United States Patent [19]
Bratz et al.

[11] Patent Number: 5,597,776
[45] Date of Patent: Jan. 28, 1997

[54] SUBSTITUTED PYRIDO[2, 3-DIPYRIMIDINES AS ANTIDOTES FOR HERBICIDAL CYCLOHEXENONES

[75] Inventors: Matthias Bratz, Speyer; Reiner Kober, Fussgoenheim; Rainer Seele, Ellerstadt; Thomas Saupe, Sandhausen; Norbert Meyer, Ladenburg; Nigel Walker, Dossenheim; Andreas Landes, Limburgerhof; Helmut Walter, Obrigheim, all of Germany

[73] Assignee: BASF Aktiengesellschaft, Ludwigshafen, Germany

[21] Appl. No.: 419,518

[22] Filed: Apr. 10, 1995

Related U.S. Application Data

[63] Continuation of Ser. No. 946,516, Sep. 16, 1992, abandoned.

[30] Foreign Application Priority Data

Sep. 18, 1991 [DE] Germany ............... 41 31 029.2

[51] Int. Cl.⁶ .................... A01N 25/32; A01N 39/04; A01N 43/90; C07D 471/02
[52] U.S. Cl. .................... 504/105; 504/106; 504/107; 504/108; 544/279
[58] Field of Search ............... 544/279; 504/105, 504/106, 107, 108

[56] References Cited

U.S. PATENT DOCUMENTS

| | | | |
|---|---|---|---|
| 2,749,345 | 6/1956 | Hitchings et al. | 544/279 |
| 3,873,545 | 3/1975 | Osselaere et al. | 260/256.5 |
| 4,249,937 | 2/1981 | Iwataki et al. | 71/97 |
| 4,867,784 | 9/1989 | Keil et al. | 504/326 |
| 4,881,969 | 11/1989 | Saupe et al. | 71/94 |
| 5,034,393 | 7/1991 | Hackler et al. | 544/279 |
| 5,059,240 | 10/1991 | Hagen et al. | 71/94 |

FOREIGN PATENT DOCUMENTS

| | | |
|---|---|---|
| 018151 | 10/1980 | European Pat. Off. |
| 387568 | 9/1990 | European Pat. Off. |
| WO92/08719 | 5/1992 | WIPO |

OTHER PUBLICATIONS

Sakamoto et al., *Chem. and Pharm. Bull.*, vol. 30, pp. 2410–16.
Brown et al., *J. Chem. Soc.*, 1975, pp. 2182–2185.
Higashino et al., (Chem. Abst., 73:66529t 1970) *Chem. Pharm. Bull.* vol. 18 No. 10, pp. 1457–1464 1970.
Ogata et al., (Chem. Abst. 78:29717k, 1973) *Chem. Pharm. Bull*, vol. 20, No. 10, pp. 2264–2268 1972.
Osselaere et al., (Chem. Abst. 83:9970n 1975) *Ann. Pharm. Franc.* vol. 32 No. 11, pp. 575–579 1974.
Stupnikova et al., (Chem. Abst, 98:179323f) *Khim. Get. Soedin.* No. 1, 1983 pp. 115–118.
J. CHem Soc., (C) 1745 (1967), Irwin et al.
Chem. Pharm. Bull. 19, 1482 (1971), Minami et al.
Chem. Pharm. Bull. 18, 1385 (1970), Nishigaki et al.
J. Org. Chem. 37, 3980 (1970), Rizkalla et al.
J. Org. Chem. 40, 1438 (1975), Evans et al.
Arch. Pharm. 316, 346 (1983), Söllhuber–Kretzer.
Bull. Chem. Soc. Jpn. 45, 1127 (1972), Nishino et al.
Chem. Ber. 96, 1868 (1963), Bredereck et al.
J. Med. Chem. 24, 382 (1981), Bennett et al.

*Primary Examiner*—S. Mark Clardy
*Attorney, Agent, or Firm*—Keil & Weinkauf

[57] ABSTRACT

Herbicides containing at least one substituted pyrido[2,3-d] pyrimidine I

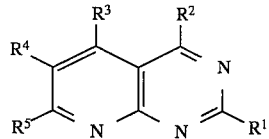

or a plant-tolerated salt of those compounds I in which at least one of the substituents $R^1$ to $R^5$ is an acidic or a basic group, and at least one herbicidal active ingredient selected from
A) the group consisting of the cyclohexenone derivatives II, or
B) the group consisting of the 2-(heteroaryloxy)- or 2-(4-aryloxy)-phenoxycarboxylic acid derivative.

9 Claims, No Drawings

SUBSTITUTED PYRIDO[2,3-DIPYRIMIDINES AS ANTIDOTES FOR HERBICIDAL CYCLOHEXENONES

This application is a continuation of application Ser. No. 07/946,516, filed on Sep. 16, 1992 abandoned.

The present invention relates to herbicides containing at least one antagonistic substituted pyrido[2,3-d]pyrimidine of the general formula I

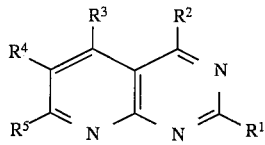

where $R^1$ and $R^2$ are each hydrogen; $C_1$–$C_8$-alkyl; $C_1$–$C_8$-haloalkyl; $C_1$–$C_6$-alkoxy; $C_1$–$C_6$-haloalkoxy; $C_1$–$C_4$-alkoxy-$C_1$–$C_6$-alkyl; $C_1$–$C_8$-alkylamino; $C_2$–$C_8$-alkenyl; $C_2$–$C_8$-alkynyl;

$C_3$–$C_8$-cycloalkyl with which a benzene radical may be fused, where this group may furthermore carry from one to three of the following radicals: hydroxyl, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

phenyl, naphthyl, phenyl-$C_1$–$C_6$-alkyl, a 5-membered aromatic ring which, in addition to carbon atoms, may contain from one to three nitrogen atoms and one oxygen or one sulfur atom as hetero atoms or which, in addition to carbon atoms, may contain from one to three nitrogen atoms or one oxygen or one sulfur atom as heteroatoms, a 6-membered aromatic ring which, in addition to carbon atoms, may contain from one to three nitrogen atoms as heteroatoms, where a benzene ring may be fused with the abovementioned 5-membered and 6-membered heteroaromatics and where the aromatic and heteroaromatic radicals may additionally carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkylthio, $C_3$–$C_6$-alkenyl and $C_3$–$C_6$-alkynyl;

$R^3$ is hydroxyl; amino; halogen; $C_1$–$C_6$-alkythio; di-$C_1$–$C_8$-alkylamino; $C_3$–$C_8$-cycloalkylamino; $C_1$–$C_8$-alkoxycarbonyl or one of the groups stated for $R^1$;

$R^4$ is one of the groups stated for $R^1$;

CN; $NO_2$; COOH; CSOH; Di-$C_1$–$C_4$-alkylamino-$C_1$–$C_4$-alkyl;

$SO_2$—$R^6$; $C(=X)$—$R^7$; $C(=Y)$—$R^8$ or $R^7$—$C(YR^9)$—$ZR^{10}$;

$R^6$ is one of the groups stated for $R^1$; hydroxyl; amino; di-$C_1$–$C_8$-alkylamino; $C_3$–$C_8$-cycloalkylamino; $C_1$–$C_6$-alkylthio;

$R^7$ amino; hydroxyamino (—NH—OH); $C_1$–$C_8$-alkylamino; di-$C_1$–$C_8$-alkylamino; $C_3$–$C_8$-cycloalkylamino; $C_1$–$C_8$-alkoxy; $C_1$–$C_6$-alkylthio; phenylamino;

$R^8$ is one of the groups stated for $R^1$;

$R^9$ and $R^{10}$ are each $C_1$–$C_8$-alkyl; $C_1$–$C_6$-haloalkyl; $C_1$–$C_4$-alkoxy-$C_2$–$C_6$-alkyl or $C_{2-8}$-alkenyl, or $R^9$ and $R^{10}$ together form —$CH_2CH_2$—, —$CH_2CH_2CH_2$— or —$CH_2CH_2CH_2CH_2$—, where one or two hydrogen atoms in these groups may be replaced by the following radicals: $=O$, $C_1$–$C_8$-alkyl, $C_1$–$C_6$-haloalkyl or $C_1$–$C_6$-alkoxy;

X is oxygen, sulfur or $NR^{11}$, where $R^{11}$ is one of the groups stated for $R^1$ or has the following meanings:

hydrogen; hydroxyl; amino; di-$C_1$–$C_8$-alkylamino; $C_3$–$C_8$-cycloalkylamino;

phenoxy, naphthyloxy, phenylamino or naphthylamino, where the aromatic radicals may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkylthio, $C_3$–$C_6$-alkenyl and $C_3$–$C_6$-alkynyl; and Y is oxygen or sulfur;

$R^5$ is one of the groups stated for $R^1$;

hydroxyl; amino; halogen; $C_1$–$C_6$-alkylthio; di-$C_1$–$C_8$-alkylamino; $C_3$–$C_8$-cycloalkylamino; pyrrolidin-1-yl; piperidin-1-yl; morpholin-1-yl; $C_1$–$C_8$-alkylcarbonyloxy; $C_1$–$C_4$-haloalkylcarbonyloxy; $C_1$–$C_8$-alkylsulfonyloxy; $C_1$–$C_8$-haloalkylsulfonyloxy;

phenoxy, napthyloxy, phenylamino, naphthylamino, benzyloxy, benzylamino, benzoyloxy, 2-naphthoyloxy or phenylsulfonyloxy, where the aromatic radicals may carry from one to three of the following groups: halogen, $C_1$–$C_4$-alkyl, $C_1$–$C_4$-haloalkyl and $C_1$–$C_4$-alkoxy;

$N(R^{12})$—$SO_2$—$R^{13}$; $N(R^{12})$—$CO$—$R^{14}$; $N(R^{12})$—$CS$—$R^{14}$;

$R^{12}$ is hydrogen; $C_1$–$C_4$-alkyl;

phenyl, which may carry from one to three of the following radicals: halogen, $C_1$–$C_4$-alkyl, $C_1$–$C_4$-haloalkyl and $C_1$–$C_4$-alkoxy;

$R^{13}$ is one of the groups stated for $R^1$;

amino, di-$C_1$–$C_8$-alkylamino or $C_3$–$C_8$-cycloalkylamino;

$R^{14}$ is one of the groups stated for $R^1$;

amino; hydroxyamino(—NH—OH); di-$C_1$–$C_6$-alkylamino or $C_3$–$C_8$-cycloalkylamino, and the plant-tolerated salts of those compounds I in which at least one of the substituents $R^1$ to $R^5$ is an acidic or basic group, and at least one herbicidal active ingredient selected from
A) the group consisting of the cylcohexenone derivatives of the general formula II

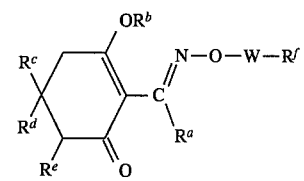

where $R^a$ is $C_1$–$C_6$-alkyl;

$R^b$ is hydrogen;

one equivalent of an agriculturally useful cation;

$C_1$–$C_8$-alkylcarbonyl; $C_1$–$C_{10}$-alkylsulfonyl; $C_1$–$C_{10}$-alkylphosphonyl;

benzoyl, benzenesulfonyl or benzenephosphonyl, where the aromatic rings may carry from 1 to 5 halogen atoms;

$R^c$ is hydrogen; CN; CHO;

$C_1$–$C_6$-alkyl which may carry one of the following radicals: $C_1$–$C_4$-alkoxy, $C_1$–$C_4$-alkylthio, phenoxy, phenylthio, pyridyloxy or pyridylthio, where the aromatic radicals in turn may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy or $NR^gR^h$;

$R^g$ is hydrogen; $C_1$–$C_4$-alkyl; $C_3$–$C_6$-alkenyl; $C_3$–$C_6$-alkynyl; $C_1$–$C_6$-alkylcarbonyl;

benzoyl which may carry from one to three of the following radicals: nitro, cyano, halogen, $C_1$–$C_4$-alkyl, $C_1$–$C_4$-haloalkyl, $C_1$–$C_4$-alkoxy and $C_1$–$C_4$-alkylthio;

$R^h$ is hydrogen; $C_1$–$C_4$-alkyl; $C_3$–$C_6$-alkenyl; $C_3$–$C_6$-alkynyl;

$R^c$ is furthermore $C_3$–$C_7$-cycloalkyl or $C_5$–$C_7$-cycloalkenyl, where these rings may carry from one to three of the following radicals: hydroxyl, halogen, $C_1$–$C_4$-alkyl, $C_1$–$C_4$-haloalkyl, $C_1$–$C_4$-alkoxy, $C_1$–$C_4$-alkylthio, benzylthio, $C_1$–$C_4$-alkylsulfonyl, $C_1$–$C_4$-alkylsulfenyl and $C_1$–$C_4$-alkylsulfinyl;

a 5-membered saturated ring which, in addition to carbon ring members, contains one or two oxygen or sulfur atoms or one oxygen and one sulfur atom and may carry from one to three of the following radicals: $C_1$–$C_4$-alkyl, $C_1$–$C_4$-haloalkyl, $C_1$–$C_4$-alkoxy and $C_1$–$C_4$-alkylthio;

a 6 - or 7 -membered saturated or monounsaturated or diunsaturated ring which, in addition to carbon ring members, contains one or two oxygen or sulfur atoms or one oxygen and one sulfur atom and may carry from one to three of the following radicals: hydroxyl, halogen, $C_1$–$C_4$-alkyl, $C_1$–$C_4$-haloalkyl, $C_1$–$C_4$-alkoxy and $C_1$–$C_4$-alkylthio;

a 5-membered aromatic ring which, in addition to carbon ring members, contains one or two nitrogen atoms and one oxygen or sulfur atom or from one to three nitrogen atoms or one oxygen or one sulfur atom and may carry from one to three of the following radicals: cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkythio, $C_2$–$C_6$-alkenyl, $C_2$–$C_6$-alkenyloxy, $C_2$–$C_6$-alkynyl, $C_2$–$C_6$-alkynyloxy and $C_1$–$C_4$-alkoxy-$C_1$–$C_4$-alkyl;

phenyl or pyridyl, where these rings may carry from one to three of the following radicals: nitro, formyl, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_2$–$C_6$-alkenyl, $C_2$–$C_6$-alkenyloxy, $C_3$–$C_6$-alkynyl, $C_3$–$C_6$-alkynyloxy and $NR^kR^l$;

$R^k$ is hydrogen; $C_1$–$C_4$-alkyl; $C_3$–$C_6$-alkenyl; $C_3$–$C_6$-alkynyl;

$R^l$ is hydrogen: $C_1$–$C_4$-alkyl; $C_3$–$C_6$-alkenyl; $C_3$–$C_6$-alkynyl; $C_1$–$C_6$-alkylcarbonyl;

benzoyl, which may carry from one to three of the following radicals: nitro, cyano, halogen, $C_1$–$C_4$-alkyl, $C_1$–$C_4$-haloalkyl, $C_1$–$C_4$-alkoxy and $C_1$–$C_4$-alkylthio;

$R^d$ is hydrogen, hydroxyl or, if $R^c$ is $C_1$–$C_6$-alkyl, also $C_1$–$C_6$-alkyl;

$R^e$ is hydrogen; cyano; halogen; $C_1$–$C_4$-alkoxycarbonyl; $C_1$–$C_4$-alkylketoxime;

W is $C_1$–$C_6$-alkylene, $C_3$–$C_6$-alkenylene or alkynylene, where these groups may carry a methylene group (=$CH_2$) and/or from one to three of the following radicals: halogen and $C_1$–$C_3$-alkyl;

$C_3$–$C_6$-alkylene or $C_3$–$C_6$-alkenylene, in each of which radicals a methylene group is replaced with oxygen, sulfur, SO, $SO_2$ or $NR^i$ and from one to three hydrogen atoms may be replaced with $C_1$–$C_3$-alkyl radicals;

$R^i$ is hydrogen; $C_1$–$C_4$-alkyl; $C_3$–$C_6$-alkenyl; $C_3$–$C_6$-alkynyl; and $R^f$ is hydrogen; CH=CH—$Z^1$, where $Z^1$ is hydrogen; cyano; carboxyl; halogen; $C_1$–$C_4$-alkyl; $C_1$–$C_4$-haloalkyl; $C_1$–$C_4$-alkoxy; $C_1$–$C_8$-alkoxycarbonyl; benzyloxycarbonyl;

$C_3$–$C_6$-cycloalkyl which in turn may carry from one to three of the following radicals: hydroxyl, halogen, $C_1$–$C_4$-alkyl, $C_1$–$C_4$-haloalkyl and $C_1$–$C_4$-alkoxy;

phenyl, halophenyl, dihalophenyl, thienyl or pyridyl, where these radicals may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_3$–$C_6$-cycloalkyl, where the cyclic radical in turn may furthermore carry from one to three of the following groups: halogen, $C_1$–$C_4$-alkyl, $C_1$–$C_4$-haloalkyl and $C_1$–$C_4$-alkoxy; $R^f$ is furthermore ethynyl, which may carry one of the following radicals: $C_1$–$C_4$-alkyl, or $C_3$–$C_6$-cycloalkyl, where these groups may furthermore carry from one to three of the following radicals: hydroxyl, halogen, $C_1$–$C_4$-alkyl, $C_1$–$C_4$-haloalkyl and $C_1$–$C_4$-alkoxy;

ethynyl which carries one of the following radicals: phenyl, thienyl or pyridyl, where the aromatic radicals may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

phenyl, halophenyl, dihalophenyl, a 5-membered aromatic ring which, in addition to carbon members, contains one or two nitrogen atoms and one oxygen or sulfur atom or from one to three nitrogen atoms or one oxygen or one sulfur atom, or a 6-membered aromatic ring which, in addition to carbon ring members, contains from one to four nitrogen atoms, where these aromatic and heteroaromatic groups may carry from one to three of the following radicals: nitro, $C_1$–$C_4$-alkoxy, $C_1$–$C_4$-haloalkoxy, $C_1$–$C_4$-alkylthio, $C_1$–$C_4$-haloalkylthio or the radicals stated for $Z^1$ and $NR^k R^l$, where $R^k$ and $R^l$ have the abovementioned meanings;

or

B) the group consisting of the 2-(4-hetaryloxy)-or 2-(4-aryloxy)-phenoxycarboxylic acid derivatives of the formula III $$R^o-O-\langle\text{phenyl}\rangle-O-\overset{R^p}{\underset{|}{CH}}-\overset{O}{\underset{\|}{C}}-OR^q \qquad \text{III}$$

where $R^o$ is phenyl, pyridyl, benzoxazolyl, benzothiazolyl or benzopyrazinyl, where these aromatic and heteroaromatic ring systems may carry one or two of the following radicals: nitro, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^p$ is hydrogen or methyl;

$R^q$ is hydrogen; $C_1$–$C_4$-alkyl; $C_3$–$C_4$-alkenyl; $C_3$–$C_4$-alkynyl; $C_1$–$C_4$-alkoxy-$_1$–$C_4$-alkyl; $C_3$–$C_4$-alkylideneiminoxy-$C_2$–$C_3$-alkyl; teztrahydrofuranylmethyl; isoxazolidinyl;

or one equivalent of an agriculturally useful cation.

The present invention furthermore relates to methods for selectively controlling undesirable plant growth on cultivated areas of crop plants with these herbicides and to novel pyrido[2,3-d]pyrimidines I'.

Substituted pyrido[2,3-d]pyrimidines of the same type as the compounds I are already known from the following publications:

W. J. Irwin et al., J. Chem. Soc. (C) (1967), 1745;
Shinsaku Minami et al., Chem. Pharm. BNull. 19 (1971), 1483 [$R_3$=hydroxyl];
Sadao Nishigaki et al., Chem. Pharm. Bull. 18 (1970), 1385;
Rizkalla et al., J. Org. Chem. 37, (1972), 3980 [$R_3$=hydroxyl];
Evans et al., J. Org. Chem. 40 (1975), 1438;
Söllhuber-Kretzer et al., Arch. Pharm. 316 (1983), 346;
Nishino et al., Bull Chem. Soc. Jpn. 45 (1972), 1127;
Bredereck et al., Chem. Ber. 96 (1963), 1868;
Bennett et al., J. Med. Chem. 24 (1981), 382;
EP-A 329 012;
EP-A 18 151 [6-aryl-7-aminopyrido[2,3-d]pyrimidines as an antihypertensive agent].

However, the stated publications do not mention an antidotal or antagonistic action of the known compounds in combination with herbicidal active ingredients.

It is an object of the present invention to provide herbicides which ensure good control of weeds without significantly damaging the crops or substantially reducing the yield thereof.

We have found that this object is achieved by the herbicides defined at the outset.

We have also found methods for treating crop plants with the antagonistic compounds I and the herbicides II or the herbicides III, whether the compounds I and II or I and III are formulated and applied together or separately and the order in which administration is effected in the case of separate application being unimportant.

The herbicides contain at least one antagonist compound I and at least one herbicide II or one herbicide III.

However, further antagonistic or herbicidal compounds may be present in the novel herbicides.

Substituted pyrido[2,3-d]pyrimidines of the formula I'

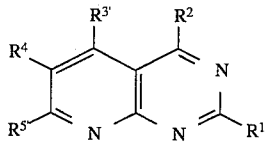

where the substituents have the following meanings, are novel:
those in which $R^1$, $R^2$ and $R^4$ have the abovementioned meanings and $R^{3'}$ and $R^{5'}$ are defined as follows:
$R^{3'}$ is halogen, $C_1$–$C_6$-alkylthio or one of the groups stated for $R^1$;
$R^{5'}$ is one of the groups stated for $R^1$;
hydroxyl; halogen; $C_1$–$C_6$-alkylthio; $C_1$–$C_8$-alkylcarbonyloxy; $C_1$–$C_8$-alkylsulfonyloxy; phenoxy; benzoyloxy;
Phenylsulfonyloxy where the aromatic radical may carry from one to three of the following groups: halogen, $C_1$–$C_4$-alkyl, $C_1$–$C_4$-haloalkyl and $C_1$–$C_4$-alkoxy;
with the proviso that $R^1$ and $R^{3'}$ are not simultaneously hydrogen when $R^2$ is hydrogen or phenyl and $R^4$ is phenyl or $R^{5'}$ is phenyl, halophenyl, naphthyl or pyridyl, and with the proviso that $R^2$, $R^{3'}$, $R^4$ and $R^{5'}$ are not simultaneously hydrogen when $R^1$ is hydrogen or pyridyl,
and the plant-tolerated salts of those compounds I' in which at least one of the substituents $R^1$, $R^2$, $R^{3'}$, $R^4$ and $R^{5'}$ is an acidic or basic group.

The substituted pyrido[2,3-d]pyrimidines I and I' are obtainable in various ways, preferably by one of the following methods:

a) Condensation of 4-aminopyrimidines IV with methylenecarbonyl compounds V

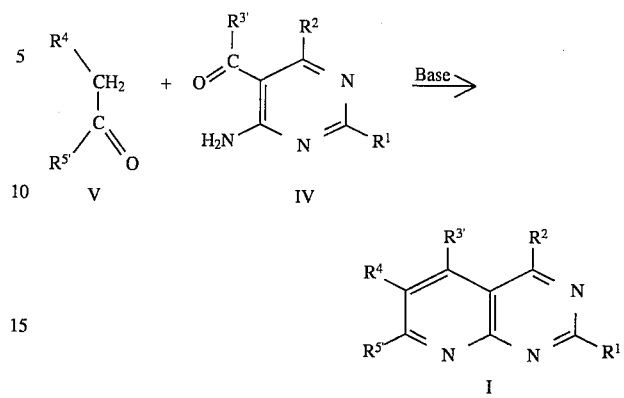

The reaction is preferably carried out in a conventional manner (cf. Caluwe et al., J. Org. Chem. 40 (1981), 1438–1439) in an inert solvent or diluent, for example in water, in an alcohol such as methanol, ethanol, propanol, isopropanol or ethoxyethanol, in liquid ammonia, in an ether, such as tetrahydrofuran or dioxane, in an aromatic hydrocarbon, such as benzene, toluene, chlorobenzene or nitrobenzene, in a polar aprotic solvent, such as acetonitrile, dimethylformamide, dimethyl sulfoxide or N-methylpyrrolidone or in a mixture. of the stated solvents.

The reactions are advantageously carried out in the presence of an organic or inorganic base, for example the hydroxides, hydrides, alkoxides, amides, carbonates and bicarbonates of the alkali and alkaline earth metals being suitable. Alkali metal hydroxides, such as lithium hydroxide, sodium hydroxide and potassium hydroxide, alkaline earth metal hydroxides, such as barium hydroxide and calcium hydroxide, alkali metal hydrides, such as sodium hydride and potassium hydride, alkaline earth metal hydrides, such as calcium hydride, alkali metal alcoholates, such as sodium methylate, sodium ethylate and potassium tert-butylate, alkali metal amides, such as sodium amide and lithium diisopropylamide, alkali metal carbonates and bicarbonates, such as sodium carbonate, sodium bicarbonate or potassium carbonate and potassium bicarbonate, are particularly suitable. Among the organic bases, aliphatic amines such as triethylamine, dimethylamine, diethylamine and diisopropylamine, cycloaliphatic amines, such as piperidine, morpholine, pyrrolidine, DBU and DABCO, and aromatic amines such as pyridine, N,N-dimethylaminopyridine and quinoline, are particularly preferred.

If the base used is an amine, the reaction can also be carried out in the absence of a solvent, in an excess of the base.

The starting materials IV and V are advantageously used in the roughly stoichiometric ratio, or an excess of up to about 100 mol % of methylene compound V is employed.

The amount of base is not critical. It is as a rule 10–50 mol %, but an excess may also be used.

When an organic base is employed, the reaction can be carried out in the absence of a solvent, in an excess of base of up to about 10 times the molar amount, based on the 4-aminopyrimidine IV.

In general, the reaction temperature is from 0° to 200° C. preferably from 20° to 150° C., in particular about 20°–30° C. (room temperature) or at the boiling point of the particular solvent.

As a rule, atmospheric pressure or the autogenous pressure of the system is used. Higher or lower pressure is possible but generally has no advantages.

The 4-aminopyrimidines IV used are known from the literature or can be prepared by methods similar to those described there (cf. for example Benett et al., J. Med. Chem. 24 (1981), 381–389 and the literature cited there).

b) Condensation of 4-aminopyrimidines IV with the acetonitriles VI and, if desired, subsequent derivatization of the amino group

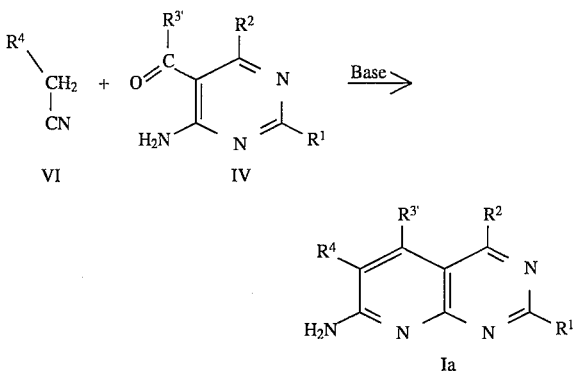

The reaction is usually carried out by conventional methods [cf. for example Benett et al., J. Med. Chem. 24 (1981), 381–389]. Subsequent derivatization can be effected, for example, by methods similar to those described in EP-A 329 012.

c) Reaction of 4-aminopyridines IV with the amides VII (cf. Söllhuber-Kretzer in Arch. Pharm. 316 (1983), 346–352]

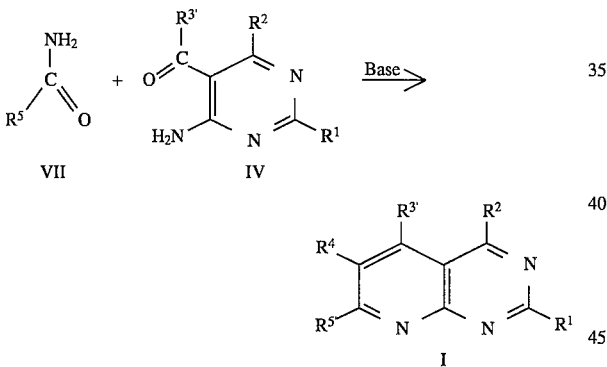

d) Reaction of 4-aminopyrimidines IV ($R^3$ and $R^{3'}$=$OC_2H_5$) with CH-acidic compounds VIIIa or VIIIb by a Claisen condensation reaction

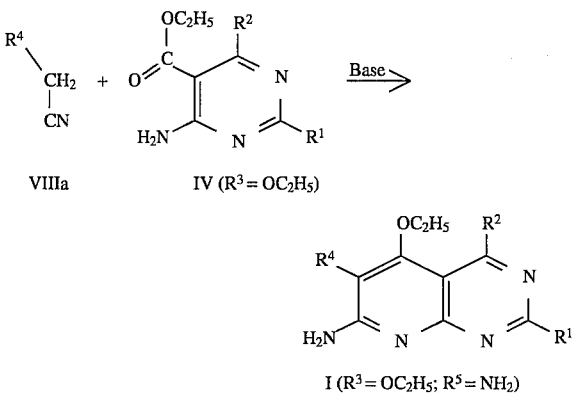

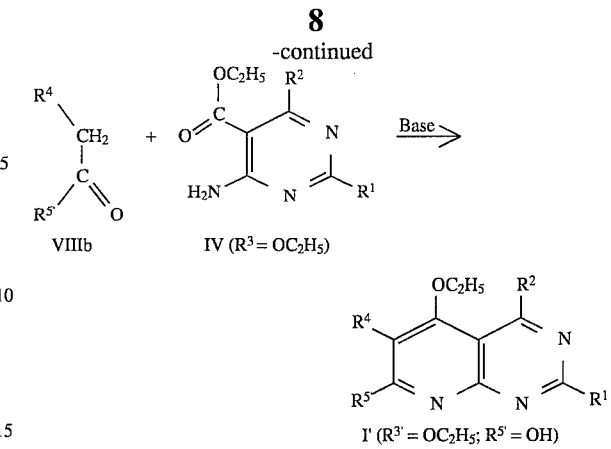

$R^5$ is preferably halogen, particularly preferably chlorine, or $C_1$–$C_4$-alkoxy, in particular ethoxy.

The reaction is carried out by conventional methods (cf. Bredereck et al., Chem. Ber. 96 (1963), 1868–1872)) in the presence of sodium or of an alkali metal alcoholate, such as sodium methylate, sodium ethylate or potassium tert-butylate.

The reaction in the presence of sodium is advantageously carried out in the absence of a solvent, in an excess of the CH-acidic compound VIIIa or VIIIb of up to about 10 times the molar amount. In the reaction in the presence of an alcoholate, it is advisable to use the corresponding alcohol as a solvent, the starting materials IV and VIIIa or VIIIb preferably being used in roughly stoichiometric amounts.

A review of further methods of preparation is given in an article by E. Lunt and C. G. Newton in Comprehensive Heterocyclic Chemistry (editors: A. Katritzky and C. W. Rees), Vol. 3, p. 215 et seq. In this context, reference may also be made to the following publications:

C. J. Blankley et al., J. Med. Chem. 24 (1990), 382–389,

M. Söllhuber-Kretzer et al., Arch. d. Pharm. 316 (1983), 346–352, and

P. Caluwe et al., J. Org. Chem. 40 (1975), 1438–1439.

With regard to the biological activity of the compounds I as antidotes, preferred derivatives are those in which the substituents have the following meanings:

$R^1$ and $R^2$ are each hydrogen;

$C_1$–$C_8$-alkyl, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpenty, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably methyl, ethyl, propyl, 1-methylethyl, butyl or 1-methylpropyl;

$C_1$–$C_8$-haloalkyl, in particular $C_1$–$C_4$-haloalkyl, in particular $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2,-difluoroethyl, 2,2,-dichloro-2-fluoroethyl, 2,2,2-trichloroethyl or pentafluoroethyl;

$C_1$–$C_6$-alkoxy, such as methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_6$-haloalkoxy, particularly $C_1$–$C_4$-haloalkoxy, in particular $C_1$–$C_2$-haloalkyloxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy;

$C_1$–$C_4$-alkoxy-$C_1$–$C_6$-alkyl is $C_1$–$C_6$-alkyl as stated above, which was substituted by $C_1$–$C_4$-alkoxy as stated above, and in particular methoxymethyl;

$C_1$–$C_8$-alkylamino, in particular $C_1$–$C_6$-alkylamino, such as methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino, in particular methylamino or ethylamino;

$C_2$–$C_8$-alkenyl, in particular $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-di-methyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular ethenyl or 2-propenyl;

$C_2$–$C_8$-alkynyl, in particular $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl, in particular 2-propynyl;

$C_3$–$C_8$-cycloalkyl such as cyclopropyl, cyclobutyl, cyclopentyl, cyclohexyl, cycloheptyl or cyclooctyl, in particular cyclopropyl, cyclopentyl or cyclohexyl, with which a benzene radical may be fused, this group may furthermore carry from one to three of the following radicals: hydroxyl;

halogen, such as fluorine, chlorine, bromine or iodine, preferably fluorine or chlorine;

$C_1$–$C_4$-alkyl, such as methyl, ethyl, propyl, 1-methylethyl, butyl, 1-methylpropyl, 2-methylpropyl or 1,1-dimethylethyl, in particular methyl, ethyl or 1-methylethyl;

$C_1$–$C_4$-haloalkyl, in particular $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy;

$C_1$–$C_4$-haloalkoxy, in particular $C_1$–$C_4$-haloalkoxy as stated above, in particular difluoromethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio or ethylthio;

phenyl, naphthyl, phenyl-$C_1$–$C_6$-alkyl (which is phenyl-substituted $C_1$–$C_6$-alkyl as stated above), a 5-membered aromatic ring which, in addition to carbon atoms, may contain from one to three nitrogen atoms and one oxygen or one sulfur atom as heteroatoms or which, in addition to carbon atoms, may contain from one to three nitrogen atoms or one oxygen or one sulfur atom as heteroatoms, a 6-membered aromatic ring which, in addition to carbon atoms, may contain from one to three nitrogen atoms as heteroatoms, where a benzene ring may be fused with the abovementioned 5- and 6-membered heteroaromatics and where the aromatic and heteroaromatic radicals may additionally carry from one to three of the following groups: nitro, cyano, halogen as stated above, preferably fluorine or chlorine;

$C_1$–$C_4$-alkyl as stated above, preferably methyl, ethyl or 1-methylethyl;

$C_1$–$C_4$-haloalkyl, in particular $C_1$–$C_2$-haloalkyl as stated above, preferably trifluoromethyl or difluoromethyl;

$C_1$–$C_4$-alkoxy as stated above, preferably methoxy, ethoxy or 1-methylethoxy;

$C_1$–$C_4$-haloalkoxy, in particular $C_1$–$C_2$-haloalkoxy as stated above, preferably difluoromethoxy or trifluoromethoxy;

$C_1$–$C_4$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1,-dimethylethoxycarbonyl, preferably methoxycarbonyl or ethoxycarbonyl;

$C_1$–$C_4$-alkylthio as stated above, preferably methylthio or ethylthio;

$C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1,methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1,-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, preferably 2-propenyl;

$C_3$–$C_6$-alynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl;

$R^3$ is hydroxyl; amino;

halogen as stated above, preferably fluorine or chlorine;

$C_1$–$C_6$-alkythio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, preferably $C_1$–$C_4$-alkylthio, in particular methylthio or ethylthio;

di-$C_1$–$C_6$-alkylamino, in particular di-$C_1$–$C_6$-alkylamino, especially di-$C_1$–$C_4$-alkylamino, such as N,N-dimethylamino, N,N-diethylamino, N,N-dipropylamino, N,N-di(1-methylethyl)-amino, N,N-dibutylamino, N,N-di-(1-methylpropyl)-amino, N,N-di-(2-methylpropyl)-amino, N,N-di-(1,1-dimethylethyl)-amino, N-ethyl-N-methylamino, N-methyl-N-propylamino, N-methyl-N-(1-methylethyl)-amino, N-butyl-N-methylamino, N-methyl-N-(1-methylpropyl)-amino, N-methnyl-N-(2-methylpropyl)-amino, N-(1,1-dimethylethyl)-N-methylamino, N-ethyl-N-propylamino, N-ethyl-N-(1-methylethyl)-amino, N-butyl-N-ethylamino, N-ethyl-N-(1-methylpropyl)-amino, N-ethyl-N-(2-methylpropyl)-amino, N-ethyl-N-(1,1-dimethylethyl)-amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)-amino, N-(1-methylethyl)-N-(1-methylpropyl)-amino, N-(1-methylethyl)-N-(2-methylpropyl)-amino, N-(1,1-dimethylethyl)-N-(1-methylethyl)-amino, N-butyl-N-(1-methylpropyl)-amino, N-butyl-N-(2-methylpropyl)-amino, N-butyl-N-(1,1-dimethylethyl)-amino, N-(1-methylpropyl)-N-(2-methylpropyl)-amino, N-(1,1-dimethylethyl)-N-(1-methylpropyl)-amino or N-(1,1,-dimethylethyl)-N-(2-methylpropyl)-amino;

$C_3$–$C_8$-cycloalkylamino, such as cyclopropylamino, cyclobutylamino, cyclopentylamino, cyclohexylamino, cycloheptylamino or cyclooctylamino, preferably cyclopropylamino, cyclopentylamino or cyclohexylamino;

$C_1$–$C_8$-alkoxycarbonyl, in particular $C_1$–$C_6$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentyloxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, preferably $C_1$–$C_4$-alkoxycarbonyl;

or one of the groups stated for $R^1$;

$R^4$ is one of the groups stated for $R^1$;

CN; $NO_2$; COOH; CSOH;

di-$C_1$–$C_4$-alkylamino-$C_1$–$C_4$-alkyl is $C_1$–$C_4$-alkyl as stated above which is substituted by di-$C_1$–$C_4$-alkylamino as stated above;

$SO_2$—$R^6$; C(=X)—$R^7$; C(=Y)—$R^8$, or $R^7$—C($YR^9$)—$ZR^{10}$;

$R^6$ is one of the groups stated for $R^1$;
hydroxyl; amino;
di-$C_1$-$C_8$-alkylamino, in particular di-$C_1$-$C_6$-alkylamino, in particular di-$C_1$-$C_4$-alkylamino as stated above;
$C_3$-$C_8$-cycloalkylamino as stated above, in particular cyclopropylamino, cyclopentylamino or cyclohexylamino;
$C_1$-$C_6$-alkylthio as stated above, preferably $C_1$-$C_4$-alkythio, in particular $C_1$-$C_2$-alkylthio;

$R^7$ is amino; hydroxyamino (—NR—OH);
$C_1$-$C_8$-alkylamino, in particular $C_1$-$C_6$-alkylamino as stated above, preferably $C_1$-$C_4$-alkylamino, especially $C_1$-$C_2$-alkylamino;
di-$C_1$-$C_8$-alkylamino, in particular di-$C_1$-$C_6$-alkylamino, especially di-$C_1$-$C_4$-alkylamino as stated above;
$C_3$-$C_8$-cycloalkylamino as stated above, preferably cyclopropylamino, cyclopentylamino or cylcohexylamino;
$C_1$-$C_8$-alkoxy as stated above, preferably $C_1$-$C_4$-alkoxy, in particular $C_1$-$C_2$-alkoxy;
$C_1$-$C_6$-alkylthio as stated above, preferably $C_1$-$C_6$-alkylthio, in particular $C_1$-$C_2$-alkylthio;
phenylamino;

$R^8$ is one of the groups stated for $R^1$;

$R^9$ and $R^{10}$ are each $C_1$-$C_8$-alkyl as stated above;
$C_1$-$C_8$-haloalkyl as stated above;
$C_1$-$C_4$-alkoxy-$C_2$-$C_6$-alkyl is $C_2$-$C_6$-alkyl as stated above which is substituted by $C_1$-$C_4$-alkoxy as stated above, preferably ethyl, propyl or 1-methylethyl which is substituted by methoxy or ethoxy;
$C_2$-$C_8$-alkenyl as stated above, or $R^9$ and $R^{10}$ together form —CH$_2$CH$_2$—, —CH$_2$CH$_2$CH$_2$— or —CH$_2$CH$_2$CH$_2$CH$_2$—, where one or two hydrogen atoms in these groups may be replaced with the following radicals: =O (vicinal H atoms);
$C_1$-$C_8$-alkyl as stated above, preferably methyl or ethyl;
$C_1$-$C_6$-haloalkyl, in particular $C_1$-$C_4$-haloalkyl, especially $C_1$-$C_2$-haloalkyl as stated above;
$C_1$-$C_6$-alkoxy as stated above, preferably methoxy or ethoxy;

X is oxygen, sulfur or NR$^{11}$, where $R^{11}$ is one of the groups stated for $R^1$ or has the following meanings:
hydrogen; hydroxyl; amino;
di-$C_1$-$C_8$-alkylamino, in particular di-$C_1$-$C_6$-alkylamino, especially di-$C_1$-$C_4$-alkylamino as stated above;
$C_3$-$C_8$-cycloalkylamino as stated above, preferably cyclopropylamino, cyclopentylamino or cyclohexylamino;
Phenoxy, naphthyloxy, phenylamino or naphthylamino, where the aromatic radicals may carry from one to three of the following groups:
Nitro, cyano;
Halogen as stated above, preferably fluorine or chlorine;
$C_1$-$C_4$-alkyl as stated above, preferably methyl or ethyl;
$C_1$-$C_4$-haloalkyl, in particular $C_1$-$C_2$-haloalkyl as stated above, preferably trifluoromethyl;
$C_1$-$C_4$-alkoxy as stated above, preferably methoxy;
$C_1$-$C_4$-haloalkoxy, in particular $C_1$-$C_2$-haloalkoxy as stated above, preferably difluoromethoxy;
$C_1$-$C_4$-alkoxycarbonyl as stated above, preferably $C_1$-$C_2$-alkoxycarbonyl;
$C_1$-$C_4$-alkylthio as stated above, preferably methylthio;
$C_3$-$C_6$-alkenyl as stated above, preferably 2-propenyl;
$C_3$-$C_6$-alkynyl as stated above, preferably 2-propynyl;

Y is oxygen or sulfur;

$R^5$
is one of the groups stated for $R^1$;
hydroxyl; amino;
halogen as stated above, preferably fluorine or chlorine;
$C_1$-$C_6$-alkylthio as stated above, preferably $C_1$-$C_4$-alkylthio, in particular $C_1$-$C_2$-alkylthio;
di-$C_1$-$C_8$-alkylamino, in particular di-$C_1$-$C_6$-alkylamino, especially di-$C_1$-$C_4$-alkylamino as stated above, preferably di-$C_1$- or $C_2$-alkylamino;
$C_3$-$C_8$-cycloalkylamino as stated above, in particular cyclopropylamino, cyclopentylamino or cyclohexylamino;
pyrrolidin-1-yl; piperidin-1-yl; morpholin-1-yl;
$C_1$-$C_8$-alkylcarbonyloxy, in particular $C_1$-$C_6$-alkylcarbonyloxy, such as methylcarbonyloxy, ethylcarbonyloxy, propylcarbonyloxy, 1-methylethylcarbonyloxy, butylcarbonyloxy, 1-methylpropylcarbonyloxy, 2-methylpropylcarbonyloxy, 1,1-dimethylethylcarbonyloxy, pentylcarbonyloxy, 1-methylbutylcarbonyloxy, 2-methylbutylcarbonyloxy, 3-methylbutylcarbonyloxy, 2,2-dimethylpropylcarbonyloxy, 1-ethylpropylcarbonyloxy, hexylcarbonyloxy, 1,1-dimethylpropylcarbonyloxy, 1,2-dimethylpropylcarbonyloxy, 1-methylpentylcarbonyloxy, 2-methylpentylcarbonyloxy, 3-methylpentylcarbonyloxy, 4-methylpentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutylcarbonyloxy, 2-ethylbutylcarbonyloxy, 1,1,2-trimethylpropylcarbonyloxy, 1,2,2-trimethylpropylcarbonyloxy, 1-ethyl-1-methylpropylcarbonyloxy or 1-ethyl-2-methylpropylcarbonyloxy, preferably $C_1$-$C_4$-alkylcarbonyloxy, in particular $C_1$-$C_2$-alkylcarbonyloxy;
$C_1$-$C_4$-haloalkylcarbonyloxy, in particular $C_1$-$C_2$-haloalkylcarbonyloxy, such as chloromethylcarbonyloxy, dichloromethylcarbonyloxy, trichloromethylcarbonyloxy, fluoromethylcarbonyloxy, difluoromethylcarbonyloxy, trifluoromethylcarbonyloxy, chlorofluoromethylcarbonyloxy, dichlorofluoromethylcarbonyloxy, chlorodifluoromethylcarbonyloxy, 1-fluoroethylcarbonyloxy, 2-fluoroethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy or pentafluoroethylcarbonyloxy, preferably trifluoromethylcarbonyloxy;
$C_1$-$C_8$-alkylsulfonyloxy, in particular $C_1$-$C_6$-alkylsulfonyloxy, such as methylsulfonyloxy, ethylsulfonyloxy, propylsulfonyloxy, 1-methylethylsulfonyloxy, butylsulfonyloxy, 1-methyl-propylsulfonyloxy, 2-methylpropylsulfonyloxy, 1,1-dimethylethylsulfonyloxy, pentylsulfonyloxy, 1-methylbutylsulfonyloxy, 2-methylbutylsulfonyloxy, 3-methylbutylsulfonyloxy, 2,2-dimethylpropylsulfonyloxy, 1-ethylpropylsulfonyloxy, hexylsulfonyloxy, 1,1-dimethylpropylsulfonyloxy, 1,2-dimethylpropylsulfonyloxy, 1-methylpentylsulfonyloxy, 2-methylpentylsulfonyloxy, 3-methylpentylsulfonyloxy, 4-methylpentylsulfonyloxy, 1,1-dimethylbutylsulfonyloxy, 1,2-dimethylbutylsulfonyloxy, 1,3-dimethylbutylsulfonyloxy, 2,2-dimethylbutylsulfonyloxy, 2,3-dimethylbutylsulfonyloxy, 3,3-dimethylbutylsulfonyloxy, 1-ethylbutylsulfonyloxy, 2-ethylbutylsulfonyloxy, 1,1,2-trimethylpropylsulfonyloxy, 1,2,2-trimethylpropylsulfonyloxy, 1-ethyl-1-methylpropylsulfonyloxy or 1-ethyl-2-methylpropylsulfonyloxy, preferably $C_1$–$C_4$-alkylsulfonyloxy, in particular $C_1$–$C_2$-alkylsulfonyloxy;

$C_1$–$C_8$haloalkylsulfonyloxy, in particular $C_1$–$C_4$-haloalkylsulfonyloxy, especially $C_1$–$C_2$-haloalkylsulfonyloxy, such as chloromethylsulfonyloxy, dichloromethylsulfonyloxy, trichloromethylsulfonyloxy, fluoromethylsulfonyloxy, difluoromethylsulfonyloxy, trifluoromethylsulfonyloxy, chlorofluoromethylsulfonyloxy, dichlorofluoromethylsulfonyloxy, chlorodifluoromethylsulfonyloxy, 1-fluoroethylsulfonyloxy, 2-fluoroethylsulfonyloxy, 2,2-difluoroethylsulfonyloxy, 2,2,2-trifluoroethylsulfonyloxy, 2-chloro-2-fluoroethylsulfonyloxy, 2-chloro-2,2-difluoroethylsulfonyloxy, 2,2-dichloro-2-fluoroethylsulfonyloxy, 2,2,2-trichloroethylsulfonyloxy or pentafluoroethylsulfonyloxy;

phenoxy, naphthyloxy, phenylamino, naphthylamino, benzyloxy, benzylamino, benzoyloxy, 2-naphthoyloxy or phenylsulfonyloxy, where the aromatic radicals may carry from one to three of the following groups:
  halogen as stated above, preferably fluorine or chlorine;
  $C_1$–$C_4$-alkyl as stated above, preferably methyl;
  $C_1$–$C_4$-haloalkyl, in particular $C_1$–$C_2$-haloalkyl as stated above, preferably trifluoromethyl;
  $C_1$–$C_4$-alkoxy as stated above, preferably methoxy;
  $N(R^{12})$—$SO_2$—$R^{13}$; $N(R^{12})$—$CO$—$R^{14}$; $N(R^{12})$—$CS$—$R^{14}$;

$R^{12}$ is hydrogen;
  $C_1$–$C_4$-alkyl as stated above, preferably $C_1$–$C_3$-alkyl;
  phenyl which may carry from one to three of the following radicals:
    halogen as stated above, preferably fluorine or chlorine;
    $C_1$–$C_4$-alkyl as stated above, preferably methyl;
    $C_1$–$C_4$-haloalkyl, in particular $C_1$–$C_2$-haloalkyl, as stated above, preferably trifluoromethyl;
    $C_1$–$C_4$-alkoxy as stated above, preferably methoxy;
$R^{13}$ is one of the groups stated for $R^1$;
  amino;
  di-$C_1$–$C_8$-alkylamino, in particular di-$C_1$–$C_6$-alkylamino, especially di-$C_1$–$C_4$-alkylamino as stated above;
  $C_3$–$C_8$-cycloalkylamino as stated above, preferably cyclopropylamino, cyclopentylamino or cyclohexylamino;
$R^{14}$ is one of the groups stated for $R^1$ amino; hydroxyamino (—NH—OH);
  di-$C_1$–$C_8$-alkylamino, in particular di-$C_1$–$C_6$-alkylamino, especially di-$C_1$–$C_4$-alkylamino, as stated above, preferably di-$C_1$- or $C_2$-alkylamino;
  $C_3$–$C_8$-cycloalkylamino as stated above, in particular cyclopropylamino, cyclopentylamino or cyclohexylamino, and the plant-tolerated salts of those compounds I in which at least one of the substituents $R^1$ to $R^5$ is an acidic or basic group.

5-membered aromatic rings which, in addition to carbon atoms, may contain from one to three nitrogen atoms and one oxygen or one sulfur atom as heteroatoms or which, in addition to carbon atoms, may contain from one to three nitrogen atoms or one oxygen or one sulfur atom as heteroatoms are understood as meaning the following groups: 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl or 1,3,4-triazol-2-yl, preferably 2-thienyl or 3-thienyl, where a benzene ring may be fused with the abovementioned 5-membered heteroaromatics if they are a radical $R^1$ or $R^2$.

6-membered aromatic rings which, in addition to carbon atoms, may contain from one to three nitrogen atoms as hetero atoms are understood as meaning the following groups: 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl, preferably 2-pyridyl, 3-pyridyl or 4-pyridyl, where a benzene ring may be fused with the abovementioned 6-membered heteroaromatics if they are a radical $R^1$ or $R^2$.

Derivatives I and I' having acidic terminal groups or having basic nitrogen atoms may be in the form of their agriculturally useful salts.

Suitable agriculturally useful salts are generally the salts of acids or bases which do not adversely affect the antagonistic reaction of I and I'.

Examples of suitable acid addition salts are the hydrochlorides and hydrobromides, sulfates, nitrates, phosphates, oxalates or dodecylbenzenesulfonates.

Examples of suitable basic salts are those of the alkali metals, in particular the sodium and potassium salts, those of the alkali earth metals, in particular calcium, magnesium and barium salts and those of the transition metals, in particular manganese, copper, zinc and iron salts, and the ammonium salts which may carry from one to three $C_1$–$C_4$-alkyl, or hydroxy-$C_1$–$C_4$-alkyl substituents and/or one phenyl or benzyl substituent, in particular diisopropylammonium, tetramethylammonium, tetrabutylammonium, trimethylbenzylammonium and trimethyl-(2-hydroxyethyl)-ammonium salts, the phosphonium salts, the sulfonium salts, in particular tri-$C_1$–$C_4$-alkylsulfonium salts, and the sulfoxonium salts, in particular tri-$C_1$–$C_4$-alkylsulfoxonium salts. Particularly preferred compounds of formula I are summarized in Tables A and B below.

TABLE A

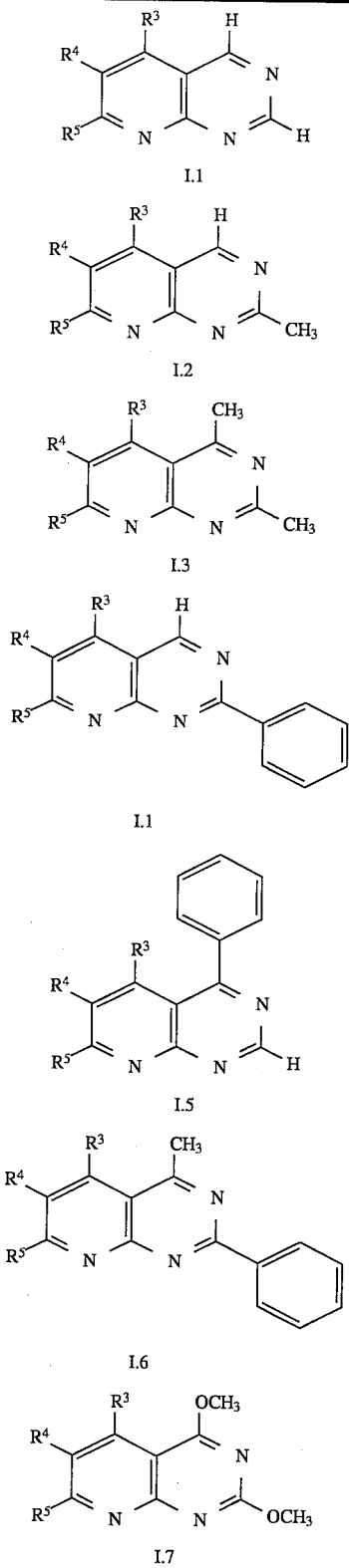

| $R^3$ | $R^4$ | $R^5$ |
|---|---|---|
| H | H | $C_6H_5$ |
| H | H | $2\text{-}CH_3\text{-}C_6H_4$ |
| H | H | $3\text{-}CH_3\text{-}C_6H_4$ |
| H | H | $4\text{-}CH_3\text{-}C_6H_4$ |
| H | H | $2\text{-}F\text{-}C_6H_4$ |
| H | H | $3\text{-}F\text{-}C_6H_4$ |
| H | H | $4\text{-}F\text{-}C_6H_4$ |
| H | H | $2\text{-}Cl\text{-}C_6H_4$ |
| H | H | $3\text{-}Cl\text{-}C_6H_4$ |
| H | H | $4\text{-}Cl\text{-}C_6H_4$ |
| H | H | $2\text{-}Br\text{-}C_6H_4$ |
| H | H | $3\text{-}Br\text{-}C_6H_4$ |
| H | H | $4\text{-}Br\text{-}C_6H_4$ |
| H | H | $2\text{-}OH\text{-}C_6H_4$ |
| H | H | $3\text{-}OH\text{-}C_6H_4$ |
| H | H | $4\text{-}OH\text{-}C_6H_4$ |
| H | H | $2\text{-}OCH_3\text{-}C_6H_4$ |
| H | H | $3\text{-}OCH_3\text{-}C_6H_4$ |
| H | H | $4\text{-}OCH_3\text{-}C_6H_4$ |
| H | H | $4\text{-}C_6H_5\text{-}C_6H_4$ |
| H | H | $3\text{-}C(CH_3)_3\text{-}C_6H_4$ |
| H | H | $4\text{-}C(CH_3)_3\text{-}C_6H_4$ |
| H | H | $2\text{-}CF_3\text{-}C_6H_4$ |
| H | H | $3\text{-}CF_3\text{-}C_6H_4$ |
| H | H | $4\text{-}CF_3\text{-}C_6H_4$ |
| H | H | $2\text{-}NO_2\text{-}C_6H_4$ |
| H | H | $3\text{-}NO_2\text{-}C_6H_4$ |
| H | H | $4\text{-}NO_2\text{-}C_6H_4$ |
| H | H | $2\text{-}CN\text{-}C_6H_4$ |
| H | H | $3\text{-}CN\text{-}C_6H_4$ |
| H | H | $4\text{-}CN\text{-}C_6H_4$ |
| H | H | $2\text{-}(CO_2C_2H_5)\text{-}C_6H_4$ |
| H | H | $3\text{-}(CO_2C_2H_5)\text{-}C_6H_4$ |
| H | H | $4\text{-}(CO_2C_2H_5)\text{-}C_6H_4$ |
| H | H | $2\text{-}Carbamoyl\text{-}C_6H_4$ |
| H | H | $3\text{-}Carbamoyl\text{-}C_6H_4$ |
| H | H | $4\text{-}Carbamoyl\text{-}C_6H_4$ |
| H | H | $2\text{-}NH_2\text{-}C_6H_4$ |
| H | H | $3\text{-}NH_2\text{-}C_6H_4$ |
| H | H | $4\text{-}NH_2\text{-}C_6H_4$ |
| H | H | $4\text{-}Pyrrolidino\text{-}C_6H_4$ |
| H | H | $2\text{-}SCH_3\text{-}C_6H_4$ |
| H | H | $3\text{-}SCH_3\text{-}C_6H_4$ |
| H | H | $4\text{-}SCH_3\text{-}C_6H_4$ |
| H | H | $2\text{-}Sulfo\text{-}C_6H_4$ |
| H | H | $3\text{-}Sulfo\text{-}C_6H_4$ |
| H | H | $4\text{-}Sulfo\text{-}C_6H_4$ |
| H | H | $3\text{-}OC(CH_3)_3\text{-}C_6H_4$ |
| H | H | $4\text{-}OC(CH_3)_3\text{-}C_6H_4$ |
| H | H | $2,4\text{-}(CH_3)_2\text{-}C_6H_3$ |
| H | H | $3,4\text{-}(CH_3)_2\text{-}C_6H_3$ |
| H | H | $2,6\text{-}(CH_3)_2\text{-}C_6H_3$ |
| H | H | $2,4\text{-}(OCH_3)_2\text{-}C_6H_3$ |
| H | H | $3,4\text{-}(OCH_3)_2\text{-}C_6H_3$ |
| H | H | $2,6\text{-}(OCH_3)_2\text{-}C_6H_3$ |
| H | H | $2,4\text{-}F_2\text{-}C_6H_3$ |
| H | H | $3,4\text{-}F_2\text{-}C_6H_3$ |
| H | H | $2,6\text{-}F_2\text{-}C_6H_3$ |
| H | H | $2,4\text{-}Cl_2\text{-}C_6H_3$ |
| H | H | $3,4\text{-}Cl_2\text{-}C_6H_3$ |
| H | H | $2,6\text{-}Cl_2\text{-}C_6H_3$ |
| H | H | $2,4\text{-}(OH)_2\text{-}C_6H_3$ |
| H | H | $3,4\text{-}(OH)_2\text{-}C_6H_3$ |
| H | H | $2,6\text{-}(OH)_2\text{-}C_6H_3$ |
| H | H | $3\text{-}NO_2\text{-}4\text{-}CH_3\text{-}C_6H_3$ |
| H | H | $3\text{-}NO_2\text{-}4\text{-}F\text{-}C_6H_3$ |
| H | H | $3\text{-}NO_2\text{-}4\text{-}Cl\text{-}C_6H_3$ |
| H | H | $3\text{-}NO_2\text{-}4\text{-}OCH_3\text{-}C_6H_3$ |

TABLE A-continued

| | | |
|---|---|---|
| H | H | 1-Naphthyl |
| H | H | 2-Naphthyl |
| H | H | Tetralin-2-yl |
| H | H | Thien-2-yl |
| H | H | Thien-3-yl |
| H | H | 5-CH$_3$-thien-2-yl |
| H | H | 5-Cl-thien-2-yl |
| H | H | 5-Br-thien-2-yl |
| H | H | 2,5-(CH$_3$)$_2$-thien-3-yl |
| H | H | 4,5-benzothien-2-yl |
| H | H | Thiazol-2-yl |
| H | H | Thiazol-4-yl |
| H | H | Thiazol-5-yl |
| H | H | 5-CH$_3$-thiazol-2-yl |
| H | H | 5-Cl-thiazol-2-yl |
| H | H | 5-Br-thiazol-2-yl |
| H | H | 2,4-(CH$_3$)$_2$-thiazol-5-yl |
| H | H | 4,5-benzothiazol-2-yl |
| H | H | Furan-2-yl |
| H | H | Furan-3-yl |
| H | H | 5-CH$_3$-furan-2-yl |
| H | H | 5-Cl-furan-2-yl |
| H | H | 5-Br-furan-2-yl |
| H | H | 2,5-(CH$_3$)$_2$-furan-3-yl |
| H | H | 4,5-benzofuran-2-yl |
| H | H | Pyrrol-2-yl |
| H | H | Pyrrol-3-yl |
| H | H | 1-CH$_3$-pyrrol-2-yl |
| H | H | 1-CH$_3$-pyrrol-3-yl |
| H | H | 2,5-(CH$_3$)$_2$-pyrrol-3-yl |
| H | H | 1,5-(CH$_3$)$_2$-pyrrol-2-yl |
| H | H | 1,5-(CH$_3$)$_2$-pyrrol-3-yl |
| H | H | Indol-2-yl |
| H | H | Indol-3-yl |
| H | H | Oxazol-2-yl |
| H | H | Oxazol-4-yl |
| H | H | 5-CH$_3$-oxazol-2-yl |
| H | H | 5-Cl-oxazol-2-yl |
| H | H | 5-Br-oxazol-2-yl |
| H | H | 2,5-(CH$_3$)$_2$-oxazol-4-yl |
| H | H | 4,5-benzoxazol-2-yl |
| H | H | Imidazol-2-yl |
| H | H | Imidazol-4-yl |
| H | H | Imidazol-5-yl |
| H | H | 5-CH$_3$-imidazol-2-yl |
| H | H | 5-Cl-imidazol-2-yl |
| H | H | 5-Br-imidazol-2-yl |
| H | H | 2,5-(CH$_3$)$_2$-imidazol-4-yl |
| H | H | 4,5-benzimidazol-2-yl |
| H | H | Pyridin-2-yl |
| H | H | Pyridin-3-yl |
| H | H | Pyridin-4-yl |
| H | H | 5-CH$_3$-pyridin-2-yl |
| H | H | 5-Cl-pyridin-2-yl |
| H | H | 5-Br-pyridin-2-yl |
| H | H | 5-CH$_3$-pyridin-3-yl |
| H | H | 5-Cl-pyridin-3-yl |
| H | H | 5-Br-pyridin-3-yl |
| H | H | 2-CH$_3$-pyridin-3-yl |
| H | H | 2-Cl-pyridin-3-yl |
| H | H | 2-Br-pyridin-3-yl |
| H | H | 2,5-(CH$_3$)$_2$-pyridin-3-yl |
| H | H | 4,5-benzopyridin-2-yl |
| H | H | Pyrazin-2-yl |
| H | H | 5-CH$_3$-pyrazin-2-yl |
| H | H | 5-Cl-pyrazin-2-yl |
| H | H | 5-Br-pyrazin-2-yl |
| H | H | Pyrimidin-2-yl |
| H | H | Pyrimidin-4-yl |
| H | H | Pyrimidin-5-yl |
| H | H | 4,5-benzopyrimidin-2-yl |
| H | CH$_3$ | C$_6$H$_5$ |
| H | CH$_3$ | 4-CH$_3$—C$_6$H$_4$ |
| H | CH$_3$ | 4-F—C$_6$H$_4$ |
| H | CH$_3$ | 4-Cl-C$_6$H$_4$ |
| H | CH$_3$ | 4-Br-C$_6$H$_4$ |
| H | CH$_3$ | 4-CH(CH$_3$)$_2$—C$_6$H$_4$ |
| H | CH$_3$ | 4-OCH$_3$—C$_6$H$_4$ |
| H | CH$_3$ | 4-C(CH$_3$)$_3$—C$_6$H$_4$ |
| H | CH$_3$ | 4-CF$_3$—C$_6$H$_4$ |
| H | CH$_3$ | 4-NO$_2$—C$_6$H$_4$ |
| H | CH$_3$ | 4-CN—C$_6$H$_4$ |
| H | CH$_3$ | 4-(NHCOCH$_3$)—C$_6$H$_4$ |
| H | CH$_3$ | 3,4-(OCH$_3$)$_2$—C$_6$H$_3$ |
| H | CH$_3$ | 2,4-Cl$_2$—C$_6$H$_3$ |
| H | CH$_3$ | 3-NO$_2$-4-CH$_3$—C$_6$H$_3$ |
| H | CH$_3$ | 2-Naphthyl |
| H | CH$_3$ | Thien-2-yl |
| H | CH$_2$CH$_3$ | C$_6$H$_5$ |
| H | CH$_2$CH$_3$ | 4-CH$_3$—C$_6$H$_4$ |
| H | CH$_2$CH$_3$ | 4-F—C$_6$H$_4$ |
| H | CH$_2$CH$_3$ | 4-Cl-C$_6$H$_4$ |
| H | CH$_2$CH$_3$ | 4-Br-C$_6$H$_4$ |
| H | CH$_2$CH$_3$ | 4-CH(CH$_3$)$_2$—C$_6$H$_4$ |
| H | CH$_2$CH$_3$ | 4-OCH$_3$—C$_6$H$_4$ |
| H | CH$_2$CH$_3$ | 4-C(CH$_3$)$_3$—C$_6$H$_4$ |
| H | CH$_2$CH$_3$ | 4-CF$_3$—C$_6$H$_4$ |
| H | CH$_2$CH$_3$ | 4-NO$_2$—C$_6$H$_4$ |
| H | CH$_2$CH$_3$ | 4-CN—C$_6$H$_4$ |
| H | CH$_2$CH$_3$ | 4-(NHCOCH$_3$)—C$_6$H$_4$ |
| H | CH$_2$CH$_3$ | 3,4-(OCH$_3$)$_2$—C$_6$H$_3$ |
| H | CH$_2$CH$_3$ | 2,4-Cl$_2$—C$_6$H$_3$ |
| H | CH$_2$CH$_3$ | 3-NO$_2$-4-CH$_3$—C$_6$H$_3$ |
| H | CH$_2$CH$_3$ | 2-Naphthyl |
| H | CH$_2$CH$_3$ | Thien-2-yl |
| H | CH$_2$CH$_2$CH$_3$ | C$_6$H$_5$ |
| H | CH$_2$CH$_2$CH$_3$ | 4-CH$_3$—C$_6$H$_4$ |
| H | CH$_2$CH$_2$CH$_3$ | 4-F—C$_6$H$_4$ |
| H | CH$_2$CH$_2$CH$_3$ | 4-Cl-C$_6$H$_4$ |
| H | CH$_2$CH$_2$CH$_3$ | 4-Br-C$_6$H$_4$ |
| H | CH$_2$CH$_2$CH$_3$ | 4-CH(CH$_3$)$_2$—C$_6$H$_4$ |
| H | CH$_2$CH$_2$CH$_3$ | 4-OCH$_3$—C$_6$H$_4$ |
| H | CH$_2$CH$_2$CH$_3$ | 4-C(CH$_3$)$_3$—C$_6$H$_4$ |
| H | CH$_2$CH$_2$CH$_3$ | 4-CF$_3$—C$_6$H$_4$ |
| H | CH$_2$CH$_2$CH$_3$ | 4-NO$_2$—C$_6$H$_4$ |
| H | CH$_2$CH$_2$CH$_3$ | 4-CN—C$_6$H$_4$ |
| H | CH$_2$CH$_2$CH$_3$ | 4-(NHCOCH$_3$)—C$_6$H$_4$ |
| H | CH$_2$CH$_2$CH$_3$ | 3,4-(OCH$_3$)$_2$—C$_6$H$_3$ |
| H | CH$_2$CH$_2$CH$_3$ | 2,4-Cl$_2$—C$_6$H$_3$ |
| H | CH$_2$CH$_2$CH$_3$ | 3-NO$_2$-4-CH$_3$—C$_6$H$_3$ |
| H | CH$_2$CH$_2$CH$_3$ | 2-Naphthyl |
| H | CH$_2$CH$_2$CH$_3$ | Thien-2-yl |
| H | CH(CH$_3$)$_2$ | C$_6$H$_5$ |
| H | CH(CH$_3$)$_2$ | 4-CH$_3$—C$_6$H$_4$ |
| H | CH(CH$_3$)$_2$ | 4-F—C$_6$H$_4$ |
| H | CH(CH$_3$)$_2$ | 4-Cl-C$_6$H$_4$ |
| H | CH(CH$_3$)$_2$ | 4-Br-C$_6$H$_4$ |
| H | CH(CH$_3$)$_2$ | 4-CH(CH$_3$)$_2$—C$_6$H$_4$ |
| H | CH(CH$_3$)$_2$ | 4-OCH$_3$—C$_6$H$_4$ |
| H | CH(CH$_3$)$_2$ | 4-C(CH$_3$)$_3$—C$_6$H$_4$ |
| H | CH(CH$_3$)$_2$ | 4-CF$_3$—C$_6$H$_4$ |
| H | CH(CH$_3$)$_2$ | 4-NO$_2$—C$_6$H$_4$ |
| H | CH(CH$_3$)$_2$ | 4-CN—C$_6$H$_4$ |
| H | CH(CH$_3$)$_2$ | 4-(NHCOCH$_3$)—C$_6$H$_4$ |
| H | CH(CH$_3$)$_2$ | 3,4-(OCH$_3$)$_2$—C$_6$H$_3$ |
| H | CH(CH$_3$)$_2$ | 2,4-Cl$_2$—C$_6$H$_3$ |
| H | CH(CH$_3$)$_2$ | 3-NO$_2$-4-CH$_3$—C$_6$H$_3$ |
| H | CH(CH$_3$)$_2$ | 2-Naphthyl |
| H | CH(CH$_3$)$_2$ | Thien-2-yl |
| H | CH$_2$CH(CH$_3$)$_2$ | C$_6$H$_5$ |
| H | CH$_2$CH(CH$_3$)$_2$ | 4-CH$_3$—C$_6$H$_4$ |
| H | CH$_2$CH(CH$_3$)$_2$ | 4-F—C$_6$H$_4$ |
| H | CH$_2$CH(CH$_3$)$_2$ | 4-Cl-C$_6$H$_4$ |
| H | CH$_2$CH(CH$_3$)$_2$ | 4-Br-C$_6$H$_4$ |
| H | CH$_2$CH(CH$_3$)$_2$ | 4-CH(CH$_3$)$_2$—C$_6$H$_4$ |
| H | CH$_2$CH(CH$_3$)$_2$ | 4-OCH$_3$—C$_6$H$_4$ |
| H | CH$_2$CH(CH$_3$)$_2$ | 4-C(CH$_3$)$_3$—C$_6$H$_4$ |
| H | CH$_2$CH(CH$_3$)$_2$ | 4-CF$_3$—C$_6$H$_4$ |
| H | CH$_2$CH(CH$_3$)$_2$ | 4-NO$_2$—C$_6$H$_4$ |
| H | CH$_2$CH(CH$_3$)$_2$ | 4-CN—C$_6$H$_4$ |
| H | CH$_2$CH(CH$_3$)$_2$ | 4-(NHCOCH$_3$)—C$_6$H$_4$ |
| H | CH$_2$CH(CH$_3$)$_2$ | 3,4-(OCH$_3$)$_2$—C$_6$H$_3$ |
| H | CH$_2$CH(CH$_3$)$_2$ | 2,4-Cl$_2$—C$_6$H$_3$ |
| H | CH$_2$CH(CH$_3$)$_2$ | 3-NO$_2$-4-CH$_3$—C$_6$H$_3$ |
| H | CH$_2$CH(CH$_3$)$_2$ | 2-Naphthyl |
| H | CH$_2$CH(CH$_3$)$_2$ | Thien-2-yl |
| H | (CH$_2$)$_3$CH$_3$ | C$_6$H$_5$ |
| H | (CH$_2$)$_3$CH$_3$ | 4-CH$_3$—C$_6$H$_4$ |

TABLE A-continued

| | | |
|---|---|---|
| H | (CH$_2$)$_3$CH$_3$ | 4-F—C$_6$H$_4$ |
| H | (CH$_2$)$_3$CH$_3$ | 4-Cl-C$_6$H$_4$ |
| H | (CH$_2$)$_3$CH$_3$ | 4-Br-C$_6$H$_4$ |
| H | (CH$_2$)$_3$CH$_3$ | 4-CH(CH$_3$)$_2$—C$_6$H$_4$ |
| H | (CH$_2$)$_3$CH$_3$ | 4-OCH$_3$—C$_6$H$_4$ |
| H | (CH$_2$)$_3$CH$_3$ | 4-C(CH$_3$)$_3$—C$_6$H$_4$ |
| H | (CH$_2$)$_3$CH$_3$ | 4-CF$_3$—C$_6$H$_4$ |
| H | (CH$_2$)$_3$CH$_3$ | 4-NO$_2$—C$_6$H$_4$ |
| H | (CH$_2$)$_3$CH$_3$ | 4-CN—C$_6$H$_4$ |
| H | (CH$_2$)$_3$CH$_3$ | 4-(NHCOCH$_3$)—C$_6$H$_4$ |
| H | (CH$_2$)$_3$CH$_3$ | 3,4-(OCH$_3$)$_2$—C$_6$H$_3$ |
| H | (CH$_2$)$_3$CH$_3$ | 2,4-Cl$_2$—C$_6$H$_3$ |
| H | (CH$_2$)$_3$CH$_3$ | 3-NO$_2$-4-CH$_3$—C$_6$H$_3$ |
| H | (CH$_2$)$_3$CH$_3$ | 2-Naphthyl |
| H | (CH$_2$)$_3$CH$_3$ | Thien-2-yl |
| H | C(CH$_3$)$_3$ | C$_6$H$_5$ |
| H | C(CH$_3$)$_3$ | 4-CH$_3$—C$_6$H$_4$ |
| H | C(CH$_3$)$_3$ | 4-F—C$_6$H$_4$ |
| H | C(CH$_3$)$_3$ | 4-Cl-C$_6$H$_4$ |
| H | C(CH$_3$)$_3$ | 4-Br-C$_6$H$_4$ |
| H | C(CH$_3$)$_3$ | 4-CH(CH$_3$)$_2$—C$_6$H$_4$ |
| H | C(CH$_3$)$_3$ | 4-OCH$_3$—C$_6$H$_4$ |
| H | C(CH$_3$)$_3$ | 4-C(CH$_3$)$_3$—C$_6$H$_4$ |
| H | C(CH$_3$)$_3$ | 4-CF$_3$—C$_6$H$_4$ |
| H | C(CH$_3$)$_3$ | 4-NO$_2$—C$_6$H$_4$ |
| H | C(CH$_3$)$_3$ | 4-CN—C$_6$H$_4$ |
| H | C(CH$_3$)$_3$ | 4-(NHCOCH$_3$)—C$_6$H$_4$ |
| H | C(CH$_3$)$_3$ | 3,4-(OCH$_3$)$_2$—C$_6$H$_3$ |
| H | C(CH$_3$)$_3$ | 2,4-Cl$_2$—C$_6$H$_3$ |
| H | C(CH$_3$)$_3$ | 3-NO$_2$-4-CH$_3$—C$_6$H$_3$ |
| H | C(CH$_3$)$_3$ | 2-Naphthyl |
| H | C(CH$_3$)$_3$ | Thien-2-yl |
| H | C$_6$H$_5$ | CH$_3$ |
| H | C$_6$H$_5$ | CH$_2$CH$_3$ |
| H | C$_6$H$_5$ | CH$_2$CH$_2$CH$_3$ |
| H | C$_6$H$_5$ | CH(CH$_3$)$_2$ |
| H | C$_6$H$_5$ | CH$_2$CH$_2$CH$_2$CH$_3$ |
| H | C$_6$H$_5$ | CH$_2$CH(CH$_3$)$_2$ |
| H | C$_6$H$_5$ | C$_6$H$_5$ |
| H | C$_6$H$_5$ | CO$_2$H |
| H | C$_6$H$_5$ | CO$_2$CH$_2$CH$_3$ |
| H | C$_6$H$_5$ | CONH$_2$ |
| H | C$_6$H$_5$ | COCH$_3$ |
| H | C$_6$H$_5$ | COCF$_3$ |
| H | C$_6$H$_5$ | COC$_6$H$_5$ |
| H | C$_6$H$_5$ | CO-(4-CH$_3$—C$_6$H$_4$) |
| H | C$_6$H$_5$ | CO$_2$C$_6$H$_5$ |
| H | C$_6$H$_5$ | CO$_2$CH$_2$C$_6$H$_5$ |
| H | C$_6$H$_5$ | F |
| H | C$_6$H$_5$ | Cl |
| H | C$_6$H$_5$ | Br |
| H | C$_6$H$_5$ | OCH$_3$ |
| H | C$_6$H$_5$ | CF$_3$ |
| H | C$_6$H$_5$ | NO$_2$ |
| H | C$_6$H$_5$ | CN |
| H | C$_6$H$_5$ | SO$_2$CH$_3$ |
| H | C$_6$H$_5$ | SO$_2$C$_6$H$_5$ |
| H | C$_6$H$_5$ | SO$_2$-(4-CH$_3$—C$_6$H$_4$) |
| H | C$_6$H$_5$ | C$_6$H$_5$ |
| H | C$_6$H$_5$ | 4-CH$_3$—C$_6$H$_4$ |
| H | C$_6$H$_5$ | 4-F—C$_6$H$_4$ |
| H | C$_6$H$_5$ | 4-Cl—C$_6$H$_4$ |
| H | C$_6$H$_5$ | 4-Br—C$_6$H$_4$ |
| H | C$_6$H$_5$ | 4-CH(CH$_3$)$_2$—C$_6$H$_4$ |
| H | C$_6$H$_5$ | 4-OCH$_3$—C$_6$H$_4$ |
| H | C$_6$H$_5$ | 4-C(CH$_3$)$_3$—C$_6$H$_4$ |
| H | C$_6$H$_5$ | 4-CF$_3$—C$_6$H$_4$ |
| H | C$_6$H$_5$ | 4-NO$_2$—C$_6$H$_4$ |
| H | C$_6$H$_5$ | 4-CN—C$_6$H$_4$ |
| H | C$_6$H$_5$ | 4-(NHCOCH$_3$)—C$_6$H$_4$ |
| H | C$_6$H$_5$ | 3,4-(OCH$_3$)$_2$—C$_6$H$_3$ |
| H | C$_6$H$_5$ | 2,4-Cl$_2$—C$_6$H$_3$ |
| H | C$_6$H$_5$ | 3-NO$_2$-4-CH$_3$—C$_6$H$_3$ |
| H | C$_6$H$_5$ | 2-Naphthyl |
| H | C$_6$H$_5$ | Thien-2-yl |
| H | CH$_2$C$_6$H$_5$ | C$_6$H$_5$ |
| H | CH$_2$C$_6$H$_5$ | 4-CH$_3$—C$_6$H$_4$ |
| H | CH$_2$C$_6$H$_5$ | 4-F—C$_6$H$_4$ |
| H | CH$_2$C$_6$H$_5$ | 4-Cl—C$_6$H$_4$ |
| H | CH$_2$C$_6$H$_5$ | 4-Br—C$_6$H$_4$ |
| H | CH$_2$C$_6$H$_5$ | 4-CH(CH$_3$)$_2$—C$_6$H$_4$ |
| H | CH$_2$C$_6$H$_5$ | 4-OCH$_3$—C$_6$H$_4$ |
| H | CH$_2$C$_6$H$_5$ | 4-C(CH$_3$)$_3$—C$_6$H$_4$ |
| H | CH$_2$C$_6$H$_5$ | 4-CF$_3$—C$_6$H$_4$ |
| H | CH$_2$C$_6$H$_5$ | 4-NO$_2$—C$_6$H$_4$ |
| H | CH$_2$C$_6$H$_5$ | 4-CN—C$_6$H$_4$ |
| H | CH$_2$C$_6$H$_5$ | 4-(NHCOCH$_3$)—C$_6$H$_4$ |
| H | CH$_2$C$_6$H$_5$ | 3,4-(OCH$_3$)$_2$—C$_6$H$_3$ |
| H | CH$_2$C$_6$H$_5$ | 2,4-Cl$_2$—C$_6$H$_3$ |
| H | CH$_2$C$_6$H$_5$ | 3-NO$_2$-4-CH$_3$—C$_6$H$_3$ |
| H | CH$_2$C$_6$H$_5$ | 2-Naphthyl |
| H | CH$_2$C$_6$H$_5$ | Thien-2-yl |
| H | CO$_2$C$_2$H$_5$ | C$_6$H$_5$ |
| H | CO$_2$C$_2$H$_5$ | 4-CH$_3$C$_6$H$_4$ |
| H | CO$_2$C$_2$H$_5$ | 4-F—C$_6$H$_4$ |
| H | CO$_2$C$_2$H$_5$ | 4-Cl—C$_6$H$_4$ |
| H | CO$_2$C$_2$H$_5$ | 4-Br—C$_6$H$_4$ |
| H | CO$_2$C$_2$H$_5$ | 4-CH(CH$_3$)$_2$—C$_6$H$_4$ |
| H | CO$_2$C$_2$H$_5$ | 4-OCH$_3$—C$_6$H$_4$ |
| H | CO$_2$C$_2$H$_5$ | 4-C(CH$_3$)$_3$—C$_6$H$_4$ |
| H | CO$_2$C$_2$H$_5$ | 4-CF$_3$—C$_6$H$_4$ |
| H | CO$_2$C$_2$H$_5$ | 4-NO$_2$—C$_6$H$_4$ |
| H | CO$_2$C$_2$H$_5$ | 4-CN—C$_6$H$_4$ |
| H | CO$_2$C$_2$H$_5$ | 4-(NHCOCH$_3$)—C$_6$H$_4$ |
| H | CO$_2$C$_2$H$_5$ | 3,4-(OCH$_3$)$_2$—C$_6$H$_3$ |
| H | CO$_2$C$_2$H$_5$ | 2,4-Cl$_2$—C$_6$H$_3$ |
| H | CO$_2$C$_2$H$_5$ | 3-NO$_2$-4-CH$_3$—C$_6$H$_3$ |
| H | CO$_2$C$_2$H$_5$ | 2-Naphthyl |
| H | CO$_2$C$_2$H$_5$ | Thien-2-yl |
| H | 2-CH$_3$—C$_6$H$_4$ | CH$_3$ |
| H | 3-CH$_3$—C$_6$H$_4$ | CH$_3$ |
| H | 4-CH$_3$—C$_6$H$_4$ | CH$_3$ |
| H | 2-F—C$_6$H$_4$ | CH$_3$ |
| H | 3-F—C$_6$H$_4$ | CH$_3$ |
| H | 4-F—C$_6$H$_4$ | CH$_3$ |
| H | 2-Cl—C$_6$H$_4$ | CH$_3$ |
| H | 3-Cl—C$_6$H$_4$ | CH$_3$ |
| H | 4-Cl—C$_6$H$_4$ | CH$_3$ |
| H | 2-Br—C$_6$H$_4$ | CH$_3$ |
| H | 3-Br—C$_6$H$_4$ | CH$_3$ |
| H | 4-Br—C$_6$H$_4$ | CH$_3$ |
| H | 2-OCH$_3$—C$_6$H$_4$ | CH$_3$ |
| H | 3-OCH$_3$—C$_6$H$_4$ | CH$_3$ |
| H | 4-OCH$_3$—C$_6$H$_4$ | CH$_3$ |
| H | 3-C(CH$_3$)$_3$—C$_6$H$_4$ | CH$_3$ |
| H | 4-C(CH$_3$)$_3$—C$_6$H$_4$ | CH$_3$ |
| H | 2-CF$_3$—C$_6$H$_4$ | CH$_3$ |
| H | 3-CF$_3$—C$_6$H$_4$ | CH$_3$ |
| H | 4-CF$_3$—C$_6$H$_4$ | CH$_3$ |
| H | 2-NO$_2$—C$_6$H$_4$ | CH$_3$ |
| H | 3-NO$_2$—C$_6$H$_4$ | CH$_3$ |
| H | 4-NO$_2$—C$_6$H$_4$ | CH$_3$ |
| H | 2-CN—C$_6$H$_4$ | CH$_3$ |
| H | 3-CN—C$_6$H$_4$ | CH$_3$ |
| H | 4-CN—C$_6$H$_4$ | CH$_3$ |
| H | 3,4-(OCH$_3$)$_2$—C$_6$H$_3$ | CH$_3$ |
| H | 2,4-Cl$_2$—C$_6$H$_3$ | CH$_3$ |
| H | 3-NO$_2$-4-CH$_3$—C$_6$H$_3$ | CH$_3$ |
| H | 2-Naphthyl | CH$_3$ |
| H | Thien-2-yl | CH$_3$ |
| H | Furan-2-yl | CH$_3$ |
| H | Isoxazol-2-yl | CH$_3$ |
| H | CH$_3$ | CH$_3$ |
| H | CH$_2$CH$_3$ | CH$_3$ |
| H | CH(CH$_3$)$_2$ | CH$_3$ |
| H | CH$_2$CH(CH$_3$)$_2$ | CH$_3$ |
| H | C(CH$_3$)$_3$ | CH$_3$ |
| H | Cyclopropyl | CH$_3$ |
| H | CH$_2$CH=CH$_2$ | CH$_3$ |
| H | CH$_2$C*CH | CH$_3$   * = triple bond |
| H | CH$_2$CH=CHCH$_3$ | CH$_3$ |
| H | CH$_2$C*CCH$_3$ | CH$_3$   * = triple bond |
| H | CH$_2$Cl | CH$_3$ |
| H | CH$_2$CH$_2$Cl | CH$_3$ |
| H | CH$_2$CH$_2$CH$_2$Cl | CH$_3$ |
| H | CH$_2$CH=CHCl | CH$_3$ |
| H | CH$_2$OH | CH$_3$ |
| H | CH$_2$CH$_2$OH | CH$_3$ |

TABLE A-continued

| | | |
|---|---|---|
| H | CH₂CH₂CH₂OH | CH₃ |
| H | CH₂OCH₃ | CH₃ |
| H | CH₂CH₂OCH₃ | CH₃ |
| H | CH₂CH₂CH₂OCH₃ | CH₃ |
| H | CH₂CO₂CH₂CH₃ | CH₃ |
| H | CH₂CH₂CO₂CH₂CH₃ | CH₃ |
| H | CH₂CH₂CH₂CO₂CH₂CH₃ | CH₃ |
| H | CH₂NH₂ | CH₃ |
| H | CH₂CH₂NH₂ | CH₃ |
| H | CH₂CH₂CH₂NH₂ | CH₃ |
| H | CH₂N(CH₃)₂ | CH₃ |
| H | CH₂CH₂N(CH₃)₂ | CH₃ |
| H | CH₂CH₂CH₂N(CH₃)₂ | CH₃ |
| H | CH₂NHCOCH₃ | CH₃ |
| H | CH₂CH₂NHCOCH₃ | CH₃ |
| H | CH₂CH₂CH₂NHCOCH₃ | CH₃ |
| H | COCH₃ | CH₃ |
| H | COCF₃ | CH₃ |
| H | COC₆H₅ | CH₃ |
| H | CO-(4-CH₃—C₆H₄) | CH₃ |
| H | CO₂C₆H₅ | CH₃ |
| H | CO₂CH₂C₆H₅ | CH₃ |
| H | F | CH₃ |
| H | Cl | CH₃ |
| H | Br | CH₃ |
| H | OCH₃ | CH₃ |
| H | CF₃ | CH₃ |
| H | NO₂ | CH₃ |
| H | CN | CH₃ |
| H | SO₂CH₃ | CH₃ |
| H | SO₂C₆H₅ | CH₃ |
| H | SO₂-(4-CH₃—C₆H₄) | CH₃ |
| H | CH₂OCH₂C₆H₅ | CH₃ |
| H | COCH₂CH₂CH₃ | CH₃ |
| H | CO₂H | CH₃ |
| H | CO₂CH₃ | CH₃ |
| H | CO₂CH₂CH₃ | CH₃ |
| H | CONH₂ | CH₃ |
| H | CONHCH₃ | CH₃ |
| H | CON(CH₃)₂ | CH₃ |
| H | CONHC₆H₅ | CH₃ |
| H | 3-Pyridyl | CH₃ |
| H | 2-Pyridyl | CH₃ |
| H | 4-SCH₃—C₆H₄ | CH₃ |
| H | 2-CH₃—C₆H₄ | C₆H₅ |
| H | 3-CH₃—C₆H₄ | C₆H₅ |
| H | 4-CH₃—C₆H₄ | C₆H₅ |
| H | 2-F—C₆H₄ | C₆H₅ |
| H | 3-F—C₆H₄ | C₆H₅ |
| H | 4-F—C₆H₄ | C₆H₅ |
| H | 2-Cl-C₆H₄ | C₆H₅ |
| H | 3-Cl-C₆H₄ | C₆H₅ |
| H | 4-Cl-C₆H₄ | C₆H₅ |
| H | 2-Br—C₆H₄ | C₆H₅ |
| H | 3-Br—C₆H₄ | C₆H₅ |
| H | 4-Br—C₆H₄ | C₆H₅ |
| H | 2-OCH₃—C₆H₄ | C₆H₅ |
| H | 3-OCH₃—C₆H₄ | C₆H₅ |
| H | 4-OCH₃—C₆H₄ | C₆H₅ |
| H | 3-C(CH₃)₃—C₆H₄ | C₆H₅ |
| H | 4-C(CH₃)₃—C₆H₄ | C₆H₅ |
| H | 2-CF₃—C₆H₄ | C₆H₅ |
| H | 3-CF₃—C₆H₄ | C₆H₅ |
| H | 4-CF₃—C₆H₄ | C₆H₅ |
| H | 2-NO₂—C₆H₄ | C₆H₅ |
| H | 3-NO₂—C₆H₄ | C₆H₅ |
| H | 4-NO₂—C₆H₄ | C₆H₅ |
| H | 2-CN—C₆H₄ | C₆H₅ |
| H | 3-CN—C₆H₄ | C₆H₅ |
| H | 4-CN—C₆H₄ | C₆H₅ |
| H | 3,4-(OCH₃)₂—C₆H₃ | C₆H₅ |
| H | 2,4-Cl₂—C₆H₃ | C₆H₅ |
| H | 3-NO₂-4-CH₃—C₆H₃ | C₆H₅ |
| H | 2-Naphthyl | C₆H₅ |
| H | Thien-2-yl | C₆H₅ |
| H | Furan-2-yl | C₆H₅ |
| H | Isoxazol-2-yl | C₆H₅ |
| H | CH₃ | C₆H₅ |
| H | CH₂CH₃ | C₆H₅ |

| | | | |
|---|---|---|---|
| H | CH(CH₃)₂ | C₆H₅ | |
| H | CH₂CH(CH₃)₂ | C₆H₅ | |
| H | C(CH₃)₃ | C₆H₅ | |
| H | Cyclopropyl | C₆H₅ | |
| H | CH₂CH=CH₂ | C₆H₅ | |
| H | CH₂C*CH | C₆H₅ | * = triple bond |
| H | CH₂CH=CHCH₃ | C₆H₅ | |
| H | CH₂C*CCH₃ | C₆H₅ | * = triple bond |
| H | CH₂Cl | C₆H₅ | |
| H | CH₂CH₂Cl | C₆H₅ | |
| H | CH₂CH₂CH₂Cl | C₆H₅ | |
| H | CH₂CH=CHCl | C₆H₅ | |
| H | CH₂OH | C₆H₅ | |
| H | CH₂CH₂OH | C₆H₅ | |
| H | CH₂CH₂CH₂OH | C₆H₅ | |
| H | CH₂OCH₃ | C₆H₅ | |
| H | CH₂CH₂OCH₃ | C₆H₅ | |
| H | CH₂CH₂CH₂OCH₃ | C₆H₅ | |
| H | CH₂CO₂CH₂CH₃ | C₆H₅ | |
| H | CH₂CH₂CO₂CH₂CH₃ | C₆H₅ | |
| H | CH₂CH₂CH₂CO₂CH₂CH₃ | C₆H₅ | |
| H | CH₂NH₂ | C₆H₅ | |
| H | CH₂CH₂NH₂ | C₆H₅ | |
| H | CH₂CH₂CH₂NH₂ | C₆H₅ | |
| H | CH₂N(CH₃)₂ | C₆H₅ | |
| H | CH₂CH₂N(CH₃)₂ | C₆H₅ | |
| H | CH₂CH₂CH₂N(CH₃)₂ | C₆H₅ | |
| H | CH₂NHCOCH₃ | C₆H₅ | |
| H | CH₂CH₂NHCOCH₃ | C₆H₅ | |
| H | CH₂CH₂CH₂NHCOCH₃ | C₆H₅ | |
| H | COCH₃ | C₆H₅ | |
| H | COCF₃ | C₆H₅ | |
| H | COC₆H₅ | C₆H₅ | |
| H | CO-(4-CH₃—C₆H₄) | C₆H₅ | |
| H | CO₂C₆H₅ | C₆H₅ | |
| H | CO₂CH₂C₆H₅ | C₆H₅ | |
| H | F | C₆H₅ | |
| H | Cl | C₆H₅ | |
| H | Br | C₆H₅ | |
| H | OCH₃ | C₆H₅ | |
| H | CF₃ | C₆H₅ | |
| H | NO₂ | C₆H₅ | |
| H | CN | C₆H₅ | |
| H | SO₂CH₃ | C₆H₅ | |
| H | SO₂C₆H₅ | C₆H₅ | |
| H | SO₂-(4-CH₃—C₆H₄) | C₆H₅ | |
| H | CH₂OCH₂C₆H₅ | C₆H₅ | |
| H | COCH₂CH₂CH₃ | C₆H₅ | |
| H | CO₂H | C₆H₅ | |
| H | CO₂CH₃ | C₆H₅ | |
| H | CO₂CH₂CH₃ | C₆H₅ | |
| H | CONH₂ | C₆H₅ | |
| H | CONHCH₃ | C₆H₅ | |
| H | CON(CH₃)₂ | C₆H₅ | |
| H | CONHC₆H₅ | C₆H₅ | |
| H | 3-Pyridyl | C₆H₅ | |
| H | 2-Pyridyl | C₆H₅ | |
| H | 4-SCH₃—C₆H₄ | C₆H₅ | |
| H | C₆H₅ | OH | |
| H | 2-CH₃—C₆H₄ | OH | |
| H | 3-CH₃—C₆H₄ | OH | |
| H | 4-CH₃—C₆H₄ | OH | |
| H | 2-F—C₆H₄ | OH | |
| H | 3-F—C₆H₄ | OH | |
| H | 4-F—C₆H₄ | OH | |
| H | 2-Cl-C₆H₄ | OH | |
| H | 3-Cl-C₆H₄ | OH | |
| H | 4-Cl-C₆H₄ | OH | |
| H | 2-Br—C₆H₄ | OH | |
| H | 3-Br—C₆H₄ | OH | |
| H | 4-Br—C₆H₄ | OH | |
| H | 2-OCH₃—C₆H₄ | OH | |
| H | 3-OCH₃—C₆H₄ | OH | |
| H | 4-OCH₃—C₆H₄ | OH | |
| H | 3-C(CH₃)₃—C₆H₄ | OH | |
| H | 4-C(CH₃)₃—C₆H₄ | OH | |
| H | 2-CF₃—C₆H₄ | OH | |
| H | 3-CF₃—C₆H₄ | OH | |
| H | 4-CF₃—C₆H₄ | OH | |

TABLE A-continued

| | | |
|---|---|---|
| H | 2-NO$_2$—C$_6$H$_4$ | OH |
| H | 3-NO$_2$—C$_6$H$_4$ | OH |
| H | 4-NO$_2$—C$_6$H$_4$ | OH |
| H | 2-CN—C$_6$H$_4$ | OH |
| H | 3-CN—C$_6$H$_4$ | OH |
| H | 4-CN—C$_6$H$_4$ | OH |
| H | 3,4-(OCH$_3$)$_2$—C$_6$H$_3$ | OH |
| H | 2,4-Cl$_2$—C$_6$H$_3$ | OH |
| H | 3-NO$_2$-4-CH$_3$—C$_6$H$_3$ | OH |
| H | 2-Naphthyl | OH |
| H | Thien-2-yl | OH |
| H | Furan-2-yl | OH |
| H | Isoxazol-2-yl | OH |
| H | CH$_3$ | OH |
| H | CH$_2$CH$_3$ | OH |
| H | CH(CH$_3$)$_2$ | OH |
| H | CH$_2$CH(CH$_3$)$_2$ | OH |
| H | C(CH$_3$)$_3$ | OH |
| H | Cyclopropyl | OH |
| H | CH$_2$CH=CH$_2$ | OH |
| H | CH$_2$C*CH | OH  * = triple bond |
| H | CH$_2$CH=CHCH$_3$ | OH |
| H | CH$_2$C*CCH$_3$ | OH  * = triple bond |
| H | CH$_2$Cl | OH |
| H | CH$_2$CH$_2$Cl | OH |
| H | CH$_2$CH$_2$CH$_2$Cl | OH |
| H | CH$_2$CH=CHCl | OH |
| H | CH$_2$OH | OH |
| H | CH$_2$CH$_2$OH | OH |
| H | CH$_2$CH$_2$CH$_2$OH | OH |
| H | CH$_2$OCH$_3$ | OH |
| H | CH$_2$CH$_2$OCH$_3$ | OH |
| H | CH$_2$CH$_2$CH$_2$OCH$_3$ | OH |
| H | CH$_2$CO$_2$CH$_2$CH$_3$ | OH |
| H | CH$_2$CH$_2$CO$_2$CH$_2$CH$_3$ | OH |
| H | CH$_2$CH$_2$CH$_2$CO$_2$CH$_2$CH$_3$ | OH |
| H | CH$_2$NH$_2$ | OH |
| H | CH$_2$CH$_2$NH$_2$ | OH |
| H | CH$_2$CH$_2$CH$_2$NH$_2$ | OH |
| H | CH$_2$N(CH$_3$)$_2$ | OH |
| H | CH$_2$CH$_2$N(CH$_3$)$_2$ | OH |
| H | CH$_2$CH$_2$CH$_2$N(CH$_3$)$_2$ | OH |
| H | CH$_2$NHCOCH$_3$ | OH |
| H | CH$_2$CH$_2$NHCOCH$_3$ | OH |
| H | CH$_2$CH$_2$CH$_2$NHCOCH$_3$ | OH |
| H | COCH$_3$ | OH |
| H | COCF$_3$ | OH |
| H | COC$_6$H$_5$ | OH |
| H | CO-(4-CH$_3$—C$_6$H$_4$) | OH |
| H | CO$_2$C$_6$H$_5$ | OH |
| H | CO$_2$CH$_2$C$_6$H$_5$ | OH |
| H | F | OH |
| H | Cl | OH |
| H | Br | OH |
| H | OCH$_3$ | OH |
| H | CF$_3$ | OH |
| H | NO$_2$ | OH |
| H | CN | OH |
| H | SO$_2$CH$_3$ | OH |
| H | SO$_2$C$_6$H$_5$ | OH |
| H | SO$_2$-(4-CH$_3$—C$_6$H$_4$) | OH |
| H | CH$_2$OCH$_2$C$_6$H$_5$ | OH |
| H | COCH$_2$CH$_3$ | OH |
| H | CO$_2$H | OH |
| H | CO$_2$CH$_3$ | OH |
| H | CO$_2$CH$_2$CH$_3$ | OH |
| H | CONH$_2$ | OH |
| H | CONHCH$_3$ | OH |
| H | CON(CH$_3$)$_2$ | OH |
| H | CONHC$_6$H$_5$ | OH |
| H | 3-Pyridyl | OH |
| H | 2-Pyridyl | OH |
| H | 4-SCH$_3$—C$_6$H$_4$ | OH |
| H | C$_6$H$_5$ | NH$_2$ |
| H | 2-CH$_3$—C$_6$H$_4$ | NH$_2$ |
| H | 3-CH$_3$—C$_6$H$_4$ | NH$_2$ |
| H | 4-CH$_3$—C$_6$H$_4$ | NH$_2$ |
| H | 2-F—C$_6$H$_4$ | NH$_2$ |
| H | 3-F—C$_6$H$_4$ | NH$_2$ |
| H | 4-F—C$_6$H$_4$ | NH$_2$ |
| H | 2-Cl-C$_6$H$_4$ | NH$_2$ |
| H | 3-Cl-C$_6$H$_4$ | NH$_2$ |
| H | 4-Cl-C$_6$H$_4$ | NH$_2$ |
| H | 2-Br—C$_6$H$_4$ | NH$_2$ |
| H | 3-Br—C$_6$H$_4$ | NH$_2$ |
| H | 4-Br—C$_6$H$_4$ | NH$_2$ |
| H | 2-OCH$_3$—C$_6$H$_4$ | NH$_2$ |
| H | 3-OCH$_3$—C$_6$H$_4$ | NH$_2$ |
| H | 4-OCH$_3$—C$_6$H$_4$ | NH$_2$ |
| H | 3-C(CH$_3$)$_3$—C$_6$H$_4$ | NH$_2$ |
| H | 4-C(CH$_3$)$_3$—C$_6$H$_4$ | NH$_2$ |
| H | 2-CF$_3$—C$_6$H$_4$ | NH$_2$ |
| H | 3-CF$_3$—C$_6$H$_4$ | NH$_2$ |
| H | 4-CF$_3$—C$_6$H$_4$ | NH$_2$ |
| H | 2-NO$_2$—C$_6$H$_4$ | NH$_2$ |
| H | 3-NO$_2$—C$_6$H$_4$ | NH$_2$ |
| H | 4-NO$_2$—C$_6$H$_4$ | NH$_2$ |
| H | 2-CN—C$_6$H$_4$ | NH$_2$ |
| H | 3-CN—C$_6$H$_4$ | NH$_2$ |
| H | 4-CN—C$_6$H$_4$ | NH$_2$ |
| H | 2,4-(OCH$_3$)$_2$—C$_6$H$_3$ | NH$_2$ |
| H | 2,4-Cl$_2$—C$_6$H$_3$ | NH$_2$ |
| H | 3-NO$_2$-4-CH$_3$—C$_6$H$_3$ | NH$_2$ |
| H | 2-Naphthyl | NH$_2$ |
| H | Thien-2-yl | NH$_2$ |
| H | Furan-2-yl | NH$_2$ |
| H | Isoxazol-2-yl | NH$_2$ |
| H | CH$_3$ | NH$_2$ |
| H | CH$_2$CH$_3$ | NH$_2$ |
| H | CH(CH$_3$)$_2$ | NH$_2$ |
| H | CH$_2$CH(CH$_3$)$_2$ | NH$_2$ |
| H | C(CH$_3$)$_3$ | NH$_2$ |
| H | Cyclopropyl | NH$_2$ |
| H | CH$_2$CH=CH$_2$ | NH$_2$ |
| H | CH$_2$C*CH | NH$_2$  * = triple bond |
| H | CH$_2$CH=CHCH$_3$ | NH$_2$ |
| H | CH$_2$C*CCH$_3$ | NH$_2$  * = triple bond |
| H | CH$_2$Cl | NH$_2$ |
| H | CH$_2$CH$_2$Cl | NH$_2$ |
| H | CH$_2$CH$_2$CH$_2$Cl | NH$_2$ |
| H | CH$_2$CH=CHCl | NH$_2$ |
| H | CH$_2$OH | NH$_2$ |
| H | CH$_2$CH$_2$OH | NH$_2$ |
| H | CH$_2$CH$_2$CH$_2$OH | NH$_2$ |
| H | CH$_2$OCH$_3$ | NH$_2$ |
| H | CH$_2$CH$_2$OCH$_3$ | NH$_2$ |
| H | CH$_2$CH$_2$CH$_2$OCH$_3$ | NH$_2$ |
| H | CH$_2$CO$_2$CH$_2$CH$_3$ | NH$_2$ |
| H | CH$_2$CH$_2$CO$_2$CH$_2$CH$_3$ | NH$_2$ |
| H | CH$_2$CH$_2$CH$_2$CO$_2$CH$_2$CH$_3$ | NH$_2$ |
| H | CH$_2$NH$_2$ | NH$_2$ |
| H | CH$_2$CH$_2$NH$_2$ | NH$_2$ |
| H | CH$_2$CH$_2$CH$_2$NH$_2$ | NH$_2$ |
| H | CH$_2$N(CH$_3$)$_2$ | NH$_2$ |
| H | CH$_2$CH$_2$N(CH$_3$)$_2$ | NH$_2$ |
| H | CH$_2$CH$_2$CH$_2$N(CH$_3$)$_2$ | NH$_2$ |
| H | CH$_2$NHCOCH$_3$ | NH$_2$ |
| H | CH$_2$CH$_2$NHCOCH$_3$ | NH$_2$ |
| H | CH$_2$CH$_2$CH$_2$NHCOCH$_3$ | NH$_2$ |
| H | COCH$_3$ | NH$_2$ |
| H | COCF$_3$ | NH$_2$ |
| H | COC$_6$H$_5$ | NH$_2$ |
| H | CO-(4-CH$_3$—C$_6$H$_4$) | NH$_2$ |
| H | CO$_2$C$_6$H$_5$ | NH$_2$ |
| H | CO$_2$CH$_2$C$_6$H$_5$ | NH$_2$ |
| H | F | NH$_2$ |
| H | Cl | NH$_2$ |
| H | Br | NH$_2$ |
| H | OCH$_3$ | NH$_2$ |
| H | CF$_3$ | NH$_2$ |
| H | NO$_2$ | NH$_2$ |
| H | CN | NH$_2$ |
| H | SO$_2$CH$_3$ | NH$_2$ |
| H | SO$_2$C$_6$H$_5$ | NH$_2$ |
| H | SO$_2$-(4-CH$_3$—C$_6$H$_4$) | NH$_2$ |
| H | CH$_2$OCH$_2$C$_6$H$_5$ | NH$_2$ |
| H | COCH$_2$CH$_3$ | NH$_2$ |
| H | CO$_2$H | NH$_2$ |

TABLE A-continued

| | | |
|---|---|---|
| H | CO$_2$CH$_3$ | NH$_2$ |
| H | CO$_2$CH$_2$CH$_3$ | NH$_2$ |
| H | CONH$_2$ | NH$_2$ |
| H | CONHCH$_3$ | NH$_2$ |
| H | CON(CH$_3$)$_2$ | NH$_2$ |
| H | CONHC$_6$H$_5$ | NH$_2$ |
| H | 3-Pyridyl | NH$_2$ |
| H | 2-Pyridyl | NH$_2$ |
| H | 4-SCH$_3$—C$_6$H$_4$ | NH$_2$ |
| H | 2,6-Cl$_2$—C$_6$H$_3$ | NH$_2$ |
| H | 2,6-OCH$_3$—C$_6$H$_3$ | NH$_2$ |
| H | 2,4-CH$_3$—C$_6$H$_3$ | NH$_2$ |
| H | 2-CO$_2$CH$_3$—C$_6$H$_4$ | NH$_2$ |
| H | 3-CF$_3$—C$_6$H$_4$ | NH$_2$ |
| H | 4-OH—C$_6$H$_4$ | NH$_2$ |
| H | 3-Cl-4-OCH$_3$—C$_6$H$_3$ | NH$_2$ |
| H | C$_6$H$_5$ | NHCHO |
| H | C$_6$H$_5$ | NHCOCH$_3$ |
| H | C$_6$H$_5$ | NHCOCH$_2$CH$_3$ |
| H | C$_6$H$_5$ | NHCOCH(CH$_3$)$_2$ |
| H | C$_6$H$_5$ | NHCO-Cyclopropyl |
| H | C$_6$H$_5$ | NHCOCH$_2$C$_6$H$_5$ |
| H | C$_6$H$_5$ | NHCOC$_6$H$_5$ |
| H | C$_6$H$_5$ | NHCO$_2$CH$_3$ |
| H | C$_6$H$_5$ | NHCO$_2$CH$_2$CH$_3$ |
| H | C$_6$H$_5$ | NHCO$_2$CH(CH$_3$)$_2$ |
| H | C$_6$H$_5$ | NHCO$_2$-Cyclopropyl |
| H | C$_6$H$_5$ | NHCO$_2$CH$_2$C$_6$H$_5$ |
| H | C$_6$H$_5$ | NHCO$_2$C$_6$H$_5$ |
| H | C$_6$H$_5$ | NHCONH$_2$ |
| H | C$_6$H$_5$ | NHCONHCH$_3$ |
| H | C$_6$H$_5$ | NHCON(CH$_3$)$_2$ |
| H | C$_6$H$_5$ | NHCONHCH$_2$CH$_3$ |
| H | C$_6$H$_5$ | NHCONHCH(CH$_3$)$_2$ |
| H | C$_6$H$_5$ | NHCONH-Cyclopropyl |
| H | C$_6$H$_5$ | NHCONHCH$_2$C$_6$H$_5$ |
| H | C$_6$H$_5$ | NHCONHC$_6$H$_5$ |
| H | C$_6$H$_5$ | OCOCH$_3$ |
| H | C$_6$H$_5$ | OCOCH$_2$CH$_3$ |
| H | C$_6$H$_5$ | OCOCH(CH$_3$)$_2$ |
| H | C$_6$H$_5$ | OCO-Cyclopropyl |
| H | C$_6$H$_5$ | OCOCH$_2$C$_6$H$_5$ |
| H | C$_6$H$_5$ | OCOC$_6$H$_5$ |
| H | C$_6$H$_5$ | OCH$_2$C$_6$H$_5$ |
| H | C$_6$H$_5$ | CO$_2$CH$_3$ |
| H | C$_6$H$_5$ | CO$_2$CH$_2$CH$_3$ |
| H | C$_6$H$_5$ | CO$_2$CH(CH$_3$)$_2$ |
| H | C$_6$H$_5$ | CO$_2$-Cyclopropyl |
| H | C$_6$H$_5$ | CO$_2$CH$_2$C$_6$H$_5$ |
| H | C$_6$H$_5$ | CO$_2$C$_6$H$_5$ |
| H | C$_6$H$_5$ | SO$_2$CH$_3$ |
| H | C$_6$H$_5$ | SO$_2$CF$_3$ |
| H | C$_6$H$_5$ | SO$_2$CH$_2$C$_6$H$_5$ |
| H | C$_6$H$_5$ | SO$_2$C$_6$H$_5$ |
| H | C$_6$H$_5$ | NHSO$_2$CH$_3$ |
| H | C$_6$H$_5$ | NHSO$_2$CF$_3$ |
| H | C$_6$H$_5$ | NHSO$_2$CH$_2$C$_6$H$_5$ |
| H | C$_6$H$_5$ | NHSO$_2$C$_6$H$_5$ |
| H | CN | NHCHO |
| H | CN | NHCOCH$_3$ |
| H | CN | NHCOCH$_2$CH$_3$ |
| H | CN | NHCOCH(CH$_3$)$_2$ |
| H | CN | NHCO-Cyclopropyl |
| H | CN | NHCOCH$_2$C$_6$H$_5$ |
| H | CN | NHCOC$_6$H$_5$ |
| H | CN | NHCO$_2$CH$_3$ |
| H | CN | NHCO$_2$CH$_2$CH$_3$ |
| H | CN | NHCO$_2$CH(CH$_3$)$_2$ |
| H | CN | NHCO$_2$-Cyclopropyl |
| H | CN | NHCO$_2$CH$_2$C$_6$H$_5$ |
| H | CN | NHCO$_2$C$_6$H$_5$ |
| H | CN | NHCONH$_2$ |
| H | CN | NHCONHCH$_3$ |
| H | CN | NHCON(CH$_3$)$_2$ |
| H | CN | NHCONHCH$_2$CH$_3$ |
| H | CN | NHCONHCH(CH$_3$)$_2$ |
| H | CN | NHCONH-Cyclopropyl |
| H | CN | NHCONHCH$_2$C$_6$H$_5$ |
| H | CN | NHCONHC$_6$H$_5$ |
| H | CN | OCOCH$_3$ |
| H | CN | OCOCH$_2$CH$_3$ |
| H | CN | OCOCH(CH$_3$)$_2$ |
| H | CN | OCO-Cyclopropyl |
| H | CN | OCOCH$_2$C$_6$H$_5$ |
| H | CN | OCOC$_6$H$_5$ |
| H | CN | OCH$_2$C$_6$H$_5$ |
| H | CN | CO$_2$CH$_3$ |
| H | CN | CO$_2$CH$_2$CH$_3$ |
| H | CN | CO$_2$CH(CH$_3$)$_2$ |
| H | CN | CO$_2$-Cyclopropyl |
| H | CN | CO$_2$CH$_2$C$_6$H$_5$ |
| H | CN | CO$_2$C$_6$H$_5$ |
| H | CN | SO$_2$CH$_3$ |
| H | CN | SO$_2$CF$_3$ |
| H | CN | SO$_2$CH$_2$C$_6$H$_5$ |
| H | CN | SO$_2$C$_6$H$_5$ |
| H | CN | NHSO$_2$CH$_3$ |
| H | CN | NHSO$_2$CF$_3$ |
| H | CN | NHSO$_2$CH$_2$C$_6$H$_5$ |
| H | CN | NHSO$_2$C$_6$H$_5$ |
| H | 2,6-Cl$_2$—C$_6$H$_3$ | NHCHO |
| H | 2,6-Cl$_2$—C$_6$H$_3$ | NHCOCH$_3$ |
| H | 2,6-Cl$_2$—C$_6$H$_3$ | NHCOCH$_2$CH$_3$ |
| H | 2,6-Cl$_2$—C$_6$H$_3$ | NHCOCH(CH$_3$)$_2$ |
| H | 2,6-Cl$_2$—C$_6$H$_3$ | NHCO-Cyclopropyl |
| H | 2,6-Cl$_2$—C$_6$H$_3$ | NHCOCH$_2$C$_6$H$_5$ |
| H | 2,6-Cl$_2$—C$_6$H$_3$ | NHCOC$_6$H$_5$ |
| H | 2,6-Cl$_2$—C$_6$H$_3$ | NHCO$_2$CH$_3$ |
| H | 2,6-Cl$_2$—C$_6$H$_3$ | NHCO$_2$CH$_2$CH$_3$ |
| H | 2,6-Cl$_2$—C$_6$H$_3$ | NHCO$_2$CH(CH$_3$)$_2$ |
| H | 2,6-Cl$_2$—C$_6$H$_3$ | NHCO$_2$-Cyclopropyl |
| H | 2,6-Cl$_2$—C$_6$H$_3$ | NHCO$_2$CH$_2$C$_6$H$_5$ |
| H | 2,6-Cl$_2$—C$_6$H$_3$ | NHCO$_2$C$_6$H$_5$ |
| H | 2,6-Cl$_2$—C$_6$H$_3$ | NHCONH$_2$ |
| H | 2,6-Cl$_2$—C$_6$H$_3$ | NHCONHCH$_3$ |
| H | 2,6-Cl$_2$—C$_6$H$_3$ | NHCON(CH$_3$)$_2$ |
| H | 2,6-Cl$_2$—C$_6$H$_3$ | NHCONHCH$_2$CH$_3$ |
| H | 2,6-Cl$_2$—C$_6$H$_3$ | NHCONHCH(CH$_3$)$_2$ |
| H | 2,6-Cl$_2$—C$_6$H$_3$ | NHCONH-Cyclopropyl |
| H | 2,6-Cl$_2$—C$_6$H$_3$ | NHCONHCH$_2$C$_6$H$_5$ |
| H | 2,6-Cl$_2$—C$_6$H$_3$ | NHCONHC$_6$H$_5$ |
| H | 2,6-Cl$_2$—C$_6$H$_3$ | OCOCH$_3$ |
| H | 2,6-Cl$_2$—C$_6$H$_3$ | OCOCH$_2$CH$_3$ |
| H | 2,6-Cl$_2$—C$_6$H$_3$ | OCOCH(CH$_3$)$_2$ |
| H | 2,6-Cl$_2$—C$_6$H$_3$ | OCO-Cyclopropyl |
| H | 2,6-Cl$_2$—C$_6$H$_3$ | OCOCH$_2$C$_6$H$_5$ |
| H | 2,6-Cl$_2$—C$_6$H$_3$ | OCOC$_6$H$_5$ |
| H | 2,6-Cl$_2$—C$_6$H$_3$ | CO$_2$CH$_3$ |
| H | 2,6-Cl$_2$—C$_6$H$_3$ | CO$_2$CH$_2$CH$_3$ |
| H | 2,6-Cl$_2$—C$_6$H$_3$ | CO$_2$CH(CH$_3$)$_2$ |
| H | 2,6-Cl$_2$—C$_6$H$_3$ | CO$_2$-Cyclopropyl |
| H | 2,6-Cl$_2$—C$_6$H$_3$ | CO$_2$CH$_2$C$_6$H$_5$ |
| H | 2,6-Cl$_2$—C$_6$H$_3$ | CO$_2$C$_6$H$_5$ |
| H | 2,6-Cl$_2$—C$_6$H$_3$ | SO$_2$CH$_3$ |
| H | 2,6-Cl$_2$—C$_6$H$_3$ | SO$_2$CF$_3$ |
| H | 2,6-Cl$_2$—C$_6$H$_3$ | SO$_2$CH$_2$C$_6$H$_5$ |
| H | 2,6-Cl$_2$—C$_6$H$_3$ | SO$_2$C$_6$H$_5$ |
| H | 2,6-Cl$_2$—C$_6$H$_3$ | NHSO$_2$CH$_3$ |
| H | 2,6-Cl$_2$—C$_6$H$_3$ | NHSO$_2$CF$_3$ |
| H | 2,6-Cl$_2$—C$_6$H$_3$ | NHSO$_2$CH$_2$C$_6$H$_5$ |
| H | 2,6-Cl$_2$—C$_6$H$_3$ | NHSO$_2$C$_6$H$_5$ |

TABLE B

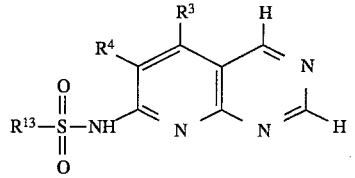

I.9

TABLE B-continued

I.10

Structure: Pyrido-pyrimidine with R³, R⁴, CH=N-C(CH₃), and R¹³-SO₂-NH-

I.11

Structure: Pyrido-pyrimidine with R³, R⁴, C(CH₃)=N-C(CH₃), and R¹³-SO₂-NH-

I.12

Structure: Pyrido-pyrimidine with R³, R⁴, CH=N-C(C₆H₅), and R¹³-SO₂-NH-

I.13

Structure: Pyrido-pyrimidine with R³, R⁴, C(CH₃)=N-C(C₆H₅), and R¹³-SO₂-NH-

I.14

Structure: Pyrido-pyrimidine with R³, R⁴, C(OCH₃)=N-C(OCH₃), and R¹³-SO₂-NH-

I.15

Structure: Pyrido-pyrimidine with R³, R⁴, CH=N-C(CH₂C₆H₅), and R¹³-SO₂-NH-

| R³ | R⁴ | R¹³ |
|---|---|---|
| H | H | C₆H₅ |
| H | H | 2-CH₃—C₆H₄ |
| H | H | 3-CH₃—C₆H₄ |
| H | H | 4-CH₃—C₆H₄ |
| H | H | 2-F—C₆H₄ |
| H | H | 3-F—C₆H₄ |
| H | H | 4-F—C₆H₄ |
| H | H | 2-Cl—C₆H₄ |
| H | H | 3-Cl—C₆H₄ |
| H | H | 4-Cl—C₆H₄ |
| H | H | 2-Br—C₆H₄ |
| H | H | 3-Br—C₆H₄ |
| H | H | 4-Br—C₆H₄ |
| H | H | 2-OH—C₆H₄ |
| H | H | 3-OH—C₆H₄ |
| H | H | 4-OH—C₆H₄ |
| H | H | 2-OCH₃—C₆H₄ |
| H | H | 3-OCH₃—C₆H₄ |
| H | H | 4-OCH₃—C₆H₄ |
| H | H | 4-C₆H₅—C₆H₄ |
| H | H | 3-C(CH₃)₃—C₆H₄ |
| H | H | 4-C(CH₃)₃—C₆H₄ |
| H | H | 2-CF₃—C₆H₄ |
| H | H | 3-CF₃—C₆H₄ |
| H | H | 4-CF₃—C₆H₄ |
| H | H | 2-NO₂—C₆H₄ |
| H | H | 3-NO₂—C₆H₄ |
| H | H | 4-NO₂—C₆H₄ |
| H | H | 2-CN—C₆H₄ |
| H | H | 3-CN—C₆H₄ |
| H | H | 4-CN—C₆H₄ |
| H | H | 2-(CO₂C₂H₅)—C₆H₄ |
| H | H | 3-(CO₂C₂H₅)—C₆H₄ |
| H | H | 4-(CO₂C₂H₅)—C₆H₄ |
| H | H | 2-(CO₂CH₃)—C₆H₄ |
| H | H | 3-(CO₂CH₃)—C₆H₄ |
| H | H | 4-(CO₂CH₃)—C₆H₄ |
| H | H | 2-CONH₂—C₆H₄ |
| H | H | 3-CONH₂—C₆H₄ |
| H | H | 4-CONH₂—C₆H₄ |
| H | H | 2-NH₂—C₆H₄ |
| H | H | 3-NH₂—C₆H₄ |
| H | H | 4-NH₂—C₆H₄ |
| H | H | 2-SCH₃—C₆H₄ |
| H | H | 3-SCH₃—C₆H₄ |
| H | H | 4-SCH₃—C₆H₄ |
| H | H | 2,4-(CH₃)₂—C₆H₃ |
| H | H | 3,4-(CH₃)₂—C₆H₃ |
| H | H | 2,6-(CH₃)₂—C₆H₃ |
| H | H | 2,4-(OCH₃)₂—C₆H₃ |
| H | H | 3,4-(OCH₃)₂—C₆H₃ |
| H | H | 2,6-(OCH₃)₂—C₆H₃ |
| H | H | 2,4-F₂—C₆H₃ |
| H | H | 3,4-F₂—C₆H₃ |
| H | H | 2,6-F₂—C₆H₃ |
| H | H | 2,4-Cl₂—C₆H₃ |
| H | H | 3,4-Cl₂—C₆H₃ |
| H | H | 2,6-Cl₂—C₆H₃ |
| H | H | 2,4-(OH)₂—C₆H₃ |
| H | H | 3,4-(OH)₂—C₆H₃ |
| H | H | 2,6-(OH)₂—C₆H₃ |
| H | H | 2-Cl-6-CH₃—C₆H₃ |
| H | H | 2-CO₂CH₃-6-CH₃—C₆H₃ |
| H | H | 3-NO₂-4-CH₃—C₆H₃ |
| H | H | 3-NO₂-4-F—C₆H₃ |
| H | H | 3-NO₂-4-Cl—C₆H₃ |
| H | H | 3-NO₂-4-OCH₃—C₆H₃ |
| H | H | 2-Naphthyl |
| H | H | Thien-2-yl |
| H | H | Thien-3-yl |
| H | H | 5-CH₃-thien-2-yl |
| H | H | 5-Cl-thien-2-yl |
| H | H | 5-Br-thien-2-yl |
| H | H | 2,5-(CH₃)₂-thien-3-yl |
| H | H | Thiazol-2-yl |
| H | H | Thiazol-4-yl |
| H | H | 5-CH₃-thiazol-2-yl |
| H | H | 5-Cl-thiazol-2-yl |
| H | H | 5-Br-thiazol-2-yl |
| H | H | 2,5-(CH₃)₂-thiazol-4-yl |
| H | H | Furan-2-yl |
| H | H | Furan-3-yl |
| H | H | 5-CH₃-furan-2-yl |
| H | H | 5-Cl-furan-2-yl |
| H | H | Pyrrol-2-yl |
| H | H | Pyrrol-3-yl |
| H | H | 5-CH₃-pyrrol-2-yl |
| H | H | 5-Br-pyrrol-2-yl |
| H | H | Oxazol-4-yl |
| H | H | Imidazol-2-yl |
| H | H | Pyridin-2-yl |

TABLE B-continued

| | | |
|---|---|---|
| H | H | Pyridin-3-yl |
| H | H | Pyridin-4-yl |
| H | H | Pyrazin-3-yl |
| H | H | Pyrazin-4-yl |
| H | H | Pyrrol-2-yl |
| H | H | Pyrimidin-2-yl |
| H | H | Pyrimidin-4-yl |
| H | H | Pyrimidin-5-yl |
| H | CN | $C_6H_5$ |
| H | CN | 2-$CH_3$—$C_6H_4$ |
| H | CN | 3-$CH_3$—$C_6H_4$ |
| H | CN | 4-$CH_3$—$C_6H_4$ |
| H | CN | 2-F—$C_6H_4$ |
| H | CN | 3-F—$C_6H_4$ |
| H | CN | 4-F—$C_6H_4$ |
| H | CN | 2-Cl—$C_6H_4$ |
| H | CN | 3-Cl—$C_6H_4$ |
| H | CN | 4-Cl—$C_6H_4$ |
| H | CN | 2-Br—$C_6H_4$ |
| H | CN | 3-Br—$C_6H_4$ |
| H | CN | 4-Br—$C_6H_4$ |
| H | CN | 2-OH—$C_6H_4$ |
| H | CN | 3-OH—$C_6H_4$ |
| H | CN | 4-OH—$C_6H_4$ |
| H | CN | 2-$OCH_3$—$C_6H_4$ |
| H | CN | 3-$OCH_3$—$C_6H_4$ |
| H | CN | 4-$OCH_3$—$C_6H_4$ |
| H | CN | 4-$C_6H_5$—$C_6H_4$ |
| H | CN | 2-Cl-6-$CH_3$—$C_6H_3$ |
| H | CN | 2-$CO_2CH_3$-6-$CH_3$—$C_6H_3$ |
| H | CN | 2,5-$(OCH_3)_2$—$C_6H_3$ |
| H | CN | 2,5-$Cl_2$—$C_6H_3$ |
| H | CN | 2,4,5-$Cl_3$—$C_6H_2$ |
| H | CN | 2-$CO_2CH_3$—$C_6H_3$ |
| H | CN | 5-Cl-2-$OCH_3$—$C_6H_3$ |
| H | CN | 5-$NO_2$-2-Cl—$C_6H_3$ |
| H | CN | 2-Cl-6-cyclopentenyl-$C_6H_3$ |
| H | CN | 3-Cl-thien-2-yl |
| H | CN | 3-$C(CH_3)_3$—$C_6H_4$ |
| H | CN | 4-$C(CH_3)_3$—$C_6H_4$ |
| H | CN | 2-$CF_3$—$C_6H_4$ |
| H | CN | 3-$CF_3$—$C_6H_4$ |
| H | CN | 4-$CF_3$—$C_6H_4$ |
| H | CN | 2-$NO_2$—$C_6H_4$ |
| H | CN | 3-$NO_2$—$C_6H_4$ |
| H | CN | 4-$NO_2$—$C_6H_4$ |
| H | CN | 2-CN—$C_6H_4$ |
| H | CN | 3-CN—$C_6H_4$ |
| H | CN | 4-CN—$C_6H_4$ |
| H | CN | 2-$(CO_2CH_3)$—$C_6H_4$ |
| H | CN | 3-$(CO_2CH_3)$—$C_6H_4$ |
| H | CN | 4-$(CO_2CH_3)$—$C_6H_4$ |
| H | CN | 2-$(CO_2C_2H_5)$—$C_6H_4$ |
| H | CN | 3-$(CO_2C_2H_5)$—$C_6H_4$ |
| H | CN | 4-$(CO_2C_2H_5)$—$C_6H_4$ |
| H | CN | 2-$CONH_2$—$C_6H_4$ |
| H | CN | 3-$CONH_2$—$C_6H_4$ |
| H | CN | 4-$CONH_2$—$C_6H_4$ |
| H | CN | 2-$NH_2$—$C_6H_4$ |
| H | CN | 3-$NH_2$—$C_6H_4$ |
| H | CN | 4-$NH_2$—$C_6H_4$ |
| H | CN | 2-$SCH_3$—$C_6H_4$ |
| H | CN | 3-$SCH_3$—$C_6H_4$ |
| H | CN | 4-$SCH_3$—$C_6H_4$ |
| H | CN | 2,4-$(CH_3)_2$—$C_6H_3$ |
| H | CN | 3,4-$(CH_3)_2$—$C_6H_3$ |
| H | CN | 2,6-$(CH_3)_2$—$C_6H_3$ |
| H | CN | 2,4-$(OCH_3)_2$—$C_6H_3$ |
| H | CN | 3,4-$(OCH_3)_2$—$C_6H_3$ |
| H | CN | 2,6-$(OCH_3)_2$—$C_6H_3$ |
| H | CN | 2,4-$F_2$—$C_6H_3$ |
| H | CN | 3,4-$F_2$—$C_6H_3$ |
| H | CN | 2,6-$F_2$—$C_6H_3$ |
| H | CN | 2,4-$Cl_2$—$C_6H_3$ |
| H | CN | 3,4-$Cl_2$—$C_6H_3$ |
| H | CN | 2,6-$Cl_2$—$C_6H_3$ |
| H | CN | 2,4-$(OH)_2$—$C_6H_3$ |
| H | CN | 3,4-$(OH)_2$—$C_6H_3$ |
| H | CN | 2,6-$(OH)_2$—$C_6H_3$ |

TABLE B-continued

| | | |
|---|---|---|
| H | CN | 3-$NO_2$-4-$CH_3$—$C_6H_3$ |
| H | CN | 3-$NO_2$-4-F—$C_6H_3$ |
| H | CN | 3-$NO_2$-4-Cl—$C_6H_3$ |
| H | CN | 3-$NO_2$-4-$OCH_3$—$C_6H_3$ |
| H | CN | 2-Naphthyl |
| H | CN | Thien-2-yl |
| H | CN | Thien-3-yl |
| H | CN | 5-$CH_3$-thien-2-yl |
| H | CN | 5-Cl-thien-2-yl |
| H | CN | 5-Br-thien-2-yl |
| H | CN | 2,5-$(CH_3)_2$-thien-3-yl |
| H | CN | Thiazol-2-yl |
| H | CN | Thiazol-4-yl |
| H | CN | 5-$CH_3$-thiazol-2-yl |
| H | CN | 5-Cl-thiazol-2-yl |
| H | CN | 5-Br-thiazol-2-yl |
| H | CN | 2,5-$(CH_3)_2$-thiazol-4-yl |
| H | CN | Furan-2-yl |
| H | CN | Furan-3-yl |
| H | CN | 5-$CH_3$-furan-2-yl |
| H | CN | 5-Cl-furan-2-yl |
| H | CN | Pyrrol-2-yl |
| H | CN | Pyrrol-3-yl |
| H | CN | 5-$CH_3$-pyrrol-2-yl |
| H | CN | 5-Br-pyrrol-2-yl |
| H | CN | Oxazol-4-yl |
| H | CN | Imidazol-2-yl |
| H | CN | Pyridin-2-yl |
| H | CN | Pyridin-3-yl |
| H | CN | Pyridin-4-yl |
| H | CN | Pyrazin-3-yl |
| H | CN | Pyrazin-4-yl |
| H | CN | Pyrrol-2-yl |
| H | CN | Pyrimidin-2-yl |
| H | CN | Pyrimidin-4-yl |
| H | CN | Pyrimidin-5-yl |
| H | $C_6H_5$ | $C_6H_5$ |
| H | $C_6H_5$ | 2-$CH_3$—$C_6H_4$ |
| H | $C_6H_5$ | 3-$CH_3$—$C_6H_4$ |
| H | $C_6H_5$ | 4-$CH_3$—$C_6H_4$ |
| H | $C_6H_5$ | 2-F—$C_6H_4$ |
| H | $C_6H_5$ | 3-F—$C_6H_4$ |
| H | $C_6H_5$ | 4-F—$C_6H_4$ |
| H | $C_6H_5$ | 2-Cl—$C_6H_4$ |
| H | $C_6H_5$ | 3-Cl—$C_6H_4$ |
| H | $C_6H_5$ | 4-Cl—$C_6H_4$ |
| H | $C_6H_5$ | 2-Br—$C_6H_4$ |
| H | $C_6H_5$ | 3-Br—$C_6H_4$ |
| H | $C_6H_5$ | 4-Br—$C_6H_4$ |
| H | $C_6H_5$ | 2-OH—$C_6H_4$ |
| H | $C_6H_5$ | 3-OH—$C_6H_4$ |
| H | $C_6H_5$ | 4-OH—$C_6H_4$ |
| H | $C_6H_5$ | 2-$OCH_3$—$C_6H_4$ |
| H | $C_6H_5$ | 3-$OCH_3$—$C_6H_4$ |
| H | $C_6H_5$ | 4-$OCH_3$—$C_6H_4$ |
| H | $C_6H_5$ | 2-Cl-6-$CH_3$—$C_6H_3$ |
| H | $C_6H_5$ | 2-$CO_2CH_3$-6-$CH_3$—$C_6H_3$ |
| H | $C_6H_5$ | 4-$C_6H_5$—$C_6H_4$ |
| H | $C_6H_5$ | 3-$C(CH_3)_3$—$C_6H_4$ |
| H | $C_6H_5$ | 4-$C(CH_3)_3$—$C_6H_4$ |
| H | $C_6H_5$ | 2-$CF_3$—$C_6H_4$ |
| H | $C_6H_5$ | 3-$CF_3$—$C_6H_4$ |
| H | $C_6H_5$ | 4-$CF_3$—$C_6H_4$ |
| H | $C_6H_5$ | 2-$NO_2$—$C_6H_4$ |
| H | $C_6H_5$ | 3-$NO_2$—$C_6H_4$ |
| H | $C_6H_5$ | 4-$NO_2$—$C_6H_4$ |
| H | $C_6H_5$ | 2-CN—$C_6H_4$ |
| H | $C_6H_5$ | 3-CN—$C_6H_4$ |
| H | $C_6H_5$ | 4-CN—$C_6H_4$ |
| H | $C_6H_5$ | 2,5-$(OCH_3)_2$—$C_6H_3$ |
| H | $C_6H_5$ | 2,5-$Cl_2$—$C_6H_3$ |
| H | $C_6H_5$ | 2,4,5-$Cl_3$—$C_6H_2$ |
| H | $C_6H_5$ | 2-$CO_2CH_3$—$C_6H_3$ |
| H | $C_6H_5$ | 5-Cl-2-$OCH_3$—$C_6H_3$ |
| H | $C_6H_5$ | 5-$NO_2$-2-Cl—$C_6H_3$ |
| H | $C_6H_5$ | 2-Cl-6-cyclopentenyl-$C_6H_3$ |
| H | $C_6H_5$ | 3-Cl-thien-2-yl |
| H | $C_6H_5$ | 2-$(CO_2CH_3)$—$C_6H_4$ |
| H | $C_6H_5$ | 3-$(CO_2CH_3)$—$C_6H_4$ |

TABLE B-continued

| | | |
|---|---|---|
| H | C₆H₅ | 4-(CO₂CH₃)—C₆H₄ |
| H | C₆H₅ | 2-(CO₂C₂H₅)—C₆H₄ |
| H | C₆H₅ | 3-(CO₂C₂H₅)—C₆H₄ |
| H | C₆H₅ | 4-(CO₂C₂H₅)—C₆H₄ |
| H | C₆H₅ | 2-CONH₂—C₆H₄ |
| H | C₆H₅ | 3-CONH₂—C₆H₄ |
| H | C₆H₅ | 4-CONH₂—C₆H₄ |
| H | C₆H₅ | 2-NH₂—C₆H₄ |
| H | C₆H₅ | 3-NH₂—C₆H₄ |
| H | C₆H₅ | 4-NH₂—C₆H₄ |
| H | C₆H₅ | 2-SCH₃—C₆H₄ |
| H | C₆H₅ | 3-SCH₃—C₆H₄ |
| H | C₆H₅ | 4-SCH₃—C₆H₄ |
| H | C₆H₅ | 2,4-(CH₃)₂—C₆H₃ |
| H | C₆H₅ | 3,4-(CH₃)₂—C₆H₃ |
| H | C₆H₅ | 2,6-(CH₃)₂—C₆H₃ |
| H | C₆H₅ | 2,4-(OCH₃)₂—C₆H₃ |
| H | C₆H₅ | 3,4-(OCH₃)₂—C₆H₃ |
| H | C₆H₅ | 2,6-(OCH₃)₂—C₆H₃ |
| H | C₆H₅ | 2,4-F₂—C₆H₃ |
| H | C₆H₅ | 3,4-F₂—C₆H₃ |
| H | C₆H₅ | 2,6-F₂—C₆H₃ |
| H | C₆H₅ | 2,4-Cl₂—C₆H₃ |
| H | C₆H₅ | 3,4-Cl₂—C₆H₃ |
| H | C₆H₅ | 2,6-Cl₂—C₆H₃ |
| H | C₆H₅ | 2,4-(OH)₂—C₆H₃ |
| H | C₆H₅ | 3,4-(OH)₂—C₆H₃ |
| H | C₆H₅ | 2,6-(OH)₂—C₆H₃ |
| H | C₆H₅ | 3-NO₂-4-CH₃—C₆H₃ |
| H | C₆H₅ | 3-NO₂-4-F—C₆H₃ |
| H | C₆H₅ | 3-NO₂-4-Cl—C₆H₃ |
| H | C₆H₅ | 3-NO₂-4-OCH₃—C₆H₃ |
| H | C₆H₅ | 2-Naphthyl |
| H | C₆H₅ | Thien-2-yl |
| H | C₆H₅ | Thien-3-yl |
| H | C₆H₅ | 5-CH₃-thien-2-yl |
| H | C₆H₅ | 5-Cl-thien-2-yl |
| H | C₆H₅ | 5-Br-thien-2-yl |
| H | C₆H₅ | 2,5-(CH₃)₂-thien-3-yl |
| H | C₆H₅ | Thiazol-2-yl |
| H | C₆H₅ | Thiazol-4-yl |
| H | C₆H₅ | 5-CH₃-thiazol-2-yl |
| H | C₆H₅ | 5-Cl-thiazol-2-yl |
| H | C₆H₅ | 5-Br-thiazol-2-yl |
| H | C₆H₅ | 2,5-(CH₃)₂-thiazol-4-yl |
| H | C₆H₅ | Furan-2-yl |
| H | C₆H₅ | Furan-3-yl |
| H | C₆H₅ | 5-CH₃-furan-2-yl |
| H | C₆H₅ | 5-Cl-furan-2-yl |
| H | C₆H₅ | Pyrrol-2-yl |
| H | C₆H₅ | Pyrrol-3-yl |
| H | C₆H₅ | 5-CH₃-pyrrol-2-yl |
| H | C₆H₅ | 5-Br-pyrrol-2-yl |
| H | C₆H₅ | Oxazol-4-yl |
| H | C₆H₅ | Imidazol-2-yl |
| H | C₆H₅ | Pyridin-2-yl |
| H | C₆H₅ | Pyridin-3-yl |
| H | C₆H₅ | Pyridin-4-yl |
| H | C₆H₅ | Pyrazin-3-yl |
| H | C₆H₅ | Pyrazin-4-yl |
| H | C₆H₅ | Pyrrol-2-yl |
| H | C₆H₅ | Pyrimidin-2-yl |
| H | C₆H₅ | Pyrimidin-4-yl |
| H | C₆H₅ | Pyrimidin-5-yl |
| H | SO₂CH₃ | C₆H₅ |
| H | SO₂CH₃ | 2-CH₃—C₆H₄ |
| H | SO₂CH₃ | 3-CH₃—C₆H₄ |
| H | SO₂CH₃ | 4-CH₃—C₆H₄ |
| H | SO₂CH₃ | 2-F—C₆H₄ |
| H | SO₂CH₃ | 3-F—C₆H₄ |
| H | SO₂CH₃ | 4-F—C₆H₄ |
| H | SO₂CH₃ | 2-Cl—C₆H₄ |
| H | SO₂CH₃ | 3-Cl—C₆H₄ |
| H | SO₂CH₃ | 4-Cl—C₆H₄ |
| H | SO₂CH₃ | 2-Br—C₆H₄ |
| H | SO₂CH₃ | 3-Br—C₆H₄ |
| H | SO₂CH₃ | 4-Br—C₆H₄ |
| H | SO₂CH₃ | 2-OH—C₆H₄ |
| H | SO₂CH₃ | 3-OH—C₆H₄ |
| H | SO₂CH₃ | 4-OH—C₆H₄ |
| H | SO₂CH₃ | 2-OCH₃—C₆H₄ |
| H | SO₂CH₃ | 3-OCH₃—C₆H₄ |
| H | SO₂CH₃ | 4-OCH₃—C₆H₄ |
| H | SO₂CH₃ | 4-C₆H₅—C₆H₄ |
| H | SO₂CH₃ | 3-C(CH₃)₃—C₆H₄ |
| H | SO₂CH₃ | 4-C(CH₃)₃—C₆H₄ |
| H | SO₂CH₃ | 2-CF₃—C₆H₄ |
| H | SO₂CH₃ | 3-CF₃—C₆H₄ |
| H | SO₂CH₃ | 4-CF₃—C₆H₄ |
| H | SO₂CH₃ | 2-NO₂—C₆H₄ |
| H | SO₂CH₃ | 3-NO₂—C₆H₄ |
| H | SO₂CH₃ | 4-NO₂—C₆H₄ |
| H | SO₂CH₃ | 2-CN—C₆H₄ |
| H | SO₂CH₃ | 3-CN—C₆H₄ |
| H | SO₂CH₃ | 4-CN—C₆H₄ |
| H | SO₂CH₃ | 2-Cl-6-CH₃—C₆H₃ |
| H | SO₂CH₃ | 2-CO₂CH₃-6-CH₃—C₆H₃ |
| H | SO₂CH₃ | 2,5-(OCH₃)₂—C₆H₃ |
| H | SO₂CH₃ | 2,5-Cl₂—C₆H₃ |
| H | SO₂CH₃ | 2,4,5-Cl₃—C₆H₂ |
| H | SO₂CH₃ | 2-CO₂CH₃—C₆H₄ |
| H | SO₂CH₃ | 5-Cl-2-OCH₃—C₆H₃ |
| H | SO₂CH₃ | 5-NO₂-2-Cl—C₆H₃ |
| H | SO₂CH₃ | 2-Cl-6-cyclopentenyl-C₆H₃ |
| H | SO₂CH₃ | 3-Cl-thien-2-yl |
| H | SO₂CH₃ | 2-(CO₂CH₃)—C₆H₄ |
| H | SO₂CH₃ | 3-(CO₂CH₃)—C₆H₄ |
| H | SO₂CH₃ | 4-(CO₂CH₃)—C₆H₄ |
| H | SO₂CH₃ | 2-(CO₂C₂H₅)—C₆H₄ |
| H | SO₂CH₃ | 3-(CO₂C₂H₅)—C₆H₄ |
| H | SO₂CH₃ | 4-(CO₂C₂H₅)—C₆H₄ |
| H | SO₂CH₃ | 2-CONH₂—C₆H₄ |
| H | SO₂CH₃ | 3-CONH₂—C₆H₄ |
| H | SO₂CH₃ | 4-CONH₂—C₆H₄ |
| H | SO₂CH₃ | 2-NH₂—C₆H₄ |
| H | SO₂CH₃ | 3-NH₂—C₆H₄ |
| H | SO₂CH₃ | 4-NH₂—C₆H₄ |
| H | SO₂CH₃ | 2-SCH₃—C₆H₄ |
| H | SO₂CH₃ | 3-SCH₃—C₆H₄ |
| H | SO₂CH₃ | 4-SCH₃—C₆H₄ |
| H | SO₂CH₃ | 2,4-(CH₃)₂—C₆H₃ |
| H | SO₂CH₃ | 3,4-(CH₃)₂—C₆H₃ |
| H | SO₂CH₃ | 2,6-(CH₃)₂—C₆H₃ |
| H | SO₂CH₃ | 2,4-(OCH₃)₂—C₆H₃ |
| H | SO₂CH₃ | 3,4-(OCH₃)₂—C₆H₃ |
| H | SO₂CH₃ | 2,6-(OCH₃)₂—C₆H₃ |
| H | SO₂CH₃ | 2,4-F₂—C₆H₃ |
| H | SO₂CH₃ | 3,4-F₂—C₆H₃ |
| H | SO₂CH₃ | 2,6-F₂—C₆H₃ |
| H | SO₂CH₃ | 2,4-Cl₂—C₆H₃ |
| H | SO₂CH₃ | 3,4-Cl₂—C₆H₃ |
| H | SO₂CH₃ | 2,6-Cl₂—C₆H₃ |
| H | SO₂CH₃ | 2,4-(OH)₂—C₆H₃ |
| H | SO₂CH₃ | 3,4-(OH)₂—C₆H₃ |
| H | SO₂CH₃ | 2,6-(OH)₂—C₆H₃ |
| H | SO₂CH₃ | 3-NO₂-4-CH₃—C₆H₃ |
| H | SO₂CH₃ | 3-NO₂-4-F—C₆H₃ |
| H | SO₂CH₃ | 3-NO₂-4-Cl—C₆H₃ |
| H | SO₂CH₃ | 3-NO₂-4-OCH₃—C₆H₃ |
| H | SO₂CH₃ | 2-Naphthyl |
| H | SO₂CH₃ | Thien-2-yl |
| H | SO₂CH₃ | Thien-3-yl |
| H | SO₂CH₃ | 5-CH₃-thien-2-yl |
| H | SO₂CH₃ | 5-Cl-thien-2-yl |
| H | SO₂CH₃ | 5-Br-thien-2-yl |
| H | SO₂CH₃ | 2,5-(CH₃)₂-thien-3-yl |
| H | SO₂CH₃ | Thiazol-2-yl |
| H | SO₂CH₃ | Thiazol-4-yl |
| H | SO₂CH₃ | 5-CH₃-thiazol-2-yl |
| H | SO₂CH₃ | 5-Cl-thiazol-2-yl |
| H | SO₂CH₃ | 5-Br-thiazol-2-yl |
| H | SO₂CH₃ | 2,5-(CH₃)₂-thiazol-4-yl |
| H | SO₂CH₃ | Furan-2-yl |
| H | SO₂CH₃ | Furan-3-yl |
| H | SO₂CH₃ | 5-CH₃-furan-2-yl |
| H | SO₂CH₃ | 5-Cl-furan-2-yl |
| H | SO₂CH₃ | Pyrrol-2-yl |
| H | SO₂CH₃ | Pyrrol-3-yl |

TABLE B-continued

| | | |
|---|---|---|
| H | $SO_2CH_3$ | 5-$CH_3$-pyrrol-2-yl |
| H | $SO_2CH_3$ | 5-Br-pyrrol-2-yl |
| H | $SO_2CH_3$ | Oxazol-4-yl |
| H | $SO_2CH_3$ | Imidazol-2-yl |
| H | $SO_2CH_3$ | Pyridin-2-yl |
| H | $SO_2CH_3$ | Pyridin-3-yl |
| H | $SO_2CH_3$ | Pyridin-4-yl |
| H | $SO_2CH_3$ | Pyrazin-3-yl |
| H | $SO_2CH_3$ | Pyrazin-4-yl |
| H | $SO_2CH_3$ | Pyrrol-2-yl |
| H | $SO_2CH_3$ | Pyrimidin-2-yl |
| H | $SO_2CH_3$ | Pyrimidin-4-yl |
| H | $SO_2CH_3$ | Pyrimidin-5-yl |
| H | $SO_2C_6H_5$ | $C_6H_5$ |
| H | $SO_2C_6H_5$ | 2-$CH_3$—$C_6H_4$ |
| H | $SO_2C_6H_5$ | 3-$CH_3$—$C_6H_4$ |
| H | $SO_2C_6H_5$ | 4-$CH_3$—$C_6H_4$ |
| H | $SO_2C_6H_5$ | 2-F—$C_6H_4$ |
| H | $SO_2C_6H_5$ | 3-F—$C_6H_4$ |
| H | $SO_2C_6H_5$ | 4-F—$C_6H_4$ |
| H | $SO_2C_6H_5$ | 2-Cl—$C_6H_4$ |
| H | $SO_2C_6H_5$ | 3-Cl—$C_6H_4$ |
| H | $SO_2C_6H_5$ | 4-Cl—$C_6H_4$ |
| H | $SO_2C_6H_5$ | 2-Br—$C_6H_4$ |
| H | $SO_2C_6H_5$ | 3-Br—$C_6H_4$ |
| H | $SO_2C_6H_5$ | 4-Br—$C_6H_4$ |
| H | $SO_2C_6H_5$ | 2-OH—$C_6H_4$ |
| H | $SO_2C_6H_5$ | 3-OH—$C_6H_4$ |
| H | $SO_2C_6H_5$ | 4-OH—$C_6H_4$ |
| H | $SO_2C_6H_5$ | 2-$OCH_3$—$C_6H_4$ |
| H | $SO_2C_6H_5$ | 3-$OCH_3$—$C_6H_4$ |
| H | $SO_2C_6H_5$ | 4-$OCH_3$—$C_6H_4$ |
| H | $SO_2C_6H_5$ | 4-$C_6H_5$—$C_6H_4$ |
| H | $SO_2C_6H_5$ | 3-$C(CH_3)_3$—$C_6H_4$ |
| H | $SO_2C_6H_5$ | 4-$C(CH_3)_3$—$C_6H_4$ |
| H | $SO_2C_6H_5$ | 2-$CF_3$—$C_6H_4$ |
| H | $SO_2C_6H_5$ | 3-$CF_3$—$C_6H_4$ |
| H | $SO_2C_6H_5$ | 4-$CF_3$—$C_6H_4$ |
| H | $SO_2C_6H_5$ | 2-$NO_2$—$C_6H_4$ |
| H | $SO_2C_6H_5$ | 3-$NO_2$—$C_6H_4$ |
| H | $SO_2C_6H_5$ | 4-$NO_2$—$C_6H_4$ |
| H | $SO_2C_6H_5$ | 2-CN—$C_6H_4$ |
| H | $SO_2C_6H_5$ | 3-CN—$C_6H_4$ |
| H | $SO_2C_6H_5$ | 4-CN—$C_6H_4$ |
| H | $SO_2C_6H_5$ | 2-Cl-6-$CH_3$—$C_6H_3$ |
| H | $SO_2C_6H_5$ | 2-$CO_2CH_3$-6-$CH_3$—$C_6H_3$ |
| H | $SO_2C_6H_5$ | 2,5-$(OCH_3)_2$—$C_6H_3$ |
| H | $SO_2C_6H_5$ | 2,5-$Cl_2$—$C_6H_3$ |
| H | $SO_2C_6H_5$ | 2,4,5-$Cl_3$—$C_6H_2$ |
| H | $SO_2C_6H_5$ | 2-$CO_2CH_3$—$C_6H_3$ |
| H | $SO_2C_6H_5$ | 5-Cl-2-$OCH_3$—$C_6H_3$ |
| H | $SO_2C_6H_5$ | 5-$NO_2$-2-Cl—$C_6H_3$ |
| H | $SO_2C_6H_5$ | 2-Cl-6-cyclopentenyl-$C_6H_3$ |
| H | $SO_2C_6H_5$ | 3-Cl-thien-2-yl |
| H | $SO_2C_6H_5$ | 2-$(CO_2C_2H_5)$—$C_6H_4$ |
| H | $SO_2C_6H_5$ | 3-$(CO_2C_2H_5)$—$C_6H_4$ |
| H | $SO_2C_6H_5$ | 4-$(CO_2C_2H_5)$—$C_6H_4$ |
| H | $SO_2C_6H_5$ | 2-$(CO_2CH_3)$—$C_6H_4$ |
| H | $SO_2C_6H_5$ | 3-$(CO_2CH_3)$—$C_6H_4$ |
| H | $SO_2C_6H_5$ | 4-$(CO_2CH_3)$—$C_6H_4$ |
| H | $SO_2C_6H_5$ | 2-$CONH_2$—$C_6H_4$ |
| H | $SO_2C_6H_5$ | 3-$CONH_2$—$C_6H_4$ |
| H | $SO_2C_6H_5$ | 4-$CONH_2$—$C_6H_4$ |
| H | $SO_2C_6H_5$ | 2-$NH_2$—$C_6H_4$ |
| H | $SO_2C_6H_5$ | 3-$NH_2$—$C_6H_4$ |
| H | $SO_2C_6H_5$ | 4-$NH_2$—$C_6H_4$ |
| H | $SO_2C_6H_5$ | 2-$SCH_3$—$C_6H_4$ |
| H | $SO_2C_6H_5$ | 3-$SCH_3$—$C_6H_4$ |
| H | $SO_2C_6H_5$ | 4-$SCH_3$—$C_6H_4$ |
| H | $SO_2C_6H_5$ | 2,4-$(CH_3)_2$—$C_6H_3$ |
| H | $SO_2C_6H_5$ | 3,4-$(CH_3)_2$—$C_6H_3$ |
| H | $SO_2C_6H_5$ | 2,6-$(CH_3)_2$—$C_6H_3$ |
| H | $SO_2C_6H_5$ | 2,4-$(OCH_3)_2$—$C_6H_3$ |
| H | $SO_2C_6H_5$ | 3,4-$(OCH_3)_2$—$C_6H_3$ |
| H | $SO_2C_6H_5$ | 2,6-$(OCH_3)_2$—$C_6H_3$ |
| H | $SO_2C_6H_5$ | 2,4-$F_2$—$C_6H_3$ |
| H | $SO_2C_6H_5$ | 3,4-$F_2$—$C_6H_3$ |
| H | $SO_2C_6H_5$ | 2,6-$F_2$—$C_6H_3$ |
| H | $SO_2C_6H_5$ | 2,4-$Cl_2$—$C_6H_3$ |
| H | $SO_2C_6H_5$ | 3,4-$Cl_2$—$C_6H_3$ |
| H | $SO_2C_6H_5$ | 2,6-$Cl_2$—$C_6H_3$ |
| H | $SO_2C_6H_5$ | 2,4-$(OH)_2$—$C_6H_3$ |
| H | $SO_2C_6H_5$ | 3,4-$(OH)_2$—$C_6H_3$ |
| H | $SO_2C_6H_5$ | 2,6-$(OH)_2$—$C_6H_3$ |
| H | $SO_2C_6H_5$ | 3-$NO_2$-4-$CH_3$—$C_6H_3$ |
| H | $SO_2C_6H_5$ | 3-$NO_2$-4-F—$C_6H_3$ |
| H | $SO_2C_6H_5$ | 3-$NO_2$-4-Cl—$C_6H_3$ |
| H | $SO_2C_6H_5$ | 3-$NO_2$-4-$OCH_3$—$C_6H_3$ |
| H | $SO_2C_6H_5$ | 2-Naphthyl |
| H | $SO_2C_6H_5$ | Thien-2-yl |
| H | $SO_2C_6H_5$ | Thien-3-yl |
| H | $SO_2C_6H_5$ | 5-$CH_3$-thien-2-yl |
| H | $SO_2C_6H_5$ | 5-Cl-thien-2-yl |
| H | $SO_2C_6H_5$ | 5-Br-thien-2-yl |
| H | $SO_2C_6H_5$ | 2,5-$(CH_3)_2$-thien-3-yl |
| H | $SO_2C_6H_5$ | Thiazol-2-yl |
| H | $SO_2C_6H_5$ | Thiazol-4-yl |
| H | $SO_2C_6H_5$ | 5-$CH_3$-thiazol-2-yl |
| H | $SO_2C_6H_5$ | 5-Cl-thiazol-2-yl |
| H | $SO_2C_6H_5$ | 5-Br-thiazol-2-yl |
| H | $SO_2C_6H_5$ | 2,5-$(CH_3)_2$-thiazol-4-yl |
| H | $SO_2C_6H_5$ | Furan-2-yl |
| H | $SO_2C_6H_5$ | Furan-3-yl |
| H | $SO_2C_6H_5$ | 5-$CH_3$-furan-2-yl |
| H | $SO_2C_6H_5$ | 5-Cl-furan-2-yl |
| H | $SO_2C_6H_5$ | Pyrrol-2-yl |
| H | $SO_2C_6H_5$ | Pyrrol-3-yl |
| H | $SO_2C_6H_5$ | 5-$CH_3$-pyrrol-2-yl |
| H | $SO_2C_6H_5$ | 5-Br-pyrrol-2-yl |
| H | $SO_2C_6H_5$ | Oxazol-4-yl |
| H | $SO_2C_6H_5$ | Imidazol-2-yl |
| H | $SO_2C_6H_5$ | Pyridin-2-yl |
| H | $SO_2C_6H_5$ | Pyridin-3-yl |
| H | $SO_2C_6H_5$ | Pyridin-4-yl |
| H | $SO_2C_6H_5$ | Pyrazin-3-yl |
| H | $SO_2C_6H_5$ | Pyrazin-4-yl |
| H | $SO_2C_6H_5$ | Pyrrol-2-yl |
| H | $SO_2C_6H_5$ | Pyrimidin-2-yl |
| H | $SO_2C_6H_5$ | Pyrimidin-4-yl |
| H | $SO_2C_6H_5$ | Pyrimidin-5-yl |

The substituted pyrido[2,3-d]pyrimidines I are suitable as antidotes, to make herbicidal active ingredients better tolerated by crop plants such as millet, rice, corn, cereal species (wheat, rye, barley and oats), cotton, sugarbeet, sugarcane and soyabean. They have an antagonistic effect on herbicides from a very wide range of classes, such as triazines, phenyl urea derivatives, carbamates, thiocarbamates, haloacetanilides, benzoic acid derivatives and in particular halophenoxy acetates, substituted phenoxyphenoxy acetates, phenoxyphenozy propionates and cyclohexenone derivatives.

Herbicidal cyclohexenone derivatives II are disclosed, for example, in EP-A 228 598, EP-A 230 235, EP-A 238 021, EP-A 368 227, U.S. Pat. No. 4,432,786, 39 104 and DE-A 38 38 309. They are used predominantly for controlling undesirable grasses in dicotyledon crops and in grasses which do not belong to the Gramineae family. Depending on the substituents and on the dosage of the compounds of the type II during their application, these cyclohexenones can also be used for selectively controlling undesirable grasses in gramineous crops, such as wheat and rice.

Further cyclohexenone derivatives II can be prepared in a conventional manner by synthesis methods disclosed in the literature (cf. for example EP-A 169 521), for example by reacting triketones IX (disclosed in, for example, EP-A 80 301, EP-A 125 094, EP-A 142 741, U.S. Pat. No. 4,249,937, EP-A 137 174 and EP-A 177 913) with hydroxylamines X (disclosed in, for example, Houben-Weyl, Methoden der Organischen Chemie, Band 10/1, page 1181 et seq.):

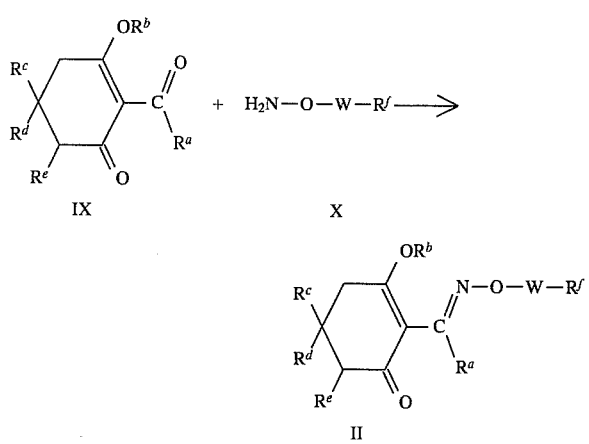

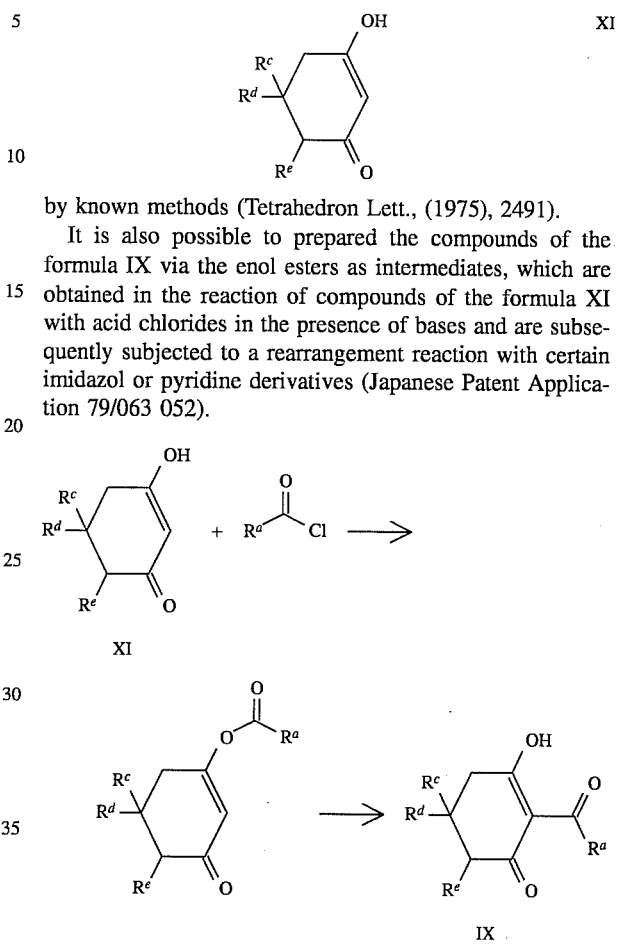

The reaction is advantageously carried out in the heterogeneous phase in a solvent, preferably in the presence of a base, hydroxylamine preferably being used as the ammonium salt.

Examples of suitable bases are the carbonates, hydrocarbonates, acetates, alcoholates and oxides of alkali metals and alkaline earth metals, such as sodium hydroxide, potassium hydroxide, magnesium oxide and calciumoxide, as well as organic bases, such as pyridine and tertiary amines, eg. triethylamine.

The triketone and hydroxylamine are preferably used in roughly stoichiometric amounts. The amount of base is not critical but is usually from about 0.5 to 2 mol equivalents, based on the amount of IX.

In general, the reaction temperature is from 0° to 80° C.

Examples of suitable solvents are dimethyl sulfoxide, alcohols, such as methanol, ethanol and isopropanol, aromatic hydrocarbons, such as benzene and toluene, aliphatic hydrocarbons such as hexane and cyclohexane, esters such as ethyl acetate, and ethers, such as diethyl ether, dioxane and tetrahydrofuran. The reaction is preferably carried out in methanol with sodium bicarbonate as the base.

The reaction is complete after a few hours. The product II can be isolated, for example, by evaporating down the mixture, distributing the residue in methylenechloride/water and distilling off the solvent under reduced pressure.

However, the free hydroxylamine base, for example in the form of an aqueous solution, may also be used directly for this reaction; depending on the solvent used for the hydroxylamine X, a one-phase or two-phase reaction mixture is obtained.

Suitable solvents for this variant are, for example, alcohols such as methanol, ethanol, isopropanol and cyclohexanol, aliphatic and aromatic hydrocarbons and chlorohydrocarbons such as hexane, cyclohexane, methylene chloride, toluene and dichloroethane, esters, such as ethyl acetate, nitriles such as acetonitrile, and cyclic ethers such as dioxane and tetrahydrofuran.

Particular conditions with regard to the pressure are not necessary; the reaction is therefore usually carried out at atmospheric pressure.

Alkali metal salts of the compounds II can be obtained by treating the 3-hydroxy compounds with sodium hydroxide, potassium hydroxide or sodium or potassium alcoholate in aqueous solution or in an organic solvent such as methanol, ethanol, acetone or toluene.

Other metal salts such as manganese, copper, zinc, iron, calcium, magnesium and barium salts, can be prepared from the sodium salts in a conventional manner, as can ammonium and phosphoniumsalts by means of ammonia or phosphonium, sulfonium or sulfoxonium hydroxides.

The compound of type IX can be prepared, for example, from the corresponding cyclohexane-1,3-diones of the formula XI

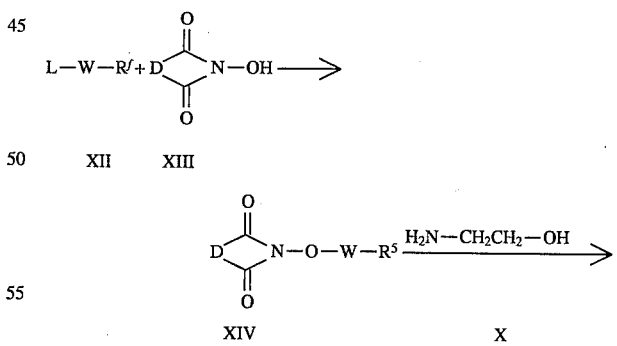

by known methods (Tetrahedron Lett., (1975), 2491).

It is also possible to prepared the compounds of the formula IX via the enol esters as intermediates, which are obtained in the reaction of compounds of the formula XI with acid chlorides in the presence of bases and are subsequently subjected to a rearrangement reaction with certain imidazol or pyridine derivatives (Japanese Patent Application 79/063 052).

The hydroxylamines of the formula X are obtained, as a rule, via a series of known process steps by starting from known intermediates:

L=the hydroxyl group or a leaving group, for example halogen, such as chlorine, bromine or iodine, or $CH_3SO_2$—O—.

The alkylating agents required for synthesizing the hydroxylamine X are known from the literature or can be prepared by known methods.

Syntheses of derivatives in which W is an aliphatic or olefinic chain which may be interrupted by heteroatoms are described in the following publications:

DE-A 3 437 919; Tetrahetron Lett. 28 (1979), 2639; Org. Synth. Coll. Vol. 1, (1944) 436; DE-A 2 654 646; DE-A 2 714 561; J. Org. Chem. 52 (1987), 3587; DE-A 948 871; DE-A 948 872; J. Med. Chem. 26 (1983), 1570; Synthesis (1983), 675; J. Org. Chem. 48 (1983), 4970; Org. Synth. Coll. Vol. V, 249; European Patents 48,911 and 143,952; U.S. Pat. No. 4,686,735.

The the preparation of compounds II in which W is an aliphatic or olefinic chain and $R^f$ is a heterocyclic structure, reference may be made to the following literature:, J. Heterocycl. Chem. 14 (1976), 525; JP 55 051 004; JP 55 047 601; Houben Weyl: Methoden der organischen Chemie, Vol. 4/3, page 424 et seq.; DE-A-2 821 409; Chem. Ber. 114. (1981), 3667 and 3674.

Preparation methods which start from suitable carbinols XII (L=OH) are disclosed, for example, in: Tetrahedron 35 (1979), 329; Chem. Lett. (1977) 423; Houben/Weyl: Methoden der organischen Chemie, Vol. 13/9B, page 964 et seq.; ibid Vol. 5/3, pages 862 and 899 et seq.; ibid. Vol. 5/4, page 361 et seq.

The preparation of alkylating agents in which W is substituted or unsubstituted $C_3$-$C_6$-alkynyl group can be carried out by classical methods [cf. J. Med. Chem. 29 (1986), 1389; ibid. 24 (1981), 678; EP-A 131 302; J. Chem. Ecol. 10 (1982), 1201] or by coupling of 1-alkynyl derivatives with aryl or hetaryl halides in the presence of palladium catalysts [cf. for example Tetrahedron Lett. 50 (1975), 4467].

XII is coupled with the cyclic hydroxylimide XIII and the resulting hydroxylamine derivative XIV is cleaved, preferably with 2-aminoethanol, to give the free hydroxylamine X.

When HO—W—$R^f$ is used, it is advisable to employ the Mitsunobu variant (cf. Synthesis (1981), 1 and J. Med. Chem. 33, (1990), 187).

In the cyclic hydroximides X, D is, for example, $C_2$- or $C_3$-alkylene, $C_2$-alkenylene or a 5-membered or 6-membered ring which contains up to three double bonds and may contain a nitrogen atom, for example phenylene, pyridylene, cyclopentylene, cyclohexylene or cyclohexenylene. For example, the following substances are suitable:

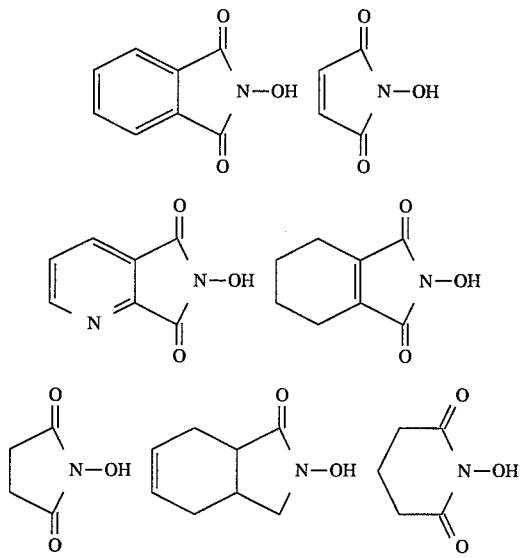

The reaction of the compound IX with the hydroximides XIII is advantageously carried out in the presence of a base. All bases which are capable of deprotonating the hydroximides XIII without attacking the imide system are in principle suitable. These are in particular the non nucleophilic bases. Examples are mineral bases, such as alkaki metal and alkaline earth metal carbonates, and alkali metal and alkaline earth metal bicarbonates, and organic bases such as aliphatic, cycloaliphatic and aromatic tertiary amines. Mixtures of these bases may also be used.

The following bases may be mentioned as examples of individual compounds: sodium carbonate, potassium carbonate, magnesiumcarbonate, calcium carbonate, barium carbonate, bicarbonates of these metals, trimethylamine, triethylamine, tributylamine, ethyldiisopropylamine, N,N-dimethylaniline, 4-N,N-dimethylaminopyridine, diazabicyclooctane, diazabicycloundecane, N-methylpiperidine, 1,4-dimethylpiperazine, pyridine, quinoline, bipyridine, and phenanthroline. The economical bases sodium carbonate and potassium carbonate are preferred.

The base is generally added in an equivalent amount to an excess of 5 equivalents based on hydroximide. A greater excess is possible but has no additional advantages. A smaller amount of base may also be used. However, from 1 to 3, in particular from 1 to 2, equivalents, based on the hydroximide XIII, of the base are preferably used.

It is also possible to use nucleophilic bases, for example alkali metal and alkaline earth metal hydroxides, in particular sodium hydroxide and potassium hydroxide. In this case, it is advantageous to use the base in equivalent amounts, based on the hydroximide XIII, in order to prevent nucleophilic attack by hydroxyl ions on the carbonyl function of the imide group.

The starting compounds XII are advantageously reacted with the hydroximides XIII in a solvent which is inert under the reaction conditions. Examples of advantageous solvents are polar, aprotic solvents, such as dimethylformamide, N-methylpyrrolidone, dimethyl sulfoxide, sulfolane and cyclic ureas. The amount of solvent is in general not critical.

The reaction of the starting compounds XII with the hydroximides XIII can also be carried out using phase transfer catalysis. In this case, solvents which form two phases with water, preferably chlorohydrocarbons, are used. Suitable phase transfer catalysts are the quaternary ammonium and phosphonium salts, polyethylene glycols, polyethylene glycol ethers and crown ethers usually used for such purposes, as described in, for example, Dehmlow et al.; Phase Transfer Catalysis, pages 37–45 and pages 86–93, Verlag Chemie, Weinheim 1980. The phase transfer catalysts are advantageously used in amounts of from 1 to 10, preferably from 3 to 5, % by volume, based on the volume of the reaction mixture.

The reaction of the starting compounds XII with the hydroximides XIII is carried out in general at from 0° to 140° C., preferably from 20° to 100° C., in particular from 40° to 80° C.

In an advantageous procedure, the hydroximide XIII is initially taken together with the base in the solvent, and the starting. material XII is metered into the solution. It may prove advantageous if the hydroximide is added at a lower temperature of, for example, from 0° to 50° C., and the reaction mixture is heated to the actual reaction temperature only after this addition.

As a rule, the reaction is carried out at atmospheric pressure or under the autogenous pressure of the solvents.

After the end of the reaction, water is advantageously added to the cooled reaction mixture, the hydroxylamine derivatives XIV formed separating out as crystalline solids or as oils. The hydroxylamine derivatives obtained in this manner can, if desired, be further purified by recrystallization or by extraction.

The hydroxylamine derivatives XIV may be temporarily stored or immediately converted into the hydroxylamine derivatives X having a free amino group. This conversion can be carried out by conventional methods, as described, for example, in DE-A 36 15 973 and in the publications cited therein. The process according to DE-A 36 15 973, in which the hydroxylamine derivatives X are liberated by means of ethanolamine, is preferably used. The liberation of the hydroxylamine derivatives X with the aid of other bases, such as aqueous mineral bases, with amines, hydrazines or hydroxylamines or by means of aqueous acids is also possible.

Hydroxylamine derivatives X can be isolated from the reaction mixtures obtained by these processes by means of conventional methods of working up, for example by extraction or by crystallization. To increase the tendency of these hydroxylamine derivatives to crystallize, it may often be necessary to convert them into their salts and mineral acids or organic acids. In general, dilute solutions of these acids are reacted with the hydroxylamine derivatives for this purpose, advantageously in equivalent amounts. The hydroxylammonium salts obtained can, as in the case of the hydroxylamine derivatives having a free amino group, be further processed directly to give the herbicides of formula II or, if desired, can be stored.

Cyclohexenone derivatives II may be obtained as isomeric mixtures in the preparation, both E-/Z-isomer mixtures and an enantiomer or diastereoisomer mixture being possible. The isomer mixtures can, if desired, be separated by the conventional methods, for example by chromatography or by crystallization.

Suitable herbicidal active ingredients (A) are both the pure enantiomers II and racemates or diastereoisomer mixtures of cyclohexanone derivatives II.

The cyclohexenone derivatives II can be represented in a plurality of tautomeric forms, the invention relating to all of these forms.

Preparation Examples (cyclohexenone derivatives)

EXAMPLE 1

2[1-(3-(4-bromophenyl)-prop-2-enyloximino)-propyl]-3-hydroxy-5-(3-tetrahydrothiopyranyl)-cyclohex-2-en-1-one

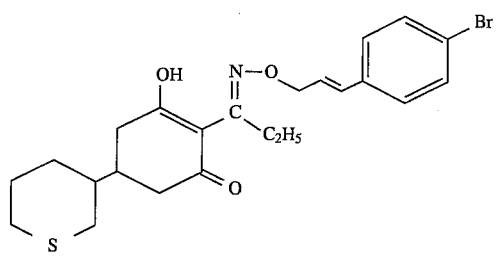

3.0 g (0.011 mol) of 2-propionyl-5-(3-tetrahydrothiopyranyl)-cyclohexane-1,3-dion and 3.0 g (0.013 mol) of 3-(4-bromophenyl)-prop-2-enyloxiamine in 100 ml of methanol were stirred at 20° C. for 16 hours. The precipitated reaction product was isolated at 0° C. washed with ice-cold methanol and petroleum ether and dried. Yield 68.4%; m.p.: 97°–99° C.

Intermediate 1.1

N-[3-(4-Bromophenyl)-prop-2-enyloxy]-phthalimide 18.5 g (0.11 mol) of N-hydroxyphthalimide and 31.4 g (0.11 mol) of 1-bromo-3-(4-bromophenyl)-prop-2-ene were added in succession to 350 ml of dry N-methylpyrrolidone, and 12.1 g (0.12 mol) of triethylamine were then added dropwise at room temperature. The reaction mixture was stirred for four days at 20° C. and then poured onto 1.5 l of ice water, and the product was filtered off and washed with water and isopropanol. Yield: 86.8%; m.p.: 161°–162° C.

Intermediate 1.2

3-(4-Bromophenyl)-prop-2-enyloxyamine 33.4 g (0.093 mol) of N-[3-(4-bromophenyl)-prop-2-enyloxy]phthalimide were introduced a little at a time in 50 ml of ethanolamine; the temperature increased to 30° C. during this procedure. Stirring was carried out for two hours at 60° C., after which the mixture was allowed to cool and 200 ml of dichloromethane were added. Extraction was effected by shaking with ice water. The organic phase was dried and evaporated down and the residue was crystallized from petroleum ether. Yield: 95.3%; m.p.: 35°–38° C.

EXAMPLE 2

2-[1-(4-(4-Fluorophenyl)-but-3-inyloximino)-butyl]-3-hydroxy-5-tetrahydropyran-4-yl-cyclohex-2-enone

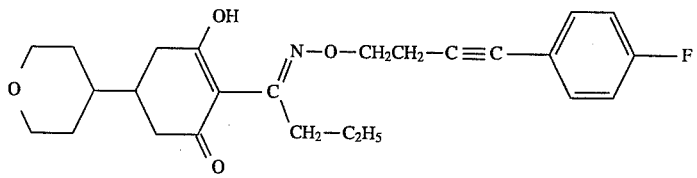

2.7 g (15 mmol) of 4-(4-fluorophenyl)-but-3-inoxyamine were added to a solution of 4 g (15 mmol) of 2-butryl-3-hydroxy-5-tetrahydropyran-4-yl-cyclohex-2-enone in 60 ml of dry methanol. After stirring for 16 hours at room temperature, the methanol was removed under reduced pressure from a water pump. The crude product was purified by

43 means of chromatography over silica gel (mobile phase: methylene chloride). Yield 81.2%.
Intermediate 2.1

4-(4-Fluorophenyl)-3-butynol 1 g of bis(triphenylphosphine)-palladium(II)-chloride, 3.8 g of copper(II)iodide and 8.7 g of triphenylphosphine were added in succession to a solution of 100 g of 4-bromofluorobenzene in 350 ml of triethylamine. This mixture was heated to the reflux temperature, after which 43.4 g of 3-butynol were added dropwise in the course of 20 minutes at this temperature (about 100° C.). Stirring was continued for a further 5 hours at this temperature. After cooling, the triethylamine was distilled off. The residue was taken up in methyl tertbutyl ether and water. The aqueous phase was extracted twice more with methyl tert-butyl ether and the combined organic extracts were washed in succession with 1N hydrochloric acid and with 10% strength sodium bicarbonate solution and was dried over sodium sulfate. After removal of the solvent, the crude product was distilled under greatly reduced pressure. Yield: 86%.
Intermediate 2.2

N-(5-(4-Fluorophenyl)-4-pentynyloxy)-phthalimide 33.4 g (0.205 mol) of N-hydroxyphthalimide and 53.8 g (0.205 mol) of triphenylphosphine were added to a solution of 33.1 g (0.186 mol) of 5-hydroxy-1-(4-fluorophenyl)-1-pentine in 430 ml of tetrahydrofuran. 35.7 g (0.205 mol) of diethyl azodicarboxylate were then added in the course of 2.5 hours with monitoring of the temperature (max. 40° C.). Stirring was carried out overnight at room temperature, the mixture was evaporated down under reduced pressure and the residue was taken up with 300 ml of dichloromethane. The solution was washed twice with sodium carbonate solution and once with saturated sodium chloride solution. After drying and evaporating down, the crude product was purified by chromategraphy over silica gel. The eluent used was initially dichloromethane/n-hexane and subsequently pure dichloromethane. Yield: 82%; mp.: 85°–88° C.

250-MHz-$^1$H-NMR (in DMSO-d$_6$): δ [ppm]=1.9–2.1 (m, 2H); 2.68 (t, 2H); 4.342 (t, 2H); 7.18 (t, 2H); 7.4–76 (m, 2H); 7.85 (s, 4H).
Intermediate 2.3

5-Aminooxy-1-(4-fluorophenyl)-1-pentine 47.7 g (0.148 mol) of the phthalimido ether prepared above were added a little at a time to a mixture of 68 ml of ethanolamine and 40 ml of dichloromethane. After stirring for 2 hours at room temperature, a clear solution had formed. The latter was added to 300 ml of ice-cold saturated sodium chloride solution. The mixture was extracted three times with 100 ml of dichloromethane and the combined organic phases were washed once with sodium chloride solution, dried and evaporated down. Yield: 95% (oil).

250-MHz-$^1$H-NMR (in CDCl$_3$): δ [ppm]=1.8–2.0 (m, 2H); 2.47 (t, 2H); 3.8 (t, 2H); 5.4 (broad s, 2H); 6.9–7.1 (m, 2H); 7.3–7.45 (m, 2H).

44

EXAMPLE 3

2-[1-[[(E)-4-(2-Thienyl)-3-butenyloxy]-imino]-butyl]-3-hydroxy-5-(2H-tetrahydropyran-4-yl)-cyclohex-2-en-1-one

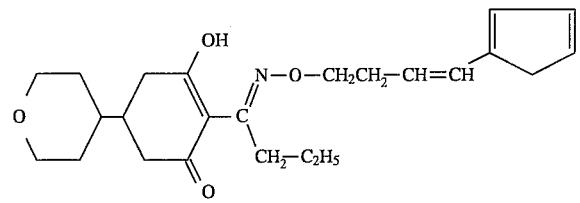

A mixture of 35 g (0.13 mol) of 2-butyryl-3-hydroxy-5-(2H-tetrahydropyran-4-yl)-2-cyclohexen-1-one and 24 g (0.14 mol) of O-[(E)-4-(2-thienyl)-3-butenyl]hydroxylamine in 300 ml of methanol was stirred for 16 hours. The mixture was evaporated down under reduced pressure and the residue was taken up in 1000 ml of 10% strength sodium hydroxide solution. The extraction was carried out with three times 200 ml of methylene chloride and the aqueous phase was brought to pH 1 with concentrated hydrochloric acid while cooling with ice. The aqueous phase was then extracted with three times 200 ml of ether and the extracts were dried over magnesium sulfate and evaporated down under reduced pressure. The crude product was purified by chromatography over 100 g of silica gel using a 30×15 cm column, (mobile phase: ethyl acetate). Yield: 85%.

200 MHz-$^1$H-NMR (in CDCl$_3$): δ [ppm]=0.95 (t, 3H), 1.17–1.96 (m, 9H), 2.13 (m, 1H), 2.36 (m, 1H), 2.43–2.70 (m, 3H), 2.88 (m, 2H), 3.36 (t, 2H), 4.02 (d, 2H), 4.15 (t, 2H), 6.00 (dt, 1H), 6.60 (d, 1H), 6.80–7.20 (m, 3H), 14.75 (s, 1H).
Intermediate 3.1

(E)-4-Bromo-1-(2-thienyl)-1-butene 225 g (1.46 mol) of cyclopropyl-2-thienylcarbinol were added dropwise to 972 ml of 48% strength hydrobromic acid at from 5° to 10° C. in the course of 1 hour. After 2 hours at room temperature, the organic phase was separated off and the aqueous solution was extracted with three times 300 ml of dichloromethane. The combined organic phases were washed neutral with dilute sodium hydroxide solution and water, dried over magnesium sulfate and evaporated under reduced pressure. 322 g (94% corrected) of crude bromide were obtained (GC: 92%).

250 MHz-$^1$H-NMR (in CDCl$_3$): δ [ppm]=2.65–2.80 (m, 2h), 3.46 (t, 2H), 5.90–6.10 (m, 1H), 6.61 (d, 1H), 6.80–7.00 (m, 2H), 7.14 (d, 1H).
Intermediate 3.2

N-[(E)-4-(2-Thienyl)-3-butenyloxy]-phthalimide 190 ml (1.37 mol) of triethylamine were added dropwise to a mixture of 283 g (1.30 mol) of the bromide prepared above, 1300 ml of N-methyl-2-pyrrolidinone, 10 g of potassium iodide and 212 g (1.30 mol) of N-hydroxyphthalimide at from 20° to 25° C. in the course of 2.5 hours. After 4 hours at from 20° to 25° C., the mixture was poured into 4000 ml of ice water and 5000 ml of 10% strength sodium hydroxide solution were added a little at a time. The extraction was then carried out with four times 500 ml of ethyl acetate. The combined ethyl acetate phases were washed neutral with dilute sodium hydroxide solution and water, dried over magnesium sulfate and evaporated down under reduced pressure. The crude product was purified by chromatography over 1000 g of silica gel using a 30×15 cm column (mobile phase: 7:3 n-hexane/dichloromethane). Yield: 29%; mp.: 69°–71° C. (Isopropanol).

250 MHz-$^1$H-NMR (in $d_6$-DMSO): δ [ppm]=2.55–2.70 (m, 2H), 4.28 (t, 2H), 6.00–6.20 (m, 1H), 6.77 (d, 1H), 7.00 (m, 2H), 7.35 (m, 1H), 7.87 (s, 4H).

Intermediate 3.3

O-[(E)-4-(2-Thienyl)-3-butenyl]-hydroxylamine

A mixture of 90.2 g (0.30 mol) of the phthalimido ether prepared above and 136 ml of ethanolamine were stirred for 3 hours at 60° C. The cold reaction mixture was poured into 200 ml of ice water. 200 ml of saturated sodium chloride solution were added and the hydrolysis product was extracted with three times 300 ml of dichloromethane. The combined organic phases were then washed with three times 100 ml of saturated sodium chloride solution, dried over magnesium sulfate and evaporated under reduced pressure. Yield: 89%.

250 MHz-$^1$H-NMR (in $CDCl_3$): δ [ppm]=2.40–2.55 (m, 2H), 3.78 (t, 2H), 5.40 (bs, 2H), 5.95–6.20 8 m, 1H), 6.57 (d, 1H), 6.80–7.15 (m, 3H).

EXAMPLE 4

2-[1-[[2-(2-Fluorobenzyloxy)-ethoxy]imino]butyl]-2-hydroxy-5-(2H-tetrahydropyran-4-yl)-2-cyclohexen-1-one

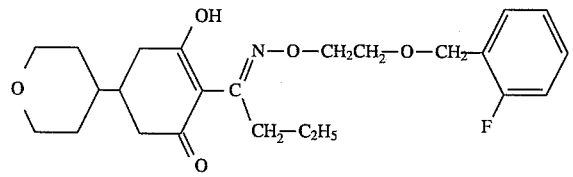

A mixture of 4.0 g (10 mmol) of 2-butyryl-3-hydroxy-5-(2H-tetrahydropyran-4-yl)-2-cyclohexen-1-one and 2.6 g (14 mmol) of 0-[2-(2-fluorobenzyloxy)ethyl]hydroxylamine in 100 ml of methanol was stirred for 24 hours. The reaction mixture was evaporated down under reduced pressure and the crude product was chromatographed over 100 g of silica gel (column 30×4 cm; mobile phase: Ether). Yield: 54%

300 MHz-$^1$H-NMR (in $CDCl_3$): δ [ppm]=0.93 (t, 3H), 1.20–1.77 (m, 7H), 1.90 (m, 1H), 2.23 (m, 2H), 2.58 (m, 2H), 2.92 (m, 2H), 3.38 (t, 2H), 3.80 (m, 2H), 4.03 (m, 2H), 4.25 (m, 2H), 4.68 (8 s, 2 h), 6.93–7.50 (m, 4H), 14.30 (s, 1H).

Intermediate 4.1

N-[2-(2-Fluorobenzyloxy)-ethoxy]-phthalimide 108 ml of triethylamine were added dropwise to a mixture of 165 g (0.71 mol) of 1-bromo-2-(2-fluorobenzyloxy)-ethane, 116 g (0.7 mol) of N-hydroxyphthalimide and 710 ml of N-methyl-2-pyrrolidone at from 20° to 25° C. in the course of 1 hour. After 5 hours at 60° C. the cold reaction mixture was poured into 200 ml of ice water and the precipitate was filtered off under suction, washed with water and isopropanol and dried under reduced pressure over phosphorus pentoxide. Yield: 82%; mp.: 62°–64° C.

250 MHz-$^1$H-NMR (in $d_6$-DMS): δ [ppm]=3.85 (m, 2H), 4.35 (m, 1H), 4.54 (s, 2H), 7.10–7.40 (m, 4H), 7.88 (s, 4H).

Intermediate 4.2

O-[2-(2-Fluorobenzyloxy)-ethyl]-hydroxylamine 184 g (0.58 mol) of the phthalimido ether prepared above were introduced a little at a time into 270 ml of ethanolamine. After 3 hours at 60° C., the cold reaction mixture was poured into 1000 ml of ice water. The hydrolysis product was extracted with three times 800 ml of dichloromethane. The combined organic phases were washed with 200 ml of saturated sodium chloride solution, and dried over magnesium sulfate and evaporated down under reduced pressure. Yield: 91%.

$^1$H-NMR (250 MHz, $CDCl_3$): δ [ppm]=3.70 (dd, 2H), 3.85 (dd, 2H), 4.54 (2H), 5.50 (bs, 2H), 7.00–7.50 (m, 4H).

The desired antidote effect of the compounds I occurs in particular during use with herbicides from the group consisting of the cyclohexenone derivatives of the general formula II when their substituents have the following meanings:

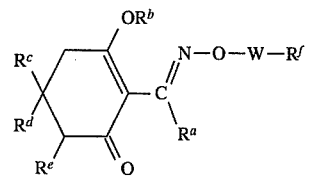

$R^a$ $C_1$–$C_6$-alkyl as stated above, preferably $C_1$–$C_4$-alkyl, in particular $C_1$–$C_2$-alkyl;

$R^b$ is hydrogen;

one equivalent of an agriculturally useful cation;

$C_1$–$C_8$-alkylcarbonyl, in particular $C_1$–$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, preferably $C_1$–$C_4$-alkylcarbonyl, in particular $C_1$–$C_2$-alkylcarbonyl;

$C_1$–$C_{10}$-alkylsulfonyl, in particular $C_1$–$C_6$-alkylsulfonyl, such as methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentyl sulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,2-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, preferably $C_1$–$C_4$-alkylsulfonyl, in particular $C_1$–$C_2$-alkylsulfonyl;

$C_1$–$C_{10}$-alkylphosphonyl, in particular $C_1$–$C_6$-alkylphosphonyl, such as methylphosphonyl, ethylphosphonyl, propylphosphonyl, 1-methylethylphosphonyl, butylphosphonyl, 1-methylpropylphosphonyl, 2-methylpropylphosphonyl, 1,1-dimethylethylphosphonyl, pentylphosphonyl, 1-methylbutylphosphonyl, 2-methylbutylphosphonyl, 3-methylbutylphosphonyl, 2,2-dimethylpropylphosphonyl, 1-ethylpropylphosphonyl, hexylphosphonyl, 1,1-dimethylpropylphosphonyl, 1,2-dimethylpropylphosphonyl, 1-methylpentylphosphonyl, 2-methylpentylphosphonyl, 3-methylpentylphosphonyl, 4-methylpentylphosphonyl, 1,1-dimethylbutylphosphonyl, 1,2-dimethylbutylphosphonyl, 1,3-dimethylbutylphosphonyl, 2,2-dimethylbutylphosphonyl, 2,3-dimethylbutylphosphonyl, 3,3-dimethylbutylphosphonyl, 1-ethylbutylphosphonyl, 2-ethylbutylphosphonyl, 1,1,2-trimethylpropylphosphonyl, 1,2,2-trimethylpropylphosphonyl, 1-ethyl-1-methylpropylphosphonyl or 1-ethyl-2-methylpropylphosphonyl, preferably $C_1$–$C_4$-alkylphosphonyl, in particular $C_1$–$C_2$-alkylphosphonyl;

benzoyl, benzenesulfonyl or benzenephosphonyl, where the aromatic rings may carry from one to five halogen atoms as stated above, preferably fluorine or chlorine;

$R^c$
is hydrogen; CN; CHO;
$C_1$–$C_6$-alkyl as stated above, preferably $C_1$–$C_4$-alkyl, in particular $C_1$–$C_2$-alkyl, which may carry one of the following radicals:
  $C_1$–$C_4$-alkoxy as stated above in general and in particular;
  $C_1$–$C_4$-alkylthio as stated above in general and in particular;
  phenoxy, phenylthio, pyridyloxy or pyridylthio, where the aromatic radicals in turn may carry from one to three of the following groups: nitro, cyano, halogen as stated above in general and in particular;
  $C_1$–$C_4$-alkyl as stated above in general and in particular;
  $C_1$–$C_4$-haloalkyl, in particular $C_1$–$C_2$-haloalkyl as stated above in general and in particular;
  $C_1$–$C_4$-alkoxy as stated above in general and in particular;
  $C_1$–$C_4$-haloalkoxy, in particular $C_1$–$C_2$-haloalkoxy as stated above in general and in particular;
  $C_1$–$C_4$-alkylthio as stated above in general and in particular;
  $C_3$–$C_6$-alkenyl as stated above in general and in particular;
  $C_3$–$C_6$-alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 3,3-dimethyl-2-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy or 1-ethyl-2-methyl-2-propenyloxy, preferably 2-propenyloxy;

$C_3$–$C_6$-alkynyl as stated above in general and in particular;
$C_3$–$C_6$-alkynyloxy, such as 2-propynyloxy, 2-butynyloxy, 3-butynyloxy, 1-methyl-2-propynyloxy, 2-pentynyloxy, 3-pentynyloxy, 4-penynyloxy, 1-methyl-2-butynyloxy, 1-methyl-3-butynyloxy, 2-methyl-3-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy or 1-ethyl-1-methyl-2-propynyloxy, preferably 2-propynyloxy, or $NR^gR^h$;

$R^g$ is hydrogen;
  $C_1$–$C_4$-alkyl as stated above in general and in particular;
  $C_3$–$C_6$-alkenyl as stated above in general and in particular;
  $C_3$–$C_6$-alkynyl as stated above in general and in particular;
  $C_1$–$C_6$-alkylcarbonyl as stated above;
  benzoyl which may carry from one to three of the following radicals: nitro, cyano,
  halogen as stated above in general and in particular;
  $C_1$–$C_4$-alkyl as stated above in general and in particular;
  $C_1$–$C_4$-haloalkyl, in particular $C_1$–$C_2$-haloalkyl as stated above in general and in particular;
  $C_1$–$C_4$-alkoxy as stated above in general and in particular;
  $C_1$–$C_4$-alkylthio as stated above in general and in particular;

$R^h$ is hydrogen;
  $C_1$–$C_4$-alkyl as stated above in general and in particular;
  $C_3$–$C_6$-alkenyl as stated above in general and in particular;

$R^c$ is furthermore
  $C_3$–$C_7$-cycloalkyl as stated above or $C_5$–$C_7$-cycloalkenyl, such as cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl or cyclohept-4-enyl, where these rings may carry from one to three of the following radicals:
hydroxyl;
halogen as stated above in general and in particular;
$C_1$–$C_4$-alkyl as stated above in general and in particular;
$C_1$–$C_4$-haloalkyl, in particular $C_1$–$C_2$-haloalkyl as stated above in general and in particular;
$C_1$–$C_4$-alkoxy as stated above in general and in particular;
$C_1$–$C_4$-alkylthio as stated above in general and in particular;
benzylthio;
$C_1$–$C_4$-alkylsulfonyl, such as methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl, preferably $C_1$–$C_2$-alkylsulfonyl;
$C_1$–$C_4$-alkylsulfenyl, such as methylsulfenyl, ethylsulfenyl, propylsulfenyl, 1-methylethylsulfenyl, butylsulfenyl, 1-methylpropylsulfenyl, 2-methylpropylsulfenyl or 1,1-dimethylethylsulfenyl, preferably $C_1$–$C_2$-alkylsulfenyl,
and $C_1$–$C_4$-alkylsulfinyl, such as methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl, preferably $C_1$–$C_2$-alkylsulfinyl;

a 5-membered saturated ring which, in addition to carbon ring members, contains one or two oxygen or sulfur atoms or one oxygen and one sulfur atom, where this ring may carry from one to three of the following radicals:
$C_1$–$C_4$-alkyl as stated above in general and in particular;
$C_1$–$C_4$-haloalkyl, in particular $C_1$–$C_2$-haloalkyl as stated above in general and in particular;
$C_1$–$C_4$-alkoxy as stated above in general and in particular;
$C_1$–$C_4$-alkylthio as stated above in general and in particular;

a 6-membered or 7-membered saturated or monounsaturated or diunsaturated ring which, in addition to carbon ring members, contains one or two oxygen or sulfur atoms or from one to three nitrogen atoms and one or two oxygen or sulfur atoms, where this ring may carry from one to three of the following radicals:
hydroxyl,
halogen as stated above in general and in particular;
$C_1$–$C_4$-alkyl as stated above in general and in particular;
$C_1$–$C_4$-haloalkyl, in particular $C_1$–$C_2$-haloalkyl as stated above in general and in particular;
$C_1$–$C_4$-alkoxy as stated above in general and in particular;
$C_1$–$C_4$-alkythio as stated above in general and in particular;

a 5-membered aromatic ring which, in addition to carbon ring members, contains one or two nitrogen atoms and one oxygen or sulfur atom or 2 nitrogen atoms or one oxygen or one sulfur atom, where this ring may carry from one to three of the following radicals:
cyano;
halogen as stated above in general and in particular;
$C_1$–$C_4$-alkyl as stated above in general and in particular;
$C_1$–$C_4$-haloalkyl, in particular $C_1$–$C_2$-haloalkyl as stated above in general and in particular;
$C_1$–$C_4$-alkoxy as stated above in general and in particular;
$C_1$–$C_4$-haloalkoxy, in particular $C_1$–$C_2$-haloalkoxy as stated above in general and in particular;
$C_1$–$C_4$-alkylthio as stated above in general and in particular;
$C_2$–$C_6$-alkenyl as stated above in general and in particular;
$C_2$–$C_6$-alkenyloxy, such as ethenyloxy, 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy or 1-ethyl-2-methyl-2-propenyloxy, preferably $C_2$–$C_4$-alkenyloxy;

$C_2$–$C_6$-alkynyl as stated above in general and in particular;

$C_2$–$C_6$-alkynyloxy, such as ethynyloxy, 1-propynyloxy, 2-propynyloxy, 1-butynyloxy, 2-butynyloxy, 3-butynyloxy, 1-methyl-2-propynyloxy, 1-pentynyloxy, 2-pentynyloxy, 3-pentynyloxy, 4-pentynyloxy, 1-methyl-2-butynyloxy, 1-methyl-3-butynyloxy, 2-methyl-3-butynyloxy, 3-methyl-1-butynyloxy, 1,1-dimethyl-2-propynyloxy, 1-ethyl-2-propynyloxy, 1-hexynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-penynyloxy, 3-methyl-1-pentynyloxy, 3-methyl-4-penynyloxy, 4-methyl-1-penynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 3,3-dimethyl-1-butynyloxy, 1-ethyl-2-butynyloxy, 1-ethyl- 3-butynyloxy, 2-ethyl-3-butynyloxy, or 1-ethyl-1-methyl-2-propynyloxy, preferably $C_2$–$C_4$-alkynyloxy;

and $C_1$–$C_4$-alkoxy-$C_1$–$C_4$-alkyl, which is $C_1$–$C_4$-alkyl as stated above and substituted by $C_1$–$C_4$-alkoxy as stated above;

phenyl or pyridyl, where these rings may carry from one to three of the following radicals: nitro, formyl, cyano, halogen as stated above in general and in particular;

$C_1$–$C_4$-alkyl as stated above in general and in particular;

$C_1$–$C_4$-haloalkyl, in particular $C_1$–$C_2$-haloalkyl as stated above in general and in particular;

$C_1$–$C_4$-alkoxy as stated above in general and in particular;

$C_1$–$C_4$-haloalkoxy, in particular $C_1$–$C_2$-haloalkoxy as stated above in general and in particular;

$C_1$–$C_4$-alkylthio as stated above in general and in particular;

$C_2$–$C_6$-alkenyl as stated above in general and in particular;

$C_2$–$C_6$-alkenyloxy as stated above in general and in particular;

$C_3$–$C_6$-alkynyl as stated above in general and in particular;

$C_3$–$C_6$-alkynyloxy as stated above in general and in particular;

and $NR^kR^l$;

$R^k$ is hydrogen;

$C_1$–$C_4$-alkyl as stated above in general and in particular;

$C_3$–$C_6$-alkenyl as stated above in general and in particular;

$C_3$–$C_6$-alkynyl as stated above in general and in particular;

$R^l$ is hydrogen;

$C_1$–$C_4$-alkyl as stated above in general and in particular;

$C_3$–$C_6$-alkenyl as stated above in general and in particular;

$C_3$–$C_6$-alkynyl as stated above in general and in particular;

$C_1$–$C_6$-alkylcarbonyl as stated above, preferably $C_1$–$C_6$-alkylcarbonyl, in particular $C_1$–$C_2$-alkylcarbonyl;

benzoyl, which may carry from one to three of the following radicals, nitro, cyano, halogen as stated above in general and in particular;

$C_1$–$C_4$-alkyl as stated above in general and in particular;

$C_1$–$C_4$-haloalkyl, in particular $C_1$–$C_2$-haloalkyl as stated above in general and in particular;

$C_1$–$C_4$-alkoxy as stated above in general and in particular;

$C_1$–$C_4$-alkylthio as stated above in general and in particular;

$R^d$ is hydrogen; hydroxyl; or, if $R^c$ is $C_1$–$C_6$-alkyl as stated above, also $C_1$–$C_6$-alkyl;

$R^e$ is hydrogen; cyano;

halogen as stated above in general and in particular;

$C_1$–$C_4$-alkoxycarbonyl as stated above in general and in particular;

$C_1$–$C_4$-alkylketoxime, such as methylketoxime, ethylketoxime, propylketoxime, 1-methylethylketoxime, butylketoxime, 1-methylpropylketoxime, 2-methylpropylketoxime or 1,1-dimethylethylketoxime;

W $C_1$–$C_6$-alkylene [—$(CH_2)_a$—; a=1, 2, 3, 4, 5 or 6], $C_3$–$C_6$-alkenylene [—$(CH_2)_b$—CH=CH—$(CH)_c$—; b=1, 2 or 3, c=0, 1, 2 or 3, and the sum b+c=1, 2, 3 or 4] or $C_3$–$C_6$-alkynylene [—$(CH_2)_b$—C*C—$(CH)_c$, where b and c have the abovementioned meanings and * is a triple bond], and these groups $X^1$ may carry a methylene group (=$CH_2$) and/or from one to three of the following radicals:

halogen as stated above in general and in particular; and $C_1$–$C_3$-alkyl, such as methyl, ethyl, propyl or 1-methylethyl, preferably methyl;

$C_3$–$C_6$-alkylene or $C_3$–$C_6$-alkenylene as stated above, where, in each of these radicals, a methylene group may be replaced with oxygen, sulfur, SO, $SO_2$ or $NR^i$ [—$(CH_2)_f$—W'—$(CH_2)_g$—; f=1, 2, 3, 4 or 5; g=0, 1, 2, 3 or 4 and the sum f+g=2, 3, 4 or 5; W'=O, S, SO, $SO_2$ or $NR^i$, or —$(CH_2)_h$—(CH=CH)$_i$—$(CH_2)_k$—W'—$(CH_2)_l$—(CH=CH)$_m$—$(CH_2)_n$— where i and m are each 0 or 1 and the sum i+m=1; h=0, 1, 2 or 3 and the sum of h, i and k may be 1, 2, 3, 4 or 5; k, and n are each 0, 1, 2 or 3 and the sum of h, k, l and n is 1, 2 or 3] and where these groups may carry from one to three $C_1$–$C_3$-alkyl radicals as stated above instead of hydrogen atoms;

$R^i$ is hydrogen;

$C_1$–$C_4$-alkyl as stated above in general and in particular;

$C_3$–$C_6$-alkenyl as stated above in general and in particular;

$C_3$–$C_6$-alkynyl as stated above in general and in particular;

$R^f$ is hydrogen; CH=CH—$Z^1$, where $Z^1$ is hydrogen; cyano; carboxyl;

halogen as stated above in general and in particular;

$C_1$–$C_4$-alkyl as stated above in general and in particular;

$C_1$–$C_4$-alkoxy as stated above in general and in particular;

$C_1$–$C_8$-alkoxycarbonyl as stated above, preferably $C_1$–$C_4$-alkoxycarbonyl, in particular $C_1$–$C_2$-alkoxycarbonyl;

benzyloxycarbonyl;

phenyl, thienyl or pyridyl, when these radicals may carry from one to three of the following groups: nitro, cyano, halogen as stated above in general and in particular;

$C_1$–$C_4$-alkyl as stated above in general and in particular;

$C_1$–$C_4$-haloalkyl, in particular $C_1$–$C_2$-haloalkyl as stated above in general and in particular;

$C_1$–$C_4$-alkoxy as stated above in general and in particular;

$C_1$–$C_4$-haloalkoxy, in particular $C_1$–$C_2$-haloalkoxy as stated above in general and in particular;

$C_1$–$C_4$-alkylthio as stated above in general and in particular;

or $C_3$–$C_6$-cycloalkyl as stated above, where the cyclic radical in turn may furthermore carry from one to three of the following groups:

halogen as stated above in general and in particular;

$C_1$–$C_4$-alkyl as stated above in general and in particular;

$C_1$–$C_4$-haloalkyl, in particular $C_1$–$C_2$-haloalkyl as stated above in general and in particular;

$C_1$–$C_4$-alkoxy as stated above in general and in particular;

R$^f$ is furthermore ethynyl, which may carry one of the following radicals:
$C_1$–$C_4$-alkyl as stated above in general and in particular;
or $C_3$–$C_6$-cycloalkyl as stated above, where these groups may furthermore carry from one to three of the following radicals: hydroxyl,
halogen as stated above in general and in particular;
$C_1$–$C_4$-alkyl as stated above in general and in particular;
$C_1$–$C_4$-haloalkyl, in particular $C_1$–$C_2$-haloalkyl as stated above in general and in particular;
$C_1$–$C_4$-alkoxy as stated above in general and in particular;

ethynyl which carries one of the following radicals:
phenyl, thienyl or pyridyl, where the aromatic radicals may carry from one to three of the following groups: nitro, cyano,
halogen as stated above in general and in particular;
$C_1$–$C_4$-alkyl as stated above in general and in particular;
$C_1$–$C_4$-haloalkyl, in particular $C_1$–$C_2$-haloalkyl as stated above in general and in particular;
$C_1$–$C_4$-alkoxy as stated above in general and in particular;
$C_1$–$C_4$-haloalkoxy, in particular $C_1$–$C_2$-haloalkoxy as stated above in general and in particular;
$C_1$–$C_4$-alkylthio as stated above in general and in particular;

phenyl, a 5-membered aromatic ring which, in addition to carbon ring members, contains one or two nitrogen atoms and one oxygen or sulfur atom or two nitrogen atoms or one oxygen or one sulfur atom, or a 6-membered aromatic ring which, in addition to carbon ring members, contains from one to four nitrogen atoms, where these aromatics and heteroaromatics may be partially or completely halogenated and may furthermore carry from one to three of the following radicals: nitro;
$C_1$–$C_4$-haloalkoxy, in particular $C_1$–$C_2$-haloalkoxy as stated above in general and in particular;
$C_1$–$C_4$-alkylthio as stated above in general and in particular;
$C_1$–$C_4$-haloalkythio, in particular $C_1$–$C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trichloromethylthio;
the radicals stated for $Z^1$
and NR$^k$R$^l$, where R$^k$ and R$^l$ have the abovementioned meanings.

5-membered saturated rings R$^c$ which, in addition to carbon members, contain one or two oxygen or sulfur atoms or one oxygen and one sulfur atom are understood as meaning the following groups: 2-tetrahydrofuranyl, 3-tetrahydrofuranyl, 2-tetrahydrothienyl, 3-tetrahydrothienyl, 1,3-dioxolan-2-yl, 1,3-dioxolan-4-yl, 1,3-dithiolan-2-yl, 1,3-dithiolan-4-yl, 1,3-thioxolan-2- yl, 1,3-thioxolan-4-yl and 1,3-thioxolan-5-yl.

6-membered or 7-membered saturated or monounsaturated or diunsaturated rings R$^c$ which, in addition to carbon ring members, contain one or two oxygen or sulfur atoms or one oxygen and one sulfur atom are understood as meaning the following groups: oxan-2-yl, oxan-3-yl, oxan-4-yl, oxepan-2-yl, oxepan-3-yl, oxepan-4-yl, oxepan-5-yl, thioxan-2-yl, thioxan-3-yl, thioxan-4-yl, thioxepan-2-yl, thioxepan-3-yl, thioxepan-4-yl, thioxepan-5-yl, 1,3-dioxan-2-yl, 1,3-dioxan-4-yl, 1,3-dioxepan-2-yl, 1,3-dioxepan-4-yl, 1,3-dioxepan-5-yl, 1,3-thioxan-2-yl, 1,3-thioxan-4-yl, 1,3-thioxan-5-yl, 1,3-thioxepan-2-yl, 1,3-thioxepan-4-yl, 1,3-thioxepan-5-yl, 1,3-thioxepan-6-yl, 1,3-thioxepan-7-yl, 1,3-dithioxan-2-yl, 1,3-dithioxan-4-yl, 1,3-dithioxepan-2-yl, 1,3-dithioxepan-4-yl, 1,3-dithioxepan-5-yl, 1,4-dioxan-2-yl, 1,4-dioxepan-2-yl, 1,4-dioxepan-5-yl, 1,4-dioxepan-6-yl, 1,4-dithioxan-2-yl, 1,4-dithioxepan-6-yl, 1,4-thioxan-2-yl, 1,4-thioxan-3-yl, 1,4-thioxan-5-yl, 1,4-thioxan-6-yl, 1,4-thioxepan-2-yl, 1,4-thioxepan-3-yl, 1,4-thioxepan-5-yl, 1,4-thioxepan-6-yl, 1,4-thioxepan-7-yl, oxin-2-yl, oxin-3-yl, oxin-4-yl, oxepin-2-yl, oxepin-3-yl, oxepin-4-yl, oxepin-5-yl, thioxin-2-yl, thioxin-3-yl, thioxin-4-yl, thioxepin-2-yl, thioxepin-3-yl, thioxepin-4-yl, thioxepin-5-yl, 1,3-dioxin-2-yl, 1,3-dioxin-4-yl, 1,3-dioxepin-2-yl, 1,3-dioxepin-4-yl, 1,3-dioxepin-5-yl, 1,3-thioxin-2-yl, 1,3-thioxin-4-yl, 1,3-thioxin-5-yl, 1,3-thioxepin-2-yl, 1,3-thioxepin-4-yl, 1,3-thioxepin-5-yl, 1,3-thioxepin-6-yl, 1,3-thioxepin-7-yl, 1,3-dithioxin-2-yl, 1,3-dithioxin-4-yl, 1,3-dithioxepin-2-yl, 1,3-dithioxepin-4-yl, 1,3-dithioxepin-5-yl, 1,4-dioxin-2-yl, 1,4-dioxepin-2-yl, 1,4-dioxepin-5-yl, 1,4-dioxepin-6-yl, 1,4-dithioxin-2-yl, 1,4-dithioxepin-2-yl, 1,4-dithioxepin-5-yl, 1,4-dithioxepin-6-yl, 1,4-thioxin-2-yl, 1,4-thioxin-3-yl, 1,4-thioxin-5-yl, 1,4-thioxin-6-yl, 1,4-thioxepin-2-yl, 1,4-thioxepin-3-yl, 1,4-thioxepin-5-yl, 1,4-thioxepin-6-yl or 1,4-thioxepin-7-yl.

5-membered aromatic rings R$^c$ and R$^f$ which, in addition to carbon atoms, may contain from one to three nitrogen atoms and one oxygen or one sulfur atom as heteroatoms or which, in addition to carbon atoms, may contain from one to three nitrogen atoms or one oxygen or one sulfur atom as heteroatoms are understood as meaning the following groups: 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4,-thiadiazol-2-yl or 1,3,4-triazol-2-yl.

6-membered aromatic rings R$^f$ which, in addition to carbon atoms, may contain from one to four nitrogen atoms as heteroatoms are preferably understood as meaning the following groups: 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl, in particular 2-pyridyl, 3-pyridyl and 4-pyridyl.

Very particularly preferred are cyclohexenone drivatives of the formula II whose toleration by crop plants can be improved by substituted pyrido[2,3-d]pyrimidines I and I' as shown in Tables II.1 to II.8 below:

TABLE II.1

[Structure: cyclohexenone with OH, =N-O-W-R^f, R^a, R^c substituents; II (R^b, R^d, R^e = H)]

| No. | R^a | R^c | W | R^f | Reference |
|---|---|---|---|---|---|
| A.001 | n-C₃H₇ | 2-(Ethylthio)propyl | —CH₂CH₂— | H | DE-A 2 822 304 |
| A.002 | C₂H₅ | 2-(Ethylthio)propyl | —CH₂CH=CCl— | H | US-A 4 440 566 |
| A.003 | n-C₃H₇ | 2-(Ethylthio)propyl | —CH₂CH=CCl— | H | US-A 4 440 566 |
| A.004 | n-C₃H₇ | Tetrahydrothiopyran-3-yl | —CH₂CH₂— | H | EP-A 71 707 |
| A.005 | C₂H₅ | Tetrahydrothiopyran-3-yl | —CH₂CH₂— | H | EP-A 71 707 |
| A.006 | CH₃ | Tetrahydrothiopyran-3-yl | —CH₂CH=CCH₃— | H | EP-A 71 707 |
| A.007 | n-C₃H₇ | Tetrahydrothiopyran-3-yl | —CH₂CH₂— | H | EP-A 71 707 |
| A.008 | C₂H₅ | Tetrahydropyran-4-yl | —CH₂CH=CCl— | H | EP-A 142 741 |
| A.009 | n-C₃H₇ | Pyridin-3-yl | —CH₂CH₂— | H | EP-A 66 195 |
| A.010 | C₂H₅ | 4-CH₃-phenyl | —CH₂CH₂— | H | DE-A 24 39 104 |
| A.011 | C₂H₅ | 4-C₂H₅-phenyl | —CH₂CH=CCH₃— | H | DE-A 38 08 072 |
| A.012 | C₂H₅ | 2,4,6-(CH₃)₃-phenyl | —CH₂CH₂— | H | EP-A 88 301 |
| A.013 | n-C₃H₇ | 4-CH₃-cyclohexyl | —CH₂CH=CCl— | H | EP-A 88 299 |
| A.014 | n-C₃H₇ | 4-CH₃-cyclohexyl | —CH₂CH=CCH₃— | H | EP-A 88 299 |
| A.015 | C₂H₅ | 3-Isopropyl-isoxazol-5-yl | —CH₂CH=CCH₃— | H | EP-A 238 021 |
| A.016 | n-C₃H₇ | 3-Isopropyl-isoxazol-5-yl | —CH₂CH=CCH₃— | H | EP-A 238 021 |
| A.017 | C₂H₅ | 4-(HC≡C—CH₂O)-pheny | —CH₂CH=CCl— | H | EP-A 137 174 |
| A.018 | n-C₃H₇ | 4-C₂H₅OCH₂-phenyl | —CH₂CH₂— | H | EP-A 2 137 200 |
| A.019 | n-C₃H₇ | 3,4-Br₂-tetrahydropyran-3-yl | —CH₂CH₂— | H | EP-A 230 235 |
| A.020 | n-C₃H₇ | 3,4-Br₂-tetrahydropyran-3-yl | —CH₂CH=CCl— | H | EP-A 230 235 |
| A.021 | n-C₃H₇ | 2,6,6-(CH₃)₃-cyclohex-1-enyl | —CH₂CH=CCl— | H | EP-A 46 860 |
| A.022 | n-C₃H₇ | Cyclohexyl | —CH₂CH₂— | H | JP-A 540 191 945 |
| A.023 | n-C₃H₇ | Cyclohex-1-enyl | —CH₂CH₂— | H | EP-A 46 860 |
| A.024 | CH₃ | 4-CH₃-cyclohexyl | —CH₂CH=CCl— | H | EP-A 88 299 |
| A.025 | n-C₃H₇ | 4-CF₃-phenyl | —CH₂CH₂— | H | EP-A 137 174 |
| A.026 | C₂H₅ | 2,6,6-(CH₃)₃-cyclohex-1-enyl | —CH₂CH=CCl— | H | EP-A 46 860 |
| A.027 | n-C₃H₇ | 2-CH₃-thiazol-4-yl | —CH₂CH=CCH₃— | H | EP-A 125 094 |
| A.028 | n-C₃H₇ | 2-CH₃-thiazol-4-yl | —CH₂CH=CCl— | H | EP-A 125 094 |
| A.029 | n-C₃H₇ | 2,4,6-(CH₃)₃-cyclohexyl | —CH₂CH₂— | H | EP-A 88 299 |
| A.030 | n-C₃H₇ | 3-C₂H₅S-4-OH-4-CH₃-cyclohexyl | —CH₂CH=CH— | H | EP-A 228 598 |
| A.031 | C₂H₅ | 3,4-(OH)₂-cyclohexyl | —CH₂CH₂— | H | EP-A 228 598 |
| A.032 | n-C₃H₇ | 1-CH₃-pyrazol-3-yl | —CH₂CH₂— | H | EP-A 66 195 |
| A.033 | n-C₃H₇ | 1-CH₃-pyrrol-3-yl | —CH₂CH=CCl— | H | EP-A 66 195 |
| A.034 | n-C₃H₇ | 2-CH₃-thiazol-4-yl | —CH₂CH=CH— | H | EP-A 125 094 |
| A.035 | n-C₃H₇ | (CH₃CH₂S)₂-methyl | —CH₂CH₂CH₂— | H | EP-A 230 260 |
| A.036 | n-C₃H₇ | 1-Oxo-tetrahydrothiopyran-3-yl | —CH₂CH₂— | H | EP-A 115 808 |
| A.037 | n-C₃H₇ | 1,1-Dioxo-tetrahydrothiopyran-3-yl | —CH₂CH₂— | H | EP-A 115 808 |
| A.038 | n-C₃H₇ | 1,1-Dioxo-tetrahydrothiopyran-3-yl | —CH₂CH=CH— | H | Proceedings Brit. Crop-Protection Conference-weeds 1985 Vol. 1 pp. 93–98 |
| A.039 | CH₃ | 4-F-phenyl-thioethyl | —CH₂CH₂— | H | EP 254 514 |
| A.040 | C₂H₅ | 4-F-phenyl-thioethyl | —CH₂CH₂— | H | EP 254 514 |
| A.041 | C₂H₅ | 4-F-phenyl-thioethyl | —CH₂CH=CH— | H | EP 254 514 |
| A.042 | C₂H₅ | 4-F-phenyl-thioethyl | —CH₂CH=CHCH₂— | H | EP 254 514 |
| A.043 | n-C₃H₇ | 4-F-phenyl-thioethyl | —CH₂CH=CH— | H | EP 254 514 |
| A.044 | n-C₃H₇ | Formyl | —CH₂CH₂— | H | EP 319 835 |
| A.045 | n-C₃H₇ | 1-CH₃S-cyclopropyl | —CH₂CH₂— | H | EP 243 313 |
| A.046 | n-C₃H₇ | 1-CH₃S-cyclopropyl | —CH₂C(H)=C(Cl)— | H | EP 243 313 |
| A.047 | C₂H₅ | 1-CH₃S-cyclopropyl | —CH₂C(H)=C(Cl)— | H | EP 243 313 |
| A.048 | C₂H₅ | 1-CH₃S-cyclopropyl | —CH₂C(H)=C(Cl)— | H | EP 243 313 |
| A.049 | C₂H₅ | 1-C₂H₅S-cyclopropyl | —CH₂C(H)=C(Cl)— | H | EP 243 313 |

TABLE II.1-continued $$\text{II} \quad (R^b, R^d, R^e = H)$$

structure: cyclohexenone with OH, R^c, H, H, =NO-W-R^f group on C, R^a substituent, =O

| No. | $R^a$ | $R^c$ | W | $R^f$ | Reference |
|---|---|---|---|---|---|
| A.050 | n-$C_3H_7$ | 1-$C_2H_5$S-cyclopropyl | —$CH_2$C=C— (H, Cl) | H | EP 243 313 |
| A.051 | $C_2H_5$ | Tetrahydrothiopyran-3-yl | —$CH_2$CH=CH$CH_2$— | 4-Cl-phenyl | EP-A 89 120 558 |
| A.052 | $C_2H_5$ | Tetrahydrothiopyran-3-yl | —$CH_2CH_2$CH=CH— | 4-Cl-phenyl | EP-A 89 120 558 |
| A.053 | $C_2H_5$ | Tetrahydrothiopyran-3-yl | —$CH_2CH_2$CH=CH— | 4-F-phenyl | EP-A 89 120 558 |
| A.054 | n-$C_3H_7$ | Tetrahydrothiopyran-3-yl | —$CH_2CH_2$CH=CH— | 4-F-phenyl | EP-A 89 120 558 |
| A.055 | $C_2H_5$ | Tetrahydrothiopyran-3-yl | —$CH_2$CH=CH$CH_2$— | Phenyl | EP-A 89 120 558 |
| A.056 | n-$C_3H_7$ | Tetrahydrothiopyran-3-yl | —$CH_2$— | 5-Cl-thien-2-yl | EP-A 177 913 |
| A.057 | $C_2H_5$ | Tetrahydrothiopyran-3-yl | —$CH_2$— | 5-Cl-thien-2-yl | EP-A 177 913 |
| A.058 | $C_2H_5$ | Tetrahydropyran-3-yl | —$CH_2$— | 5-Cl-thien-2-yl | EP-A 177 913 |
| A.059 | n-$C_3H_7$ | Tetrahydropyran-4-yl | —$CH_2$— | 5-Cl-thien-2-yl | EP-A 177 913 |
| A.060 | n-$C_3H_7$ | Tetrahydrothiopyran-3-yl | —$CH_2$— | Thien-2-yl | EP-A 177 913 |
| A.061 | $CH_3$ | Tetrahydropyran-3-yl | —$CH_2$— | Thien-2-yl | EP-A 177 913 |
| A.062 | $C_2H_5$ | Tetrahydropyran-4-yl | —$CH_2$— | Thien-2-yl | EP-A 117 913 |
| A.063 | $C_2H_5$ | Tetrahydropyran-3-yl | —$(CH_2)_4$— | 4-F-phenyl | DE-A 38 38 309 |
| A.064 | n-$C_3H_7$ | Tetrahydropyran-3-yl | —$(CH_2)_4$— | 4-F-phenyl | DE-A 38 38 309 |
| A.065 | $C_2H_5$ | Tetrahydrothiopyran-3-yl | —$(CH_2)_4$— | 4-F-phenyl | DE-A 38 38 309 |
| A.066 | n-$C_3H_7$ | Tetrahydrothiopyran-3-yl | —$(CH_2)_4$— | 4-F-phenyl | DE-A 38 38 309 |
| A.067 | $C_2H_5$ | Tetrahydropyran-3-yl | —$(CH_2)_4$— | 4-F-phenyl | DE-A 38 38 309 |
| A.068 | n-$C_3H_7$ | Tetrahydropyran-3-yl | —$(CH_2)_4$— | 4-F-phenyl | DE-A 38 38 309 |
| A.069 | $C_2H_5$ | Tetrahydropyran-3-yl | —$(CH_2)_4$— | 4-Cl-phenyl | DE-A 38 38 309 |
| A.070 | n-$C_3H_7$ | Tetrahydropyran-3-yl | —$(CH_2)_4$— | 4-Cl-phenyl | DE-A 38 38 309 |
| A.071 | $C_2H_5$ | Tetrahydropyran-4-yl | —$(CH_2)_4$— | 4-Cl-phenyl | DE-A 38 38 309 |
| A.072 | n-$C_3H_7$ | Tetrahydropyran-4-yl | —$(CH_2)_4$— | 4-Cl-phenyl | DE-A 38 38 309 |
| A.073 | $C_2H_5$ | Tetrahydrothiopyran-3-yl | —$(CH_2)_4$— | 4-Cl-phenyl | DE-A 38 38 309 |
| A.074 | n-$C_3H_7$ | Tetrahydrothiopyran-3-yl | —$(CH_2)_4$— | 4-Cl-phenyl | DE-A 38 38 309 |

TABLE II.2

$$(R^b, R^d, R^e = H)$$
$$(R^c = \text{Tetrahydropyran-3-yl})$$

| Ex. | $R^a$ | W | $R^f$ | phys. data (NMR data in ppm) (M.p. in °C.) |
|---|---|---|---|---|
| A.075 | $C_2H_5$ | —$CH_2$—CH=CH— | Phenyl | 103–104 |
| A.076 | n-$C_3H_7$ | —$CH_2$—CH=CH— | Phenyl | 4.7(d, 2H), 6.3(dt, 1H), 6.7(d, 1H), 7.2–7.5(2m, 5H) |
| A.077 | $C_2H_5$ | —$CH_2$—CH=CH— | 4-Cl-phenyl | 106–107 |
| A.078 | n-$C_3H_7$ | —$CH_2$—CH=CH— | 4-Cl-phenyl | 4.7(d, 2H), 6.3(dt, 1H), 6.65(d, 1H), 7.2–7.5(m, 4H) |
| A.079 | $C_2H_5$ | —$CH_2$—CH=CH— | 4-F-phenyl | 90–91 |
| A.080 | n-$C_3H_7$ | —$CH_2$—CH=CH— | 4-F-phenyl | 4.6(d, 2H), 6.2(dt, 1H), 6.6(d, 1H), 7.0(m, 2H), 7.4(m, 2H) |
| A.081 | $C_2H_5$ | —$CH_2$—CH=CH— | 2,4-$Cl_2$-phenyl | 123–124 |
| A.082 | n-$C_3H_7$ | —$CH_2$—CH=CH— | 2,4-$Cl_2$-phenyl | 80–82 |
| A.083 | $C_2H_5$ | —$(CH_2)_3$CH=CH— | Phenyl | 80–82 |
| A.084 | n-$C_3H_7$ | —$(CH_2)_3$CH=CH— | Phenyl | 4.1(t, 2H), 6.2(dt, 1H), 6.4(d, 1H), 7.2–7.4(m, 5H) |
| A.085 | $C_2H_5$ | —$(CH_2)_3$CH=CH— | 4-Cl-phenyl | 108–110 |
| A.086 | n-$C_3H_7$ | —$(CH_2)_3$CH=CH— | 4-Cl-phenyl | 4.1(t, 2H), 6.2(dt, 1H), 6.4(d, 1H), 7.3(s, 4H) |
| A.087 | $C_2H_5$ | —$(CH_2)_3$— | Phenyl | 4.0(t, 2H), 7.0–7.4(m, 5H) |
| A.088 | n-$C_3H_7$ | —$(CH_2)_3$— | Phenyl | 4.0(t, 2H), 7.0–7.4(m, 5H) |
| A.089 | $C_2H_5$ | —$CH_2$C(=$CH_2$)—$CH_2$— | Phenyl | 3.3(s, 2H), 4.4(s, 2H), 5.1 and 5.2(2s, 2H), 7.1–7.4(m, 5H) |
| A.090 | n-$C_3H_7$ | —$CH_2$C(=$CH_2$)—$CH_2$— | Phenyl | 3.35(s, 2H), 4.4(s, 2H), 5.0 and 5.1(2s, 2H), 7.0–7.4(m, 5H) |
| A.091 | $C_2H_5$ | —$CH_2$CH=CH— | 4-Br-phenyl | 89–91 |

TABLE II.2-continued $$\text{structure with } R^c, \text{ OH, NO-W-R}^f, R^a, \text{ring with H, H, O}$$

($R^b, R^d, R^e$ = H)
($R^c$ = Tetrahydropyran-3-yl)

| Ex. | $R^a$ | W | $R^f$ | phys. data (NMR data in ppm) (M.p. in °C.) |
|---|---|---|---|---|
| A.092 | n-C$_3$H$_7$ | —CH$_2$CH=CH— | 4-Br-phenyl | 97–99 |
| A.093 | C$_2$H$_5$ | —CH$_2$CH=CH— | 4-CH$_3$-phenyl | 103–105 |
| A.094 | n-C$_3$H$_7$ | —CH$_2$CH=CH— | 4-CH$_3$-phenyl | 88–90 |
| A.095 | C$_2$H$_5$ | —CH$_2$CH=CH— | 4-CF$_3$-phenyl | 97–98 |
| A.096 | n-C$_3$H$_7$ | —CH$_2$CH=CH— | 4-CF$_3$-phenyl | 4.75(d, 2H), 6.45(dt, 1H), 6.75(d, 1H), 7.4–7.8(m, 4H) |
| A.097 | C$_2$H$_5$ | —CH$_2$CH=CH— | 4-C$_6$H$_5$O-phenyl | 4.65(d, 2H), 6.25(dt, 1H), 6.65(d, 1H), 6.9–7.6(3m, 9H) |
| A.098 | n-C$_3$H$_7$ | —CH$_2$CH=CH— | 4-C$_6$H$_5$O-phenyl | 4.65(d, 2H), 6.25(dt, 1H), 6.65(d, 1H), 6.9–7.5(3m, 9H) |
| A.099 | C$_2$H$_5$ | —CH$_2$CH=C(CH$_3$)— | Phenyl | 77–78 |
| A.100 | n-C$_3$H$_7$ | —CH$_2$CH=C(CH$_3$)— | Phenyl | 2.15(s, 3H), 4.75(d, 2H), 5.95(t, 1H), 7.2–7.6(m, 5H) |
| A.101 | C$_2$H$_5$ | —CH$_2$CH=CH— | 2-Cl-phenyl | 97–98 |
| A.102 | n-C$_3$H$_7$ | —CH$_2$CH=CH— | 2-Cl-phenyl | 87–89 |
| A.103 | C$_2$H$_5$ | —(CH$_2$)$_3$— | 4-F-phenyl | 4.05(t, 2H), 6.9–7.2(2m, 4H) |
| A.104 | n-C$_3$H$_7$ | —(CH$_2$)$_3$— | 4-F-phenyl | 4.05(t, 2H), 6.9–7.2(2m, 4H) |
| A.105 | C$_2$H$_5$ | —(CH$_2$)$_3$— | 2,4-Cl$_2$-phenyl | 63–65 |
| A.106 | n-C$_3$H$_7$ | —(CH$_2$)$_3$— | 2,4-Cl$_2$-phenyl | 4.05(t, 2H), 7.05–7.4(2m, 3H) |
| A.107 | C$_2$H$_5$ | —(CH$_2$)$_3$— | 4-Br-phenyl | 4.05(t, 2H), 7.05 and 7.45(2m, 4H) |
| A.108 | n-C$_3$H$_7$ | —(CH$_2$)$_3$— | 4-Br-phenyl | 4.05(t, 2H), 7.05 and 7.45(2m, 4H) |
| A.109 | C$_2$H$_5$ | —(CH$_2$)$_3$— | 2-Cl-phenyl | 4.1(t, 2H), 7.05–7.4(m, 4H) |
| A.110 | n-C$_3$H$_7$ | —(CH$_2$)$_3$— | 2-Cl-phenyl | 4.1(t, 2H), 7.05–7.4(m, 4H) |
| A.111 | C$_2$H$_5$ | —(CH$_2$)$_3$— | 4-Cl-phenyl | 4 05(t, 2H), 7.0–7.4(m, 4H) |
| A.112 | n-C$_3$H$_7$ | —(CH$_2$)$_3$— | 4-Cl-phenyl | 4.05(t, 2H), 7.0–7.4(m, 4H) |
| A.113 | C$_2$H$_5$ | —CH$_2$CH=CH— | 3,5-Cl$_2$-phenyl | 75–77 |
| A.114 | n-C$_3$H$_7$ | —CH$_2$CH=CH— | 3,5-Cl$_2$-phenyl | 70–73 |
| A.115 | C$_2$H$_5$ | —CH$_2$CH$_2$CH(CH$_3$)— | Phenyl | 1.25(d, 3H), 3.95(m, 2H), 7.05–7.4(m, 5H) |
| A.116 | n-C$_3$H$_7$ | —CH$_2$CH$_2$CH(CH$_3$)— | Phenyl | 1.25(d, 3H), 3.95(m, 2H), 7.05–7.4(m, 5H) |
| A.117 | C$_2$H$_5$ | —(CH$_2$)$_3$— | 3,5-Cl$_2$-phenyl | 82–84 |
| A.118 | n-C$_3$H$_7$ | —(CH$_2$)$_3$— | 3,5-Cl$_2$-phenyl | 4.05(t, 2H), 7.0–7.25(m, 3H) |
| A.119 | C$_2$H$_5$ | —CH$_2$CH$_2$C(=CH$_2$)— | Phenyl | 4.15(t, 2H), 5.15(s, 1H), 5.25(s, 1H), 7.2–7.6(m, 5H) |
| A.120 | n-C$_3$H$_7$ | —CH$_2$CH$_2$C(=CH$_2$)— | Phenyl | 4.15(t, 2H), 5.15(s, 1H), 5.25(s, 1H), 7.2–7.6(m, 5H) |
| A.121 | CH$_3$ | —CH$_2$CH=CH— | 2,4-Cl$_2$-phenyl | 107–108 |
| A.122 | CH$_3$ | —CH$_2$CH=CH— | 4-Cl-phenyl | 104–106 |
| A.123 | C$_2$H$_5$ | —(CH$_2$)$_5$— | 4-Cl-phenyl | 4.05(t, 2H), 7.0–7.4(2m, 4H) |
| A.124 | n-C$_3$H$_7$ | —(CH$_2$)$_5$— | 4-Cl-phenyl | 64–66 |
| A.125 | C$_2$H$_5$ | —CH$_2$CH=CH— | 3,4-Cl$_2$-phenyl | 4.7(d, 2H), 6.3(dt, 1H), 6.55(d, 1H), 7.2–7.6(m, 3H) |
| A.126 | n-C$_3$H$_7$ | —CH$_2$CH=CH— | 3,4-Cl$_2$-phenyl | 4.7(d, 2H), 6.3(dt, 1H), 6.55(d, 1H), 7.2–7.6(m, 3H) |
| A.127 | C$_2$H$_5$ | —CH$_2$CH(CH$_3$)CH$_2$— | Phenyl | 0.95(d, 3H), 3.9(m, 2H), 7.0–7.5(m, 5H) |
| A.128 | n-C$_3$H$_7$ | —CH$_2$CH(CH$_3$)CH$_2$— | Phenyl | 0.95(d, 3H), 3.9(m, 2H), 7.0–7.5(m, 5H) |
| A.129 | C$_2$H$_5$ | —(CH$_2$)$_3$— | 3,4-Cl$_2$-phenyl | 4.05(t, 2H), 7.0–7.1 and 7.2–7.4(2m, 3H) |
| A.130 | n-C$_3$H$_7$ | —(CH$_2$)$_3$— | 3,4-Cl$_2$-phenyl | 4.05(t, 2H), 6.95–7.1 and 7.2–7.45(2m, 3H) |
| A.131 | C$_2$H$_5$ | —CH$_2$CH(CH$_3$)CH$_2$— | 4-F-phenyl | 0.95(d, 3H), 3.9(dd, 2H), 6.8–7.2(m, 4H) |
| A.132 | n-C$_3$H$_7$ | —CH$_2$CH(CH$_3$)CH$_2$— | 4-F-phenyl | 0.95(d, 3H), 3.9(dd, 2H), 6.8–7.2(m, 4H) |
| A.133 | C$_2$H$_5$ | —CH$_2$CH(CH$_3$)CH$_2$— | 4-Cl-phenyl | 0.9(d, 3H), 3.9(m, 2H), 7.0–7.4(2m, 4H) |
| A.134 | n-C$_3$H$_7$ | —CH$_2$CH(CH$_3$)CH$_2$— | 4-Cl-phenyl | 0.9(d, 3H), 3.9(m, 2H), 7.0–7.4(2m, 4H) |
| A.135 | C$_2$H$_5$ | —CH$_2$CH$_2$C(CH$_3$)$_2$— | 4-F-phenyl | 1.35(s, 6H), 3.85(t, 2H), 7.0 and 7.3(2m, 4H) |
| A.136 | n-C$_3$H$_7$ | —CH$_2$CH$_2$C(CH$_3$)$_2$— | 4-F-phenyl | 1.35(s, 6H), 3.85(t, 2H), 7.0 and 7.3(2m, 4H) |
| A.137 | C$_2$H$_5$ | —CH$_2$CH$_2$C(CH$_3$)$_2$— | 4-Cl-phenyl | 1.35(s, 6H), 3.85(t, 2H), 7.25(s, 4H) |
| A.138 | n-C$_3$H$_7$ | —CH$_2$CH$_2$C(CH$_3$)$_2$— | 4-Cl-phenyl | 1.35(s, 6H), 3.85(t, 2H), 7.25(s, 4H) |
| A.139 | C$_2$H$_5$ | —(CH$_2$)$_6$— | 4-Cl-phenyl | 1.15(t, 3H), 4.05(t, 2H), 7.1(d, 2H), 7.25(d, 2H) |
| A.140 | n-C$_3$H$_7$ | —(CH$_2$)$_6$— | 4-Cl-phenyl | 0.95(t, 3H), 4.05(t, 2H), 7.1(d, 2H), 7.25(d, 2H) |
| A.141 | C$_2$H$_5$ | —(CH$_2$)$_6$— | 4-F-phenyl | 1.1(t, 3H), 4.0(t, 2H) |
| A.142 | n-C$_3$H$_7$ | —(CH$_2$)$_6$— | 4-F-phenyl | 0.95(t, 3H), 4.0(t, 2H) |
| A.143 | C$_2$H$_5$ | —(CH$_2$)$_5$— | 4-F-phenyl | 1.1(t, 3H), 4.05(t, 2H), 6.95 and 7.1(2m, 4H) |
| A.144 | n-C$_3$H$_7$ | —(CH$_2$)$_5$— | 4-F-phenyl | 0.9(t, 3H), 4.05(t, 2H), 6.95 and 7.1(2m, 4H) |
| A.145 | C$_2$H$_5$ | —CH$_2$CH(CH$_3$)—(CH$_2$)$_3$— | 2-CH$_3$-phenyl | 2.3(s, 3H), 3.95(t, 1H), 7.1(m, 4H) |
| A.146 | n-C$_3$H$_7$ | —CH$_2$CH(CH$_3$)—(CH$_2$)$_3$— | 2-CH$_3$-phenyl | 2.3(s, 3H), 3.9(t, 1H), 7.05(m, 4H) |
| A.147 | C$_2$H$_5$ | —CH$_2$CH=CH— | 3-Br-phenyl | 96–98 |
| A.148 | n-C$_3$H$_7$ | —CH$_2$CH=CH— | 3-Br-phenyl | 0.95(t, 3H), 4.65(d, 2H), 6.3(dt, 1H), 6.6(d, 1H), 7.1–7.6(m, 4H) |
| A.149 | C$_2$H$_5$ | —CH$_2$CH=CH— | 3-Cl-phenyl | 98–100 |
| A.150 | n-C$_3$H$_7$ | —CH$_2$CH=CH— | 3-Cl-phenyl | 1.0(t, 3H), 4.7(d, 2H), 6.35(dt, 1H), 6.65(d, 1H), 7.2–7.5(m, 4H) |
| A.151 | C$_2$H$_5$ | —CH$_2$CH=CH— | 3-F-phenyl | 77–78 |
| A.152 | n-C$_3$H$_7$ | —CH$_2$CH=CH— | 3-F-phenyl | 0.95(t, 3H), 4.65(d, 2H), 6.3(dt, 1H), 6.6(d, 1H), 6.9–7.3(m, 4H) |

TABLE II.3

(R^b, R^d, R^e = H)
(R^c = Tetrahydropyran-3-yl)

| Ex. | R^a | W | R^f | phys. data (NMR data in ppm) (M.p. in °C.) |
|---|---|---|---|---|
| A.153 | C₂H₅ | —CH₂—CH=CH— | Phenyl | |
| A.154 | n-C₃H₇ | —CH₂—CH=CH— | Phenyl | 4.7(d, 2H), 6.3(dt, 1H), 6.7(d, 1H), 7.2–7.5(m, 5H) |
| A.155 | C₂H₅ | —CH₂—CH=CH— | 4-Cl-phenyl | 106–108 |
| A.156 | n-C₃H₇ | —CH₂—CH=CH— | 4-Cl-phenyl | 4.7(d, 2H), 6.3(dt, 1H), 6.65(d, 1H), 7.2–7.5(m, 4H) |
| A.157 | C₂H₅ | —CH₂—CH=CH— | 4-F-phenyl | |
| A.158 | n-C₃H₇ | —CH₂—CH=CH— | 4-F-phenyl | 4.65(d, 2H), 6.2(dt, 1H), 6.7(d, 1H), 7.0(m, 2H), 7.4(m, 2H) |
| A.159 | C₂H₅ | —CH₂—CH=CH— | 2,4-Cl₂-phenyl | 135–137 |
| A.160 | n-C₃H₇ | —CH₂—CH=CH— | 2,4-Cl₂-phenyl | 4.75(d, 2H), 6.3(dt, 1H), 7.0(d, 1H), 7.05–7.5(m, 3H) |
| A.161 | C₂H₅ | —(CH₂)₃CH=CH— | Phenyl | 4.1(t, 2H), 6.2(dt, 1H), 6.4(d, 1H), 7.2–7.4(m, 5H) |
| A.162 | n-C₃H₇ | —(CH₂)₃CH=CH— | Phenyl | 4.1(t, 2H), 6.2(dt, 1H), 6.4(d, 1H), 7.1–7.4(m, 5H) |
| A.163 | C₂H₅ | —(CH₂)₃CH=CH— | 4-Cl-phenyl | 92–95 |
| A.164 | n-C₃H₇ | —(CH₂)₃CH=CH— | 4-Cl-phenyl | 4.1(t, 2H), 6.2(dt, 1H), 6.35(d, 1H), 7.3(s, 4H) |
| A.165 | C₂H₅ | —(CH₂)₃— | Phenyl | 4.05(t, 2H), 7.1–7.4(m, 5H) |
| A.166 | n-C₃H₇ | —(CH₂)₃— | Phenyl | 4.05(t, 2H), 7.1–7.4(m, 5H) |
| A.167 | C₂H₅ | —CH₂C(=CH₂)—CH₂— | Phenyl | 3.35(s, 2H), 4.4(s, 2H), 5.0 and 5.2(2s, 2H), 7.1–7.4(m, 5H) |
| A.168 | n-C₃H₇ | —CH₂C(=CH₂)—CH₂— | Phenyl | 3.35(s, 2H), 4.4(s, 2H), 5.0 and 5.2(2s, 2H), 7.1–7.4(m, 5H) |
| A.169 | C₂H₅ | —CH₂CH=CH— | 4-Br-phenyl | 114–116° C. |
| A.170 | n-C₃H₇ | —CH₂CH=CH— | 4-Br-phenyl | 99–100° C. |
| A.171 | C₂H₅ | —CH₂CH=CH— | 4-CH₃-phenyl | 123–125 |
| A.172 | n-C₃H₇ | —CH₂CH=CH— | 4-CH₃-phenyl | 70–72 |
| A.173 | C₂H₅ | —CH₂CH=CH— | 4-CF₃-phenyl | 104–106 |
| A.174 | n-C₃H₇ | —CH₂CH=CH— | 4-CF₃-phenyl | 4.75(d, 2H), 6.4(dt, 1H), 6.75(d, 1H), 7.4–7.8(m, 4H) |
| A.175 | C₂H₅ | —CH₂CH=CH— | 4-C₆H₅O-phenyl | 89–91 |
| A.176 | n-C₃H₇ | —CH₂CH=CH— | 4-C₆H₅O-phenyl | 4.65(d, 2H), 6.25(dt, 1H), 6.65(d, 1H), 6.9–7.5(3m, 9H) |
| A.177 | C₂H₅ | —CH₂CH=C(CH₃)— | Phenyl | 2.15(s, 3H), 4.75(d, 2H), 5.95(t, 1H), 7.2–7.6(m, 5H) |
| A.178 | n-C₃H₇ | —CH₂CHC(CH₃)— | Phenyl | 2.15(s, 3H), 4.75(d, 2H), 5.95(t, 1H), 7.2–7.6(m, 5H) |
| A.179 | C₂H₅ | —CH₂CH=CH— | 2-Cl-phenyl | 113–118 |
| A.180 | n-C₃H₇ | —CH₂CH=CH— | 2-Cl-phenyl | 4.75(d, 2H), 6.3(dt, 1H), 7.05(d, 1H), 7.05–7.6(m, 4H) |
| A.181 | C₂H₅ | —(CH₂)₃— | 4-F-phenyl | 4.1(t, 2H), 6.9–7.2(2m, 4H) |
| A.182 | n-C₃H₇ | —(CH₂)₃— | 4-F-phenyl | 4.1(t, 2H), 6.8–7.15(2m, 4H) |
| A.183 | C₂H₅ | —(CH₂)₃— | 2,4-Cl₂-phenyl | 75–77 |
| A.184 | n-C₃H₇ | —(CH₂)₃— | 2,4-Cl₂-phenyl | 4.05(t, 2H), 7.05–7.5(2m, 3H) |
| A.185 | C₂H₅ | —(CH₂)₃— | 2-Cl-phenyl | 4.1(t, 2H), 7.0–7.4(m, 4H) |
| A.186 | n-C₃H₇ | —(CH₂)₃— | 2-Cl-phenyl | 4.1(t, 2H), 7.0–7.4(m, 4H) |
| A.187 | C₂H₅ | —(CH₂)₃— | 4-Cl-phenyl | 62–64 |
| A.188 | n-C₃H₇ | —(CH₂)₃— | 4-Cl-phenyl | 4.05(t, 2H), 7.05–7.3(2m, 4H) |
| A.189 | C₂H₅ | —CH₂CH=CH₂— | 3,5-Cl₂-phenyl | 126–127 |
| A.190 | n-C₃H₇ | —CH₂CH=CH₂— | 3,5-Cl₂-phenyl | 4.7(d, 2H), 6.3(dt, 1H), 6.55(d, 1H), 7.1(m, 3H) |
| A.191 | C₂H₅ | —(CH₂)₃— | 3,5-Cl₂-phenyl | 79–80 |
| A.192 | n-C₃H₇ | —(CH₂)₃— | 3,5-Cl₂-phenyl | 4.05(t, 2H), 7.0–7.25(m, 3H) |
| A.193 | C₂H₅ | —CH₂CH₂C(=CH₂)— | Phenyl | 4.15(t, 2H), 5.15(s, 1H), 5.3(s, 1H), 7.2–7.5(m, 5H) |
| A.194 | n-C₃H₇ | —CH₂CH₂C(=CH₂)— | Phenyl | 4.15(t, 2H), 5.15(s, 1H), 5.3(s, 1H), 7.2–7.5(m, 5H) |
| A.195 | CH₃ | —CH₂CH=CH₂— | 4-Br-phenyl | 135–137 |
| A.196 | C₂H₅ | —(CH₂)₅— | 4-Cl-phenyl | 66–67 |
| A.197 | n-C₃H₇ | —(CH₂)₅— | 4-Cl-phenyl | 60–62 |
| A.198 | C₂H₅ | —CH₂C(CH₃)—CH₂— | Phenyl | 0.95(d, 3H), 3.9(m, 2H), 7.0–7.4(m, 5H) |
| A.199 | n-C₃H₇ | —CH₂C(CH₃)—CH₂— | Phenyl | 0.95(d, 3H), 3.9(m, 2H), 7.0–7.4(m, 5H) |
| A.200 | C₂H₅ | —CH₂CH=CH₂— | 3,4-Cl₂-phenyl | 4.65(d, 2H), 6.3(dt, 1H), 6.55(d, 1H), 7.2–7.6(m, 3H) |
| A.201 | n-C₃H₇ | —CH₂CH=CH₂— | 3,4-Cl₂-phenyl | 4.65(d, 2H), 6.3(dt, 1H), 6.55(d, 1H), 7.2–7.6(m, 3H) |
| A.202 | C₂H₅ | —CH₂C(CH₃)—CH₂— | 4-F-phenyl | 0.95(d, 3H), 3.9(dd, 2H), 6.8–7.2(m, 4H) |
| A.203 | n-C₃H₇ | —CH₂C(CH₃)—CH₂— | 4-F-phenyl | 0.95(d, 3H), 3.9(dd, 2H), 6.8–7.2(m, 4H) |
| A.204 | C₂H₅ | —CH₂C(CH₃)—CH₂— | 4-Cl-phenyl | 0.95(d, 3H), 3.9(m with dd, 4H), 7.0–7.4(m, 4H) |
| A.205 | n-C₃H₇ | —CH₂C(CH₃)—CH₂— | 4-Cl-phenyl | 0.95(d, 3H), 3.9(m with dd, 4H), 7.0–7.4(m, 4H) |
| A.206 | C₂H₅ | —CH₂CH₂C(CH₃)₂— | 4-F-phenyl | 1.3(s, 6H), 3.85(m with t, 4H), 6.9 and 7.3(2m, 4H) |
| A.207 | n-C₃H₇ | —CH₂CH₂C(CH₃)₂— | 4-F-phenyl | 1.3(s, 6H), 3.85(m with t, 4H), 6.9 and 7.3(2m, 4H) |
| A.208 | C₂H₅ | —CH₂CH₂C(CH₃)₂— | 4-Cl-phenyl | 1.35(s, 6H), 3.9(m with t, 4H), 7.25(s, 4H) |
| A.209 | n-C₃H₇ | —CH₂CH₂C(CH₃)₂— | 4-Cl-phenyl | 1.35(s, 6H), 3.9(m with t, 4H), 7.25(s, 4H) |
| A.210 | C₂H₅ | —(CH₂)₅— | 4-F-phenyl | 1.1(t, 3H), 4.05(t, 2H), 6.95 and 7.1(2m, 4H) |
| A.211 | n-C₃H₇ | —(CH₂)₅— | 4-F-phenyl | 0.95(t, 3H), 4.05(t, 2H), 6.95 and 7.1(2m, 4H) |
| A.212 | C₂H₅ | —CH₂CH=CH— | 3-Br-phenyl | 1.1(t, 3H), 4.65(d, 2H), 6.35(dt, 1H), 6.6(d, 1H), 7.2–7.6(m, 4H) |
| A.213 | n-C₃H₇ | —CH₂CH=CH— | 3-Br-phenyl | 1.0(t, 3H), 4.65(d, 2H), 6.35(dt, 1H), 6.6(d, 1H), 7.1–7.5(m, 4H) |

TABLE II.3-continued (R$^b$,R$^d$,R$^e$ = H)
(R$^c$ = Tetrahydropyran-3-yl)

| Ex. | R$^a$ | W | R$^f$ | phys. data (NMR data in ppm) (M.p. in °C.) |
|---|---|---|---|---|
| A.214 | C$_2$H$_5$ | —CH$_2$CH=CH— | 3-Cl-phenyl | 1.1(t, 3H), 4.7(d, 2H), 6.35(dt, 1H), 6.6(d, 1H), 7.2–7.5(m, 4H) |
| A.215 | n-C$_3$H$_7$ | —CH$_2$CH=CH— | 3-Cl-phenyl | 1.0(t, 3H), 4.7(d, 2H), 6.3(dt, 1H), 6.6(d, 1H), 7.2–7.5(m, 4H) |
| A.216 | C$_2$H$_5$ | —CH$_2$CH=CH— | 3-F-phenyl | 66–68 |
| A.217 | n-C$_3$H$_7$ | —CH$_2$CH=CH— | 3-F-phenyl | 1.0(t, 3H), 4.7(d, 2H), 6.3(dt, 1H), 6.6(d, 1H), 6.8–7.4(m, 4H) |

TABLE II.4

(R$^b$,R$^d$,R$^e$ = H)
(R$^c$ = Tetrahydropyran-4-yl)

| Ex. | R$^a$ | W | R$^f$ | phys. data (NMR data in ppm) (M.p. in °C.) |
|---|---|---|---|---|
| A.218 | C$_2$H$_5$ | —CH$_2$—CH=CH— | Phenyl | 129–130 |
| A.219 | n-C$_3$H$_7$ | —CH$_2$—CH=CH— | Phenyl | 85–87 |
| A.220 | C$_2$H$_5$ | —CH$_2$—CH=CH— | 4-Cl-phenyl | 130–131 |
| A.221 | n-C$_3$H$_7$ | —CH$_2$—CH=CH— | 4-Cl-phenyl | 108–110 |
| A.222 | C$_2$H$_5$ | —CH$_2$—CH=CH— | 4-F-phenyl | 118–120 |
| A.223 | n-C$_3$H$_7$ | —CH$_2$—CH=CH— | 4-F-phenyl | 87–89 |
| A.224 | C$_2$H$_5$ | —CH$_2$—CH=CH— | 2,4-Cl$_2$-phenyl | 95–97 |
| A.225 | n-C$_3$H$_7$ | —CH$_2$—CH=CH— | 2,4-Cl$_2$-phenyl | 93–95 |
| A.226 | C$_2$H$_5$ | —(CH$_2$)$_3$CH=CH— | Phenyl | 77–78 |
| A.227 | n-C$_3$H$_7$ | —(CH$_2$)$_3$CH=CH— | Phenyl | 67–68 |
| A.228 | C$_2$H$_5$ | —(CH$_2$)$_3$CH=CH— | 4-Cl-phenyl | 99–100 |
| A.229 | n-C$_3$H$_7$ | —(CH$_2$)$_3$CH=CH— | 4-Cl-phenyl | 4.05(t, 2H), 6.2(dt, 1H), 6.4(d, 1H), 7.3(s, 4H) |
| A.230 | C$_2$H$_5$ | —(CH$_2$)$_3$— | Phenyl | 4.1(t, 2H), 7.0–7.4(m, 5H) |
| A.231 | n-C$_3$H$_7$ | —(CH$_2$)$_3$— | Phenyl | 4.1(t, 2H), 7.0–7.4(m, 5H) |
| A.232 | C$_2$H$_5$ | —CH$_2$C(=CH$_2$)—CH$_2$— | Phenyl | 3.4(s, 2H), 4.4(s, 2H), 5.0 and 5.2(2s, 2H), 7.1–7.4 (m, 5H) |
| A.233 | n-C$_3$H$_7$ | —CH$_2$C(=CH$_2$)—CH$_2$— | Phenyl | 3.35(s, 2H), 4.4(s, 2H), 5.0 and 5.1(2s, 2H), 7.1–7.4(m, 5H) |
| A.234 | C$_2$H$_5$ | —CH$_2$CH=CH | 4-Br-phenyl | 140–142 |
| A.235 | n-C$_3$H$_7$ | —CH$_2$CH=CH | 4-Br-phenyl | 117–119 |
| A.236 | C$_2$H$_5$ | —CH$_2$CH=CH | 4-CH$_3$-phenyl | 135–137 |
| A.237 | n-C$_3$H$_7$ | —CH$_2$CH=CH | 4-CH$_3$-phenyl | 97–98 |
| A.238 | C$_2$H$_5$ | —CH$_2$CH=CH | 4-CF$_3$-phenyl | 103–104 |
| A.239 | n-C$_3$H$_7$ | —CH$_2$CH=CH | 4-CF$_3$-phenyl | 114–116 |
| A.240 | C$_2$H$_5$ | —CH$_2$CH=CH | 4-C$_6$H$_5$O-phenyl | 64–66 |
| A.241 | n-C$_3$H$_7$ | —CH$_2$CH=CH | 4-C$_6$H$_5$O-phenyl | 4.65(d, 2H), 6.2(dt, 1H), 6.65(d, 1H), 6.9–7.5(3m, 9H) |
| A.242 | C$_2$H$_5$ | —CH$_2$CH=C(CH$_3$)— | Phenyl | 70–72 |
| A.243 | n-C$_3$H$_7$ | —CH$_2$CH=C(CH$_3$)— | Phenyl | 2.15(s, 3H), 4.75(d, 2H), 5.95(t, 1H), 7.2–7.6(m, 5H) |
| A.244 | C$_2$H$_5$ | —CH$_2$CH=CH— | 2-Cl-phenyl | 85–87 |
| A.245 | n-C$_3$H$_7$ | —CH$_2$CH=CH— | 2-Cl-phenyl | 90–92 |
| A.246 | C$_2$H$_5$ | —(CH$_2$)$_3$— | 4-F-phenyl | 65–67 |
| A.247 | n-C$_3$H$_7$ | —(CH$_2$)$_3$— | 4-F-phenyl | 64–66 |
| A.248 | C$_2$H$_5$ | —(CH$_2$)$_3$— | 2,4-Cl$_2$-phenyl | 4.05(t, 2H), 7.05–7.4(2m, 3H) |
| A.249 | n-C$_3$H$_7$ | —(CH$_2$)$_3$— | 2,4-Cl$_2$-phenyl | 65–67 |
| A.250 | C$_2$H$_5$ | —(CH$_2$)$_3$— | 4-Br-phenyl | 111–112 |
| A.251 | C$_2$H$_5$ | —(CH$_2$)$_3$— | 2-Cl-phenyl | 4.1(t, 2H), 7.0–7.4(m, 4H) |
| A.252 | n-C$_3$H$_7$ | —(CH$_2$)$_3$— | 2-Cl-phenyl | 4.1(t, 2H), 7.05–7.45(m, 4H) |
| A.253 | C$_2$H$_5$ | —(CH$_2$)$_3$— | 4-Cl-phenyl | 97–99 |
| A.254 | n-C$_3$H$_7$ | —(CH$_2$)$_3$— | 4-Cl-phenyl | 84–86 |
| A.255 | C$_2$H$_5$ | —CH$_2$CH=CH— | 3,5-Cl$_2$-phenyl | 127–128 |
| A.256 | n-C$_3$H$_7$ | —CH$_2$CH=CH— | 3,5-Cl$_2$-phenyl | 80–81 |
| A.257 | C$_2$H$_5$ | —CH$_2$CH$_2$CH(CH$_3$)— | Phenyl | 1.25(d, 3H), 4.0(m, 2H), 7.05–7.4(m, 5H) |

TABLE II.4-continued $$R^c \text{—cyclohexenone with OH, NO—W—R}^f, R^l, (R^b, R^d, R^e = H), (R^c = \text{Tetrahydropyran-4-yl})$$

| Ex. | $R^a$ | W | $R^f$ | phys. data (NMR data in ppm) (M.p. in °C.) |
|---|---|---|---|---|
| A.258 | n-$C_3H_7$ | —$CH_2CH_2CH(CH_3)$— | Phenyl | 1.25(d, 3H), 4.0(m, 2H), 7.0–7.4(m, 5H) |
| A.259 | $C_2H_5$ | —$(CH_2)_3$— | 3,5-$Cl_2$-phenyl | 105–107 |
| A.260 | n-$C_3H_7$ | —$(CH_2)_3$— | 3,5-$Cl_2$-phenyl | 73–75 |
| A.261 | $C_2H_5$ | —$CH_2CH_2C(=CH_2)$— | Phenyl | 4.15(t, 2H), 5.15(s, 1H), 5.3(s, 1H), 7.2–7.6(m, 5H) |
| A.262 | n-$C_3H_7$ | —$CH_2CH_2C(=CH_2)$— | Phenyl | 4.15(t, 2H), 5.15(s, 1H), 5.3(s, 1H), 7.2–7.6(m, 5H) |
| A.263 | $C_2H_5$ | —$(CH_2)_5$— | 4-Cl-phenyl | 66–67 |
| A.264 | n-$C_3H_7$ | —$(CH_2)_5$— | 4-Cl-phenyl | 61–63 |
| A.265 | $C_2H_5$ | —$CH_2C(CH_3)$—$CH_2$— | Phenyl | 0.9(d, 3H), 3.9(m, 2H), 7.0–7.4(m, 5H) |
| A.266 | n-$C_3H_7$ | —$CH_2C(CH_3)$—$CH_2$— | Phenyl | 0.9(d, 3H), 3.9(m, 2H), 7.0–7.4(m, 5H) |
| A.267 | $C_2H_5$ | —$CH_2CH=CH$— | 3,4-$Cl_2$-phenyl | 103–105 |
| A.268 | n-$C_3H_7$ | —$CH_2CH=CH$— | 3,4-$Cl_2$-phenyl | 4.65(d, 2H), 6.3(dt, 1H), 6.55(d, 1H), 7.2–7.6(m, 3H) |
| A.269 | $C_2H_5$ | —$(CH_2)_3$— | 3,4-$Cl_2$-phenyl | 3.95–4.1(m, 4H), 7.0–7.1 and 7.2–7.45(2m, 3H) |
| A.270 | $C_2H_5$ | —$CH_2C(CH_3)$—$CH_2$— | 4-F-phenyl | 0.90(d, 3H), 3.85(dd, 2H), 6.8–7.2(m, 4H) |
| A.271 | n-$C_3H_7$ | —$CH_2C(CH_3)$—$CH_2$— | 4-F-phenyl | 0.90(d, 3H), 3.85(dd, 2H), 6.8–7.2(m, 4H) |
| A.272 | $C_2H_5$ | —$CH_2C(CH_3)$—$CH_2$— | 4-Cl-phenyl | 0.90(d, 3H), 3.85(dd, 2H), 7.0–7.4(2m, 4H) |
| A.273 | n-$C_3H_7$ | —$CH_2C(CH_3)$—$CH_2$— | 4-Cl-phenyl | 0.90(d, 3H), 3.85(dd, 2H), 7.0–7.4(2m, 4H) |
| A.274 | $C_2H_5$ | —$CH_2CH_2C(CH_3)_2$— | 4-F-phenyl | 1.35(s, 6H), 3.85(t, 2H), 7.0 and 7.3(2m, 4H) |
| A.275 | n-$C_3H_7$ | —$CH_2CH_2C(CH_3)_2$— | 4-F-phenyl | 1.35(s, 6H), 3.85(t, 2H), 7.0 and 7.3(2m, 4H) |
| A.276 | $C_2H_5$ | —$CH_2CH_2C(CH_3)_2$— | 4-Cl-phenyl | 1.35(s, 6H), 3.85(t, 2H), 7.25(s, 4H) |
| A.277 | n-$C_3H_7$ | —$CH_2CH_2C(CH_3)_2$— | 4-Cl-phenyl | 1.35(s, 6H), 3.85(t, 2H), 7.25(s, 4H) |
| A.278 | $C_2H_5$ | —$(CH_2)_6$— | 4-Cl-phenyl | 1.15(t, 3H), 3.35(t, 2H), 7.1(d, 2H), 7.25(d, 2H) |
| A.279 | n-$C_3H_7$ | —$(CH_2)_6$— | 4-Cl-phenyl | 0.95(t, 3H), 3.35(t, 2H), 7.1(d, 2H), 7.25(d, 2H) |
| A.280 | $C_2H_5$ | —$(CH_2)_6$— | 4-F-phenyl | 1.1(t, 3H), 3.35(t, 2H) |
| A.281 | n-$C_3H_7$ | —$(CH_2)_6$— | 4-F-phenyl | 0.95(t, 3H), 3.35(t, 2H) |
| A.282 | $C_2H_5$ | —$(CH_2)_5$— | 4-F-phenyl | 1.15(t, 3H), 3.35(t, 2H), 6.95 and 7.1(2m, 4H) |
| A.283 | n-$C_3H_7$ | —$(CH_2)_5$— | 4-F-phenyl | 0.95(t, 3H), 3.35(t, 2H), 6.95 and 7.1(2m, 4H) |
| A.284 | $C_2H_5$ | —$CH_2CH(CH_3)$—$CH_2CH_2CH_2$— | 2-$CH_3$-phenyl | 2.3(s, 3H), 7.05(m, 4H) |
| A.285 | n-$C_3H_7$ | —$CH_2CH(CH_3)$—$CH_2CH_2CH_2$— | 2-$CH_3$-phenyl | 2.3(s, 3H), 7.1(m, 4H) |
| A.286 | n-$C_3H_7$ | —$CH_2CH=CH$— | 3-F-phenyl | 61–62 |
| A.287 | $C_2H_5$ | —$CH_2CH=CH$— | 3-Br-phenyl | 103–105 |
| A.288 | n-$C_3H_7$ | —$CH_2CH=CH$— | 3-Br-phenyl | 80–82 |
| A.289 | $C_2H_5$ | —$CH_2CH=CH$— | 3-Cl-phenyl | 109–111 |
| A.290 | n-$C_3H_7$ | —$CH_2CH=CH$— | 3-Cl-phenyl | 89–91 |
| A.291 | $C_2H_5$ | —$CH_2CH=CH$— | 3-F-phenyl | 122–123 |

TABLE II.5

$$R^c \text{—cyclohexenone with OH, NO—W—R}^f, R^a, (R^b, R^d, R^e = H)$$

| Ex. | $R^c$ | $R^a$ | W | $R^f$ | phys. data (NMR data in ppm) (M.p. in °C.) |
|---|---|---|---|---|---|
| A.292 | 2-Ethylthiopropyl | n-$C_3H_7$ | —$(CH_2)_3$— | Phenyl | 4.05(t, 2H), 7.15–7.4(m, 5H) |
| A.293 | 2,4,6-Trimethyl-phenyl | $C_2H_5$ | —$CH_2CH=CH$— | 2,4-$Cl_2$-phenyl | 106–107 |
| A.294 | 2,4,6-Trimethyl-phenyl | $C_2H_5$ | —$CH_2CH=CH$— | 4-F-phenyl | 2.2(s, 3H), 2.35(s, 6H), 4.7(d, 2H), 6.3(dt, 1H), 6.65(d, 1H), 7.0(m, 2H), 7.4(m, 2H) |
| A.295 | Phenyl | n-$C_3H_7$ | —$CH_2CH=CH$— | 4-F-phenyl | 55–57 |
| A.296 | 4-(Benzoylamino)-phenyl | n-$C_3H_7$ | —$CH_2CH=CH$— | 4-F-phenyl | 80–82 |
| A.297 | 5,6-Dihydrothio-pyran-3-yl | $C_2H_5$ | —$CH_2CH=CH$— | 4-F-phenyl | 94–96 |
| A.298 | Cyclohexyl | n-$C_3H_7$ | —$CH_2CH=CH$— | 4-F-phenyl | 67–69 |
| A.299 | 3-Isopropyl-isoxazol-5-yl | n-$C_3H_7$ | —$CH_2CH=CH$— | 4-F-phenyl | 103–104 |
| A.300 | 5,6-Dihydrothio-pyran-3-yl | $C_2H_5$ | —$CH_2CH=CH$— | 2,4-$Cl_2$-phenyl | 88–89 |
| A.301 | Cyclohex-3-enyl | n-$C_3H_7$ | —$CH_2CH=CH$— | 2,4-$Cl_2$-phenyl | 75–77 |
| A.302 | 3-Isopropyl- | n-$C_3H_7$ | —$CH_2CH=CH$— | 2,4-$Cl_2$-phenyl | 113–115 |

TABLE II.5-continued ($R^b, R^d, R^e$ = H)

| Ex. | $R^c$ | $R^a$ | W | $R^f$ | phys. data (NMR data in ppm) (M.p. in °C.) |
|---|---|---|---|---|---|
| | isoxazol-5-yl | | | | |
| A.303 | 3-Isopropyl-isothiazol-5-yl | $C_2H_5$ | $-CH_2CH=CH-$ | 2,4-$Cl_2$-phenyl | 82–83 |
| A.304 | 4-Ethylphenyl | $C_2H_5$ | $-CH_2CH=CH-$ | 2,4-$Cl_2$-phenyl | 81–82 |
| A.305 | 3-Isopropyl-isothiazol-5-yl | $C_2H_5$ | $-CH_2CH=CH-$ | 4-F-phenyl | 98–101 |
| A.306 | N-Isopropyl-pyrrol-3-yl | n-$C_3H_7$ | $-CH_2CH=CH-$ | 4-F-phenyl | 54–56 |
| A.307 | 3-Nitro-4-fluor-phenyl | n-$C_3H_7$ | $-CH_2CH=CH-$ | 4-Br-phenyl | 124–126 |
| A.308 | Cyclohex-3-enyl | n-$C_3H_7$ | $-CH_2CH=CH-$ | 4-Br-phenyl | 68–71 |
| A.309 | Thien-3-yl | n-$C_3H_7$ | $-CH_2CH=CH-$ | 4-Br-phenyl | 85–87 |
| A.310 | 4-(Prop-2-inoxy)-phenyl | $C_2H_5$ | $-CH_2CH=CH-$ | 4-Br-phenyl | 126–129 |
| A.311 | 2-Ethylthiopropyl | $C_2H_5$ | $-CH_2CH=CH-$ | 2,4-$Cl_2$-phenyl | 4.7(d, 2H), 6.3(dt, 1H), 7.0(d, 1H), 7.2–7.6(m, 3H) |
| A.312 | 3-Isopropyl-isoxazol-5-yl | $CH_3$ | $-CH_2CH=CH-$ | 4-Cl-phenyl | 113–115 |
| A.313 | Ethoxycarbonyl | n-$C_3H_7$ | $-CH_2CH=CH-$ | 4-Cl-phenyl | 44–45 |
| A.314 | 4-Ethylphenyl | $C_2H_5$ | $-CH_2CH=CH-$ | 4-Cl-phenyl | 104–106 |
| A.315 | (dioxane-substituted ring) | $C_2H_5$ | $-CH_2CH=CH-$ | 4-Cl-phenyl | 68–70 |
| A.316 | Cyclohex-1-enyl | n-$C_3H_7$ | $-CH_2CH=CH-$ | 4-Cl-phenyl | 63–64 |
| A.317 | 4-(Benzoylamino)-phenyl | n-$C_3H_7$ | $-CH_2CH=CH-$ | 4-Cl-phenyl | 132–134 |
| A.318 | 4-(Prop-2-ynoxy)-phenyl | $C_2H_5$ | $-CH_2CH=CH-$ | 4-Cl-phenyl | 122–124 |
| A.319 | 2-Ethylthiophenyl | n-$C_3H_7$ | $-(CH_2)_6-$ | 4-Cl-phenyl | 0.95(t, 3H), 4.0(t, 2H), 7.1(d, 2H), 7.25(d, 2H) |
| A.320 | 2,4,6-Trimethyl-phenyl | $C_2H_5$ | $-(CH_2)_6-$ | 4-Cl-phenyl | 1.15(t, 3H), 2.25(s, 3H), 6.85(s, 2H) |
| A.321 | 2,4,6-Trimethyl-phenyl | $C_2H_5$ | $-(CH_2)_6-$ | 4-F-phenyl | 1.2(t, 3H), 2.25(s, 3H), 4.05(t, 2H) |
| A.322 | 2-Ethylthiopropyl | n-$C_3H_7$ | $-(CH_2)_6-$ | 4-F-phenyl | 0.95(t, 3H), 4.0(t, 2H) |

TABLE II.6

($R^b, R^d, R^e$ = H)

| Comp. No. | $R^c$ | $R^a$ | W | $R^f$ | $^1$H-NMR*) [δ ppm] | M.p. [°C.] |
|---|---|---|---|---|---|---|
| A.323 | Tetrahydrothiopyran-3-yl | n-$C_3H_7$ | $-CH_2-C\equiv C-$ | Phenyl | 4.9(s, 2H); 7.2–7.6(2m, 5H) | |
| A.324 | Tetrahydrothiopyran-3-yl | n-$C_3H_7$ | $-CH_2-C\equiv C-CH_2-$ | Phenyl | 3.6(s, 2H); 4.7(s, 2H), 7.2–7.5(m, 5H) | |
| A.325 | Tetrahydrothiopyran-3-yl | $C_2H_5$ | $-CH_2-C\equiv C-CH_2-$ | Phenyl | 3.65(s, 2H); 4.7(s, 2H); 7.2–7.5(m, 5H) | |
| A.326 | Tetrahydropyran-3-yl | n-$C_3H_7$ | $-CH_2-C\equiv C-CH_2-$ | Phenyl | 3.65(s, 2H); 4.7(s, 2H); 7.2–7.5(m, 5H) | |
| A.327 | 2-Ethylthiopropyl | n-$C_3H_7$ | $-CH_2-C\equiv C-$ | Phenyl | 4.9(s, 2H); 7.3–7.6(m, 5H) | |
| A.328 | 2-Ethylthiopropyl | n-$C_3H_7$ | $-CH_2-C\equiv C-CH_2-$ | Phenyl | 3.65(s, 2H); 4.7(s, 2H); | |

TABLE II.6-continued

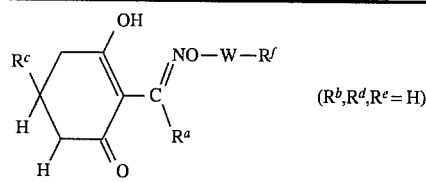

($R^b, R^d, R^e = H$)

| Comp. No. | $R^c$ | $R^a$ | W | $R^f$ | $^1$H-NMR*) [δ ppm] | M.p. [°C.] |
|---|---|---|---|---|---|---|
| A.329 | Tetrahydropyran-4-yl | $C_2H_5$ | —$CH_2$—C≡C—$CH_2$— | Phenyl | 7.2–7.5(m, 5H) 3.65(s, 2H); 4.7(s, 2H); | |
| A.330 | Tetrahydropyran-4-yl | n-$C_3H_7$ | —$CH_2$—C≡C—$CH_2$— | Phenyl | 7.2–7.5(m, 5H) 3.6(s, 2H); 4.65(s, 2H); | |
| A.331 | Tetrahydropyran-4-yl | n-$C_3H_7$ | —$(CH_2)_3$—C≡C— | 4-F-phenyl | 7.1–7.6(m, 5H) 4.25(t, 2H); 6.8–7.5(2m, 4H) | |
| A.332 | Tetrahydropyran-4-yl | $C_2H_5$ | —$(CH_2)_3$—C≡C— | 4-F-phenyl | 4.25(t, 2H); 6.8–7.5(2m, 4H) | |
| A.333 | Tetrahydrothiopyran-3-yl | $C_2H_5$ | —$(CH_2)_3$—C≡C— | 4-F-phenyl | 4.25(t, 2H); 6.8–7.5(2m, 4H) | |
| A.334 | Tetrahydrothiopyran-3-yl | n-$C_3H_7$ | —$(CH_2)_3$—C≡C— | 4-F-phenyl | 4.25(t, 2H); 6.8–7.5(2m, 4H) | |
| A.335 | Tetrahydropyran-3-yl | $C_2H_5$ | —$(CH_2)_3$—C≡C— | 4-F-phenyl | 4.25(t, 2H); 6.8–7.5(2m, 4H) | |
| A.336 | Tetrahydropyran-3-yl | n-$C_3H_7$ | —$(CH_2)_3$—C≡C— | 4-F-phenyl | 4.25(t, 2H); 6.8–7.5(2m, 4H) | |
| A.337 | Tetrahydrothiopyran-3-yl | $C_2H_5$ | —$CH_2CH_2$—C≡C— | 4-F-phenyl | 4.25(t); 6.98(dd); 7.35(dd) | 74–90 |
| A.338 | Tetrahydrothiopyran-3-yl | n-$C_3H_7$ | —$CH_2CH_2$—C≡C— | 4-F-phenyl | 4.25(t); 6.98(dd); 7.35(dd) | — |
| A.339 | Tetrahydropyran-3-yl | $C_2H_5$ | —$CH_2CH_2$—C≡C— | 4-F-phenyl | 4.25(t); 6.98(dd); 7.35(dd) | 55–61 |
| A.340 | Tetrahydropyran-3-yl | n-$C_3H_7$ | —$CH_2CH_2$—C≡C— | 4-F-phenyl | 4.25(t); 6.98(dd); 7.35(dd) | — |
| A.341 | Tetrahydropyran-4-yl | $C_2H_5$ | —$CH_2CH_2$—C≡C— | 4-F-phenyl | 4.25(t); 6.98(dd); 7.35(dd) | 83–87 |
| A.342 | Tetrahydropyran-4-yl | n-$C_3H_7$ | —$CH_2CH_2$—C≡C— | 4-F-phenyl | 4.25(t); 6.98(dd); 7.35(dd) | 98–102 |
| A.343 | 3-Isopropylisoxazol-5-yl | n-$C_3H_7$ | —$CH_2CH_2$—C≡C— | 4-F-phenyl | 4.25(t); 5.94(s); 7.0(dd); 7.37(dd) | — |
| A.344 | 4-Methylphenyl | n-$C_3H_7$ | —$CH_2CH_2$—C≡C— | 4-F-phenyl | 4.25(t); 6.98(dd); 7.15(m); 7.35(dd) | 65–69 |
| A.345 | 3,4-Dibromotetrahydro-pyran-3-yl | n-$C_3H_7$ | —$CH_2CH_2$—C≡C— | 4-F-phenyl | 4.25(t); 6.98(dd); 7.35(dd) | — |
| A.346 | Tetrahydrothiopyran-3-yl | n-$C_3H_7$ | —$CH_2CH_2$—C≡C— | 4-Cl-phenyl | 4.25(t); 7.25(d); 7.35(d) | — |
| A.347 | Tetrahydrothiopyran-3-yl | $C_2H_5$ | —$CH_2CH_2$—C≡C— | 4-Cl-phenyl | 4.25(t); 7.25(d); 7.35(d) | 82–86 |
| A.348 | Tetrahydropyran-3-yl | $C_2H_5$ | —$CH_2CH_2$—C≡C— | 4-Cl-phenyl | 4.25(t); 7.25(d); 7.35(d) | 99–101 |
| A.349 | Tetrahydropyran-3-yl | n-$C_3H_7$ | —$CH_2CH_2$—C≡C— | 4-Cl-phenyl | 4.25(t); 7.25(d); 7.35(d) | |
| A.350 | Tetrahydropyran-4-yl | $C_2H_5$ | —$CH_2CH_2$—C≡C— | 4-Cl-phenyl | 4.25(t); 7.25(d); 7.35(d) | 98–101 |
| A.351 | Tetrahydropyran-4-yl | n-$C_3H_7$ | —$CH_2CH_2$—C≡C— | 4-Cl-phenyl | 4.25(t); 7.25(d); 7.35(d) | 115–118 |
| A.352 | 3-Isopropylisoxazol-5-yl | n-$C_3H_7$ | —$CH_2CH_2$—C≡C— | 4-Cl-phenyl | 4.25(t); 5.9(s); 7.25(d); 7.35(d) | 71–74 |
| A.353 | 4-Methylphenyl | n-$C_3H_7$ | —$CH_2CH_2$—C≡C— | 4-Cl-phenyl | 4.25(t); 7.45(m); 7.28(M) | 93–6 |
| A.354 | 3,4-Dibromotetrahydro-pyran-3-yl | n-$C_3H_7$ | —$CH_2CH_2$—C≡C— | 4-Cl-phenyl | 4.25(t); 7.25(d); 7.25(d) | — |
| A.355 | Tetrahydrothiopyran-3-yl | $C_2H_5$ | —$(CH_2)_3$—C≡C— | 4-Cl-phenyl | 1.15(t); 4.2(t); 7.25(d); 7.35(d) | |
| A.356 | Tetrahydrothiopyran-3-yl | n-$C_3H_7$ | —$(CH_2)_3$—C≡C— | 4-Cl-phenyl | 0.98(t); 4.2(t); 7.25(d); 7.35(d) | |
| A.357 | Tetrahydropyran-3-yl | $C_2H_5$ | —$(CH_2)_3$—C≡C— | 4-Cl-phenyl | 1.15(t); 4.2(t); 7.25(d); 7.35(d) | |
| A.358 | Tetrahydropyran-3-yl | n-$C_3H_7$ | —$(CH_2)_3$—C≡C— | 4-Cl-phenyl | 0.95(t); 4.2(t); 7.25(d); 7.35(d) | |
| A.359 | Tetrahydropyran-4-yl | $C_2H_5$ | —$(CH_2)_3$—C≡C— | 4-Cl-phenyl | 1.15(t); 4.2(t); 7.25(d); 7.35(d) | |
| A.360 | Tetrahydropyran-4-yl | n-$C_3H_7$ | —$(CH_2)_3$—C≡C— | 4-Cl-phenyl | 0.98(t); 4.2(t); 7.25(d); 7.35(d) | |

TABLE II.6-continued $(R^b, R^d, R^e = H)$

| Comp. No. | $R^c$ | $R^a$ | W | $R^f$ | $^1$H-NMR*) [δ ppm] | M.p. [°C.] |
|---|---|---|---|---|---|---|
| A.361 | Tetrahydrothiopyran-3-yl | $C_2H_5$ | $-CH_2-CH_2-C\equiv C-$ | 2-Thienyl | 1.15(t); 2.75(t); 4.25(t); 7.05(m); 7.2(m) | |
| A.362 | Tetrahydrothiopyran-3-yl | n-$C_3H_7$ | $-CH_2-CH_2-C\equiv C-$ | 2-Thienyl | 0.95(t); 2.75(t); 4.25(t); 7.05(m); 7.2(m) | |
| A.363 | Tetrahydropyran-3-yl | $C_2H_5$ | $-CH_2-CH_2-C\equiv C-$ | 2-Thienyl | 1.15(t); 2.75(t); 4.25(t); 7.05(m); 7.2(m) | |
| A.364 | Tetrahydropyran-3-yl | n-$C_3H_7$ | $-CH_2-CH_2-C\equiv C-$ | 2-Thienyl | 0.95(t); 2.75(t); 4.25(t); 7.05(m); 7.2(m) | |
| A.365 | Tetrahydropyran-4-yl | $C_2H_5$ | $-CH_2-CH_2-C\equiv C-$ | 2-Thienyl | 1.15(t); 2.75(t); 4.25(t); 7.05(m); 7.2(m) | |
| A.366 | Tetrahydropyran-4-yl | n-$C_3H_7$ | $-CH_2-CH_2-C\equiv C-$ | 2-Thienyl | 0.95(t); 2.75(t); 4.25(t); 7.05(m); 7.2(m) | |
| 3.45 | Tetrahydrothiopyran-3-yl | $C_2H_5$ | $-CH_2CH=C(CH_3)-C\equiv C-$**) | 4-Cl-phenyl | 1.15(t); 2.0(s); 4.8(d); 5.9(t) | |
| 3.46 | Tetrahydrothiopyran-3-yl | n-$C_3H_7$ | $-CH_2CH=C(CH_3)-C\equiv C-$**) | 4-Cl-phenyl | 0.95(t); 2.0(s); 4.8(d); 5.9(t) | |
| 3.47 | Tetrahydropyran-4-yl | $C_2H_5$ | $-CH_2CH=C(CH_3)-C\equiv C-$**) | 4-Cl-phenyl | 1.15(t); 2.0(s); 4.8(d); 5.9(t) | |
| 3.48 | Tetrahydropyran-4-yl | n-$C_3H_7$ | $-CH_2CH=C(CH_3)-C\equiv C-$**) | 4-Cl-phenyl | 0.95(t); 2.0(s); 4.8(d); 5.9(t) | |
| 3.49 | 2-Ethylthiopropyl | n-$C_3H_7$ | $-CH_2CH=C(CH_3)-C\equiv C-$**) | 4-Cl-phenyl | 0.95(t); 2.0(s); 4.8(d); 5.9(t) | |
| 3.50 | 2,4,6-Trimethylphenyl | $C_2H_5$ | $-CH_2CH=C(CH_3)-C\equiv C-$**) | 4-Cl-phenyl | 1.2(t); 2.0(s); 4.8(d); 5.95(t) | |
| 3.51 | Tetrahydrothiopyran-3-yl | $C_2H_5$ | $-CH_2CH=C(CH_3)-C\equiv C-$**) | 4-F-phenyl | 1.1(t); 2.0(s); 4.8(d); 5.9(t) | |
| 3.52 | Tetrahydrothiopyran-3-yl | n-$C_3H_7$ | $-CH_2CH=C(CH_3)-C\equiv C-$**) | 4-F-phenyl | 0.95(t); 2.0(s); 4.8(d); 5.9(t) | |
| A.375 | Tetrahydropyran-4-yl | n-$C_3H_7$ | $-CH_2-CH=C(CH_3)-C\equiv C-$**) | 4-F-phenyl | 0.95(t); 2.0(s); 4.8(d); 5.9(t) | |
| A.376 | Tetrahydropyran-4-yl | $C_2H_5$ | $-CH_2-CH=C(CH_3)-C\equiv C-$**) | 4-F-phenyl | 1.15(t); 2.0(s); 4.8(d); 5.9(t) | |
| A.377 | 2-Ethylthiopropyl | n-$C_3H_7$ | $-CH_2-CH=C(CH_3)-C\equiv C-$**) | 4-F-phenyl | 0.95(t); 2.0(s); 4.8(d); 5.9(t) | |

*) selected signals
**) Z configuration about the double fond

TABLE II.7

$(R^b, R^d, R^e = H)$

| No. | $R^a$ | $R^c$ | W | $R^f$ | phys. data NMR data in ppm M.p. in °C. |
|---|---|---|---|---|---|
| A.378 | $C_2H_5$ | Tetrahydropyran-3-yl | $-(CH_2)_2-$ | Furan-2-yl | |
| A.379 | n-$C_3H_7$ | Tetrahydropyran-3-yl | $-(CH_2)_2-$ | Furan-2-yl | |
| A.380 | $C_2H_5$ | Tetrahydropyran-4-yl | $-(CH_2)_2-$ | Furan-2-yl | |
| A.381 | n-$C_3H_7$ | Tetrahydropyran-4-yl | $-(CH_2)_2-$ | Furan-2-yl | |
| A.382 | $C_2H_5$ | Tetrahydrothiopyran-3-yl | $-(CH_2)_2-$ | Furan-2-yl | |
| A.383 | n-$C_3H_7$ | Tetrahydrothiopyran-3-yl | $-(CH_2)_2-$ | Furan-2-yl | |
| A.384 | $C_2H_5$ | Tetrahydropyran-3-yl | $-(CH_2)_2-$ | Thien-2-yl | 3.92(m, 2H), 4.33(t, 2H), 6.82(m, 1H), 6.93(m, 1H), 7.13(m, 1H) |
| A.385 | n-$C_3H_7$ | Tetrahydropyran-3-yl | $-(CH_2)_2-$ | Thien-2-yl | 3.92(m, 2H), 4.33(t, 2H), 6.82(m, 1H), 6.93(m, 1H), 7.13(m, 1H) |

TABLE II.7-continued $$\text{(structure shown with } R^c, H, H, OH, NO-W-R^f, R^a, O \text{ substituents)} \quad (R^b, R^d, R^e = H)$$

| No. | $R^a$ | $R^c$ | W | $R^f$ | phys. data NMR data in ppm M.p. in °C. |
|---|---|---|---|---|---|
| A.386 | $C_2H_5$ | Tetrahydropyran-4-yl | —(CH$_2$)$_2$— | Thien-2-yl | 4.00(m, 2H), 4.33(t, 2H), 6.82(m, 1H), 6.93(m, 1H), 7.13(m, 1H) |
| A.387 | n-$C_3H_7$ | Tetrahydropyran-4-yl | —(CH$_2$)$_2$— | Thien-2-yl | 4.00(m, 2H), 4.33(t, 2H), 6.82(m, 1H), 6.93(m, 1H), 7.13(m, 1H) |
| A.388 | $C_2H_5$ | Tetrahydrothiopyran-3-yl | —(CH$_2$)$_2$— | Thien-2-yl | 4.30(t, 2H), 6.82(m, 1H), 6.93(m, 1H), 7.13(m, 1H) |
| A.389 | n-$C_3H_7$ | Tetrahydrothiopyran-3-yl | —(CH$_2$)$_2$— | Thien-2-yl | 4.30(t, 2H), 6.82(m, 1H), 6.93(m, 1H), 7.13(m, 1H) |
| A.390 | $C_2H_5$ | Tetrahydropyran-3-yl | —(CH$_2$)$_2$— | Pyrid-2-yl | 3.90(m, 2H), 4.46(t, 2H), 7.20(m, 2H), 7.67(m, 1H), 8.50(m, 1H) |
| A.391 | n-$C_3H_7$ | Tetrahydropyran-3-yl | —(CH$_2$)$_2$— | Pyrid-2-yl | |
| A.392 | $C_2H_5$ | Tetrahydropyran-4-yl | —(CH$_2$)$_2$— | Pyrid-2-yl | 4.00(m, 2H), 4.46(t, 2H), 7.20(m, 2H), 7.67(m, 1H), 8.50(m, 1H) |
| A.393 | n-$C_3H_7$ | Tetrahydropyran-4-yl | —(CH$_2$)$_2$— | Pyrid-2-yl | |
| A.394 | $C_2H_5$ | Tetrahydrothiopyran-3-yl | —(CH$_2$)$_2$— | Pyrid-2-yl | 4.46(t, 2H), 7.20(m, 2H), 7.67(m, 1H), 8.50(m, 1H) |
| A.395 | n-$C_3H_7$ | Tetrahydrothiopyran-3-yl | —(CH$_2$)$_2$— | Pyrid-2-yl | |
| A.396 | $C_2H_5$ | Tetrahydropyran-3-yl | —(CH$_2$)$_3$— | Furan-2-yl | 3.93(m, 2H), 4.10(t, 2H), 6.00(m, 1H), 6.26(m, 1H), 7.33(m, 1H) |
| A.397 | n-$C_3H_7$ | Tetrahydropyran-3-yl | —(CH$_2$)$_3$— | Furan-2-yl | 3.93(m, 2H), 4.10(t, 2H), 6.00(m, 1H), 6.26(m, 1H), 7.33(m, 1H) |
| A.398 | $C_2H_5$ | Tetrahydropyran-4-yl | —(CH$_2$)$_3$— | Furan-2-yl | 78–82 |
| A.399 | n-$C_3H_7$ | Tetrahydropyran-4-yl | —(CH$_2$)$_3$— | Furan-2-yl | 48–52 |
| A.400 | $C_2H_5$ | Tetrahydrothiopyran-3-yl | —(CH$_2$)$_3$— | Furan-2-yl | 54–58 |
| A.401 | n-$C_3H_7$ | Tetrahydrothiopyran-3-yl | —(CH$_2$)$_3$— | Furan-2-yl | 4.10(t, 2H), 6.00(m, 1H), 6.26(m, 1H), 7.33(m, 1H) |
| A.402 | $C_2H_5$ | Tetrahydropyran-3-yl | —(CH$_2$)$_3$— | Thien-2-yl | 72–74 |
| A.403 | n-$C_3H_7$ | Tetrahydropyran-3-yl | —(CH$_2$)$_3$— | Thien-2-yl | 3.93(m, 2H), 4.10(t, 2H), 6.82(m, 1H), 6.93(m, 1H), 7.33(m, 1H) |
| A.404 | $C_2H_5$ | Tetrahydropyran-4-yl | —(CH$_2$)$_3$— | Thien-2-yl | 86–90 |
| A.405 | n-$C_3H_7$ | Tetrahydropyran-4-yl | —(CH$_2$)$_3$— | Thien-2-yl | 55–58 |
| A.406 | $C_2H_5$ | Tetrahydrothiopyran-3-yl | —(CH$_2$)$_3$— | Thien-2-yl | 4.12(t, 2H), 6.82(m, 1H), 6.93(m, 1H), 7.13(m, 1H), |
| A.407 | n-$C_3H_7$ | Tetrahydrothiopyran-3-yl | —(CH$_2$)$_3$— | Thien-2-yl | 4.12(t, 2H), 6.82(m, 1H), 6.93(m, 1H), 7.13(m, 1H), |
| A.408 | $C_2H_5$ | Tetrahydropyran-3-yl | —(CH$_2$)$_3$— | Thien-3-yl | 73–74 |
| A.409 | n-$C_3H_7$ | Tetrahydropyran-3-yl | —(CH$_2$)$_3$— | Thien-3-yl | 4.05(t, 2H), 6.95(m, 2H), 7.25(m, 1H) |
| A.410 | $C_2H_5$ | Tetrahydropyran-4-yl | —(CH$_2$)$_3$— | Thien-3-yl | 105–107 |
| A.411 | n-$C_3H_7$ | Tetrahydropyran-4-yl | —(CH$_2$)$_3$— | Thien-3-yl | 68–70 |
| A.412 | $C_2H_5$ | Tetrahydrothiopyran-3-yl | —(CH$_2$)$_3$— | Thien-3-yl | 57–59 |
| A.413 | n-$C_3H_7$ | Tetrahydrothiopyran-3-yl | —(CH$_2$)$_3$— | Thien-3-yl | 4.05(t, 5H), 6.95(m, 2H), 7.25(m, 1H) |
| A.414 | $C_2H_5$ | Tetrahydropyran-3-yl | —(CH$_2$)$_3$— | 1-CH$_3$-pyrrol-2-yl | 3.90(m, 2H), 4.12(t, 2H), 5.90(m, 1H), 6.06(m, 1H), 6,53(m, 1H) |
| A.415 | n-$C_3H_7$ | Tetrahydropyran-3-yl | —(CH$_2$)$_3$— | 1-CH$_3$-pyrrol-2-yl | 3.90(m, 2H), 4.12(t, 2H), 5.90(m, 1H), 6.06(m, 1H), 6,53(m, 1H) |
| A.416 | $C_2H_5$ | Tetrahydropyran-4-yl | —(CH$_2$)$_3$— | 1-CH$_3$-pyrrol-2-yl | 4.00(m, 2H), 4.12(t, 2H), 5.90(m, 1H), 6.06(m, 1H), 6,53(m, 1H) |
| A.417 | n-$C_3H_7$ | Tetrahydropyran-4-yl | —(CH$_2$)$_3$— | 1-CH$_3$-pyrrol-2-yl | 4.00(m, 2H), 4.12(t, 2H), 5.90(m, 1H), 6.06(m, 1H), 6,53(m, 1H) |
| A.418 | $C_2H_5$ | Tetrahydropyran-3-yl | —(CH$_2$)$_3$— | 1-CH$_3$-pyrrol-2-yl | 4.12(t, 2H), 5.90(m, 1H), 6.06(m, 1H), 6,53(m, 1H) |
| A.419 | n-$C_3H_7$ | Tetrahydropyran-3-yl | —(CH$_2$)$_3$— | 1-CH$_3$-pyrrol-2-yl | 4.12(t, 2H), 5.90(m, 1H), 6.06(m, 1H), 6,53(m, 1H) |
| A.420 | $C_2H_5$ | Tetrahydropyran-3-yl | —CH$_2$CH(CH$_3$)—CH$_2$— | Thien-2-yl | 35 |
| A.421 | n-$C_3H_7$ | Tetrahydropyran-3-yl | —CH$_2$CH(CH$_3$)—CH$_2$— | Thien-2-yl | 6.85–7.20(m, 3H) |
| A.422 | $C_2H_5$ | Tetrahydropyran-4-yl | —CH$_2$CH(CH$_3$)—CH$_2$— | Thien-2-yl | 59–61 |
| A.423 | n-$C_3H_7$ | Tetrahydropyran-4-yl | —CH$_2$CH(CH$_3$)—CH$_2$— | Thien-2-yl | 6.70–7.20(m, 3H) |
| A.424 | $C_2H_5$ | Tetrahydrothiopyran-3-yl | —CH$_2$CH(CH$_3$)—CH$_2$— | Thien-2-yl | 6.70–7.20(m, 3H) |
| A.425 | n-$C_3H_7$ | Tetrahydrothiopyran-3-yl | —CH$_2$CH(CH$_3$)—CH$_2$— | Thien-2-yl | 6.70–7,20(m, 3H) |
| A.426 | $C_2H_5$ | Tetrahydropyran-3-yl | —CH$_2$CH(CH$_3$)—CH$_2$— | Thien-3-yl | 38–40 |
| A.427 | n-$C_3H_7$ | Tetrahydropyran-3-yl | —CH$_2$CH(CH$_3$)—CH$_2$— | Thien-3-yl | 6.80–7.30(m, 3H) |
| A.428 | $C_2H_5$ | Tetrahydropyran-4-yl | —CH$_2$CH(CH$_3$)—CH$_2$— | Thien-3-yl | 58–60 |
| A.429 | n-$C_3H_7$ | Tetrahydropyran-4-yl | —CH$_2$CH(CH$_3$)—CH$_2$— | Thien-3-yl | 6.80–7.40(m, 3H) |
| A.430 | $C_2H_5$ | Tetrahydrothiopyran-3-yl | —CH$_2$CH(CH$_3$)—CH$_2$— | Thien-3-yl | 6.90(m, 2H), 7.25(m, 1H) |
| A.431 | n-$C_3H_7$ | Tetrahydrothiopyran-3-yl | —CH$_2$CH(CH$_3$)—CH$_2$— | Thien-3-yl | 6.90(m, 2H), 7.30(m, 1H) |
| A.432 | $C_2H_5$ | Tetrahydropyran-3-yl | —CH$_2$CH(CH$_3$)—CH$_2$— | 5-CH$_3$-thien-2-yl | 48–50 |

TABLE II.7-continued

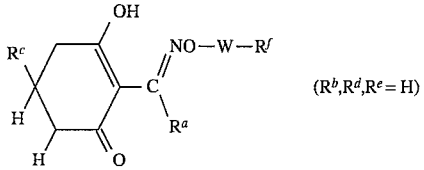

($R^b, R^d, R^e = H$)

| No. | $R^a$ | $R^c$ | W | $R^f$ | phys. data NMR data in ppm M.p. in °C. |
|---|---|---|---|---|---|
| A.433 | n-$C_3H_7$ | Tetrahydropyran-3-yl | —$CH_2CH(CH_3)$—$CH_2$— | 5-$CH_3$-thien-2-yl | 2.40(s, 3H), 6.55(s, 2H) |
| A.434 | $C_2H_5$ | Tetrahydropyran-4-yl | —$CH_2CH(CH_3)$—$CH_2$— | 5-$CH_3$-thien-2-yl | 2.40(s, 3H), 6.55(s, 2H) |
| A.435 | n-$C_3H_7$ | Tetrahydropyran-4-yl | —$CH_2CH(CH_3)$—$CH_2$— | 5-$CH_3$-thien-2-yl | 2.40(s, 3H), 6.55(s, 2H) |
| A.436 | $C_2H_5$ | Tetrahydrothiopyran-3-yl | —$CH_2CH(CH_3)$—$CH_2$— | 5-$CH_3$-thien-2-yl | 2.45(s, 3H), 6.75(s, 2H) |
| A.437 | n-$C_3H_7$ | Tetrahydrothiopyran-3-yl | —$CH_2CH(CH_3)$—$CH_2$— | 5-$CH_3$-thien-2-yl | 56–58 |
| A.438 | $C_2H_5$ | Tetrahydropyran-3-yl | —$CH_2CH$=$CH$— | Furan-2-yl | 4.70(d, 2H), 6.10–6.60(m, 4H), 7.40(s, 1H) |
| A.439 | n-$C_3H_7$ | Tetrahydropyran-3-yl | —$CH_2CH$=$CH$— | Furan-2-yl | 4.70(d, 2H), 6.00–6.60(m, 4H), 7.40(s, 1H) |
| A.440 | $C_2H_5$ | Tetrahydropyran-4-yl | —$CH_2CH$=$CH$— | Furan-2-yl | 99–100 |
| A.441 | n-$C_3H_7$ | Tetrahydropyran-4-yl | —$CH_2CH$=$CH$— | Furan-2-yl | 4.70(d, 2H), 6.10–6.60(m, 4H), 7.40(s, 1H) |
| A.442 | $C_2H_5$ | Tetrahydrothiopyran-3-yl | —$CH_2CH$=$CH$— | Furan-2-yl | 4.65(d, 2H), 6.10–6.60(m, 4H), 7.40(s, 1H) |
| A.443 | n-$C_3H_7$ | Tetrahydrothiopyran-3-yl | —$CH_2CH$=$CH$— | Furan-2-yl | 4.70(d, 2H), 6.10–6.60(m, 4H), 7.40(s, 1H) |
| A.444 | $C_2H_5$ | Tetrahydrothiopyran-3-yl | —$CH_2CH$=$CH$— | 5-Cl-thien-2-yl | 4.60(d, 2H), 6.00(dt, 1H), 6.70(d, 1H), 6.80(m, 2H) |
| A.445 | n-$C_3H_7$ | Tetrahydrothiopyran-3-yl | —$CH_2CH$=$CH$— | 5-Cl-thien-2-yl | 4.60(d, 2H), 6.00(dt, 1H), 6.70(d, 1H), 6.80(m, 2H) |
| A.446 | $C_2H_5$ | Tetrahydropyran-3-yl | —$CH_2CH$=$CH$— | Thien-2-yl | 112–114 |
| A.447 | n-$C_3H_7$ | Tetrahydropyran-3-yl | —$CH_2CH$=$CH$— | Thien-2-yl | 67–68 |
| A.448 | $C_2H_5$ | Tetrahydropyran-4-yl | —$CH_2CH$=$CH$— | Thien-2-yl | 123–125 |
| A.449 | n-$C_3H_7$ | Tetrahydropyran-4-yl | —$CH_2CH$=$CH$— | Thien-2-yl | 70–72 |
| A.450 | $C_2H_5$ | Tetrahydrothiopyran-3-yl | —$CH_2CH$=$CH$— | Thien-2-yl | 104–106 |
| A.451 | n-$C_3H_7$ | Tetrahydrothiopyran-3-yl | —$CH_2CH$=$CH$— | Thien-2-yl | 85–88 |
| A.452 | $C_2H_5$ | 2,4,6-Trimethylphenyl | —$CH_2CH$=$CH$— | Thien-2-yl | 4.65(d, 2H), 6.10–6.30(m, 1H), 6.70–7.20(m, 6H) |
| A.453 | $C_2H_5$ | Tetrahydropyran-3-yl | —$CH_2CH$=$CH$— | Thien-3-yl | 87–90 |
| A.454 | n-$C_3H_7$ | Tetrahydropyran-3-yl | —$CH_2CH$=$CH$— | Thien-3-yl | 3.90(m, 2H), 4.67(d, 2H), 6.12(dt, 1H), 6.63(d, 1H), 7.20(m, 3H) |
| A.455 | $C_2H_5$ | Tetrahydropyran-4-yl | —$CH_2CH$=$CH$— | Thien-3-yl | 128–135 |
| A.456 | n-$C_3H_7$ | Tetrahydropyran-4-yl | —$CH_2CH$=$CH$— | Thien-3-yl | 92–95 |
| A.457 | $C_2H_5$ | Tetrahydrothiopyran-3-yl | —$CH_2CH$=$CH$— | Thien-3-yl | 79–81 |
| A.458 | n-$C_3H_7$ | Tetrahydrothiopyran-3-yl | —$CH_2CH$=$CH$— | Thien-3-yl | 86–92 |
| A.459 | $C_2H_5$ | Tetrahydropyran-3-yl | —$CH_2CH$=$CH$— | 5-$CH_3$-thien-2-yl | 88–89 |
| A.460 | n-$C_3H_7$ | Tetrahydropyran-3-yl | —$CH_2CH$=$CH$— | 5-$CH_3$-thien-2-yl | 70–71 |
| A.461 | $C_2H_5$ | Tetrahydropyran-4-yl | —$CH_2CH$=$CH$— | 5-$CH_3$-thien-2-yl | 108–110 |
| A.462 | n-$C_3H_7$ | Tetrahydropyran-4-yl | —$CH_2CH$=$CH$— | 5-$CH_3$-thien-2-yl | 104–105 |
| A.463 | $C_2H_5$ | Tetrahydrothiopyran-3-yl | —$CH_2CH$=$CH$— | 5-$CH_3$-thien-2-yl | 111–112 |
| A.464 | n-$C_3H_7$ | Tetrahydrothiopyran-3-yl | —$CH_2CH$=$CH$— | 5-$CH_3$-thien-2-yl | 75–77 |
| A.465 | $C_2H_5$ | Tetrahydropyran-3-yl | —$CH_2CH$=$CH$— | 4-Br-thien-2-yl | 78–80 |
| A.466 | n-$C_3H_7$ | Tetrahydropyran-3-yl | —$CH_2CH$=$CH$— | 4-Br-thien-2-yl | 6.70(d, 1H), 6.95(s, 1H), 7.05(s, 1H) |
| A.467 | $C_2H_5$ | Tetrahydropyran-4-yl | —$CH_2CH$=$CH$— | 4-Br-thien-2-yl | 122–124 |
| A.468 | n-$C_3H_7$ | Tetrahydropyran-4-yl | —$CH_2CH$=$CH$— | 4-Br-thien-2-yl | 88–90 |
| A.469 | $C_2H_5$ | Tetrahydrothiopyran-3-yl | —$CH_2CH$=$CH$— | 4-Br-thien-2-yl | 72–74 |
| A.470 | n-$C_3H_7$ | Tetrahydrothiopyran-3-yl | —$CH_2CH$=$CH$— | 4-Br-thien-2-yl | 6.70(d, 1H), 6.90(s, 1H), 7.05(s, 1H) |
| A.471 | $C_2H_5$ | Tetrahydropyran-3-yl | —$CH_2CH$=$CH$— | Pyrid-3-yl | 146–148 |
| A.472 | n-$C_3H_7$ | Tetrahydropyran-3-yl | —$CH_2CH$=$CH$— | Pyrid-3-yl | 6.40(dt, 1H), 7.30, 7.75, 8.40–8.70(3m, 4H) |
| A.473 | $C_2H_5$ | Tetrahydropyran-4-yl | —$CH_2CH$=$CH$— | Pyrid-3-yl | 164–165 |
| A.474 | n-$C_3H_7$ | Tetrahydropyran-4-yl | —$CH_2CH$=$CH$— | Pyrid-3-yl | 73–78 |
| A.475 | $C_2H_5$ | Tetrahydrothiopyran-3-yl | —$CH_2CH$=$CH$— | Pyrid-3-yl | 6.40(dt, 1H), 7.30, 7.75, 8.40–8.70(3m, 4H) |
| A.476 | n-$C_3H_7$ | Tetrahydrothiopyran-3-yl | —$CH_2CH$=$CH$— | Pyrid-3-yl | 6.40(dt, 1H), 7.30, 7.75, 8.40–8.70(3m, 4H) |
| A.477 | $C_2H_5$ | Tetrahydropyran-3-yl | —$CH_2C(CH_3)$=$CH$— | Thien-2-yl | |
| A.478 | n-$C_3H_7$ | Tetrahydropyran-3-yl | —$CH_2C(CH_3)$=$CH$— | Thien-2-yl | |
| A.479 | $C_2H_5$ | Tetrahydropyran-4-yl | —$CH_2C(CH_3)$=$CH$— | Thien-2-yl | 97–98 |
| A.480 | n-$C_3H_7$ | Tetrahydropyran-4-yl | —$CH_2C(CH_3)$=$CH$— | Thien-2-yl | 6.65(s, 1H), 6.90–7.30(2m, 3H), |
| A.481 | $C_2H_5$ | Tetrahydrothiopyran-3-yl | —$CH_2C(CH_3)$=$CH$— | Thien-2-yl | 88–90 |
| A.482 | n-$C_3H_7$ | Tetrahydrothiopyran-3-yl | —$CH_2C(CH_3)$=$CH$— | Thien-2-yl | 6.65(s, 1H), 6.90–7.80(2m, 3H), |
| A.483 | $C_2H_5$ | Tetrahydropyran-3-yl | —$CH_2C(CH_3)$=$CH$— | Thien-3-yl | 6.50(s, 1H), 7.00–7.40(m, 3H) |
| A.484 | n-$C_3H_7$ | Tetrahydropyran-3-yl | —$CH_2C(CH_3)$=$CH$— | Thien-3-yl | 6.50(s, 1H), 7.00–7.40(m, 3H) |
| A.485 | $C_2H_5$ | Tetrahydropyran-4-yl | —$CH_2C(CH_3)$=$CH$— | Thien-3-yl | 88–90 |
| A.486 | n-$C_3H_7$ | Tetrahydropyran-4-yl | —$CH_2C(CH_3)$=$CH$— | Thien-3-yl | 6.55(s, 1H), 7.00–7.40(m, 3H), |
| A.487 | $C_2H_5$ | Tetrahydrothiopyran-3-yl | —$CH_2C(CH_3)$=$CH$— | Thien-3-yl | 6.55(s, 1H), 7.00–7.40(m, 3H), |
| A.488 | n-$C_3H_7$ | Tetrahydrothiopyran-3-yl | —$CH_2C(CH_3)$=$CH$— | Thien-3-yl | 6.50(s, 1H), 7.00–7.40(m, 3H), |
| A.489 | $C_2H_5$ | Tetrahydropyran-3-yl | —$CH_2C(CH_3)$=$CH$— | 5-$CH_3$-thien-2-yl | 108–110 |

TABLE II.7-continued

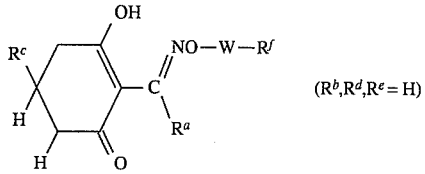

($R^b, R^d, R^e = H$)

| No. | $R^a$ | $R^c$ | W | $R^f$ | phys. data NMR data in ppm M.p. in °C. |
|---|---|---|---|---|---|
| A.490 | n-$C_3H_7$ | Tetrahydropyran-3-yl | —$CH_2C(CH_3)$=CH— | 5-$CH_3$-thien-2-yl | 6.60(s, 1H), 6.65–7.00(m, 2H) |
| A.491 | $C_2H_5$ | Tetrahydropyran-4-yl | —$CH_2C(CH_3)$=CH— | 5-$CH_3$-thien-2-yl | 111–112 |
| A.492 | n-$C_3H_7$ | Tetrahydropyran-4-yl | —$CH_2C(CH_3)$=CH— | 5-$CH_3$-thien-2-yl | 6.60(s, 1H), 6.65–7.00(m, 2H), |
| A.493 | $C_2H_5$ | Tetrahydrothiopyran-3-yl | —$CH_2C(CH_3)$=CH— | 5-$CH_3$-thien-2-yl | 119–120 |
| A.494 | n-$C_3H_7$ | Tetrahydrothiopyran-3-yl | —$CH_2C(CH_3)$=CH— | 5-$CH_3$-thien-2-yl | 6.55(s, 1H), 6.60–7.00(m, 2H), |
| A.495 | $C_2H_5$ | Tetrahydropyran-3-yl | —$CH_2C(CH_3)$=CH— | 5-Cl-thien-2-yl | 82–85 |
| A.496 | n-$C_3H_7$ | Tetrahydropyran-3-yl | —$CH_2C(CH_3)$=CH— | 5-Cl-thien-2-yl | 6.70(s, 1H), 6.90(m, 2H) |
| A.497 | $C_2H_5$ | Tetrahydropyran-4-yl | —$CH_2C(CH_3)$=CH— | 5-Cl-thien-2-yl | 124–126 |
| A.498 | n-$C_3H_7$ | Tetrahydropyran-4-yl | —$CH_2C(CH_3)$=CH— | 5-Cl-thien-2-yl | 97–98 |
| A.499 | $C_2H_5$ | Tetrahydrothiopyran-3-yl | —$CH_2C(CH_3)$=CH— | 5-Cl-thien-2-yl | 103–105 |
| A.500 | n-$C_3H_7$ | Tetrahydrothiopyran-3-yl | —$CH_2C(CH_3)$=CH— | 5-Cl-thien-2-yl | 6.65(s, 1H), 6.90(m, 2H), |
| A.501 | $C_2H_5$ | Tetrahydropyran-3-yl | —$(CH_2)_4$— | Furan-2-yl | 3.93(m, 2H), 4.07(m, 2H), 6.00(m, 1H), 6.26(m, 1H), 7.30(m, 1H) |
| A.502 | n-$C_3H_7$ | Tetrahydropyran-3-yl | —$(CH_2)_4$— | Furan-2-yl | 3.93(m, 2H), 4.07(m, 2H), 6.00(m, 1H), 6.26(m, 1H), 7.30(m, 1H) |
| A.503 | $C_2H_5$ | Tetrahydropyran-4-yl | —$(CH_2)_4$— | Furan-2-yl | 3.90–4.13(m, 4H), 6.00(m, 1H), 6.26(m, 1H), 7.30(m, 1H) |
| A.504 | n-$C_3H_7$ | Tetrahydropyran-4-yl | —$(CH_2)_4$— | Furan-2-yl | 3.90–4.13(m, 4H), 6.00(m, 1H), 6.26(m, 1H), 7.30(m, 1H) |
| A.505 | $C_2H_5$ | Tetrahydrothiopyran-3-yl | —$(CH_2)_4$— | Furan-2-yl | 4.05(m, 2H), 6.00(m, 1H) 6.26(m, 1H), 7.30(m, 1H) |
| A.506 | n-$C_3H_7$ | Tetrahydrothiopyran-3-yl | —$(CH_2)_4$— | Furan-2-yl | 4.05(m, 2H), 6.00(m, 1H) 6.26(m, 1H), 7.30(m, 1H) |
| A.507 | $C_2H_5$ | Tetrahydropyran-3-yl | —$(CH_2)_4$— | 5-$CH_3$-furan-2-yl | 62–64 |
| A.508 | n-$C_3H_7$ | Tetrahydropyran-3-yl | —$(CH_2)_4$— | 5-$CH_3$-furan-2-yl | 3.93(m, 2H), 4.07(m, 2H), 5.87(m, 2H) |
| A.509 | $C_2H_5$ | Tetrahydropyran-4-yl | —$(CH_2)_4$— | 5-$CH_3$-furan-2-yl | 76–78 |
| A.510 | n-$C_3H_7$ | Tetrahydropyran-4-yl | —$(CH_2)_4$— | 5-$CH_3$-furan-2-yl | 3.90–4.15(m, 4H), 5.87(m, 2H) |
| A.511 | $C_2H_5$ | Tetrahydrothiopyran-3-yl | —$(CH_2)_4$— | 5-$CH_3$-furan-2-yl | 4.07(m, 2H), 5.87(m, 2H) |
| A.512 | n-$C_3H_7$ | Tetrahydrothiopyran-3-yl | —$(CH_2)_4$— | 5-$CH_3$-furan-2-yl | 4.07(m, 2H), 5.87(m, 2H) |
| A.513 | $C_2H_5$ | Tetrahydropyran-3-yl | —$(CH_2)_4$— | Thien-2-yl | 3.80–4.15(m, 4H), 6.80(dd, 1H), 6.93(dd, 1H), 7.13(dd, 1H) |
| A.514 | n-$C_3H_7$ | Tetrahydropyran-3-yl | —$(CH_2)_4$— | Thien-2-yl | 3.80–4.15(m, 4H), 6.80(dd, 1H), 6.93(dd, 1H), 7.13(dd, 1H) |
| A.515 | $C_2H_5$ | Tetrahydropyran-4-yl | —$(CH_2)_4$— | Thien-2-yl | 3.90–4.23(m, 4H), 6.80(dd, 1H), 6.93(dd, 1H), 7.13(dd, 1H) |
| A.516 | n-$C_3H_7$ | Tetrahydropyran-4-yl | —$(CH_2)_4$— | Thien-2-yl | 3.90–4.23(m, 4H), 6.80(dd, 1H), 6.93(dd, 1H), 7.13(dd, 1H) |
| A.517 | $C_2H_5$ | Tetrahydrothiopyran-3-yl | —$(CH_2)_4$— | Thien-2-yl | 4.06(m, 2H), 6.80(dd, 1H), 6.93(dd, 1H), 7.13(dd, 1H) |
| A.518 | n-$C_3H_7$ | Tetrahydrothiopyran-3-yl | —$(CH_2)_4$— | Thien-2-yl | 4.06(m, 2H), 6.80(dd, 1H), 6.93(dd, 1H), 7.13(dd, 1H) |
| A.519 | $C_2H_5$ | Tetrahydropyran-3-yl | —$(CH_2)_4$— | 5-$CH_3$-thien-2-yl | 3.85–4.13(m, 4H), 6.53(s, 2H) |
| A.520 | n-$C_3H_7$ | Tetrahydropyran-3-yl | —$(CH_2)_4$— | 5-$CH_3$-thien-2-yl | 3.80–4.13(m, 4H), 6.53(s, 2H) |
| A.521 | $C_2H_5$ | Tetrahydropyran-4-yl | —$(CH_2)_4$— | 5-$CH_3$-thien-2-yl | 3.90–4.15(m, 4H), 6.50(s, 2H) |
| A.522 | n-$C_3H_7$ | Tetrahydropyran-4-yl | —$(CH_2)_4$— | 5-$CH_3$-thien-2-yl | 3.94–4.15(m, 4H), 6.53(s, 2H) |
| A.523 | $C_2H_5$ | Tetrahydrothiopyran-3-yl | —$(CH_2)_4$— | 5-$CH_3$-thien-2-yl | 4.08(m, 2H), 6.56(s, 2H) |
| A.524 | n-$C_3H_7$ | Tetrahydrothiopyran-3-yl | —$(CH_2)_4$— | 5-$CH_3$-thien-2-yl | 4.08(m, 2H), 6.56(s, 2H) |
| A.525 | $C_2H_5$ | Tetrahydropyran-3-yl | —$(CH_2)_4$— | 5-Cl-thien-2-yl | 3.93(m, 2H), 4.10(m, 2H), 6.53(d, 1H), 6.70(d, 1H) |
| A.526 | n-$C_3H_7$ | Tetrahydropyran-3-yl | —$(CH_2)_4$— | 5-Cl-thien-2-yl | 3.93(m, 2H), 4.10(m, 2H), 6.53(d, 1H), 6.70(d, 1H) |
| A.527 | $C_2H_5$ | Tetrahydropyran-4-yl | —$(CH_2)_4$— | 5-Cl-thien-2-yl | 3.90–4.10(m, 4H), 6.53(d, 1H) 6.70(d, 1H) |
| A.528 | n-$C_3H_7$ | Tetrahydropyran-4-yl | —$(CH_2)_4$— | 5-Cl-thien-2-yl | 3.90–4.10(m, 4H), 6.53(d, 1H) 6.70(d, 1H) |
| A.529 | $C_2H_5$ | Tetrahydrothiopyran-3-yl | —$(CH_2)_4$— | 5-Cl-thien-2-yl | 4.10(m, 2H), 6.53(d, 1H), 6.70(d, 1H) |
| A.530 | n-$C_3H_7$ | Tetrahydrothiopyran-3-yl | —$(CH_2)_4$— | 5-Cl-thien-2-yl | 4.10(m, 2H), 6.53(d, 1H), 6.70(d, 1H) |
| A.531 | $C_2H_5$ | Tetrahydropyran-3-yl | —$(CH_2)_4$— | 5-$C_2H_5$-thien-2-yl | 3.80–4.09(m, 4H), 6.60(s, 2H) |
| A.532 | n-$C_3H_7$ | Tetrahydropyran-3-yl | —$(CH_2)_4$— | 5-$C_2H_5$-thien-2-yl | 3.80–4.09(m, 4H), 6.60(s, 2H) |
| A.533 | $C_2H_5$ | Tetrahydropyran-4-yl | —$(CH_2)_4$— | 5-$C_2H_5$-thien-2-yl | 3.93–4.09(m, 4H), 6.60(s, 2H) |
| A.534 | n-$C_3H_7$ | Tetrahydropyran-4-yl | —$(CH_2)_4$— | 5-$C_2H_5$-thien-2-yl | 3.93–4.09(m, 4H), 6.60(s, 2H) |
| A.535 | $C_2H_5$ | Tetrahydrothiopyran-3-yl | —$(CH_2)_4$— | 5-$C_2H_5$-thien-2-yl | 4.03(m, 2H), 6.60(s, 2H) |
| A.536 | n-$C_3H_7$ | Tetrahydrothiopyran-3-yl | —$(CH_2)_4$— | 5-$C_2H_5$-thien-2-yl | 4.03(m, 2H), 6.60(s, 2H) |
| A.537 | $C_2H_5$ | Tetrahydropyran-3-yl | —$(CH_2)_4$— | 1-$CH_3$-pyrrol-2-yl | 64–66 |

TABLE II.7-continued

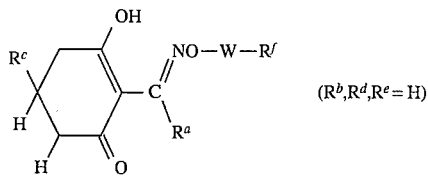

($R^b, R^d, R^e = H$)

| No. | $R^a$ | $R^c$ | W | $R^f$ | phys. data NMR data in ppm M.p. in °C. |
|---|---|---|---|---|---|
| A.538 | n-$C_3H_7$ | Tetrahydropyran-3-yl | —$(CH_2)_4$— | 1-$CH_3$-pyrrol-2-yl | 3.90(m, 2H), 4.09(t, 2H), 5.87(m, 1H), 6.03(m, 1H), 6.53(m, 1H) |
| A.539 | $C_2H_5$ | Tetrahydropyran-4-yl | —$(CH_2)_4$— | 1-$CH_3$-pyrrol-2-yl | 82–84 |
| A.540 | n-$C_3H_7$ | Tetrahydropyran-4-yl | —$(CH_2)_4$— | 1-$CH_3$-pyrrol-2-yl | 4.00(m, 22), 4.09(t, 2H), 5.87(m, 1H), 6.03(m, 1H), 6.53(m, 1H) |
| A.541 | $C_2H_5$ | Tetrahydrothiopyran-3-yl | —$(CH_2)_4$— | 1-$CH_3$-pyrrol-2-yl | 4.09(t, 2H), 5.87(m, 1H), 6.03(m, 1H), 6.53(m, 1H) |
| A.542 | n-$C_3H_7$ | Tetrahydrothiopyran-3-yl | —$(CH_2)_4$— | 1-$CH_3$-pyrrol-2-yl | 4.09(t, 2H), 5.87(m, 1H), 6.03(m, 1H), 6.53(m, 1H) |
| A.543 | $C_2H_5$ | Tetrahydropyran-4-yl | —$CH_2CH_2CH=CH$— | Furan-2-yl | 4.13(t, 2H), 6.00–6.42(m, 4H), 7.33(bs, 1H) |
| A.544 | $C_2H_5$ | Tetrahydropyran-3-yl | —$CH_2CH_2CH=CH$— | Furan-3-yl | 4.13(t, 2H), 5.92(m, 1H), 6.33(d, 1H), 6.55(bs, 1H), 7.40(d, 2H) |
| A.545 | $C_2H_5$ | Tetrahydropyran-4-yl | —$CH_2CH_2CH=CH$— | Furan-3-yl | 4.13(m, 2H), 5.92(m, 1H), 6.33(d, 1H), 6.55(s, 1H), 7.40(d, 2H) |
| A.546 | $C_2H_5$ | Tetrahydrothiopyran-3-yl | —$CH_2CH_2CH=CH$— | Furan-3-yl | 4.13(t, 2H), 5.92(m, 1H), 6.33(d, 1H), 6.55(bs, 1H), 7.40(d, 2H) |
| A.547 | $C_2H_5$ | Tetrahydropyran-3-yl | —$CH_2CH_2CH=CH$— | Thien-2-yl | 4.15(t, 2H), 6.00(dt, 1H), 6.60(d, 1H), 6.90(m, 2H), 7.10(d, 1H) |
| A.548 | n-$C_3H_7$ | Tetrahydropyran-3-yl | —$CH_2CH_2CH=CH$— | Thien-2-yl | 4.10(t, 2H), 6.00(dt, 1H), 6.60(d, 1H), 6.80–7.20(m, 3H) |
| A.549 | $C_2H_5$ | Tetrahydropyran-4-yl | —$CH_2CH_2CH=CH$— | Thien-2-yl | 4.15(t, 2H), 6.00(dt, 1H), 6.60(d, 1H), 6.80–7.20(m, 3H), |
| A.550 | n-$C_3H_7$ | Tetrahydropyran-4-yl | —$CH_2CH_2CH=CH$— | Thien-2-yl | 4.15(t, 2H), 6.00(dt, 1H), 6.60(d, 1H), 6.80–7.20(m, 3H), |
| A.551 | $C_2H_5$ | Tetrahydrothiopyran-3-yl | —$CH_2CH_2CH=CH$— | Thien-2-yl | 4.15(t, 2H), 6.00(dt, 1H), 6.60(d, 1H), 6.80–7.20(m, 3H), |
| A.552 | n-$C_3H_7$ | Tetrahydrothiopyran-3-yl | —$CH_2CH_2CH=CH$— | Thien-2-yl | 4.15(t, 2H), 6.00(dt, 1H), 6.60(d, 1H), 6.80–7.20(m, 3H) |
| A.553 | $C_2H_5$ | 2,4,6-Trimethylphenyl | —$CH_2CH_2CH=CH$— | Thien-2-yl | 4.20(t, 2H), 6.10(dt, 1H), 6.60(d, 1H), 6.80–7.20(m, 5H) |
| A.554 | $C_2H_5$ | Tetrahydropyran-3-yl | —$CH_2CH_2CH=CH$— | 5-$CH_3$-thien-2-yl | 4.13(t, 2H), 5.87(dt, 1H) 6.37–6.73(m, 3H) |
| A.555 | n-$C_3H_7$ | Tetrahydropyran-3-yl | —$CH_2CH_2CH=CH$— | 5-$CH_3$-thien-2-yl | 4.13(t, 2H), 5.87(dt, 1H) 6.37–6.73(m, 3H) |
| A.556 | $C_2H_5$ | Tetrahydropyran-4-yl | —$CH_2CH_2CH=CH$— | 5-$CH_3$-thien-2-yl | 4.13(t, 2H), 5.87(dt, 1H) 6.37–6.73(m, 3H) |
| A.557 | n-$C_3H_7$ | Tetrahydropyran-4-yl | —$CH_2CH_2CH=CH$— | 5-$CH_3$-thien-2-yl | 4.13(t, 2H), 5.87(dt, 1H) 6.37–6.73(m, 3H) |
| A.558 | $C_2H_5$ | Tetrahydrothiopyran-3-yl | —$CH_2CH_2CH=CH$— | 5-$CH_3$-thien-2-yl | 4.13(t, 2H), 5.88(dt, 1H) 6.37–6.73(m, 3H) |
| A.559 | n-$C_3H_7$ | Tetrahydrothiopyran-3-yl | —$CH_2CH_2CH=CH$— | 5-$CH_3$-thien-2-yl | 4.13(t, 2H), 5.88(dt, 1H) 6.37–6.73(m, 3H) |
| A.560 | $C_2H_5$ | Tetrahydropyran-3-yl | —$CH_2CH_2CH=CH$— | 5-Cl-thien-2-yl | 4.15(t, 2H), 5.93(dt, 1H), 6.46(d, 1H), 6.63(d, 1H), 6.75(d, 1H) |
| A.561 | n-$C_3H_7$ | Tetrahydropyran-3-yl | —$CH_2CH_2CH=CH$— | 5-Cl-thien-2-yl | 4.15(t, 2H), 5.93(dt, 1H), 6.46(d, 1H), 6.63(d, 1H), 6.75(d, 1H) |
| A.562 | $C_2H_5$ | Tetrahydropyran-4-yl | —$CH_2CH_2CH=CH$— | 5-Cl-thien-2-yl | 4.15(t, 2H), 5.93(dt, 1H), 6.46(d, 1H), 6.63(d, 1H), 6.75(d, 1H) |
| A.563 | n-$C_3H_7$ | Tetrahydropyran-4-yl | —$CH_2CH_2CH=CH$— | 5-Cl-thien-2-yl | 4.15(t, 2H), 5.93(dt, 1H), 6.46(d, 1H), 6.63(d, 1H), 6.75(d, 1H) |
| A.564 | $C_2H_5$ | Tetrahydrothiopyran-3-yl | —$CH_2CH_2CH=CH$— | 5-Cl-thien-2-yl | 4.15(t, 2H), 5.93(dt, 1H), 6.46(d, 1H), 6.63(d, 1H), 6.75(d, 1H) |
| A.565 | n-$C_3H_7$ | Tetrahydrothiopyran-3-yl | —$CH_2CH_2CH=CH$— | 5-Cl-thien-2-yl | 4.15(t, 2H), 5.93(dt, 1H), 6.46(d, 1H), 6.63(d, 1H), 6.75(d, 1H) |
| A.566 | $C_2H_5$ | Tetrahydropyran-3-yl | —$CH_2CH_2CH=CH$— | Thien-3-yl | 4.15(t, 2H), 6.07(dt, 1H), |

TABLE II.7-continued

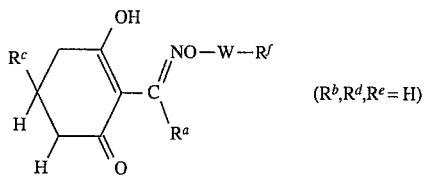

(R$^b$, R$^d$, R$^e$ = H)

| No. | R$^a$ | R$^c$ | W | R$^f$ | phys. data NMR data in ppm M.p. in °C. |
|---|---|---|---|---|---|
| A.567 | n-C$_3$H$_7$ | Tetrahydropyran-3-yl | —CH$_2$CH$_2$CH=CH— | Thien-3-yl | 6.50(d, 1H), 7.00–7.32(m, 3H) 4.15(t, 2H), 6.07(dt, 1H), |
| A.568 | C$_2$H$_5$ | Tetrahydropyran-4-yl | —CH$_2$CH$_2$CH=CH— | Thien-3-yl | 6.50(d, 1H), 7.00–7.32(m, 3H) 4.20(t, 2H), 6.07(dt, 1H), |
| A.569 | n-C$_3$H$_7$ | Tetrahydropyran-4-yl | —CH$_2$CH$_2$CH=CH— | Thien-3-yl | 6.50(d, 1H), 7.03–7.32(m, 3H) 4.20(t, 2H), 6.07(dt, 1H), |
| A.570 | C$_2$H$_5$ | Tetrahydrothiopyran-3-yl | —CH$_2$CH$_2$CH=CH— | Thien-3-yl | 6.50(d, 1H), 7.03–7.32(m, 3H) 4.17(t, 2H), 6.07(dt, 1H), |
| A.571 | n-C$_3$H$_7$ | Tetrahydrothiopyran-3-yl | —CH$_2$CH$_2$CH=CH— | Thien-3-yl | 6.50(d, 1H), 7.00–7.36(m, 3H) 4.17(t, 2H), 6.07(dt, 1H), |
| A.572 | C$_2$H$_5$ | Tetrahydropyran-3-yl | —CH$_2$CH$_2$CH=CH— | 2-Cl-thien-3-yl | 6.50(d, 1H), 7.00–7.36(m, 3H) 4.20(t, 2H), 6.10(dt, 1H), |
| A.573 | n-C$_3$H$_7$ | Tetrahydropyran-3-yl | —CH$_2$CH$_2$CH=CH— | 2-Cl-thien-3-yl | 6.52(d, 1H), 7.05(s, 2H), 4.20(t, 2H), 6.10(dt, 1H), |
| A.574 | C$_2$H$_5$ | Tetrahydropyran-4-yl | —CH$_2$CH$_2$CH=CH— | 2-Cl-thien-3-yl | 6.52(d, 1H), 7.05(s, 2H), 4.20(t, 2H), 6.13(dt, 1H), |
| A.575 | n-C$_3$H$_7$ | Tetrahydropyran-4-yl | —CH$_2$CH$_2$CH=CH— | 2-Cl-thien-3-yl | 6.52(d, 1H), 7.07(s, 2H), 4.20(t, 2H), 6.13(dt, 1H), |
| A.576 | C$_2$H$_5$ | Tetrahydrothiopyran-3-yl | —CH$_2$CH$_2$CH=CH— | 2-Cl-thien-3-yl | 6.52(d, 1H), 7.07(s, 2H), 4.20(t, 2H), 6.12(dt, 1H), |
| A.577 | n-C$_3$H$_7$ | Tetrahydrothiopyran-3-yl | —CH$_2$CH$_2$CH=CH— | 2-Cl-thien-3-yl | 6.53(d, 1H), 7.10(s, 2H), 4.20(t, 2H), 6.12(dt, 1H), |
| A.578 | C$_2$H$_5$ | Tetrahydropyran-3-yl | —CH$_2$CH$_2$CH=CH— | 5-Cl-thien-3-yl | 6.53(d, 1H), 7.10(s, 2H), 4.17(t, 2H), 6.00(dt, 1H), 6.33(d, 1H), 6.83(s, 1H), 7.03(s, 1H) |
| A.579 | n-C$_3$H$_7$ | Tetrahydropyran-3-yl | —CH$_2$CH$_2$CH=CH— | 5-Cl-thien-3-yl | 4.17(t, 2H), 6.00(dt, 1H), 6.33(d, 1H), 6.83(s, 1H), 7.03(s, 1H) |
| A.580 | C$_2$H$_5$ | Tetrahydropyran-4-yl | —CH$_2$CH$_2$CH=CH— | 5-Cl-thien-3-yl | 4.17(t, 2H), 6.00(dt, 1H), 6.33(d, 1H), 6.83(s, 1H), 7.03(s, 1H) |
| A.581 | n-C$_3$H$_7$ | Tetrahydropyran-4-yl | —CH$_2$CH$_2$CH=CH— | 5-Cl-thien-3-yl | 4.17(t, 2H), 6.00(dt, 1H), 6.33(d, 1H), 6.83(s, 1H), 7.03(s, 1H) |
| A.582 | C$_2$H$_5$ | Tetrahydrothiopyran-3-yl | —CH$_2$CH$_2$CH=CH— | 5-Cl-thien-3-yl | 4.20(t, 2H), 6.00(dt, 1H), 6.33(d, 1H), 6.83(s, 1H), 7.03(s, 1H) |
| A.583 | n-C$_3$H$_7$ | Tetrahydrothiopyran-3-yl | —CH$_2$CH$_2$CH=CH— | 5-Cl-thien-3-yl | 4.20(t, 2H), 6.00(dt, 1H), 6.33(d, 1H), 6.83(s, 1H), 7.03(s, 1H) |
| A.584 | C$_2$H$_5$ | Tetrahydropyran-3-yl | —CH$_2$CH$_2$CH=CH— | Thien-2-yl | 3.90(m, 2H), 6.90(m, 2H), 7.10(d, 1H) |
| A.585 | n-C$_3$H$_7$ | Tetrahydropyran-3-yl | —CH$_2$CH$_2$CH=CH— | Thien-2-yl | 3.90(m, 2H), 6.90(m, 2H), 7.10(d, 1H) |
| A.586 | C$_2$H$_5$ | Tetrahydropyran-4-yl | —CH$_2$CH$_2$CH=CH— | Thien-2-yl | |
| A.587 | n-C$_3$H$_7$ | Tetrahydropyran-4-yl | —CH$_2$CH$_2$CH=CH— | Thien-2-yl | |
| A.588 | C$_2$H$_5$ | Tetrahydrothiopyran-3-yl | —CH$_2$CH$_2$CH=CH— | Thien-3-yl | 6.90(m, 2H), 7.10(d, 1H) |
| A.589 | n-C$_3$H$_7$ | Tetrahydrothiopyran-3-yl | —CH$_2$CH$_2$CH=CH— | Thien-3-yl | 6.90(m, 2H), 7.10(d, 1H) |
| A.590 | C$_2$H$_5$ | Tetrahydropyran-3-yl | —(CH$_2$)$_5$— | Furan-2-yl | 5.93(m, 1H), 6.27(m, 1H), 7.27(m, 1H) |
| A.591 | n-C$_3$H$_7$ | Tetrahydropyran-3-yl | —(CH$_2$)$_5$— | Furan-2-yl | 5.93(m, 1H), 6.27(m, 1H), 7.27(m, 1H) |
| A.592 | C$_2$H$_5$ | Tetrahydropyran-4-yl | —(CH$_2$)$_5$— | Furan-2-yl | 5.90(m, 1H), 6.24(m, 1H), 7.24(m, 1H) |
| A.593 | n-C$_3$H$_7$ | Tetrahydropyran-4-yl | —(CH$_2$)$_5$— | Furan-2-yl | 50–53 |
| A.594 | C$_2$H$_5$ | Tetrahydrothiopyran-3-yl | —(CH$_2$)$_5$— | Furan-2-yl | 5.93(m, 1H), 6.27(m, 1H), 7.27(m, 1H) |
| A.595 | n-C$_3$H$_7$ | Tetrahydrothiopyran-3-yl | —(CH$_2$)$_5$— | Furan-2-yl | 5.93(m, 1H), 6.27(m, 1H), 7.27(m, 1H) |
| A.596 | C$_2$H$_5$ | Tetrahydropyran-3-yl | —(CH$_2$)$_5$— | Thien-2-yl | 43–45 |
| A.597 | n-C$_3$H$_7$ | Tetrahydropyran-3-yl | —(CH$_2$)$_5$— | Thien-2-yl | 73–75 |
| A.598 | C$_2$H$_5$ | Tetrahydropyran-4-yl | —(CH$_2$)$_5$— | Thien-2-yl | 91–93 |
| A.599 | n-C$_3$H$_7$ | Tetrahydropyran-4-yl | —(CH$_2$)$_5$— | Thien-2-yl | 74–75 |
| A.600 | C$_2$H$_5$ | Tetrahydrothiopyran-3-yl | —(CH$_2$)$_5$— | Thien-2-yl | 4.07(t, 2H), 6.80(m, 1H), 6.90(m, 1H), 7.10(m, 1H) |

TABLE II.7-continued $$\text{(structure shown)} \quad (R^b, R^d, R^e = H)$$

| No. | $R^a$ | $R^c$ | W | $R^f$ | phys. data NMR data in ppm M.p. in °C. |
|---|---|---|---|---|---|
| A.601 | n-$C_3H_7$ | Tetrahydrothiopyran-3-yl | —$(CH_2)_5$— | Thien-2-yl | 4.07(t, 2H), 6.80(m, 1H), 6.90(m, 1H), 7.10(m, 1H) |
| A.602 | $C_2H_5$ | Tetrahydropyran-3-yl | —$(CH_2)_5$— | 1-$CH_3$-pyrrol-2-yl | 3.90(m, 2H), 4.12(t, 2H), 5.90(m, 1H), 6.06(m, 1H), 6.53(m, 1H) |
| A.603 | n-$C_3H_7$ | Tetrahydropyran-3-yl | —$(CH_2)_5$— | 1-$CH_3$-pyrrol-2-yl | 3.90(m, 2H), 4.12(t, 2H), 5.90(m, 1H), 6.06(m, 1H), 6.53(m, 1H) |
| A.604 | $C_2H_5$ | Tetrahydropyran-4-yl | —$(CH_2)_5$— | 1-$CH_3$-pyrrol-2-yl | 4.00(m, 2H), 4.12(t, 2H), 5.90(m, 1H), 6.06(m, 1H), 6.53(m, 1H) |
| A.605 | n-$C_3H_7$ | Tetrahydropyran-4-yl | —$(CH_2)_5$— | 1-$CH_3$-pyrrol-2-yl | 4.00(m, 2H), 4.12(t, 2H), 5.90(m, 1H), 6.06(m, 1H), 6.53(m, 1H) |
| A.606 | $C_2H_5$ | Tetrahydrothiopyran-3-yl | —$(CH_2)_5$— | 1-$CH_3$-pyrrol-2-yl | 4.12(t, 2H), 5.90(m, 1H), 6.06(m, 1H), 6.53(m, 1H) |
| A.607 | n-$C_3H_7$ | Tetrahydrothiopyran-3-yl | —$(CH_2)_5$— | 1-$CH_3$-pyrrol-2-yl | 4.12(t, 2H), 5.90(m, 1H), 6.06(m, 1H), 6.53(m, 1H) |
| A.608 | $C_2H_5$ | Tetrahydropyran-3-yl | —$(CH_2)_6$— | Furan-2-yl | 5.90(m, 1H), 6.27(m, 1H), 7.27(m, 1H) |
| A.609 | n-$C_3H_7$ | Tetrahydropyran-3-yl | —$(CH_2)_6$— | Furan-2-yl | 5.90(m, 1H), 6.27(m, 1H), 7.27(m, 1H) |
| A.610 | $C_2H_5$ | Tetrahydropyran-4-yl | —$(CH_2)_6$— | Furan-2-yl | 5.93(m, 1H), 6.27(m, 1H), 7.27(m, 1H) |
| A.611 | n-$C_3H_7$ | Tetrahydropyran-4-yl | —$(CH_2)_6$— | Furan-2-yl | 5.93(m, 1H), 6.27(m, 1H), 7.27(m, 1H) |
| A.612 | $C_2H_5$ | Tetrahydrothiopyran-3-yl | —$(CH_2)_6$— | Furan-2-yl | 5.93(m, 1H), 6.27(m, 1H), 7.27(m, 1H) |
| A.613 | n-$C_3H_7$ | Tetrahydrothiopyran-3-yl | —$(CH_2)_6$— | Furan-2-yl | 5.93(m, 1H), 6.27(m, 1H), 7.27(m, 1H) |
| A.614 | $C_2H_5$ | Tetrahydropyran-3-yl | —$(CH_2)_6$— | Thien-2-yl | 6.77(m, 1H), 6.90(m, 1H), 7.10(m, 1H) |
| A.615 | n-$C_3H_7$ | Tetrahydropyran-3-yl | —$(CH_2)_6$— | Thien-2-yl | 6.77(m, 1H), 6.90(m, 1H), 7.10(m, 1H) |
| A.616 | $C_2H_5$ | Tetrahydropyran-4-yl | —$(CH_2)_6$— | Thien-2-yl | 50–52 |
| A.617 | n-$C_3H_7$ | Tetrahydropyran-4-yl | —$(CH_2)_6$— | Thien-2-yl | 6.80(m, 1H), 6.90(m, 1H), 7.10(m, 1H) |
| A.618 | $C_2H_5$ | Tetrahydrothiopyran-3-yl | —$(CH_2)_6$— | Thien-2-yl | 6.80(m, 1H), 6.90(m, 1H), 7.10(m, 1H) |
| A.619 | n-$C_3H_7$ | Tetrahydrothiopyran-3-yl | —$(CH_2)_6$— | Thien-2-yl | 6.80(m, 1H), 6.90(m, 1H), 7.10(m, 1H) |
| A.620 | $C_2H_5$ | Tetrahydropyran-3-yl | —$(CH_2)_6$— | 1-$CH_3$-pyrrol-2-yl | 5.90(m, 1H), 6.06(m, 1H), 6.53(m, 1H) |
| A.621 | n-$C_3H_7$ | Tetrahydropyran-3-yl | —$(CH_2)_6$— | 1-$CH_3$-pyrrol-2-yl | 5.90(m, 1H), 6.06(m, 1H), 6.53(m, 1H) |
| A.622 | $C_2H_5$ | Tetrahydropyran-4-yl | —$(CH_2)_6$— | 1-$CH_3$-pyrrol-2-yl | 5.87(m, 1H), 6.06(m, 1H), 6.53(m, 1H) |
| A.623 | n-$C_3H_7$ | Tetrahydropyran-4-yl | —$(CH_2)_6$— | 1-$CH_3$-pyrrol-2-yl | 5.87(m, 1H), 6.06(m, 1H), 6.53(m, 1H) |
| A.624 | $C_2H_5$ | Tetrahydrothiopyran-3-yl | —$(CH_2)_6$— | 1-$CH_3$-pyrrol-2-yl | 5.90(m, 1H), 6.06(m, 1H), 6.50(m, 1H) |
| A.625 | n-$C_3H_7$ | Tetrahydrothiopyran-3-yl | —$(CH_2)_6$— | 1-$CH_3$-pyrrol-2-yl | 5.90(m, 1H), 6.06(m, 1H), 6.50(m, 1H) |
| A.626 | $C_2H_5$ | Tetrahydropyran-3-yl | —$CH_2CH_2$—O— | Phenyl | 42–45 |
| A.627 | n-$C_3H_7$ | Tetrahydropyran-3-yl | —$CH_2CH_2$—O— | Phenyl | 3.90(m, 2H), 4.20(t, 2H), 4.40(m, 2H), 6.80–7.00(m, 3H), 7.13–7.37(m, 2H) |
| A.628 | $C_2H_5$ | Tetrahydropyran-4-yl | —$CH_2CH_2$—O— | Phenyl | 106–107 |
| A.629 | n-$C_3H_7$ | Tetrahydropyran-4-yl | —$CH_2CH_2$—O— | Phenyl | 72–73 |
| A.630 | $C_2H_5$ | Tetrahydrothiopyran-3-yl | —$CH_2CH_2$—O— | Phenyl | 52–55 |
| A.631 | n-$C_3H_7$ | Tetrahydrothiopyran-3-yl | —$CH_2CH_2$—O— | Phenyl | 92 |
| A.632 | $C_2H_5$ | Tetrahydropyran-3-yl | —$CH_2CH_2$—O— | 2-F-phenyl | 76–78 |
| A.633 | n-$C_3H_7$ | Tetrahydropyran-3-yl | —$CH_2CH_2$—O— | 2-F-phenyl | 72–77 |
| A.634 | $C_2H_5$ | Tetrahydropyran-4-yl | —$CH_2CH_2$—O— | 2-F-phenyl | 121–125 |
| A.635 | n-$C_3H_7$ | Tetrahydropyran-4-yl | —$CH_2CH_2$—O— | 2-F-phenyl | 103–107 |
| A.636 | $C_2H_5$ | Tetrahydrothiopyran-3-yl | —$CH_2CH_2$—O— | 2-F-phenyl | 82–86 |
| A.637 | n-$C_3H_7$ | Tetrahydrothiopyran-3-yl | —$CH_2CH_2$—O— | 2-F-phenyl | 81–85 |
| A.638 | $C_2H_5$ | Tetrahydropyran-3-yl | —$CH_2CH_2$—O— | 3-F-phenyl | 62–68 |
| A.639 | n-$C_3H_7$ | Tetrahydropyran-3-yl | —$CH_2CH_2$—O— | 3-F-phenyl | 3.90(m, 2H), 4.20(t, 2H), 4.40(m, 2H) 6.70(m, 3H), 7.25(m, 1H), |
| A.640 | $C_2H_5$ | Tetrahydropyran-4-yl | —$CH_2CH_2$—O— | 3-F-phenyl | 103–109 |
| A.641 | n-$C_3H_7$ | Tetrahydropyran-4-yl | —$CH_2CH_2$—O— | 3-F-phenyl | 73–79 |
| A.642 | $C_2H_5$ | Tetrahydrothiopyran-3-yl | —$CH_2CH_2$—O— | 3-F-phenyl | 4.20(t, 2H), 4.40(m, 2H), 6.70(m, 3H), 7.25(m, 1H) |
| A.643 | n-$C_3H_7$ | Tetrahydrothiopyran-3-yl | —$CH_2CH_2$—O— | 3-F-phenyl | |
| A.644 | $C_2H_5$ | Tetrahydropyran-3-yl | —$CH_2CH_2$—O— | 4-F-phenyl | 64–67 |
| A.645 | n-$C_3H_7$ | Tetrahydropyran-3-yl | —$CH_2CH_2$—O— | 4-F-phenyl | 70–72 |
| A.646 | $C_2H_5$ | Tetrahydropyran-4-yl | —$CH_2CH_2$—O— | 4-F-phenyl | 101–103 |
| A.647 | n-$C_3H_7$ | Tetrahydropyran-4-yl | —$CH_2CH_2$—O— | 4-F-phenyl | 107–109 |
| A.648 | $C_2H_5$ | Tetrahydrothiopyran-3-yl | —$CH_2CH_2$—O— | 4-F-phenyl | 105–108 |
| A.649 | n-$C_3H_7$ | Tetrahydrothiopyran-3-yl | —$CH_2CH_2$—O— | 4-F-phenyl | 82–84 |
| A.650 | $C_2H_5$ | Tetrahydropyran-3-yl | —$CH_2CH_2$—O— | 2-Cl-phenyl | 74–80 |
| A.651 | n-$C_3H_7$ | Tetrahydropyran-3-yl | —$CH_2CH_2$—O— | 2-Cl-phenyl | 67–71 |
| A.652 | $C_2H_5$ | Tetrahydropyran-4-yl | —$CH_2CH_2$—O— | 2-Cl-phenyl | 4.00(m, 2H), 4.27(t, 2H), 4.47(m, 2H), 7.20(t, 1H), 7.37(d, 1H) |
| A.653 | n-$C_3H_7$ | Tetrahydropyran-4-yl | —$CH_2CH_2$—O— | 2-Cl-phenyl | 68–72 |
| A.654 | $C_2H_7$ | Tetrahydrothiopyran-3-yl | —$CH_2CH_2$—O— | 2-Cl-phenyl | 74–78 |
| A.655 | n-$C_3H_7$ | Tetrahydrothiopyran-3-yl | —$CH_2CH_2$—O— | 2-Cl-phenyl | 72–78 |

TABLE II.7-continued $(R^b, R^d, R^e = H)$

| No. | $R^a$ | $R^c$ | W | $R^f$ | phys. data NMR data in ppm M.p. in °C. |
|---|---|---|---|---|---|
| A.656 | $C_2H_5$ | Tetrahydropyran-3-yl | $-CH_2CH_2-O-$ | 3-Cl-phenyl | |
| A.657 | n-$C_3H_7$ | Tetrahydropyran-3-yl | $-CH_2CH_2-O-$ | 3-Cl-phenyl | |
| A.658 | $C_2H_5$ | Tetrahydropyran-4-yl | $-CH_2CH_2-O-$ | 3-Cl-phenyl | |
| A.659 | n-$C_3H_7$ | Tetrahydropyran-4-yl | $-CH_2CH_2-O-$ | 3-Cl-phenyl | |
| A.660 | $C_2H_5$ | Tetrahydrothiopyran-3-yl | $-CH_2CH_2-O-$ | 3-Cl-phenyl | |
| A.661 | n-$C_3H_7$ | Tetrahydrothiopyran-3-yl | $-CH_2CH_2-O-$ | 3-Cl-phenyl | |
| A.662 | $C_2H_5$ | Tetrahydropyran-3-yl | $-CH_2CH_2-O-$ | 4-Cl-phenyl | 3.93(m, 2H), 4.20(t, 2H), 4.43(m, 2H), 6.90(m, 2H), 7.25(m, 2H) |
| A.663 | n-$C_3H_7$ | Tetrahydropyran-3-yl | $-CH_2CH_2-O-$ | 4-Cl-phenyl | 3.93(m, 2H), 4.20(t, 2H), 4.43(m, 2H), 6.90(m, 2H), 7.25(m, 2H) |
| A.664 | $C_2H_5$ | Tetrahydropyran-4-yl | $-CH_2CH_2-O-$ | 4-Cl-phenyl | 116–118 |
| A.665 | n-$C_3H_7$ | Tetrahydropyran-4-yl | $-CH_2CH_2-O-$ | 4-Cl-phenyl | 104–106 |
| A.666 | $C_2H_5$ | Tetrahydrothiopyran-3-yl | $-CH_2CH_2-O-$ | 4-Cl-phenyl | 74–77 |
| A.667 | n-$C_3H_7$ | Tetrahydrothiopyran-3-yl | $-CH_2CH_2-O-$ | 4-Cl-phenyl | 86–88 |
| A.668 | $C_2H_5$ | Tetrahydropyran-3-yl | $-CH_2CH_2-O-$ | 2-$CF_3$-phenyl | |
| A.669 | n-$C_3H_7$ | Tetrahydropyran-3-yl | $-CH_2CH_2-O-$ | 2-$CF_3$-phenyl | |
| A.670 | $C_2H_5$ | Tetrahydropyran-4-yl | $-CH_2CH_2-O-$ | 2-$CF_3$-phenyl | |
| A.671 | n-$C_3H_7$ | Tetrahydropyran-4-yl | $-CH_2CH_2-O-$ | 2-$CF_3$-phenyl | |
| A.672 | $C_2H_5$ | Tetrahydrothiopyran-3-yl | $-CH_2CH_2-O-$ | 2-$CF_3$-phenyl | |
| A.673 | n-$C_3H_7$ | Tetrahydrothiopyran-3-yl | $-CH_2CH_2-O-$ | 2-$CF_3$-phenyl | |
| A.674 | $C_2H_5$ | Tetrahydropyran-3-yl | $-CH_2CH_2-O-$ | 3-$CF_3$-phenyl | |
| A.675 | n-$C_3H_7$ | Tetrahydropyran-3-yl | $-CH_2CH_2-O-$ | 3-$CF_3$-phenyl | |
| A.676 | $C_2H_5$ | Tetrahydropyran-4-yl | $-CH_2CH_2-O-$ | 3-$CF_3$-phenyl | |
| A.677 | n-$C_3H_7$ | Tetrahydropyran-4-yl | $-CH_2CH_2-O-$ | 3-$CF_3$-phenyl | |
| A.678 | $C_2H_5$ | Tetrahydrothiopyran-3-yl | $-CH_2CH_2-O-$ | 3-$CF_3$-phenyl | |
| A.679 | n-$C_3H_7$ | Tetrahydrothiopyran-3-yl | $-CH_2CH_2-O-$ | 3-$CF_3$-phenyl | |
| A.680 | $C_2H_5$ | Tetrahydropyran-3-yl | $-CH_2CH_2-O-$ | 4-$CF_3$-phenyl | 72–77 |
| A.681 | n-$C_3H_7$ | Tetrahydropyran-3-yl | $-CH_2CH_2-O-$ | 4-$CF_3$-phenyl | 3.90(m, 2H), 4.27(t, 2H), 4.47(m, 2H) 7.00(d, 2H), 7.55(d, 2H) |
| A.682 | $C_2H_5$ | Tetrahydropyran-4-yl | $-CH_2CH_2-O-$ | 4-$CF_3$-phenyl | |
| A.683 | n-$C_3H_7$ | Tetrahydropyran-4-yl | $-CH_2CH_2-O-$ | 4-$CF_3$-phenyl | 90–94 |
| A.684 | $C_2H_5$ | Tetrahydrothiopyran-3-yl | $-CH_2CH_2-O-$ | 4-$CF_3$-phenyl | 73–79 |
| A.685 | n-$C_3H_7$ | Tetrahydrothiopyran-3-yl | $-CH_2CH_2-O-$ | 4-$CF_3$-phenyl | 4.27(t, 2H), 4.47(m, 2H), 7.00(d, 2H) 7.55(d, 2H) |
| A.686 | $C_2H_5$ | Tetrahydropyran-3-yl | $-CH_2CH_2-O-$ | 2,4-$Cl_2$-phenyl | 73–75 |
| A.687 | n-$C_3H_7$ | Tetrahydropyran-3-yl | $-CH_2CH_2-O-$ | 2,4-$Cl_2$-phenyl | 69–73 |
| A.688 | $C_2H_5$ | Tetrahydropyran-4-yl | $-CH_2CH_2-O-$ | 2,4-$Cl_2$-phenyl | 4.00(m, 2H), 4.25(t, 2H), 4.45(t, 2H) 6.87(d, 1H), 7.17(d, 1H), 7.37(d, 1H) |
| A.689 | n-$C_3H_7$ | Tetrahydropyran-4-yl | $-CH_2CH_2-O-$ | 2,4-$Cl_2$-phenyl | 4.00(m, 2H), 4.25(t, 2H), 4.45(t, 2H) 6.87(d, 1H), 7.17(d, 1H), 7.37(d, 1H) |
| A.690 | $C_2H_5$ | Tetrahydrothiopyran-3-yl | $-CH_2CH_2-O-$ | 2,4-$Cl_2$-phenyl | 4.25(t, 2H), 4.45(t, 2H), 6.87(d, 1H) 7.17(d, 1H), 7.37(d, 1H) |
| A.691 | n-$C_3H_7$ | Tetrahydrothiopyran-3-yl | $-CH_2CH_2-O-$ | 2,4-$Cl_2$-phenyl | 4.25(t, 2H), 4.45(t, 2H), 6.87(d, 1H), 7.17(d, 1H), 7.37(d, 1H) |
| A.692 | $C_2H_5$ | Tetrahydropyran-3-yl | $-CH_2CH_2-O-$ | 2,4,6-$Cl_3$-phenyl | 90–93 |
| A.693 | n-$C_3H_7$ | Tetrahydropyran-3-yl | $-CH_2CH_2-O-$ | 2,4,6-$Cl_3$-phenyl | 83–87 |
| A.694 | $C_2H_5$ | Tetrahydropyran-4-yl | $-CH_2CH_2-O-$ | 2,4,6-$Cl_3$-phenyl | 79–82 |
| A.695 | n-$C_3H_7$ | Tetrahydropyran-4-yl | $-CH_2CH_2-O-$ | 2,4,6-$Cl_3$-phenyl | 4.00(m, 2H), 4.27(t, 2H), 4.45(m, 2H), 7.32(s, 2H) |
| A.696 | $C_2H_5$ | Tetrahydrothiopyran-3-yl | $-CH_2CH_2-O-$ | 2,4,6-$Cl_3$-phenyl | 105–108 |
| A.697 | n-$C_3H_7$ | Tetrahydrothiopyran-3-yl | $-CH_2CH_2-O-$ | 2,4,6-$Cl_3$-phenyl | 4.27(t, 2H), 4.45(m, 2H), 7.82(s, 2H) |
| A.698 | $C_2H_5$ | Tetrahydropyran-3-yl | $-CH_2CH_2-O-$ | 4-$NO_2$-phenyl | 3.90(m, 2H), 4.32(m, 2H), 4.50(m, 2H), 7.00(d, 2H), 8.20(d, 2H) |
| A.699 | n-$C_3H_7$ | Tetrahydropyran-3-yl | $-CH_2CH_2-O-$ | 4-$NO_2$-phenyl | 3.90(m, 2H), 4.32(m, 2H), 4.50(m, 2H) 7.00(d, 2H), 8.20(d, 2H) |
| A.700 | $C_2H_5$ | Tetrahydropyran-4-yl | $-CH_2CH_2-O-$ | 4-$NO_2$-phenyl | 126–129 |
| A.701 | n-$C_3H_7$ | Tetrahydropyran-4-yl | $-CH_2CH_2-O-$ | 4-$NO_2$-phenyl | 138–141 |
| A.702 | $C_2H_5$ | Tetrahydrothiopyran-3-yl | $-CH_2CH_2-O-$ | 4-$NO_2$-phenyl | 4.32(m, 2H), 4.50(m, 2H), 7.00(d, 2H), 8.20(d, 2H) |
| A.703 | n-$C_3H_7$ | Tetrahydrothiopyran-3-yl | $-CH_2CH_2-O-$ | 4-$NO_2$-phenyl | 4.32(m, 2H), 4.50(m, 2H), 7.00(d, 2H), 8.20(d, 2H) |
| A.704 | $C_2H_5$ | Tetrahydropyran-3-yl | $-CH_2CH(CH_3)-O-$ | Phenyl | |
| A.705 | n-$C_3H_7$ | Tetrahydropyran-3-yl | $-CH_2CH(CH_3)-O-$ | Phenyl | |
| A.706 | $C_2H_5$ | Tetrahydropyran-4-yl | $-CH_2CH(CH_3)-O-$ | Phenyl | |
| A.707 | n-$C_3H_7$ | Tetrahydropyran-4-yl | $-CH_2CH(CH_3)-O-$ | Phenyl | |
| A.708 | $C_2H_5$ | Tetrahydrothiopyran-3-yl | $-CH_2CH(CH_3)-O-$ | Phenyl | |

TABLE II.7-continued

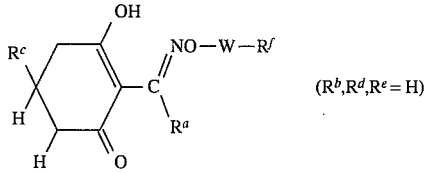

($R^b, R^d, R^e = H$)

| No. | $R^a$ | $R^c$ | W | $R^f$ | phys. data NMR data in ppm M.p. in °C. |
|---|---|---|---|---|---|
| A.709 | n-$C_3H_7$ | Tetrahydrothiopyran-3-yl | —$CH_2CH(CH_3)$—O— | Phenyl | |
| A.710 | $C_2H_5$ | Tetrahydropyran-3-yl | —$CH_2CH(CH_3)$—O— | 4-F-phenyl | |
| A.711 | n-$C_3H_7$ | Tetrahydropyran-3-yl | —$CH_2CH(CH_3)$—O— | 4-F-phenyl | |
| A.712 | $C_2H_5$ | Tetrahydropyran-4-yl | —$CH_2CH(CH_3)$—O— | 4-F-phenyl | |
| A.713 | n-$C_3H_7$ | Tetrahydropyran-4-yl | —$CH_2CH(CH_3)$—O— | 4-F-phenyl | |
| A.714 | $C_2H_5$ | Tetrahydrothiopyran-3-yl | —$CH_2CH(CH_3)$—O— | 4-F-phenyl | |
| A.715 | n-$C_3H_7$ | Tetrahydrothiopyran-3-yl | —$CH_2CH(CH_3)$—O— | 4-F-phenyl | |
| A.716 | $C_2H_5$ | Tetrahydropyran-3-yl | —$CH_2CH(CH_3)$—O— | 4-Cl-phenyl | |
| A.717 | n-$C_3H_7$ | Tetrahydropyran-3-yl | —$CH_2CH(CH_3)$—O— | 4-Cl-phenyl | |
| A.718 | $C_2H_5$ | Tetrahydropyran-4-yl | —$CH_2CH(CH_3)$—O— | 4-Cl-phenyl | 1.35(m, 3H), 4.05–4.30(m, 2H), 4.60(m, 1H), 6.80–7.40(m, 4H) |
| A.719 | n-$C_3H_7$ | Tetrahydropyran-4-yl | —$CH_2CH(CH_3)$—O— | 4-Cl-phenyl | 1.35(m, 3H), 4.05–4.30(m, 2H), 4.60(m, 1H), 6.80–7.40(m, 4H) |
| A.720 | $C_2H_5$ | Tetrahydrothiopyran-3-yl | —$CH_2CH(CH_3)$—O— | 4-Cl-phenyl | 1.35(m, 3H), 4.05–4.25(m, 2H), 4.60(m, 1H), 6.80–7.40(m, 4H) |
| A.721 | n-$C_3H_7$ | Tetrahydrothiopyran-3-yl | —$CH_2CH(CH_3)$—O— | 4-Cl-phenyl | 1.35(m, 3H), 4.05–4.30(m, 2H), 4.60(m, 1H), 6.80–7.40(m, 4H) |
| A.722 | $C_2H_5$ | Tetrahydropyran-3-yl | —$CH_2CH_2$—S— | Phenyl | 3.90(m, 2H), 4.23(t, 2H), 7.17–7.43(m, 5H) |
| A.723 | n-$C_3H_7$ | Tetrahydropyran-3-yl | —$CH_2CH_2$—S— | Phenyl | 65 |
| A.724 | $C_2H_5$ | Tetrahydropyran-4-yl | —$CH_2CH_2$—S— | Phenyl | 3.97(m, 2H), 4.23(t, 2H), 7.17–7.43(m, 5H) |
| A.725 | n-$C_3H_7$ | Tetrahydropyran-4-yl | —$CH_2CH_2$—S— | Phenyl | 3.97(m, 2H), 4.23(t, 2H), 7.17–7.43(m, 5H) |
| A.726 | $C_2H_5$ | Tetrahydrothiopyran-3-yl | —$CH_2CH_2$—S— | Phenyl | 4.23(t, 2H), 7.17–7.43(m, 5H) |
| A.727 | n-$C_3H_7$ | Tetrahydrothiopyran-3-yl | —$CH_2CH_2$—S— | Phenyl | 4.23(t, 2H), 7.17–7.43(m, 5H) |
| A.728 | $C_2H_5$ | Tetrahydropyran-3-yl | —$CH_2CH_2$—S— | 4-F-phenyl | 3.90(m, 2H), 4.17(t, 2H), 7.00(m, 2H), 7.40(m, 2H) |
| A.729 | n-$C_3H_7$ | Tetrahydropyran-3-yl | —$CH_2CH_2$—S— | 4-F-phenyl | 3.90(m, 2H), 4.17(t, 2H), 7.00(m, 2H), 7.40(m, 2H) |
| A.730 | $C_2H_5$ | Tetrahydropyran-4-yl | —$CH_2CH_2$—S— | 4-F-phenyl | 4.00(m, 2H), 4.17(t, 2H), 7.00(m, 2H), 7.40(m, 2H) |
| A.731 | n-$C_3H_7$ | Tetrahydropyran-4-yl | —$CH_2CH_2$—S— | 4-F-phenyl | 4.00(m, 2H), 4.17(t, 2H), 7.00(m, 2H), 7.40(m, 2H) |
| A.732 | $C_2H_5$ | Tetrahydrothiopyran-3-yl | —$CH_2CH_2$—S— | 4-F-phenyl | 4.17(t, 2H), 7.00(m, 2H), 7.40(m, 2H), |
| A.733 | n-$C_3H_7$ | Tetrahydrothiopyran-3-yl | —$CH_2CH_2$—S— | 4-F-phenyl | 4.17(t, 2H), 7.00(m, 2H), 7.40(m, 2H), |
| A.734 | $C_2H_5$ | Tetrahydropyran-3-yl | —$CH_2CH_2$—S— | 4-Cl-phenyl | 71–75 |
| A.735 | n-$C_3H_7$ | Tetrahydropyran-3-yl | —$CH_2CH_2$—S— | 4-Cl-phenyl | 63–65 |
| A.736 | $C_2H_5$ | Tetrahydropyran-4-yl | —$CH_2CH_2$—S— | 4-Cl-phenyl | 4.00(m, 2H), 4.20(t, 2H), 7.30(m, 4H) |
| A.737 | n-$C_3H_7$ | Tetrahydropyran-4-yl | —$CH_2CH_2$—S— | 4-Cl-phenyl | 4.00(m, 2H), 4.20(t, 2H), 7.30(m, 4H) |
| A.738 | $C_2H_5$ | Tetrahydrothiopyran-3-yl | —$CH_2CH_2$—S— | 4-Cl-phenyl | 4.20(t, 2H), 7.30(m, 4H) |
| A.739 | n-$C_3H_7$ | Tetrahydrothiopyran-3-yl | —$CH_2CH_2$—S— | 4-Cl-phenyl | 4.20(t, 2H), 7.30(m, 4H) |
| A.740 | $C_2H_5$ | Tetrahydropyran-3-yl | —$CH_2CH_2$—S— | 2-Cl-phenyl | 3.90(m, 2H), 4.25(t, 2H), 7.10–7.50(m, 4H) |
| A.741 | n-$C_3H_7$ | Tetrahydropyran-3-yl | —$CH_2CH_2$—S— | 2-Cl-phenyl | 3.90(m, 2H), 4.25(t, 2H), 7.10–7.50(m, 4H) |
| A.742 | $C_2H_5$ | Tetrahydropyran-4-yl | —$CH_2CH_2$—S— | 2-Cl-phenyl | 4.00(m, 2H), 4.25(t, 2H), 7.10–7.50(m, 4H) |
| A.743 | n-$C_3H_7$ | Tetrahydropyran-4-yl | —$CH_2CH_2$—S— | 2-Cl-phenyl | 4.00(m, 2H), 4.25(t, 2H), 7.10–7.50(m, 4H) |
| A.744 | $C_2H_5$ | Tetrahydrothiopyran-3-yl | —$CH_2CH_2$—S— | 2-Cl-phenyl | 4.25(t, 2H), 7.10–7.50(m, 4H) |
| A.745 | n-$C_3H_7$ | Tetrahydrothiopyran-3-yl | —$CH_2CH_2$—S— | 2-Cl-phenyl | 4.25(t, 2H), 7.10–7.50(m, 4H) |
| A.746 | $C_2H_5$ | Tetrahydropyran-3-yl | —$CH_2CH_2$—S— | 2,6-$Cl_2$-phenyl | 3.90(m, 2H) 4.20(t, 2H), 7.20(t, 1H) 7.40(d, 2H) |
| A.747 | n-$C_3H_7$ | Tetrahydropyran-3-yl | —$CH_2CH_2$—S— | 2,6-$Cl_2$-phenyl | 3.90(m, 2H) 4.20(t, 2H), 7.20(t, 1H) 7.40(d, 2H) |
| A.748 | $C_2H_5$ | Tetrahydropyran-4-yl | —$CH_2CH_2$—S— | 2,6-$Cl_2$-phenyl | 61–64 |
| A.749 | n-$C_3H_7$ | Tetrahydropyran-4-yl | —$CH_2CH_2$—S— | 2,6-$Cl_2$-phenyl | 4.00(m, 2H) 4.20(t, 2H), 7.20(t, 1H) 7.40(d, 2H) |
| A.750 | $C_2H_5$ | Tetrahydrothiopyran-3-yl | —$CH_2CH_2$—S— | 2,6-$Cl_2$-phenyl | 4.20(t, 2H) 7.20(t, 2H), 7.40(d, 2H) |
| A.751 | n-$C_3H_7$ | Tetrahydrothiopyran-3-yl | —$CH_2CH_2$—S— | 2,6-$Cl_2$-phenyl | 4.20(t, 2H) 7.20(t, 2H), 7.40(d, 2H) |
| A.752 | $C_2H_5$ | Tetrahydropyran-3-yl | —$(CH_2)_3$—O— | Phenyl | 3.90(m, 2H), 4.03(t, 2H), 4.23(t, 2H), 6.90(m, 3H), 7.27(m, 2H) |
| A.753 | n-$C_3H_7$ | Tetrahydropyran-3-yl | —$(CH_2)_3$—O— | Phenyl | 3.90(m, 2H), 4.03(t, 2H), 4.23(t, 2H), 6.90(m, 3H), 7.27(m, 2H) |
| A.754 | $C_2H_5$ | Tetrahydropyran-4-yl | —$(CH_2)_3$—O— | Phenyl | 3.97(m, 2H), 4.03(t, 2H), 4.23(t, 2H), 6.90(m, 3H), 7.27(m, 2H) |
| A.755 | n-$C_3H_7$ | Tetrahydropyran-4-yl | —$(CH_2)_3$—O— | Phenyl | 3.97(m, 2H), 4.03(t, 2H), 4.23(t, 2H), 6.90(m, 3H), 7.27(m, 2H) |
| A.756 | $C_2H_5$ | Tetrahydrothiopyran-3-yl | —$(CH_2)_3$—O— | Phenyl | 4.03(t, 2H), 4.23(t, 2H), 6.90(m, 3H), 7.27(m, 2H) |
| A.757 | n-$C_3H_7$ | Tetrahydrothiopyran-3-yl | —$(CH_2)_3$—O— | Phenyl | 4.03(t, 2H), 4.23(t, 2H), 6.90(m, 3H), 7.27(m, 2H) |

TABLE II.7-continued $(R^b, R^d, R^e = H)$

| No. | $R^a$ | $R^c$ | W | $R^f$ | phys. data NMR data in ppm M.p. in °C. |
|---|---|---|---|---|---|
| A.758 | $C_2H_5$ | Tetrahydropyran-3-yl | $-(CH_2)_3-O-$ | 2-F-phenyl | 3.90(m, 2H), 4.10(t, 2H), 4.27(t, 2H), 6.80–7.15(m, 4H) |
| A.759 | n-$C_3H_7$ | Tetrahydropyran-3-yl | $-(CH_2)_3-O-$ | 2-F-phenyl | 3.90(m, 2H), 4.10(t, 2H), 4.27(t, 2H), 6.80–7.15(m, 4H) |
| A.760 | $C_2H_5$ | Tetrahydropyran-4-yl | $-(CH_2)_3-O-$ | 2-F-phenyl | 4.00(m, 2H), 4.10(t, 2H), 4.27(t, 2H), 6.80–7.15(m, 4H) |
| A.761 | n-$C_3H_7$ | Tetrahydropyran-4-yl | $-(CH_2)_3-O-$ | 2-F-phenyl | 76–80 |
| A.762 | $C_2H_5$ | Tetrahydrothiopyran-3-yl | $-(CH_2)_3-O-$ | 2-F-phenyl | 4.10(t, 2H), 4.27(t, 2H), 6.80–7.15(m, 4H), |
| A.763 | n-$C_3H_7$ | Tetrahydrothiopyran-3-yl | $-(CH_2)_3-O-$ | 2-F-phenyl | 4.10(t, 2H), 4.27(t, 2H), 6.80–7.15(m, 4H), |
| A.764 | $C_2H_5$ | Tetrahydropyran-3-yl | $-(CH_2)_3-O-$ | 3-F-phenyl | 3.90(m, 2H), 4.05(t, 2H), 4.27(t, 2H), 6.67(m, 3H), 7.23(m, 1H) |
| A.765 | n-$C_3H_7$ | Tetrahydropyran-3-yl | $-(CH_2)_3-O-$ | 3-F-phenyl | 3.90(m, 2H), 4.05(t, 2H), 4.27(t, 2H), 6.67(m, 3H), 7.23(m, 1H) |
| A.766 | $C_2H_5$ | Tetrahydropyran-4-yl | $-(CH_2)_3-O-$ | 3-F-phenyl | 3.90–4.10(m, 4H), 4.27(t, 2H), 6.67(m, 3H), 7.23(m, 1H) |
| A.767 | n-$C_3H_7$ | Tetrahydropyran-4-yl | $-(CH_2)_3-O-$ | 3-F-phenyl | 3.90–4.10(m, 4H), 4.27(t, 2H), 6.67(m, 3H), 7.23(m, 1H) |
| A.768 | $C_2H_5$ | Tetrahydrothiopyran-3-yl | $-(CH_2)_3-O-$ | 3-F-phenyl | 4.05(t, 2H), 4.27(t, 2H), 6.67(m, 3H) 7.23(m, 1H) |
| A.769 | n-$C_3H_7$ | Tetrahydrothiopyran-3-yl | $-(CH_2)_3-O-$ | 3-F-phenyl | 4.05(t, 2H), 4.27(t, 2H), 6.67(m, 3H) 7.23(m, 1H) |
| A.770 | $C_2H_5$ | Tetrahydropyran-3-yl | $-(CH_2)_3-O-$ | 4-F-phenyl | 3.90(m, 2H), 4.03(t, 2H), 4.27(t, 2H), 6.90(m, 2H), 7.00(m, 2H) |
| A.771 | n-$C_3H_7$ | Tetrahydropyran-3-yl | $-(CH_2)_3-O-$ | 4-F-phenyl | 3.90(m, 2H), 4.03(t, 2H), 4.27(t, 2H), 6.90(m, 2H), 7.00(m, 2H) |
| A.772 | $C_2H_5$ | Tetrahydropyran-4-yl | $-(CH_2)_3-O-$ | 4-F-phenyl | 3.90–4.06(m, 4H), 4.23(t, 2H), 6.90(m, 2H), 7.00(m, 2H) |
| A.773 | n-$C_3H_7$ | Tetrahydropyran-4-yl | $-(CH_2)_3-O-$ | 4-F-phenyl | 3.90–4.06(m, 4H), 4.28(t, 2H), 6.90(m, 2H), 7.00(m, 2H) |
| A.774 | $C_2H_5$ | Tetrahydrothiopyran-3-yl | $-(CH_2)_3-O-$ | 4-F-phenyl | 4.03(t, 2H), 4.27(t, 2H), 6.90(m, 2H), 7.00(m, 2H) |
| A.775 | n-$C_3H_7$ | Tetrahydrothiopyran-3-yl | $-(CH_2)_3-O-$ | 4-F-phenyl | 4.03(t, 2H), 4.27(t, 2H), 6.90(m, 2H), 7.00(m, 2H) |
| A.776 | $C_2H_5$ | Tetrahydropyran-3-yl | $-(CH_2)_3-O-$ | 2-Cl-phenyl | |
| A.777 | n-$C_3H_7$ | Tetrahydropyran-3-yl | $-(CH_2)_3-O-$ | 2-Cl-phenyl | |
| A.778 | $C_2H_5$ | Tetrahydropyran-4-yl | $-(CH_2)_3-O-$ | 2-Cl-phenyl | |
| A.779 | n-$C_3H_7$ | Tetrahydropyran-4-yl | $-(CH_2)_3-O-$ | 2-Cl-phenyl | |
| A.780 | $C_2H_5$ | Tetrahydrothiopyran-3-yl | $-(CH_2)_3-O-$ | 2-Cl-phenyl | |
| A.781 | n-$C_3H_7$ | Tetrahydrothiopyran-3-yl | $-(CH_2)_3-O-$ | 2-Cl-phenyl | |
| A.782 | $C_2H_5$ | Tetrahydropyran-3-yl | $-(CH_2)_3-O-$ | 3-Cl-phenyl | 3.90(m, 2H), 4.06(t, 2H), 4.27(t, 2H), 6.77(m, 1H), 6.90(m, 2H), 7.17(m, 1H) |
| A.783 | n-$C_3H_7$ | Tetrahydropyran-3-yl | $-(CH_2)_3-O-$ | 3-Cl-phenyl | 3.90(m, 2H), 4.06(t, 2H), 4.27(t, 2H), 6.77(m, 1H), 6.90(m, 2H), 7.17(m, 1H) |
| A.784 | $C_2H_5$ | Tetrahydropyran-4-yl | $-(CH_2)_3-O-$ | 3-Cl-phenyl | 3.90–4.10(m, 4H), 4.27(t, 2H), 6.77(m, 1H), 6.90(m, 2H), 7.17(m, 1H) |
| A.785 | n-$C_3H_7$ | Tetrahydropyran-4-yl | $-(CH_2)_3-O-$ | 3-Cl-phenyl | 3.90–4.10(m, 4H), 4.27(t, 2H), 6.77(m, 1H), 6.90(m, 2H), 7.17(m, 1H) |
| A.786 | $C_2H_5$ | Tetrahydrothiopyran-3-yl | $-(CH_2)_3-O-$ | 3-Cl-phenyl | 4.06(t, 2H), 4.27(t, 2H), 6.77(m, 1H), 6.90(m, 2H), 7.17(m, 1H) |
| A.787 | n-$C_3H_7$ | Tetrahydrothiopyran-3-yl | $-(CH_2)_3-O-$ | 3-Cl-phenyl | 4.06(t, 2H), 4.27(t, 2H), 6.77(m, 1H), 6.90(m, 2H), 7.17(m, 1H) |
| A.788 | $C_2H_5$ | Tetrahydropyran-3-yl | $-(CH_2)_3-O-$ | 4-Cl-phenyl | 3.90(m, 2H), 4.03(t, 2H), 4.23(t, 2H), 6.80(m, 2H), 7.20(m, 2H) |
| A.789 | n-$C_3H_7$ | Tetrahydropyran-3-yl | $-(CH_2)_3-O-$ | 4-Cl-phenyl | 3.90(m, 2H), 4.03(t, 2H), 4.23(t, 2H), 6.80(m, 2H), 7.20(m, 2H) |
| A.790 | $C_2H_5$ | Tetrahydropyran-4-yl | $-(CH_2)_3-O-$ | 4-Cl-phenyl | 3.90–4.09(m, 4H), 4.23(t, 2H), 6.80(m, 2H), 7.20(m, 2H) |
| A.791 | n-$C_3H_7$ | Tetrahydropyran-4-yl | $-(CH_2)_3-O-$ | 4-Cl-phenyl | 3.90–4.09(m, 4H), 4.23(t, 2H), 6.80(m, 2H), 7.20(m, 2H) |
| A.792 | $C_2H_5$ | Tetrahydrothiopyran-3-yl | $-(CH_2)_3-O-$ | 4-Cl-phenyl | 4.03(t, 2H), 4.23(t, 2H), 6.80(m, 2H), 7.20(m, 2H) |
| A.793 | n-$C_3H_7$ | Tetrahydrothiopyran-3-yl | $-(CH_2)_3-O-$ | 4-Cl-phenyl | 4.03(t, 2H), 4.23(t, 2H), 6.80(m, 2H), 7.20(m, 2H) |
| A.794 | $C_2H_5$ | Tetrahydropyran-3-yl | $-(CH_2)_3-O-$ | 4-$NO_2$-phenyl | 3.90(m, 2H), 4.20(t, 2H), 4.28(t, 2H), 6.93(d, 2H), 8.20(d, H) |
| A.795 | n-$C_3H_7$ | Tetrahydropyran-3-yl | $-(CH_2)_3-O-$ | 4-$NO_2$-phenyl | 3.90(m, 2H), 4.20(t, 2H), 4.28(t, 2H), |

TABLE II.7-continued $(R^b, R^d, R^e = H)$

| No. | $R^a$ | $R^c$ | W | $R^f$ | phys. data NMR data in ppm M.p. in °C. |
|---|---|---|---|---|---|
| A.796 | $C_2H_5$ | Tetrahydropyran-4-yl | $-(CH_2)_3-O-$ | 4-$NO_2$-phenyl | 6.93(d, 2H), 8.20(d, 2H) 4.00(m, 2H), 4.20(t, 2H), 4.28(t, 2H), 6.93(d, 2H), 8.20(d, 2H) |
| A.797 | n-$C_3H_7$ | Tetrahydropyran-4-yl | $-(CH_2)_3-O-$ | 4-$NO_2$-phenyl | 4.00(m, 2H), 4.20(t, 2H), 4.28(t, 2H), 6.93(d, 2H), 8.20(d, 2H) |
| A.798 | $C_2H_5$ | Tetrahydrothiopyran-3-yl | $-(CH_2)_3-O-$ | 4-$NO_2$-phenyl | 4.20(t, 2H), 4.28(t, 2H), 6.93(d, 2H), 8.20(d, 2H) |
| A.799 | n-$C_3H_7$ | Tetrahydrothiopyran-3-yl | $-(CH_2)_3-O-$ | 4-$NO_2$-phenyl | 4.20(t, 2H), 4.28(t, 2H), 6.93(d, 2H), 8.20(d, 2H) |
| A.800 | $C_2H_5$ | Tetrahydropyran-3-yl | $-(CH_2)_3-O-$ | 4-Br-phenyl | 3.90(m, 2H), 4.00(t, 2H), 4.27(t, 2H), 6.80(d, 2H), 7.37(d, 2H) |
| A.801 | n-$C_3H_7$ | Tetrahydropyran-3-yl | $-(CH_2)_3-O-$ | 4-Br-phenyl | 3.90(m, 2H), 4.00(t, 2H), 4.27(t, 2H), 6.80(d, 2H), 7.37(d, 2H) |
| A.802 | $C_2H_5$ | Tetrahydropyran-4-yl | $-(CH_2)_3-O-$ | 4-Br-phenyl | 3.90–4.10(m, 4H), 4.27(t, 2H), 6.80(d, 2H), 7.37(d, 2H) |
| A.803 | n-$C_3H_7$ | Tetrahydropyran-4-yl | $-(CH_2)_3-O-$ | 4-Br-phenyl | 3.90–4.10(m, 4H), 4.27(t, 2H), 6.80(d, 2H), 7.37(d, 2H) |
| A.804 | $C_2H_5$ | Tetrahydrothiopyran-4-yl | $-(CH_2)_3-O-$ | 4-Br-phenyl | 4.00(t, 2H), 4.27(t, 2H), 6.80(d, 2H), 7.37(d, 2H) |
| A.805 | n-$C_3H_7$ | Tetrahydrothiopyran-4-yl | $-(CH_2)_3-O-$ | 4-Br-phenyl | 4.00(t, 2H), 4.27(t, 2H), 6.80(d, 2H), 7.37(d, 2H) |
| A.806 | $C_2H_5$ | Tetrahydropyran-3-yl | $-(CH_2)_3-S-$ | Phenyl | 3.90(m, 2H), 4.17(t, 2H), 7.10–7.40(m, 5H) |
| A.807 | n-$C_3H_7$ | Tetrahydropyran-3-yl | $-(CH_2)_3-S-$ | Phenyl | 3.90(m, 2H), 4.17(t, 2H), 7.10–7.40(m, 5H) |
| A.808 | $C_2H_5$ | Tetrahydropyran-4-yl | $-(CH_2)_3-S-$ | Phenyl | 4.00(m, 2H), 4.17(t, 2H), 7.10–7.40(m, 5H) |
| A.809 | n-$C_3H_7$ | Tetrahydropyran-4-yl | $-(CH_2)_3-S-$ | Phenyl | 4.00(m, 2H), 4.17(t, 2H), 7.10–7.40(m, 5H) |
| A.810 | $C_2H_5$ | Tetrahydrothiopyran-3-yl | $-(CH_2)_3-S-$ | Phenyl | 4.17(t, 2H), 7.10–7.40(m, 5H) |
| A.811 | n-$C_3H_7$ | Tetrahydrothiopyran-3-yl | $-(CH_2)_3-S-$ | Phenyl | 4.17(t, 2H), 7.10–7.40(m, 5H) |
| A.812 | $C_2H_5$ | Tetrahydropyran-3-yl | $-(CH_2)_3-S-$ | 4-F-phenyl | 3.90(m, 2H), 4.17(t, 2H), 7.00(t, 2H), 7.33(m, 2H) |
| A.813 | n-$C_3H_7$ | Tetrahydropyran-3-yl | $-(CH_2)_3-S-$ | 4-F-phenyl | 3.90(m, 2H), 4.17(t, 2H), 7.00(t, 2H), 7.33(m, 2H) |
| A.814 | $C_2H_5$ | Tetrahydropyran-4-yl | $-(CH_2)_3-S-$ | 4-F-phenyl | 4.00(m, 2H), 4.17(t, 2H), 7.00(t, 2H), 7.33(m, 2H) |
| A.815 | n-$C_3H_7$ | Tetrahydropyran-4-yl | $-(CH_2)_3-S-$ | 4-F-phenyl | 4.00(m, 2H), 4.17(t, 2H), 7.00(t, 2H), 7.33(m, 2H) |
| A.816 | $C_2H_5$ | Tetrahydrothiopyran-3-yl | $-(CH_2)_3-S-$ | 4-F-phenyl | 4.17(t, 2H), 7.00(t, 2H), 7.33(m, 2H) |
| A.817 | n-$C_3H_7$ | Tetrahydrothiopyran-3-yl | $-(CH_2)_3-S-$ | 4-F-phenyl | 4.17(t, 2H), 7.00(t, 2H), 7.33(m, 2H) |
| A.818 | $C_2H_5$ | Tetrahydropyran-3-yl | $-(CH_2)_3-S-$ | 4-Cl-phenyl | 3.90(m, 2H), 4.17(t, 2H), 7.27(s, 4H) |
| A.819 | n-$C_3H_7$ | Tetrahydropyran-3-yl | $-(CH_2)_3-S-$ | 4-Cl-phenyl | 3.90(m, 2H), 4.17(t, 2H), 7.27(s, 4H) |
| A.820 | $C_2H_5$ | Tetrahydropyran-4-yl | $-(CH_2)_3-S-$ | 4-Cl-phenyl | 4.00(m, 2H), 4.17(t, 2H), 7.27(s, 4H) |
| A.821 | n-$C_3H_7$ | Tetrahydropyran-4-yl | $-(CH_2)_3-S-$ | 4-Cl-phenyl | 4.00(m, 2H), 4.17(t, 2H), 7.27(s, 4H) |
| A.822 | $C_2H_5$ | Tetrahydrothiopyran-3-yl | $-(CH_2)_3-S-$ | 4-Cl-phenyl | 4.17(t, 2H), 7.27(s, 4H) |
| A.823 | n-$C_3H_7$ | Tetrahydrothiopyran-3-yl | $-(CH_2)_3-S-$ | 4-Cl-phenyl | 4.17(t, 2H), 7.27(s, 4H) |
| A.824 | $C_2H_5$ | Tetrahydropyran-3-yl | $-(CH_2)_3-S-$ | 2-Cl-phenyl | 3.90(m, 2H), 4.20(t, 2H), 7.07–7.40(m, 4H) |
| A.825 | n-$C_3H_7$ | Tetrahydropyran-3-yl | $-(CH_2)_3-S-$ | 2-Cl-phenyl | 3.90(m, 2H), 4.20(t, 2H), 7.07–7.40(m, 4H) |
| A.826 | $C_2H_5$ | Tetrahydropyran-4-yl | $-(CH_2)_3-S-$ | 2-Cl-phenyl | 4.00(m, 2H), 4.20(t, 2H), 7.07–7.40(m, 4H) |
| A.827 | n-$C_3H_7$ | Tetrahydropyran-4-yl | $-(CH_2)_3-S-$ | 2-Cl-phenyl | 4.00(m, 2H), 4.20(t, 2H), 7.07–7.40(m, 4H) |
| A.828 | $C_2H_5$ | Tetrahydrothiopyran-3-yl | $-(CH_2)_3-S-$ | 2-Cl-phenyl | 4.20(t, 2H), 7.07–7.40(m, 4H) |
| A.829 | n-$C_3H_7$ | Tetrahydrothiopyran-3-yl | $-(CH_2)_3-S-$ | 2-Cl-phenyl | 4.20(t, 2H), 7.07–7.40(m, 4H) |
| A.830 | $C_2H_5$ | Tetrahydropyran-3-yl | $-(CH_2)_3-S-$ | 3-Cl-phenyl | 3.90(m, 2H), 4.20(t, 2H), 7.17(m, 3H) 7.30(m, 1H) |
| A.831 | n-$C_3H_7$ | Tetrahydropyran-3-yl | $-(CH_2)_3-S-$ | 3-Cl-phenyl | 3.90(m, 2H), 4.20(t, 2H), 7.17(m, 3H) 7.30(m, 1H) |
| A.832 | $C_2H_5$ | Tetrahydropyran-4-yl | $-(CH_2)_3-S-$ | 3-Cl-phenyl | 4.00(m, 2H), 4.20(t, 2H), 7.17(m, 3H) 7.30(m, 1H) |
| A.833 | n-$C_3H_7$ | Tetrahydropyran-4-yl | $-(CH_2)_3-S-$ | 3-Cl-phenyl | 4.00(m, 2H), 4.20(t, 2H), 7.17(m, 3H) 7.30(m, 1H) |
| A.834 | $C_2H_5$ | Tetrahydrothiopyran-3-yl | $-(CH_2)_3-S-$ | 3-Cl-phenyl | 4.20(t, 2H), 7.17(m, 3H), 7.30(m, 1H) |
| A.835 | n-$C_3H_7$ | Tetrahydrothiopyran-3-yl | $-(CH_2)_3-S-$ | 3-Cl-phenyl | 4.20(t, 2H), 7.17(m, 3H), 7.30(m, 1H) |
| A.836 | $C_2H_5$ | Tetrahydropyran-3-yl | $-(CH_2)_3-S-$ | 2,5-$Cl_2$-phenyl | 3.90(m, 2H), 4.20(t, 2H), 7.07(dd, 1H), 7.20(d, 1H), 7.30(d, 1H) |
| A.837 | n-$C_3H_7$ | Tetrahydropyran-3-yl | $-(CH_2)_3-S-$ | 2,5-$Cl_2$-phenyl | 3.90(m, 2H), 4.20(t, 2H), 7.07(dd, 1H), 7.20(d, 1H), 7.30(d, 1H) |
| A.838 | $C_2H_5$ | Tetrahydropyran-4-yl | $-(CH_2)_3-S-$ | 2,5-$Cl_2$-phenyl | 4.00(m, 2H), 4.20(t, 2H), 7.07(dd, 1H), 7.20(d, 1H), 7.30(d, 1H) |
| A.839 | n-$C_3H_7$ | Tetrahydropyran-4-yl | $-(CH_2)_3-S-$ | 2,5-$Cl_2$-phenyl | 4.00(m, 2H), 4.20(t, 2H), 7.07(dd, 1H), |

TABLE II.7-continued

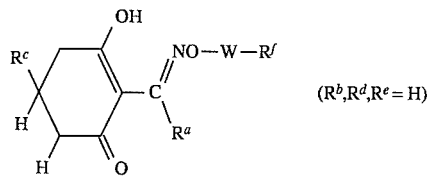

($R^b$, $R^d$, $R^e$ = H)

| No. | $R^a$ | $R^c$ | W | $R^f$ | phys. data NMR data in ppm M.p. in °C. |
|---|---|---|---|---|---|
| A.840 | $C_2H_5$ | Tetrahydrothiopyran-3-yl | $-(CH_2)_3-S-$ | 2,5-$Cl_2$-phenyl | 7.20(d, 1H), 7.30(d, 1H) 4.20(t, 2H), 7.07(dd, 1H), 7.20(d, 1H) 7.30(d, 1H) |
| A.841 | n-$C_3H_7$ | Tetrahydrothiopyran-3-yl | $-(CH_2)_3-S-$ | 2,5-$Cl_2$-phenyl | 4.20(t, 2H), 7.07(dd, 1H), 7.20(d, 1H) 7.30(d, 1H) |
| A.842 | $C_2H_5$ | Tetrahydropyran-3-yl | $-(CH_2)_3-S-$ | 2,6-$Cl_2$-phenyl | 3.90(m, 2H), 4.20(t, 2H), 7.20(t, 1H) 7.40(d, 2H) |
| A.843 | n-$C_3H_7$ | Tetrahydropyran-3-yl | $-(CH_2)_3-S-$ | 2,6-$Cl_2$-phenyl | 3.90(m, 2H), 4.20(t, 2H), 7.20(t, 1H) 7.40(d, 2H) |
| A.844 | $C_2H_5$ | Tetrahydropyran-4-yl | $-(CH_2)_3-S-$ | 2,6-$Cl_2$-phenyl | 4.00(m, 2H), 4.20(t, 2H), 7.20(t, 1H) 7.40(d, 2H) |
| A.845 | n-$C_3H_7$ | Tetrahydropyran-4-yl | $-(CH_2)_3-S-$ | 2,6-$Cl_2$-phenyl | 4.00(m, 2H), 4.20(t, 2H), 7.20(t, 1H) 7.40(d, 2H) |
| A.846 | $C_2H_7$ | Tetrahydrothiopyran-3-yl | $-(CH_2)_3-S-$ | 2,6-$Cl_2$-phenyl | 4.20(t, 2H), 7.20(t, 1H), 7.40(d, 2H) |
| A.847 | n-$C_3H_7$ | Tetrahydrothiopyran-3-yl | $-(CH_2)_3-S-$ | 2,6-$Cl_2$-phenyl | 4.20(t, 2H), 7.20(t, 1H), 7.40(d, 2H) |
| A.848 | $C_2H_5$ | Tetrahydropyran-3-yl | $-CH_2CH_2OCH_2-$ | Phenyl | 3.90(m, 2H), 4.25(t, 2H), 4.58(s, 2H), 7.38(s, 5H) |
| A.849 | n-$C_3H_7$ | Tetrahydropyran-3-yl | $-CH_2CH_2OCH_2-$ | Phenyl | 3.90(m, 2H), 4.25(t, 2H), 4.58(s, 2H), 7.38(s, 5H) |
| A.850 | $C_2H_5$ | Tetrahydropyran-4-yl | $-CH_2CH_2OCH_2-$ | Phenyl | 4.03(m, 2H), 4.33(m, 2H), 4.60(s, 2H), 7.40(s, 5H) |
| A.851 | n-$C_3H_7$ | Tetrahydropyran-4-yl | $-CH_2CH_2OCH_2-$ | Phenyl | 4.03(m, 2H), 4.33(m, 2H), 4.60(s, 2H), 7.40(s, 5H) |
| A.852 | $C_2H_5$ | Tetrahydrothiopyran-3-yl | $-CH_2CH_2OCH_2-$ | Phenyl | 4.27(m, 2H), 4.57(s, 2H), 7.35(s, 5H) |
| A.853 | n-$C_3H_7$ | Tetrahydrothiopyran-3-yl | $-CH_2CH_2OCH_2-$ | Phenyl | 4.27(m, 2H), 4.57(s, 2H), 7.35(s, 5H) |
| A.854 | $C_2H_5$ | Tetrahydropyran-3-yl | $-CH_2CH_2OCH_2-$ | 2-F-phenyl | 3.93(m, 2H), 4.27(m, 2H), 4.67(s, 2H), 6.93–7.50(m, 4H) |
| A.855 | n-$C_3H_7$ | Tetrahydropyran-3-yl | $-CH_2CH_2OCH_2-$ | 2-F-phenyl | 3.93(m, 2H), 4.27(m, 2H), 4.67(s, 2H), 6.93–7.50(m, 4H) |
| A.856 | $C_2H_5$ | Tetrahydropyran-4-yl | $-CH_2CH_2OCH_2-$ | 2-F-phenyl | 4.03(m, 2H), 4.27(m, 2H), 4.63(s, 2H), 6.97–7.50(m, 4H) |
| A.857 | n-$C_3H_7$ | Tetrahydropyran-4-yl | $-CH_2CH_2OCH_2-$ | 2-F-phenyl | 4.03(m, 2H), 4.27(m, 2H), 4.63(s, 2H), 6.97–7.50(m, 4H) |
| A.858 | $C_2H_5$ | Tetrahydrothiopyran-3-yl | $-CH_2CH_2OCH_2-$ | 2-F-phenyl | 4.27(m, 2H), 4.67(s, 2H), 6.97–7.50(m, 4H) |
| A.859 | n-$C_3H_7$ | Tetrahydrothiopyran-3-yl | $-CH_2CH_2OCH_2-$ | 2-F-phenyl | 4.27(m, 2H), 4.67(s, 2H), 6.97–7.50(m, 4H) |
| A.860 | $C_2H_5$ | Tetrahydropyran-3-yl | $-CH_2CH_2OCH_2-$ | 3-F-phenyl | 3.93(m, 2H), 4.27(m, 2H), 4.57(s, 2H), 6.90–7.15(m, 3H), 7.23–7.40(m, 1H) |
| A.861 | n-$C_3H_7$ | Tetrahydropyran-3-yl | $-CH_2CH_2OCH_2-$ | 3-F-phenyl | 3.93(m, 2H), 4.27(m, 2H), 4.57(s, 2H), 6.90–7.15(m, 3H), 7.23–7.40(m, 1H) |
| A.862 | $C_2H_5$ | Tetrahydropyran-4-yl | $-CH_2CH_2OCH_2-$ | 3-F-phenyl | 4,03(m, 2H), 4,25(m, 2H), 4,60(s, 2H), 6.90–7,18(m, 3H), 7,26–7,40(m, 1H) |
| A.863 | n-$C_3H_7$ | Tetrahydropyran-4-yl | $-CH_2CH_2OCH_2-$ | 3-F-phenyl | 4.03(m, 2H), 4.25(m, 2H), 4.60(s, 2H), 6.90–7.18(m, 3H), 7.26–7.40(m, 1H) |
| A.864 | $C_2H_5$ | Tetrahydrothiopyran-3-yl | $-CH_2CH_2OCH_2-$ | 3-F-phenyl | 4.27(m, 2H), 4.60(s, 2H), 6.90–7.15(m, 3H), 7.23–7.40(m, 1H) |
| A.865 | n-$C_3H_7$ | Tetrahydrothiopyran-3-yl | $-CH_2CH_2OCH_2-$ | 3-F-phenyl | 4.27(m, 2H), 4.60(s, 2H), 6.90–7.15(m, 3H), 7.23–7.40(m, 1H) |
| A.866 | $C_2H_5$ | Tetrahydropyran-3-yl | $-CH_2CH_2OCH_2-$ | 4-F-phenyl | 3.93(m, 2H), 4.23(m, 2H), 4.53(s, 2H), 7.00(m, 2H), 7.30(m, 2H) |
| A.867 | n-$C_3H_7$ | Tetrahydropyran-3-yl | $-CH_2CH_2OCH_2-$ | 4-F-phenyl | 3.93(m, 2H), 4.23(m, 2H), 4.53(s, 2H), 7.00(m, 2H), 7.30(m, 2H) |
| A.868 | $C_2H_5$ | Tetrahydropyran-4-yl | $-CH_2CH_2OCH_2-$ | 4-F-phenyl | 92 |
| A.869 | n-$C_3H_7$ | Tetrahydropyran-4-yl | $-CH_2CH_2OCH_2-$ | 4-F-phenyl | 4.00(m, 2H), 4.23(m, 2H), 4.53(s, 2H), 7.03(m, 2H), 7.30(m, 2H) |
| A.870 | $C_2H_5$ | Tetrahydrothiopyran-3-yl | $-CH_2CH_2OCH_2-$ | 4-F-phenyl | 4.27(m, 2H), 4.53(s, 2H), 7.03(m, 2H), 7.30(m, 2H) |
| A.871 | n-$C_3H_7$ | Tetrahydrothiopyran-3-yl | $-CH_2CH_2OCH_2-$ | 4-F-phenyl | 4.27(m, 2H), 4.53(s, 2H), 7.03(m, 2H), 7.30(m, 2H) |
| A.872 | $C_2H_5$ | Tetrahydropyran-3-yl | $-CH_2CH_2OCH_2-$ | 2-Cl-phenyl | |
| A.873 | n-$C_3H_7$ | Tetrahydropyran-3-yl | $-CH_2CH_2OCH_2-$ | 2-Cl-phenyl | |
| A.874 | $C_2H_5$ | Tetrahydropyran-4-yl | $-CH_2CH_2OCH_2-$ | 2-Cl-phenyl | |
| A.875 | n-$C_3H_7$ | Tetrahydropyran-4-yl | $-CH_2CH_2OCH_2-$ | 2-Cl-phenyl | |
| A.876 | $C_2H_5$ | Tetrahydrothiopyran-3-yl | $-CH_2CH_2OCH_2-$ | 2-Cl-phenyl | |
| A.877 | n-$C_3H_7$ | Tetrahydrothiopyran-3-yl | $-CH_2CH_2OCH_2-$ | 2-Cl-phenyl | |
| A.878 | $C_2H_5$ | Tetrahydropyran-3-yl | $-CH_2CH_2OCH_2-$ | 3-Cl-phenyl | |
| A.879 | n-$C_3H_7$ | Tetrahydropyran-3-yl | $-CH_2CH_2OCH_2-$ | 3-Cl-phenyl | |

TABLE II.7-continued $(R^b, R^d, R^e = H)$

| No. | $R^a$ | $R^c$ | W | $R^f$ | phys. data NMR data in ppm M.p. in °C. |
|---|---|---|---|---|---|
| A.880 | C₂H₅ | Tetrahydropyran-4-yl | —CH₂CH₂OCH₂— | 3-Cl-phenyl | |
| A.881 | n-C₃H₇ | Tetrahydropyran-4-yl | —CH₂CH₂OCH₂— | 3-Cl-phenyl | |
| A.882 | C₂H₅ | Tetrahydrothiopyran-3-yl | —CH₂CH₂OCH₂— | 3-Cl-phenyl | |
| A.883 | n-C₃H₇ | Tetrahydrothiopyran-3-yl | —CH₂CH₂OCH₂— | 3-Cl-phenyl | |
| A.884 | C₂H₅ | Tetrahydropyran-3-yl | —CH₂CH₂OCH₂— | 4-Cl-phenyl | 3.93(m, 2H), 4.27(m, 2H), 4.53(s, 2H), 7.28(m, 4H) |
| A.885 | n-C₃H₇ | Tetrahydropyran-3-yl | —CH₂CH₂OCH₂— | 4-Cl-phenyl | 3.93(m, 2H), 4.27(m, 2H), 4.53(s, 2H), 7.28(m, 4H) |
| A.886 | C₂H₇ | Tetrahydropyran-4-yl | —CH₂CH₂OCH₂— | 4-Cl-phenyl | 67–72 |
| A.887 | n-C₃H₇ | Tetrahydropyran-4-yl | —CH₂CH₂OCH₂— | 4-Cl-phenyl | 4.00(m, 2H), 4.23(m, 2H), 4.53(s, 2H), 7.28(m, 4H) |
| A.888 | C₂H₅ | Tetrahydrothiopyran-3-yl | —CH₂CH₂OCH₂— | 4-Cl-phenyl | 4.27(m, 2H), 4.53(s, 2H), 7.28(m, 4H) |
| A.889 | n-C₃H₇ | Tetrahydrothiopyran-3-yl | —CH₂CH₂OCH₂— | 4-Cl-phenyl | 4.27(m, 2H), 4.53(s, 2H), 7.28(m, 4H) |
| A.890 | C₂H₅ | Tetrahydropyran-3-yl | —CH₂CH₂OCH₂— | 2-CH₃-phenyl | 3.93(m, 2H), 4.23(m, 2H), 4.57(s, 2H), 7.09–7.33(m, 4H) |
| A.891 | n-C₃H₇ | Tetrahydropyran-3-yl | —CH₂CH₂OCH₂— | 2-CH₃-phenyl | 3.93(m, 2H), 4.23(m, 2H), 4.57(s, 2H), 7.09–7.33(m, 4H) |
| A.892 | C₂H₅ | Tetrahydropyran-4-yl | —CH₂CH₂OCH₂— | 2-CH₃-phenyl | 4.00(m, 2H), 4.23(m, 2H), 4.57(s, 2H), 7.09–7.33(m, 4H) |
| A.893 | n-C₃H₇ | Tetrahydropyran-4-yl | —CH₂CH₂OCH₂— | 2-CH₃-phenyl | 4.00(m, 2H), 4.23(m, 2H), 4.57(s, 2H), 7.09–7.33(m, 4H) |
| A.894 | C₂H₅ | Tetrahydrothiopyran-3-yl | —CH₂CH₂OCH₂— | 2-CH₃-phenyl | 4.23(m, 2H), 4.57(s, 2H), 7.09–7.33(m, 4H) |
| A.895 | n-C₃H₇ | Tetrahydrothiopyran-3-yl | —CH₂CH₂OCH₂— | 2-CH₃-phenyl | 4.23(m, 2H), 4.57(s, 2H), 7.09–7.33(m, 4H) |
| A.896 | C₂H₅ | Tetrahydropyran-3-yl | —CH₂CH₂OCH₂— | 3-CH₃-phenyl | 3.93(m, 2H), 4.25(m, 2H), 4.57(s, 2H), 7.00–7.32(m, 4H) |
| A.897 | n-C₃H₇ | Tetrahydropyran-3-yl | —CH₂CH₂OCH₂— | 3-CH₃-phenyl | 3.93(m, 2H), 4.25(m, 2H), 4.57(s, 2H), 7.00–7.32(m, 4H) |
| A.898 | C₂H₅ | Tetrahydropyran-4-yl | —CH₂CH₂OCH₂— | 3-CH₃-phenyl | 4.00(m, 2H), 4.27(m, 2H), 4.57(s, 2H), 7.00–7.32(m, 4H) |
| A.899 | n-C₃H₇ | Tetrahydropyran-4-yl | —CH₂CH₂OCH₂— | 3-CH₃-phenyl | 4.00(m, 2H), 4.27(m, 2H), 4.57(s, 2H), 7.00–7.32(m, 4H) |
| A.900 | C₂H₅ | Tetrahydrothiopyran-3-yl | —CH₂CH₂OCH₂— | 3-CH₃-phenyl | 4.27(m, 2H), 4.60(s, 2H), 7.00–7.32(m, 4H) |
| A.901 | n-C₃H₇ | Tetrahydrothiopyran-3-yl | —CH₂CH₂OCH₂— | 3-CH₃-phenyl | 4.27(m, 2H), 4.60(s, 2H), 7.00–7.32(m, 4H) |
| A.902 | C₂H₇ | Tetrahydropyran-3-yl | —CH₂CH₂OCH₂— | 4-CH₃-phenyl | 3.93(m, 2H), 4.20(m, 2H), 4.53(s, 2H), 7.07–7.30(m, 4H) |
| A.903 | n-C₃H₇ | Tetrahydropyran-3-yl | —CH₂CH₂OCH₂— | 4-CH₃-phenyl | 3.93(m, 2H), 4.20(m, 2H), 4.53(s, 2H), 7.07–7.30(m, 4H) |
| A.904 | C₂H₇ | Tetrahydropyran-4-yl | —CH₂CH₂OCH₂— | 4-CH₃-phenyl | 4.00(m, 2H), 4.23(m, 2H), 4.57(s, 2H), 7.03–7.27(m, 4H) |
| A.905 | n-C₃H₇ | Tetrahydropyran-4-yl | —CH₂CH₂OCH₂— | 4-CH₃-phenyl | 4.00(m, 2H), 4.23(m, 2H), 4.57(s, 2H), 7.03–7.27(m, 4H) |
| A.906 | C₂H₅ | Tetrahydrothiopyran-3-yl | —CH₂CH₂OCH₂— | 4-CH₃-phenyl | 4.23(m, 2H), 4.57(s, 2H), 7.07–7.30(m, 4H) |
| A.907 | n-C₃H₇ | Tetrahydrothiopyran-3-yl | —CH₂CH₂OCH₂— | 4-CH₃-phenyl | 4.28(m, 2H), 4.57(s, 2H), 7.07–7.30(m, 4H) |
| A.908 | C₂H₅ | Tetrahydropyran-3-yl | —CH₂CH₂OCH₂— | 4-tert.-C₄H₉ | 3.93(m, 2H), 4.23(m, 2H), 4.53(s, 2H), 7.20–7.40(m, 4H) |
| A.909 | n-C₃H₇ | Tetrahydropyran-3-yl | —CH₂CH₂OCH₂— | 4-tert.-C₄H₉ | 3.93(m, 2H), 4.23(m, 2H), 4.53(s, 2H), 7.20–7.40(m, 4H) |
| A.910 | C₂H₅ | Tetrahydropyran-4-yl | —CH₂CH₂OCH₂— | 4-tert.-C₄H₉ | 4.00(m, 2H), 4.23(m, 2H), 4.53(s, 2H), 7.20–7.40(m, 4H) |
| A.911 | n-C₃H₇ | Tetrahydropyran-4-yl | —CH₂CH₂OCH₂— | 4-tert.-C₄H₉ | 4.00(m, 2H), 4.23(m, 2H), 4.53(s, 2H), 7.20–7.40(m, 4H) |
| A.912 | C₂H₅ | Tetrahydrothiopyran-3-yl | —CH₂CH₂OCH₂— | 4-tert.-C₄H₉ | 4.23(m, 2H), 4.53(s, 2H), 7.20–7.40(m, 4H) |
| A.913 | n-C₃H₇ | Tetrahydrothiopyran-3-yl | —CH₂CH₂OCH₂— | 4-tert.-C₄H₉ | 4.23(m, 2H), 4.53(s, 2H), 7.20–7.40(m, 4H) |
| A.914 | C₂H₅ | Tetrahydropyran-3-yl | —CH₂CH₂SCH₂— | Phenyl | 3.73(s, 2H), 3.90(m, 2H), 4.17(t, 2H), 7.28(s, 5H) |
| A.915 | n-C₃H₇ | Tetrahydropyran-3-yl | —CH₂CH₂SCH₂— | Phenyl | 3.73(s, 2H), 3.90(m, 2H), 4.17(t, 2H), 7.28(s, 5H) |
| A.916 | C₂H₅ | Tetrahydropyran-4-yl | —CH₂CH₂SCH₂— | Phenyl | 3.77(s, 2H), 4.00(m, 2H), 4.13(t, 2H), 7.28(s, 5H) |
| A.917 | n-C₃H₇ | Tetrahydropyran-4-yl | —CH₂CH₂SCH₂— | Phenyl | 3.77(s, 2H), 4.00(m, 2H), 4.13(t, 2H), 7.28(s, 5H) |
| A.918 | C₂H₅ | Tetrahydrothiopyran-3-yl | —CH₂CH₂SCH₂— | Phenyl | 3.80(s, 2H), 4.13(t, 2H), 7.28(s, 5H) |
| A.919 | n-C₃H₇ | Tetrahydrothiopyran-3-yl | —CH₂CH₂SCH₂— | Phenyl | 3.80(s, 2H), 4.13(t, 2H), 7.28(s, 5H) |
| A.920 | C₂H₅ | Tetrahydropyran-3-yl | —CH₂CH₂SCH₂— | 4-F-phenyl | 3.72(s, 2H), 3.90(m, 2H), 4.13(t, 2H), 7.00(m, 2H), 7.30(m, 2H) |
| A.921 | n-C₃H₇ | Tetrahydropyran-3-yl | —CH₂CH₂SCH₂— | 4-F-phenyl | 3.72(s, 2H), 3.90(m, 2H), 4.13(t, 2H), |

TABLE II.7-continued $(R^b, R^d, R^e = H)$

| No. | $R^a$ | $R^c$ | W | $R^f$ | phys. data NMR data in ppm M.p. in °C. |
|---|---|---|---|---|---|
| A.922 | $C_2H_5$ | Tetrahydropyran-4-yl | —CH₂CH₂SCH₂— | 4-F-phenyl | 7.00(m, 2H), 7.30(m, 2H) 63–65 |
| A.923 | n-$C_3H_7$ | Tetrahydropyran-4-yl | —CH₂CH₂SCH₂— | 4-F-phenyl | 3.73(s, 2H), 4.00(m, 2H), 4.13(t, 2H), 7.00(m, 2H), 7.30(m, 2H) |
| A.924 | $C_2H_5$ | Tetrahydrothiopyran-3-yl | —CH₂CH₂SCH₂— | 4-F-phenyl | 3.75(s, 2H), 4.13(t, 2H), 7.00(m, 2H), 7.30(m, 2H) |
| A.925 | n-$C_3H_7$ | Tetrahydrothiopyran-3-yl | —CH₂CH₂SCH₂— | 4-F-phenyl | 3.75(s, 2H), 4.13(t, 2H), 7.00(m, 2H), 7.30(m, 2H) |
| A.926 | $C_2H_5$ | Tetrahydropyran-3-yl | —CH₂CH₂SCH₂— | 4-Cl-phenyl | 3.77(s, 2H), 3.93(m, 2H), 4.13(t, 2H), 7.30(s, 4H) |
| A.927 | n-$C_3H_7$ | Tetrahydropyran-3-yl | —CH₂CH₂SCH₂— | 4-Cl-phenyl | 3.77(s, 2H), 3.93(m, 2H), 4.13(t, 2H), 7.30(s, 4H) |
| A.928 | $C_2H_5$ | Tetrahydropyran-4-yl | —CH₂CH₂SCH₂— | 4-Cl-phenyl | 3.73(s, 2H), 4.00(m, 2H), 4.17(t, 2H), 7.30(s, 4H) |
| A.929 | n-$C_3H_7$ | Tetrahydropyran-4-yl | —CH₂CH₂SCH₂— | 4-Cl-phenyl | 3.73(s, 2H), 4.00(m, 2H), 4.17(t, 2H), 7.30(s, 4H) |
| A.930 | $C_2H_7$ | Tetrahydrothiopyran-3-yl | —CH₂CH₂SCH₂— | 4-Cl-phenyl | 3.73(s, 2H), 4.13(m, 2H), 7.30(s, 4H) |
| A.931 | n-$C_3H_7$ | Tetrahydrothiopyran-3-yl | —CH₂CH₂SCH₂— | 4-Cl-phenyl | 3.73(s, 2H), 4.13(m, 2H), 7.30(s, 4H) |
| A.932 | $C_2H_5$ | Tetrahydropyran-3-yl | —(CH₂)₄—O— | Phenyl | 3.70–4.20(m, 6H), 6.90(m, 3H), 7.30(m, 2H) |
| A.933 | n-$C_3H_7$ | Tetrahydropyran-3-yl | —(CH₂)₄—O— | Phenyl | 3.70–4.20(m, 6H), 6.90(m, 3H), 7.30(m, 2H) |
| A.934 | $C_2H_5$ | Tetrahydropyran-4-yl | —(CH₂)₄—O— | Phenyl | 3.83–4.23(m, 6H), 6.90(m, 3H), 7.30(m, 2H) |
| A.935 | n-$C_3H_7$ | Tetrahydropyran-4-yl | —(CH₂)₄—O— | Phenyl | 3.83–4.23(m, 6H), 6.90(m, 3H), 7.30(m, 2H) |
| A.936 | $C_2H_5$ | Tetrahydrothiopyran-3-yl | —(CH₂)₄—O— | Phenyl | 4.00(bs, 2H), 4.13(bs, 2H), 6.90(m, 3H), 7.30(m, 2H) |
| A.937 | n-$C_3H_7$ | Tetrahydrothiopyran-3-yl | —(CH₂)₄—O— | Phenyl | 4.00(bs, 2H), 4.13(bs, 2H), 6.90(m, 3H), 7.30(m, 2H) |
| A.938 | $C_2H_5$ | Tetrahydropyran-3-yl | —(CH₂)₄—O— | 2-F-phenyl | 3.93(m, 2H), 4.00–4.20(m, 4H), 6.80–7.15(m, 4H) |
| A.939 | n-$C_3H_7$ | Tetrahydropyran-3-yl | —(CH₂)₄—O— | 2-F-phenyl | 3.93(m, 2H), 4.00–4.20(m, 4H), 6.80–7.15(m, 4H) |
| A.940 | $C_2H_5$ | Tetrahydropyran-4-yl | —(CH₂)₄—O— | 2-F-phenyl | 68–72 |
| A.941 | n-$C_3H_7$ | Tetrahydropyran-4-yl | —(CH₂)₄—O— | 2-F-phenyl | 3.90–4.20(m, 6H), 6.80–7.15(m, 4H) |
| A.942 | $C_2H_5$ | Tetrahydrothiopyran-3-yl | —(CH₂)₄—O— | 2-F-phenyl | 4.00–4.20(m, 4H), 6.80–7.15(m, 4H) |
| A.943 | n-$C_3H_7$ | Tetrahydrothiopyran-3-yl | —(CH₂)₄—O— | 2-F-phenyl | 4.00–4.20(m, 4H), 6.80–7.15(m, 4H) |
| A.944 | $C_2H_5$ | Tetrahydropyran-3-yl | —(CH₂)₄—O— | 3-F-phenyl | |
| A.945 | n-$C_3H_7$ | Tetrahydropyran-3-yl | —(CH₂)₄—O— | 3-F-phenyl | |
| A.946 | $C_2H_5$ | Tetrahydropyran-4-yl | —(CH₂)₄—O— | 3-F-phenyl | |
| A.947 | n-$C_3H_7$ | Tetrahydropyran-4-yl | —(CH₂)₄—O— | 3-F-phenyl | |
| A.948 | $C_2H_5$ | Tetrahydrothiopyran-3-yl | —(CH₂)₄—O— | 3-F-phenyl | |
| A.949 | n-$C_3H_7$ | Tetrahydrothiopyran-3-yl | —(CH₂)₄—O— | 3-F-phenyl | |
| A.950 | $C_2H_5$ | Tetrahydropyran-3-yl | —(CH₂)₄—O— | 4-F-phenyl | 3.80–4.20(m, 6H), 6.75–7.05(m, 4H) |
| A.951 | n-$C_3H_7$ | Tetrahydropyran-3-yl | —(CH₂)₄—O— | 4-F-phenyl | 3.80–4.20(m, 6H), 6.75–7.05(m, 4H) |
| A.952 | $C_2H_5$ | Tetrahydropyran-4-yl | —(CH₂)₄—O— | 4-F-phenyl | 3.90–4.20(m, 6H), 6.75–7.05(m, 4H) |
| A.953 | n-$C_3H_7$ | Tetrahydropyran-4-yl | —(CH₂)₄—O— | 4-F-phenyl | 3.90–4.20(m, 6H), 6.75–7.05(m, 4H) |
| A.954 | $C_2H_5$ | Tetrahydrothiopyran-3-yl | —(CH₂)₄—O— | 4-F-phenyl | 3.90–4.20(m, 4H), 6.75–7.05(m, 4H) |
| A.955 | n-$C_3H_7$ | Tetrahydrothiopyran-3-yl | —(CH₂)₄—O— | 4-F-phenyl | 3.90–4.20(m, 4H), 6.75–7.05(m, 4H) |
| A.956 | $C_2H_5$ | Tetrahydropyran-3-yl | —(CH₂)₄—O— | 4-Cl-phenyl | 3.80–4.20(m, 6H), 6.80(m, 2H), 7.20(m, 2H) |
| A.957 | n-$C_3H_7$ | Tetrahydropyran-3-yl | —(CH₂)₄—O— | 4-Cl-phenyl | 3.80–4.20(m, 6H), 6.80(m, 2H), 7.20(m, 2H) |
| A.958 | $C_2H_7$ | Tetrahydropyran-4-yl | —(CH₂)₄—O— | 4-Cl-phenyl | 3.90–4.20(m, 6H), 6.80(m, 2H), 7.20(m, 2H) |
| A.959 | n-$C_3H_7$ | Tetrahydropyran-4-yl | —(CH₂)₄—O— | 4-Cl-phenyl | 3.90–4.20(m, 6H), 6.80(m, 2H), 7.20(m, 2H) |
| A.960 | $C_2H_5$ | Tetrahydrothiopyran-3-yl | —(CH₂)₄—O— | 4-Cl-phenyl | 3.90–4.20(m, 4H), 6.80(m, 2H), 7.20(m, 2H) |
| A.961 | n-$C_3H_7$ | Tetrahydrothiopyran-3-yl | —(CH₂)₄—O— | 4-Cl-phenyl | 3.90–4.20(m, 4H), 6.80(m, 2H), 7.20(m, 2H) |
| A.962 | $C_2H_7$ | Tetrahydropyran-3-yl | —(CH₂)₄—O— | 2,6-Cl₂-phenyl | 3.93(m, 2H), 4.00–4.25(m, 4H), 7.00(t, 1H), 7.30(d, 2H) |
| A.963 | n-$C_3H_7$ | Tetrahydropyran-3-yl | —(CH₂)₄—O— | 2,6-Cl₂-phenyl | 3.93(m, 2H), 4.00–4.25(m, 4H), 7.00(t, 1H), 7.30(d, 2H) |

TABLE II.7-continued (R$^b$, R$^d$, R$^e$ = H)

| No. | R$^a$ | R$^c$ | W | R$^f$ | phys. data NMR data in ppm M.p. in °C. |
|---|---|---|---|---|---|
| A.964 | C$_2$H$_5$ | Tetrahydropyran-4-yl | —(CH$_2$)$_4$—O— | 2,6-Cl$_2$-phenyl | 3.90–4.25(m, 6H), 7.00(t, 1H), 7.30(d, 2H) |
| A.965 | n-C$_3$H$_7$ | Tetrahydropyran-4-yl | —(CH$_2$)$_4$—O— | 2,6-Cl$_2$-phenyl | 3.90–4.25(m, 6H), 7.00(t, 1H), 7.30(d, 2H) |
| A.966 | C$_2$H$_5$ | Tetrahydrothiopyran-3-yl | —(CH$_2$)$_4$—O— | 2,6-Cl$_2$-phenyl | 4.00–4.20(m, 4H), 7.00(t, 1H), 7.30(d, 2H) |
| A.967 | n-C$_3$H$_7$ | Tetrahydrothiopyran-3-yl | —(CH$_2$)$_4$—O— | 2,6-Cl$_2$-phenyl | 4.00–4.20(m, 4H), 7.00(t, 1H), 7.30(d, 2H) |
| A.968 | C$_2$H$_5$ | Tetrahydropyran-3-yl | —CH$_2$CH$_2$OCH$_2$CH$_2$— | Phenyl | 3.90(m, 2H), 4.20(m, 2H), 7.25(m, 5H) |
| A.969 | n-C$_3$H$_7$ | Tetrahydropyran-3-yl | —CH$_2$CH$_2$OCH$_2$CH$_2$— | Phenyl | 3.90(m, 2H), 4.20(m, 2H), 7.25(m, 5H) |
| A.970 | C$_2$H$_5$ | Tetrahydropyran-4-yl | —CH$_2$CH$_2$OCH$_2$CH$_2$— | Phenyl | |
| A.971 | n-C$_3$H$_7$ | Tetrahydropyran-4-yl | —CH$_2$CH$_2$OCH$_2$CH$_2$— | Phenyl | |
| A.972 | C$_2$H$_5$ | Tetrahydrothiopyran-3-yl | —CH$_2$CH$_2$OCH$_2$CH$_2$— | Phenyl | 4.20(m, 2H), 7.25(m, 5H) |
| A.973 | n-C$_3$H$_7$ | Tetrahydrothiopyran-3-yl | —CH$_2$CH$_2$OCH$_2$CH$_2$— | Phenyl | 4.20(m, 2H), 7.25(m, 5H) |
| A.974 | C$_2$H$_5$ | Tetrahydropyran-3-yl | —CH$_2$CH$_2$OCH$_2$CH$_2$— | 4-F-phenyl | 3.90(m, 2H), 4.17(m, 2H), 6.93(m, 2H), 7.13(m, 2H) |
| A.975 | n-C$_3$H$_7$ | Tetrahydropyran-3-yl | —CH$_2$CH$_2$OCH$_2$CH$_2$— | 4-F-phenyl | 3.90(m, 2H), 4.17(m, 2H), 6.93(m, 2H), 7.13(m, 2H) |
| A.976 | C$_2$H$_5$ | Tetrahydropyran-4-yl | —CH$_2$CH$_2$OCH$_2$CH$_2$— | 4-F-phenyl | |
| A.977 | n-C$_3$H$_7$ | Tetrahydropyran-4-yl | —CH$_2$CH$_2$OCH$_2$CH$_2$— | 4-F-phenyl | |
| A.978 | C$_2$H$_5$ | Tetrahydrothiopyran-3-yl | —CH$_2$CH$_2$OCH$_2$CH$_2$— | 4-F-phenyl | 4.17(m, 2H), 6.93(m, 2H), 7.13(m, 2H) |
| A.979 | n-C$_3$H$_7$ | Tetrahydrothiopyran-3-yl | —CH$_2$CH$_2$OCH$_2$CH$_2$— | 4-F-phenyl | 4.17(m, 2H), 6.93(m, 2H), 7.13(m, 2H) |
| A.980 | C$_2$H$_5$ | Tetrahydropyran-3-yl | —CH$_2$CH$_2$OCH$_2$CH$_2$— | 4-Cl-phenyl | 3.90(m, 2H), 4.17(m, 2H), 7.13(m, 4H) |
| A.981 | n-C$_3$H$_7$ | Tetrahydropyran-3-yl | —CH$_2$CH$_2$OCH$_2$CH$_2$— | 4-Cl-phenyl | 3.90(m, 2H), 4.17(m, 2H), 7.13(m, 4H) |
| A.982 | C$_2$H$_5$ | Tetrahydropyran-4-yl | —CH$_2$CH$_2$OCH$_2$CH$_2$— | 4-Cl-phenyl | |
| A.983 | n-C$_3$H$_7$ | Tetrahydropyran-4-yl | —CH$_2$CH$_2$OCH$_2$CH$_2$— | 4-Cl-phenyl | |
| A.984 | C$_2$H$_5$ | Tetrahydrothiopyran-3-yl | —CH$_2$CH$_2$OCH$_2$CH$_2$— | 4-Cl-phenyl | 4.17(m, 2H), 7.13(m, 4H) |
| A.985 | n-C$_3$H$_7$ | Tetrahydrothiopyran-3-yl | —CH$_2$CH$_2$OCH$_2$CH$_2$— | 4-Cl-phenyl | 4.17(m, 2H), 7.13(m, 4H) |
| A.986 | C$_2$H$_7$ | Tetrahydropyran-3-yl | —(CH$_2$)$_5$—O— | Phenyl | 3.80–4.17(m, 6H), 6.90(m, 3H), 7.27(m, 2H) |
| A.987 | n-C$_3$H$_7$ | Tetrahydropyran-3-yl | —(CH$_2$)$_5$—O— | Phenyl | 3.80–4.17(m, 6H), 6.90(m, 3H), 7.27(m, 2H) |
| A.988 | C$_2$H$_5$ | Tetrahydropyran-4-yl | —(CH$_2$)$_5$—O— | Phenyl | 3.90–4.17(m, 6H), 6.90(m, 3H), 7.27(m, 2H) |
| A.989 | n-C$_3$H$_7$ | Tetrahydropyran-4-yl | —(CH$_2$)$_5$—O— | Phenyl | 3.90–4.17(m, 6H), 6.90(m, 3H), 7.27(m, 2H) |
| A.990 | C$_2$H$_5$ | Tetrahydrothiopyran-3-yl | —(CH$_2$)$_5$—O— | Phenyl | 3.97(t, 2H), 4.07(t, 2H), 6.90(m, 3H), 7.27(m, 2H) |
| A.991 | n-C$_3$H$_7$ | Tetrahydrothiopyran-3-yl | —(CH$_2$)$_5$—O— | Phenyl | 3.97(t, 2H), 4.07(t, 2H), 6.90(m, 3H), 7.27(m, 2H) |
| A.992 | C$_2$H$_7$ | Tetrahydropyran-3-yl | —(CH$_2$)$_5$—O— | 4-F-phenyl | 3.90(m, 4H), 4.03(t, 2H), 6.70–7.03(m, 4H) |
| A.993 | n-C$_3$H$_7$ | Tetrahydropyran-3-yl | —(CH$_2$)$_5$—O— | 4-F-phenyl | 3.90(m, 4H), 4.03(t, 2H), 6.70–7.03(m, 4H) |
| A.994 | C$_2$H$_7$ | Tetrahydropyran-4-yl | —(CH$_2$)$_5$—O— | 4-F-phenyl | 3.83–4.13(m, 6H), 6.70–7.03(m, 4H) |
| A.995 | n-C$_3$H$_7$ | Tetrahydropyran-4-yl | —(CH$_2$)$_5$—O— | 4-F-phenyl | 3.83–4.13(m, 6H), 6.70–7.03(m, 4H) |
| A.996 | C$_2$H$_5$ | Tetrahydrothiopyran-3-yl | —(CH$_2$)$_5$—O— | 4-F-phenyl | 3.90(t, 2H), 4.03(t, 2H) 6.70–7.03(m, 4H) |
| A.997 | n-C$_3$H$_7$ | Tetrahydrothiopyran-3-yl | —(CH$_2$)$_5$—O— | 4-F-phenyl | 3.90(t, 2H), 4.03(t, 2H) 6.70–7.03(m, 4H) |
| A.998 | C$_2$H$_5$ | Tetrahydropyran-3-yl | —(CH$_2$)$_5$—O— | 4-Cl-phenyl | 3.80–4.10(m, 6H), 6.80(d, 2H), 7.20(d, 2H) |
| A.999 | n-C$_3$H$_7$ | Tetrahydropyran-3-yl | —(CH$_2$)$_5$—O— | 4-Cl-phenyl | 3.80–4.10(m, 6H), 6.80(d, 2H), 7.20(d, 2H) |
| A.1000 | C$_2$H$_5$ | Tetrahydropyran-4-yl | —(CH$_2$)$_5$—O— | 4-Cl-phenyl | 3.87–4.10(m, 6H), 6.80(d, 2H), 7.20(d, 2H) |
| A.1001 | n-C$_3$H$_7$ | Tetrahydropyran-4-yl | —(CH$_2$)$_5$—O— | 4-Cl-phenyl | 3.87–4.10(m, 6H), 6.80(d, 2H), 7.20(d, 2H) |
| A.1002 | C$_2$H$_5$ | Tetrahydrothiopyran-3-yl | —(CH$_2$)$_5$—O— | 4-Cl-phenyl | 54–61 |
| A.1003 | n-C$_3$H$_7$ | Tetrahydrothiopyran-3-yl | —(CH$_2$)$_5$—O— | 4-Cl-phenyl | 3.90(t, 2H), 4.07(t, 2H), 6.80(d, 2H) 7.20(d, 2H) |

TABLE II.8

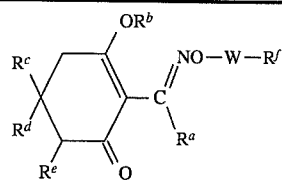

| No. | $R^a$ | $R^b$ | $R^c$ | $R^d$ | $R^e$ | W | $R^f$ | Ref./$^1$H-NMR-data[ppm] |
|---|---|---|---|---|---|---|---|---|
| A.1004 | n-$C_3H_7$ | Na | Methyl | $CH_3$ | $COOCH_3$ | $-CH_2CH=CH-$ | H | DE-A 2 439 104 |
| A.1005 | n-$C_3H_7$ | H | Methyl | $CH_3$ | $C(CH_3)=NOCH_3$ | $-CH_2CH_2-$ | H | EP-A 172 551 |
| A.1006 | n-$C_3H_7$ | Na | Tetrahydro-thiopyran-3-yl | H | H | $-CH_2CH=CH-$ | 4-F-phenyl | 0.8(t, 3H), 4.5(d, 2H), 6.35(dt, 1H), 6.6(d, 1H), 7.0–7.6(2m, 4H) |
| A.1007 | $C_2H_5$ | Na | Tetrahydro-thiopyran-3-yl | H | H | $-CH_2CH=CH-$ | 4-F-phenyl | 0.8(t, 3H), 4.5(d, 2H), 6.35(dt, 1H), 6.6(d, 1H), 7.0–7.6(2m, 4H) |
| A.1008 | n-$C_3H_7$ | O—CO—phenyl | Tetrahydro-thiopyran-3-yl | H | H | $-CH_2CH=CH-$ | 4-F-phenyl | 0.9(t, 3H), 4.75(d, 2H), 6.1(dt, 1H), 6.4(d, 1H), 6.9–8.0(5m, 9H) |
| A.1009 | $C_2H_5$ | O—CO—phenyl | Tetrahydro-thiopyran-3-yl | H | H | $-CH_2CH=CH-$ | 4-F-phenyl | 0.95(t, 3H), 4.75(d, 2H), 6.1(dt, 1H), 6.4(d, 1H), 6.9–8.0(5m, 9H) |

In addition, the desired antidote effect for the compounds I occurs in particular during use with herbicides selected from the group consisting of the 2-(4-heteroaryloxy)- or 2-(4-aryloxy)-phenoxycarboxylic acid derivatives of the formula III when their substitutes have the following meanings:

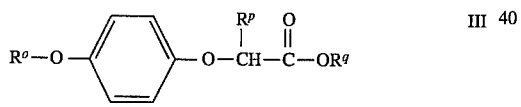

$R^o$ is phenyl, pyridyl, benzoxazolyl, benzothiazolyl or benzopyrazinyl, where these aromatic and heteroaromatic ring systems may carry one or two of the following radicals:
nitro;
halogen as stated above in general and in particular;
$C_1$–$C_4$-alkyl as stated above in general and in particular;
$C_1$–$C_4$-haloalkyl, in particular $C_1$–$C_2$-haloalkyl as stated above in general and in particular;
$C_1$–$C_4$-alkoxy as stated above in general and in particular;
$C_1$–$C_4$-haloalkoxy, in particular $C_1$–$C_2$-haloalkoxy as stated above in general and in particular;
$C_1$–$C_4$-alkylthio as stated above in general and in particular;

$R^p$ is hydrogen or methyl; and $R^q$ is hydrogen;
$C_1$–$C_4$-alkyl as stated above in general and in particular;
$C_3$–$C_4$-alkenyl, such as allyl, 2-butenyl or 3-butenyl;
$C_3$–$C_4$-alkynyl, such as propargyl, 2-butynyl or 3-butynyl;
$C_1$–$C_4$-alkoxy-$C_1$–$C_4$-alkyl as stated above in general and in particular;
$C_3$–$C_4$-alkylideneiminooxy-$C_2$- or $C_3$-alkyl is propylideneiminooxy-substituted or butylideneiminooxy-substituted $C_2$–$C_3$-alkyl such as ethyl, propyl or 1-methylethyl; tetrahydrofuranylmethyl; isoxazolidinyl;
or one equivalent of an agriculturally useful cation.

Such compounds are known from the literature (cf. for example DE-A 22 23 894, DE-A 24 33 067, DE-A 25 76 251, DE-A 30 04 770, DE-A 32 46 847, BE-A 868 875, BE-A 858 618, EP-A 054 715, EP-A 248 968, EP-A 323 127 and U.S. Pat. No. 4,753,673).

The 2-(4-Heteroaryloxy)- and 2-(4-aryloxy)-phenoxycarboxylic acid derivatives III may contain one or more centers of asymmetry. They act as racemates, as obtained in most preparation processes, but can, if desired, also be prepared as pure isomers or resolved by the conventional methods.

Both the racemates and the pure isomers were used for controlling undesirable plants from the Gramineae family. Further, the toleration of these substances by crop plants varies from commercially acceptable to nontolerated, depending on the substituents and application rate.

Specific examples of herbicides are 2-(4-heteroaryloxy)- and 2-(4-aryloxy)-phenoxycarboxylic acid derivatives of the formula III whose toleration by crop plants can be improved by substituted 3-pyrido[2,3-d]pyrimidine I are shown in Table III.1 below:

TABLE III.1

$$R^o-O-\underset{}{\underset{}{\bigcirc}}-O-CH(R^p)-C(=O)-O-R^q \quad \text{III}$$

| No. | R° | R$^p$ | R$^q$ | Reference |
|---|---|---|---|---|
| 8.01 | 3,4-dichlorophenyl | CH$_3$ | —CH$_3$ | DE-A 22 23 894 |
| 8.02 | 3-trifluoromethyl-pyridin-2-yl | CH$_3$ | -n-C$_4$H$_9$ | BE-A 868 875 |
| 8.03 | 3-trifluoromethyl-pyridin-2-yl | CH$_3$ | —CH$_2$CH$_2$OCH$_2$H$_5$ | US-A 4 753 673 |
| 8.04 | 4-chloro-2-(oxazolinyl)phenyl | CH$_3$ | —C$_2$H$_5$ | BE-A 858 618 |
| 8.05 | 3-chloro-5-trifluoromethyl-pyridin-2-yl | CH$_3$ | —CH$_3$ | BE-A 868 875 |
| 8.06 | 3-fluoro-5-chloro-pyridin-2-yl | CH$_3$ | —CH$_2$—C≡CH | EP-A 248 968 |
| 8.07 | 3,6-dichloro-pyridin-2-yl | CH$_3$ | —N(pyrrolidinyl)O | DE-A 32 46 847 |
| 8.08 | 6-chloro-quinoxalin-2-yl | CH$_3$ | —C$_2$H$_5$ | DE-A 30 04 770 |
| 8.09 | 6-chloro-quinoxalin-2-yl | CH$_3$ | —CH$_2$CH$_2$—ON=C(CH$_3$)$_2$ | EP 54 715 |
| 8.10 | 6-chloro-quinoxalin-2-yl | CH$_3$ | —CH$_2$-(tetrahydrofuran-2-yl) | EP-A 323 727 |

The herbicidal active ingredients and the antidote compound can be applied together or separately, after emergence, to the leaves and shoots of the crop plants and undesirable grasses. However, the herbicidal and antidote active ingredients are preferably applied simultaneously to the field. In the case of separate application of antidote and herbicidal active ingredient, the antidote is preferably applied first.

The antidote and the herbicidal active ingredient can be formulated together or separately and may then be in suspendable, emulsifiable or soluble form for the preparation of spray agents.

Antidote effects are also achieved by treating the seeds of the crop plants or the seedlings with the antidote prior to sowing or prior to planting out. The herbicidal ingredient is then applied alone in the conventional manner.

In the case of seed treatment, in general from 0.1 to 10 g, preferably from 1 to 2 g of active ingredient per kilogram of seed are required.

When the antidote is applied by seed swelling or when seedlings are treated, solutions which contain the antagonistic active ingredient in a concentration of from 1 to 10,000 ppm, in particular from 100 to 10,000 ppm, are preferably used.

Different amounts of antidote compound I and herbicidal compounds II and III are usually required in the various crops, the ratios being variable within wide ranges. They are dependent on the structure of the cyclohexenone derivatives II and of the heteroaryloxy- and aryloxyphenoxy acetic acid derivatives III, the substituted pyrido[2,3-d]pyrimidines I and the particular crop to which the compounds are applied. Suitable ratios of herbicidal active ingredient to substituted pyrido[2,3-d]pyrimidines I having an antidote effect are from 1:10 to 1:0.01, preferably from 1:4 to 1:0.1.

The novel agents or, in the case of separate application, the herbicidal active ingredients or the antidote are used, for example, in the form of directly sprayable solutions, powders, suspensions, including concentrated aqueous, oily or other dispensions, dispersions, emulsions, oil dispersions, pastes, dusting agents, broadcasting agents or granules, by spraying, nebulizing, dusting, broadcasting or pouring. The application form depends entirely on the particular intended use.

Mineral oil fractions having a medium to high boiling point such as kerosene and diesel oil, as well as coaltar oils and oils and fats of vegetable or animal origin, aliphatic or cyclic or aromatic hydrocarbons, for example methanol, ethanol, isopropanol, butanol, chloroform, carbon tetrachloride, cyclohexanol, cyclohexanone, chlorobenzene, toluene, xylenes, paraffin, tetrahydronaphthalene, alkylated naphthalenes or derivatives thereof or isophorone, and strong polar solvents, such as dimethylformamide, dimethyl sulfoxide, N-methylpyrrolidone and preferably water, are suitable for the preparation or directly sprayable solutions from emulsions, pastes and oil dispersions.

Aqueous application forms can be prepared from emulsion concentrates, pastes, wettable powders or oil dispersions by adding water. For the preparation of emulsions, pastes or oil dispersions, the herbicidal active ingredient and/or the antidote, as such or dissolved in an oil or solvent, can be homogenized with water using wetting agents, adherents, dispersants or emulsifiers. However, concentrates consisting of herbicidal active ingredient and/or antidote, wetting agents, adherents, and dispersants or emulsifiers and, if desired, copolymer solvents or oil and suitable for dilution with water can also be prepared.

Suitable surfactant salts are alkali metal, alkaline earth metal and ammonium salts of ligninsulfonic acid, naphthalene sulfonic acid, phenolsulfonic acid, alkylarylsufonates, alkylsufates, alkylsufonates, alkali metal and alkaline earth metal salts of dibutylnaphthalene sulfonic acid, lauryl ether sulfate, fatty alcohol sulfates, alkali metal and alkaline earth metal salts or fatty acids, salts of sulfated hexadecanols, heptadeconals, octadecanols, salts of sulfated fatty alcohol glycol ethers, condensates of sulfonated naphthalene and napthalene derivatives with formaldehyde, condensates of naphthalene or naphthalene sulfonic acids with phenol and formaldehyde, polyoxyethylene octylphenol ethers, ethoxylated isooctylphenol, octylphenol or nonylphenol, alkylphenolpolyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin sulfite waste liquors and methylcellulose.

Powders, broadcasting agents and dusting agents can be prepared by mixing or milling the herbicidal active ingredient and/or the antidote together with a solid carrier.

Granules, for example coated, impregnated and homogenous granules, can be prepared by binding their active ingredients to solid carriers. Examples of solid carriers are mineral earths, such as silica gel, silicas, silicates, talc, kaolin, attaclay, lime, chalk, talc, boles, loess, clay, dolomite, kieselguhr, calcium sulfate, magnesium sulfate, magnesium oxide, milled plastics, fertilizers, such as ammonium sulfate, ammonium phosphate or ammonium nitrate and ureas, and vegetable products, such as grain flours, barkmeal, woodmeal and nutshell meal, cellulosic powders and other solid carriers.

The formulations contain from 0.02 to 95, preferably 0.5 to 90% by weight of herbicidal active ingredient and antidote. The application rates of herbicidal active ingredient are from 0.05 to 5 kg/ha.

In addition to the antagonistic substituted pyrido[2,3-d]pyrimidines I and herbicide from the group consisting of cyclohexenones II or of the heteroaryloxy- or aryloxyphenoxycarboxylic acids III, the herbicides may contain further herbicidal or growth-regulating active ingredients with a different chemical structure, the antagonistic effect of the substituted pyrido[2,3-d]pyrimidines I being retained.

Preparation Examples (novel substituted pyrido[2,3-d]pyrimidines I):

EXAMPLE 1

7-(4-Fluorophenyl)-2-methylpyrido[2,3-d]pyrimidine

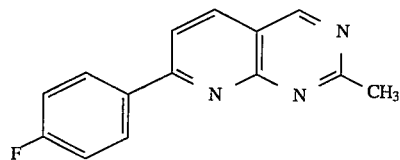

15 ml of 40% strength by weight aqueous potassium hydroxide solution were slowly added to a suspension of 30.1 g (0.22 mol) of 4-amino-5-formyl-2-methylpyrimidine and 31.7 g (0.23 mol) of 4-fluoroacetophenone in 395 ml of methanol at 20°–25° C., a homogeneous solution being formed. After the mixture had been stirred for 20 hours at about 20° C., the solid formed was isolated and was recrystallized from ethanol. Yield: 50%; mp.>200° C.

EXAMPLE 2

2-Methyl-7-(2-thienyl)-pyrido[2,3-d]pyrimidine

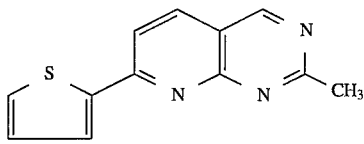

1 ml of 40% strength by weight aqueous potassium hydroxide solution was added to a suspension of 2.0 g (14.6 mmol) of 4-amino-5-formyl-2-methylpyrimidine and 1.93 g. (15.3 mmol) of 2-acetylthiophene in 25 ml of methanol. The reaction mixture was then stirred for 20 hours at 20°–25° C. after which the solvent was removed After the residue had been taken up in dichloromethane, the organic phase was washed with water, dried and evaporated down. Yield: 17%; mp.: 175°–180° C.

EXAMPLE 3

7-Amino-6-(4-fluorophenyl)-2-methyl-pyrido [2,3-d]pyrimidine

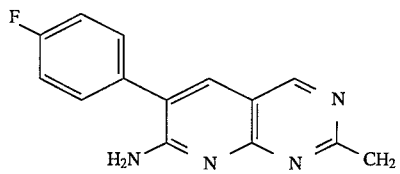

60 ml of 40% strength by weight aqueous potassium hydroxide solution were added to a suspension of 90 g (0.66 mol) of 4-amino-5-formyl-2-methylpyrimidine and 88.7 g (0.66 mol) of p-fluorophenylacetonitrile in 900 ml of methanol at 40° C., a homogeneous solution being formed. After cooling to about 20° C., the precipitate formed was separated off. 1 l of water was added to the alcoholic phase, with the result that further product crystallized out. Yield: 78%; mp.: 252°–254° C.

EXAMPLE 4

-7-Amino-6-(3-methylphenyl)-2-methylpyrido [2,3-d]pyrimidine

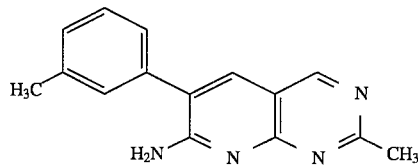

1 ml of 40% strength by weight aqueous potassium hydroxide solution was added to a mixture of 1.52 g (11.6 mmol) of m-methylphenylacetonitrile and 1.59 g (11.6 mmol) of 4-amino-5-formyl-2-methylpyridine in 15 ml of methanol at 42° C. After cooling to about 20° C. the solid formed was isolated and was washed with diethyl ether. Yield: 60%; mp.: 177°–180° C.

EXAMPLE 5

6–Cyano-7-hydroxy-2-methylpyrido [2,3-d]pyrimidine

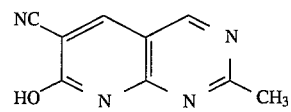

A suspension of 3 g (22 mmol) of 4-amino-5-formyl-3-methylpyrimidine, 5 g (44 mmol) of ethylcyanoacetate and 850 mg (100 mmol) of piperidine in 20 ml of ethanol was stirred for 20 hours at 20°–25° C. The fine-particled solid formed was separated off, freed from solvent residues under reduced pressure and suspended twice in 20 ml of ethanol each time. The crude product was finally washed with diethyl ether. Yield: 50% (fine powder); mp.: >200° C.

EXAMPLE 6

7-Hydroxy-6-(4-methylphenylsulfonyl)-2-methylpyrido [2,3-d]pyrimidine

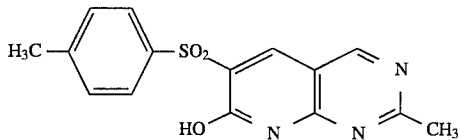

A suspension of 3 g (22 mmol) of 4-amino-5-formyl-3-methylpyrimidine and 10.6 g (44 mmol) of ethyl p-tolylsulfonyl acetate and 1.5 g (176 mmol) of piperidine in 30 ml of ethanol was stirred for 1 hour at the reflux temperature. The reaction mixture was then added to diethyl ether, after which the resulting solid was separated off and washed with diethyl ether. Yield: 45%; mp.: >200° C.

Further compounds which were prepared, or can be prepared, by the same methods are shown in Tables 1 to 5 below.

TABLE 1

$R^4 = H$

| Example No. | $R^1$ | $R^2$ | $R^3$ | $R^5$ | M.p. [°C.] | Ref. |
|---|---|---|---|---|---|---|
| 1.001 | H | H | H | $C_6H_5$ | 188 | a) |
| 1.002 | H | H | H | $4\text{-}CH_3\text{-}C_6H_4$ | 230 | |
| 1.003 | H | H | H | 1-Naphthyl | 272 | a) |
| 1.004 | H | H | H | Thien-2-yl | 194–195 | |
| 1.005 | H | H | H | Pyridin-2-yl | 200 | a) |
| 1.006 | H | H | OH | $C_6H_5$ | 294 | d) |
| 1.007 | $CH_3$ | H | H | $C_6H_5$ | >200 | |
| 1.008 | $CH_3$ | H | H | $2\text{-}CH_3\text{-}C_6H_4$ | 184 | |
| 1.009 | $CH_3$ | H | H | $4\text{-}CH_3\text{-}C_6H_4$ | >200 | |
| 1.010 | $CH_3$ | H | H | $2\text{-}F\text{-}C_6H_4$ | 200–201 | |
| 1.011 | $CH_3$ | H | H | $3\text{-}F\text{-}C_6H_4$ | 198–200 | |
| 1.012 | $CH_3$ | H | H | $4\text{-}F\text{-}C_6H_4$ | >200 | |
| 1.013 | $CH_3$ | H | H | $2\text{-}Cl\text{-}C_6H_4$ | 174–178 | |
| 1.014 | $CH_3$ | H | H | $3\text{-}Cl\text{-}C_6H_4$ | 156–160 | |
| 1.015 | $CH_3$ | H | H | $4\text{-}Cl\text{-}C_6H_4$ | >200 | |
| 1.016 | $CH_3$ | H | H | $3\text{-}Br\text{-}C_6H_4$ | 178–181 | |
| 1.017 | $CH_3$ | H | H | $3\text{-}CH_3O\text{-}C_6H_4$ | 150–155 | |
| 1.018 | $CH_3$ | H | H | $4\text{-}CH_3O\text{-}C_6H_4$ | >200 | |
| 1.019 | $CH_3$ | H | H | 4-Biphenylyl | >200 | |
| 1.020 | $CH_3$ | H | H | $4\text{-}t\text{-}Butyl\text{-}C_6H_4$ | >200 | |
| 1.021 | $CH_3$ | H | H | $4\text{-}NO_2\text{-}C_6H_4$ | >200 | |
| 1.022 | $CH_3$ | H | H | $4\text{-}CN\text{-}C_6H_4$ | >200 | |
| 1.023 | $CH_3$ | H | H | $3,4\text{-}Cl_2\text{-}C_6H_3$ | >200 | |
| 1.024 | $CH_3$ | H | H | $2,4\text{-}(OCH_3)_2\text{-}C_6H_3$ | 165–167 | |
| 1.025 | $CH_3$ | H | H | $3,4\text{-}(OCH_3)_2\text{-}C_6H_3$ | 188–192 | |
| 1.026 | $CH_3$ | H | H | 3,4-Methylenedioxy-$C_6H_3$ | | |
| 1.027 | $CH_3$ | H | H | $3\text{-}NO_2\text{-}4\text{-}Cl\text{-}C_6H_3$ | >200 | |
| 1.028 | $CH_3$ | H | H | $3\text{-}NO_2\text{-}4\text{-}OCH_3\text{-}C_6H_3$ | >200 | |
| 1.029 | $CH_3$ | H | H | 2-Naphthyl | >200 | |
| 1.030 | $CH_3$ | H | H | Thien-2-yl | 175–180 | |
| 1.031 | $CH_3$ | H | H | Thien-3-yl | 191–193 | |
| 1.032 | $CH_3$ | H | H | 5-Cl-thien-2-yl | >200 | |
| 1.033 | $CH_3$ | H | H | 5-$CH_3$-isoxazol-3-yl | >200 | |
| 1.034 | $CH_3$ | $CH_3$ | H | Pyridin-2-yl | 184 | |
| 1.035 | $CH_3$ | $CH_3$ | H | Pyridin-3-yl | 191–197 | |
| 1.036 | $CH_3$ | $CH_3$ | H | Pyridin-4-yl | 190–191 | |
| 1.037 | $CH_3$ | $CH_3$ | H | $C_6H_5$ | 135–136 | |
| 1.038 | $CH_3$ | $CH_3$ | H | $2\text{-}CH_3\text{-}C_6H_4$ | 131 | |
| 1.039 | $CH_3$ | $CH_3$ | H | $4\text{-}CH_3\text{-}C_6H_4$ | 162–165 | |
| 1.040 | $CH_3$ | $CH_3$ | H | Thien-2-yl | 167–168 | |
| 1.041 | $CH_3$ | $CH_3$ | H | Furan-2-yl | 157–160 | |
| 1.042 | $C_6H_5$ | H | H | $C_6H_5$ | 190 | |
| 1.043 | $C_6H_5$ | H | H | $4\text{-}CH_3\text{-}C_6H_4$ | 226 | |
| 1.044 | $C_6H_5$ | H | H | Thien-2-yl | 172–176 | |
| 1.045 | $C_6H_5$ | H | H | Pyridin-2-yl | 200 | |
| 1.046 | H | $C_6H_5$ | H | $C_6H_5$ | 128–130 | b) |
| 1.047 | H | $C_6H_5$ | H | $4\text{-}Cl\text{-}C_6H_4$ | 202–204 | b) |
| 1.048 | H | $C_6H_5$ | H | $4\text{-}F\text{-}C_6H_4$ | 153–155 | b) |
| 1.049 | $C_6H_5$ | $CH_3$ | H | $C_6H_5$ | 210–213 | |
| 1.050 | $C_6H_5$ | $CH_3$ | H | $4\text{-}CH_3\text{-}C_6H_4$ | 194–197 | |
| 1.051 | $C_6H_5$ | $CH_3$ | H | Thien-2-yl | 188–191 | |
| 1.052 | $OCH_3$ | $OCH_3$ | H | $C_6H_5$ | >250 | |
| 1.053 | $OCH_3$ | $OCH_3$ | H | $4\text{-}CH_3\text{-}C_6H_4$ | >250 | |
| 1.054 | $OCH_3$ | $OCH_3$ | H | Thien-2-yl | 201–204 | |
| 1.055 | $CH_2C_6H_5$ | H | H | $C_6H_5$ | 135–137 | |
| 1.056 | $CH_2C_6H_5$ | H | H | $4\text{-}CH_3\text{-}C_6H_4$ | 181–182 | |
| 1.057 | $CH_2C_6H_5$ | H | H | Thienyl | 190–191 | |
| 1.058 | $CH_3$ | H | H | Tetralin-2-yl | 223–226 | |
| 1.059 | $CH_3$ | H | H | $2\text{-}Cl\text{-}5\text{-}NO_2\text{-}C_6H_3$ | 209–211 | |
| 1.060 | $CH_3$ | H | H | $2,5\text{-}(CH_3)_2\text{-}thien\text{-}3\text{-}yl$ | 170 | |
| 1.061 | $CH_3$ | H | H | 3-$CH_3$-thien-2-yl | 120 | |
| 1.062 | $CH_3$ | H | H | 5-$CH_3$-thien-2-yl | Ol | |
| 1.063 | $CH_3$ | H | H | $2,5\text{-}Cl_2\text{-}thien\text{-}3\text{-}yl$ | 211–212 | |
| 1.064 | $CH_3$ | H | H | Benzothien-2-yl | 176–178 | |
| 1.065 | $CH_3$ | H | H | $2,5\text{-}Cl_2\text{-}C_6H_3$ | 152–156 | |
| 1.066 | $CH_3$ | H | H | $3,5\text{-}Cl_2\text{-}C_6H_3$ | 166 | |
| 1.067 | $CH_3$ | H | H | $2,3,4\text{-}Cl_3\text{-}C_6H_2$ | >200 | |
| 1.068 | $CH_3$ | H | H | $2\text{-}CH_3O\text{-}3,5\text{-}Cl_2\text{-}C_6H_2$ | 196–197 | |
| 1.069 | $CH_3$ | H | H | $2\text{-}CH_3O\text{-}C_6H_4$ | 160–165 | |

TABLE 1-continued

R⁴ = H

| Example No. | R¹ | R² | R³ | R⁵ | M.p. [°C.] | Ref. |
|---|---|---|---|---|---|---|
| 1.070 | CH₃ | H | H | 4-CF₃—C₆H₄ | 182 | |
| 1.071 | CH₃ | H | H | 4-N(CH₂)₅—C₆H₄ | >200 | |

TABLE 2

R³ = H

| Ex. No. | R⁴ | R¹ | R² | R⁵ | M.p. [°C.] | Ref. |
|---|---|---|---|---|---|---|
| 2.001 | H | H | H | NHSO₂—C₆H₅ | 188 | |
| 2.002 | CH₃ | H | H | C₆H₅ | 169 | a) |
| 2.003 | C₆H₅ | H | H | CH₃ | 203 | a) |
| 2.004 | C₆H₅ | H | H | C₆H₅ | 157 | a) |
| 2.005 | 2,6-Cl₂—C₆H₃ | H | H | NHCOCH₃ | 215–217 | f) |
| 2.006 | CH₃ | CH₃ | H | C₆H₅ | 175–178 | |
| 2.007 | C₂H₅ | CH₃ | H | C₆H₅ | 92–94 | |
| 2.008 | n-C₃H₇ | CH₃ | H | C₆H₅ | 77–81 | |
| 2.009 | 2,6-Cl₂—C₆H₃ | CH₃ | H | NHCOH | 257–259 | f) |
| 2.010 | 2,6-Cl₂—C₆H₃ | CH₃ | H | NHCOCH₃ | 202–203 | f) |
| 2.011 | 2,6-Cl₂—C₆H₃ | CH₃ | H | NHCOC₂H₅ | 192–193 | f) |
| 2.012 | 2,6-Cl₂—C₆H₃ | CH₃ | H | NHCO₂CH₃ | 136–139 | f) |
| 2.013 | H | CH₃ | CH₃ | NHSO₂-(2-Cl-6-CH₃—C₆H₃) | >215 | e) |
| 2.014 | H | CH₃ | CH₃ | NHSO₂-(2-Carbomethoxy-6-CH₃—C₆H₃) | 171–173 | e) |
| 2.015 | H | CH₃ | CH₃ | NHSO₂-(2,6-Cl₂—C₆H₃) | >230 | e) |
| 2.016 | H | CH₃ | CH₃ | NHSO₂-(2-Cl-6-CH₃—C₆H₃) | >215 | e) |
| 2.017 | H | CH₃ | CH₃ | NHSO₂-(3-OCH₃—C₆H₄) | 193–194 | |
| 2.018 | H | CH₃ | CH₃ | NHSO₂-(2-Cl—C₆H₄) | 231–232 | |
| 2.019 | H | CH₃ | CH₃ | NHSO₂-(2-F—C₆H₄) | 172–173 | |
| 2.020 | CH₃ | CH₃ | CH₃ | C₆H₅ | 120–123 | |
| 2.021 | C₆H₅ | CH₃ | CH₃ | CH₃ | 120–123 | |
| 2.022 | SO₂CH₃ | CH₃ | CH₃ | NHSO₂-(2-Cl—C₆H₄) | >230 | e) |
| 2.023 | SO₂CH₃ | CH₃ | CH₃ | NHSO₂-(2,5-Cl₂—C₆H₃) | >230 | e) |
| 2.024 | SO₂CH₃ | CH₃ | CH₃ | NHSO₂-(2-F—C₆H₄) | 107–109 | e) |
| 2.025 | SO₂CH₃ | CH₃ | CH₃ | NHSO₂-(2-Carbomethoxyphenyl) | 220–222 | e) |
| 2.026 | SO₂CH₃ | CH₃ | CH₃ | NHSO₂-(2-Cl-6-cyclopentyl-C₆H₃) | >215 | e) |
| 2.027 | SO₂CH₃ | CH₃ | CH₃ | NHSO₂-(2,6-Cl₂—C₆H₃) | >230 | e) |
| 2.028 | C₆H₅ | OCH₃ | OCH₃ | NHSO₂-(2-Cl₂—C₆H₄) | 226–228 | e) |
| 2.029 | C₆H₅ | OCH₃ | OCH₃ | NHSO₂-(2-F—C₆H₄) | 198–199 | e) |
| 2.030 | C₆H₅ | OCH₃ | OCH₃ | NHSO₂-(2,6-Cl₂—C₆H₃) | >230 | e) |
| 2.031 | C₆H₅ | OCH₃ | OCH₃ | NHSO₂-(2-Carbomethoxyphenyl) | 108–111 | e) |
| 2.032 | SO₂CH₃ | OCH₃ | OCH₃ | NHSO₂-(2-Cl—C₆H₄) | >215 | e) |
| 2.033 | SO₂CH₃ | OCH₃ | OCH₃ | NHSO₂-(2-F—C₆H₄) | 155–157 | e) |
| 2.034 | SO₂CH₃ | OCH₃ | OCH₃ | NHSO₂-(2,6-Cl₂—C₆H₃) | 213–214 | e) |
| 2.035 | SO₂CH₃ | OCH₃ | OCH₃ | NHSO₂-(2,5-Cl₂—C₆H₃) | 172–175 | e) |
| 2.036 | SO₂CH₃ | OCH₃ | OCH₃ | NHSO₂-(2-Cl-6-CH₃—C₆H₃) | 226–227 | e) |
| 2.037 | SO₂CH₃ | OCH₃ | OCH₃ | NHSO₂-(2,5-(OCH₃)₂—C₆H₃) | 128 | e) |
| 2.038 | C₆H₅ | OC₂H₅ | OC₂H₅ | NHSO₂-(2-F—C₆H₄) | 198 | e) |
| 2.039 | C₆H₅ | OC₂H₅ | OC₂H₅ | NHSO₂-(2-Cl—C₆H₄) | 169–173 | e) |
| 2.040 | CH₃ | CH₃ | H | 3-Thienyl | 172–175 | |
| 2.041 | CH₃ | CH₃ | H | 2-Thienyl | 152–154 | |

TABLE 3

$R^5 = OH$

| Ex. No. | $R^1$ | $R^2$ | $R^3$ | $R^4$ | M.p. [°C.] | Ref. |
|---|---|---|---|---|---|---|
| 3.001 | H | H | H | $CO_2C_2H_5$ | 196–199 | |
| 3.002 | H | H | H | CN | >250 | |
| 3.003 | H | H | OH | H | >340 | d) |
| 3.004 | H | H | OH | $CH_3$ | >360 | d) |
| 3.005 | H | H | OH | $C_2H_5$ | 317 | d) |
| 3.006 | H | H | OH | $C_6H_5$ | >360 | d) |
| 3.007 | H | H | OH | $CO_2C_2H_5$ | 246–248 | d) |
| 3.008 | $CH_3$ | H | H | $CO_2C_2H_5$ | >200 | c) |
| 3.009 | $CH_3$ | H | H | CN | >200 | |
| 3.010 | $CH_3$ | H | H | $SO_2CH_3$ | >250 | |
| 3.011 | $CH_3$ | H | H | $SO_2$-(4-$CH_3$—$C_6H_4$) | >200 | |
| 3.012 | $CH_3$ | H | H | 4-F—$C_6H_4$ | >260 | |
| 3.013 | $CH_3$ | $CH_3$ | H | $CO_2C_2H_5$ | 176–177 | |
| 3.014 | $CH_3$ | $CH_3$ | H | CN | >250 | |
| 3.015 | $C_6H_5$ | H | H | $CO_2C_2H_5$ | >250 | |
| 3.016 | $C_6H_5$ | H | H | CN | >250 | |
| 3.017 | $C_6H_5$ | $CH_3$ | H | $CO_2C_2H_5$ | >230 | |
| 3.018 | $C_6H_5$ | $CH_3$ | H | CN | >250 | |
| 3.019 | $OCH_3$ | $OCH_3$ | H | $CO_2C_2H_5$ | 240–243 | |
| 3.020 | $OCH_3$ | $OCH_3$ | H | CN | >250 | |
| 3.021 | $CH_2C_6H_5$ | H | H | $CO_2C_2H_5$ | 193 | |
| 3.022 | $CH_2C_6H_5$ | H | H | CN | 180–185 | |
| 3.023 | $CH_3$ | H | H | 2-Pyridyl | >220 | |

TABLE 4

$R^5 = NH_2$

| Ex. No. | $R^1$ | $R^2$ | $R^3$ | $R^4$ | M.p. [°C.] | Ref. |
|---|---|---|---|---|---|---|
| 4.001 | H | H | OH | H | >340 | d) |
| 4.002 | H | H | OH | $C_6H_5$ | >340 | d) |
| 4.003 | H | H | H | $C_6H_5$ | 289–290 | g) |
| 4.004 | H | H | H | 2-$CH_3$—$C_6H_4$ | 253–255 | f) |
| 4.005 | H | H | H | 2-Cl—$C_6H_4$ | 269–270 | g) |
| 4.006 | H | H | H | 2-Br—$C_6H_4$ | 265–267 | g) |
| 4.007 | H | H | H | 4-Br—$C_6H_4$ | 265–267 | g) |
| 4.008 | H | H | H | 2,6-$Cl_2$—$C_6H_3$ | 328–330 | f) |
| 4.009 | H | H | H | Pyridin-3-yl | 295–297 | g) |
| 4.010 | $CH_3$ | H | H | $C_6H_5$ | 229–230 | g) |
| 4.011 | $CH_3$ | H | H | 2-$CH_3$—$C_6H_4$ | 234–235 | f) |
| 4.012 | $CH_3$ | H | H | 3-$CH_3$—$C_6H_4$ | 180–188 | |
| 4.013 | $CH_3$ | H | H | 2-Cl—$C_6H_4$ | 256–260 | f) |
| 4.014 | $CH_3$ | H | H | 3-Cl—$C_6H_4$ | 208–209 | |
| 4.015 | $CH_3$ | H | H | 4-Cl—$C_6H_4$ | 262–264 | g) |
| 4.016 | $CH_3$ | H | H | 2-F—$C_6H_4$ | 278–279 | g) |
| 4.017 | $CH_3$ | H | H | 4-F—$C_6H_4$ | 252–254 | |
| 4.018 | $CH_3$ | H | H | 2-Br—$C_6H_4$ | 228–230 | f) |
| 4.019 | $CH_3$ | H | H | 3-$CH_3O$—$C_6H_4$ | 175–180 | |
| 4.020 | $CH_3$ | H | H | 4-$CH_3O$—$C_6H_4$ | >200 | |
| 4.021 | $CH_3$ | H | H | 4-$NO_2$—$C_6H_4$ | 299–301 | g) |
| 4.022 | $CH_3$ | H | H | 2,4-$Cl_2$—$C_6H_4$ | 259–261 | f) |
| 4.023 | $CH_3$ | H | H | 2,6-$Cl_2$—$C_6H_3$ | 288–290 | g) |
| 4.024 | $CH_3$ | H | H | Carbamoyl | 232–233 | g) |
| 4.025 | $CH_3$ | H | H | Pyridin-3-yl | 296–298 | g) |
| 4.026 | $CH_3$ | $CH_3$ | H | 2-$CH_3$—$C_6H_4$ | 234–235 | g) |
| 4.027 | $CH_3$ | $CH_3$ | H | 2-F—$C_6H_4$ | 222–223 | |
| 4.028 | $CH_3$ | $CH_3$ | H | 3-F—$C_6H_4$ | >230 | |
| 4.029 | $CH_3$ | $CH_3$ | H | 2-$CH_3O$—$C_6H_4$ | 210–212 | |
| 4.030 | $CH_3$ | $CH_3$ | H | 3-$CH_3O$—$C_6H_4$ | 211–214 | |
| 4.031 | $CH_3$ | $CH_3$ | H | 4-$CH_3O$—$C_6H_4$ | >250 | |
| 4.032 | $CH_3$ | $CH_3$ | H | 2,6-$Cl_2$—$C_6H_3$ | 239–240 | f) |
| 4.033 | $CH_3$ | $CH_3$ | H | CN | >210 | |

TABLE 5

$R^4 = CN$

[Structure: pyrido-pyrimidine with substituents $R^3$, $R^2$, $R^4$, $R^5$, $R^1$]

| Ex. No. | $R^3$ | $R^1$ | $R^2$ | $R^5$ | M.p. [°C.] | Ref. |
|---|---|---|---|---|---|---|
| 5.001 | H | CH$_3$ | CH$_3$ | NHSO$_2$-(2-Cl—C$_6$H$_4$) | >230 | e) |
| 5.002 | H | CH$_3$ | CH$_3$ | NHSO$_2$-(2-F—C$_6$H$_4$) | 210–212 | e) |
| 5.003 | H | CH$_3$ | CH$_3$ | NHSO$_2$-(2,6-Cl$_2$—C$_6$H$_3$) | >230 | e) |
| 5.004 | H | CH$_3$ | CH$_3$ | NHSO$_2$-(2,5-Cl$_2$—C$_6$H$_3$) | >230 | e) |
| 5.005 | H | CH$_3$ | CH$_3$ | NHSO$_2$-(2,5-(CH$_3$O)$_2$—C$_6$H$_3$) | 137 | e) |
| 5.006 | H | CH$_3$ | CH$_3$ | NHSO$_2$-(2-Cl-6-CH$_3$—C$_6$H$_3$) | 233–235 | e) |
| 5.007 | H | CH$_3$ | CH$_3$ | NHSO$_2$-(2-carbomethoxy-C$_6$H$_4$) | 220–225 | e) |
| 5.008 | H | OCH$_3$ | OCH$_3$ | NHSO$_2$-C$_6$H$_5$ | 199–201 | e) |
| 5.009 | H | OCH$_3$ | OCH$_3$ | NHSO$_2$-(2-F—C$_6$H$_4$) | 153–156 | e) |
| 5.010 | H | OCH$_3$ | OCH$_3$ | NHSO$_2$-(2,6-Cl$_2$—C$_6$H$_3$) | 218–220 | e) |
| 5.011 | H | OCH$_3$ | OCH$_3$ | NHSO$_2$-(2-carbomethoxy-C$_6$H$_4$) | 211–215 | e) |

References:
a) Evans et al., J. Org. Chem. 40 (1975), 1438
b) Söllhuber-Kretzer et al., Arch. Pharm. 316 (1983), 346
c) Nishino et al., Bull. Chem. Soc. Jpn. 45 (1972), 1127
d) Bredereck et al., Chem. Ber. 96 (1963), 1868
e) EP-A 329 012 (BASF)
f) EP-A 18 151 (Warner-Lambert)
g) Bennett et al., J. Med. Chem. 24 (1981), 382

Examples of biological action

The effect of various members of the novel herbicides or herbicide combinations, consisting of herbicide and antidote compound, on the growth of desired and undesirable plants in comparison with the herbicidal active ingredient alone is demonstrated by the following biological examples from greenhouse experiments:

In greenhouse experiments, plastic flowerpots having a capacity of about 300 cm$^3$ and containing loamy sand with about 3.0% by weight of humus as substrate served as culture vessels. Seeds of the test plants were separated according to species, shown shallowly and moistened. Thereafter, the vessels were covered with transparent plastic covers until the seeds had uniformly germinated and the plants had begun to grow.

| List of test plants | |
|---|---|
| Botanical Name | Common Name |
| Setaria viridis | green foxtail |
| Triticum aestivum | spring wheat |
| Zea mays | corn | le;2qFor the postemergence treatment, the test plants were first grown to a height of from 3 to 20 cm depending on the form of growth, and then treated. The herbicide was suspended or emulsified in water as a distributing agent and was sprayed by means of finely distributing nozzles.

The following were used as example herbicides of cyclohexenone derivatives II:

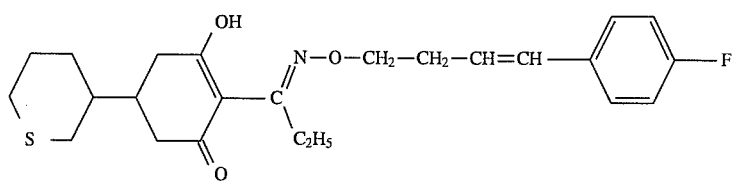

No. A.053

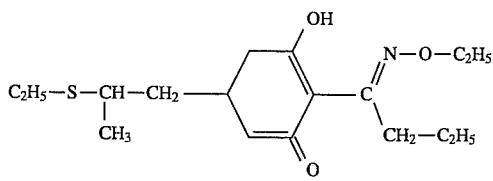

No. A.001

(Trade name: Sethoxydim)

For the postemergence treatment, all antidote compounds were prepared in a mixture consisting of 80% by weight of cyclohexanone as diluent and 20% by weight of surfactant (Emulphor EL*)) with 10% by weight of active ingredient.
* ethoxylated castor oil For comparison, the herbicidal active ingredient was formulated as a 10 to 20% by weight emulsion concentrate and was used with the addition of that amount of solvent system to the spray liquor with which the antidote compound was applied at the application rates shown on the tables. The solution was prepared by mixing the active ingredient into a solution of 93% by weight of xylene and 7% by weight of Lutensol AP-8 **).
**) nonionic surfactant based on alkylphenol polyethylene glycol ether After application of the particular active ingredient mixture, the test plants were cultivated in the greenhouse, heat-loving species at from about 18° to 30° C. and those from more temperate climates at from about 10° to 25° C.

The test period extended over from 3 to 5 weeks. During this time, the plants were tended and their reactions to the active-ingredient treatments were recorded.

The damage by the chemical agents was rated on a scale from 0 to 100% in comparison with the untreated control plants. 0 means no damage and 100 means complete destruction of the plants.

The improvement in the toleration of herbicidal cyclohexenone derivatives II by crop plants from the Gramineae family (grasses) such as wheat and corn, by pyrido[2,3-d] pyrimidines I is shown in tables X.1 to X.5 below:

TABLE X.1

Improvement in the toleration of herbicide No. A.001 by corn as a result of admixing an antidote example compound during post emergence use; greenhouse

| Anti- | Application rate [Kg/ha a.s.] | | Test plants and damage [%] | |
|---|---|---|---|---|
| dote No. | Anti-dote | Herb-icide | corn (variety: "Lixis") | weed *Setaria viridis* |
| — | — | 0.015 | 90 | 85 |
| 2.039 | 0.015 | 0.015 | 15 | 75 |
| 4.026 | 0.015 | 0.015 | 55 | 85 |
| 4.013 | 0.015 | 0.015 | 55 | 80 |
| 4.010 | 0.015 | 0.015 | 40 | 80 |
| 4.015 | 0.015 | 0,015 | 50 | 85 |
| 4.019 | 0.015 | 0.015 | 25 | 85 |
| 1.007 | 0.015 | 0.015 | 15 | 70 |
| 1.009 | 0.015 | 0.015 | 40 | 75 |
| 1.030 | 0.015 | 0.015 | 25 | 75 |
| 1.012 | 0.013 | 0.015 | 55 | 75 |

TABLE X.2

Improvement in the toleration of herbicide No. A.001 by corn and wheat as a result of admixing in antidote example compound during post emergence use; greenhouse experiment

| Anti- | Application rate [Kg/ha a.s.] | | Test plants and damage [%] | | |
|---|---|---|---|---|---|
| dote No. | Anti-dote | Herb-icide | crop plants | | weed |
| | | | corn*) | wheat**) | *Setaria viridis* |
| — | — | 0.06 | 95 | 75 | 95 |
| 2.039 | 0.06 | 0.06 | 65 | 40 | 95 |
| 4.033 | 0.06 | 0.06 | 75 | 40 | 95 |
| 4.019 | 0.06 | 0.06 | — | 45 | 98 |
| 1.007 | 0.06 | 0.06 | — | 0 | 95 |
| 1.009 | 0.06 | 0.06 | — | 20 | 95 |
| 1.030 | 0.06 | 0.06 | 60 | 15 | 90 |

*)Lixis variety
**)Spring wheat, Star variety, Table 7

TABLE X.3

Improvement in the toleration of herbicide No. A.053 by corn and wheat as a result of admixing an antidote example compound during post emergence use; greenhouse experiment

| Anti- | Application rate [Kg/ha a.s.] | | Test plants and damage [%] | | |
|---|---|---|---|---|---|
| dote No. | Anti-dote | Herb-icide | crop plants | | weed |
| | | | corn*) | wheat**) | *Setaria viridis* |
| — | — | 0.03 | 90 | 70 | 98 |
| 1.015 | 0.03 | 0.03 | 50 | 30 | 98 |
| 1.009 | 0.03 | 0.03 | 20 | 20 | 90 |
| 1.030 | 0.03 | 0.03 | 10 | 20 | 70 |
| 1.021 | 0.03 | 0.03 | — | 20 | 90 |
| 1.020 | 0.03 | 0.03 | — | 35 | 95 |
| 1.008 | 0.03 | 0.03 | — | 30 | 95 |
| 1.031 | 0.03 | 0.03 | — | 10 | 85 |
| 1.019 | 0.03 | 0.03 | — | 30 | 90 |
| 1.023 | 0.03 | 0.03 | — | 10 | 85 |
| 1.024 | 0.03 | 0.03 | — | 0 | 80 |
| 1.013 | 0.03 | 0.03 | — | 20 | 75 |
| 1.032 | 0.03 | 0.03 | — | 20 | 80 |
| 1.022 | 0.03 | 0.03 | — | 40 | 98 |

*)variety: "Lixis"
**)spring wheat, variety: "Star"

TABLE X.4

Improvement in the toleration of herbicide No. A.721 by corn and wheat as a result of admixing an antidote example compound during post emergence use; greenhouse experiment

| Anti-dote No. | Application rate [Kg/ha a.s.] Anti-dote | Application rate [Kg/ha a.s.] Herb-icide | Test plants and damage [%] crop plants corn*) | Test plants and damage [%] crop plants wheat**) | Test plants and damage [%] weed Setaria viridis |
|---|---|---|---|---|---|
| — | — | 0.125 | 35 | 90 | 100 |
| 1.001 | 0.125 | 0.125 | — | 20 | 100 |
| 1.004 | 0.125 | 0.125 | — | 25 | 98 |
| 1.044 | 0.125 | 0.125 | 0 | 45 | 100 |
| 1.052 | 0,125 | 0.125 | 0 | — | 100 |
| 1.062 | 0.125 | 0.125 | 0 | — | 100 |
| 3.002 | 0.125 | 0.125 | 0 | 10 | 98 |
| 3.013 | 0.125 | 0.125 | 0 | 45 | 100 |
| 3.014 | 0,125 | 0.125 | 0 | 65 | 100 |
| 3.018 | 0.125 | 0.125 | 0 | 45 | 100 |

*Merlin variety
**Spring wheat, Star variety

TABLE X.5

Improvement in the toleration of herbicide No. A.721 by corn as a result of admixing an antidote example compound during post emergence use; greenhouse experiment

| Anti-dote No. | Application rate [Kg/ha a.s.] Anti-dote | Application rate [Kg/ha a.s.] Herb-icide | Test plants and damage [%] crop plant corn* | Test plants and damage [%] weed Setaria viridis |
|---|---|---|---|---|
| — | — | 0.125 | 40 | 100 |
| 2.014 | 0.125 | 0.125 | 0 | 85 |
| 2.023 | 0.125 | 0.125 | 20 | 95 |
| 2.024 | 0.125 | 0.125 | 0 | 100 |
| 2.025 | 0.125 | 0.125 | 0 | 85 |
| 2.027 | 0.125 | 0.125 | 15 | 95 |
| 2.028 | 0.125 | 0.125 | 10 | 100 |
| 2.029 | 0.125 | 0.125 | 0 | 85 |
| 2.033 | 0.125 | 0.125 | 0 | 95 |
| 2.036 | 0.125 | 0.125 | 0 | 90 |
| 2.037 | 0.125 | 0.125 | 25 | 95 |
| 5.005 | 0.125 | 0.125 | 10 | 95 |

*Merlin variety

We claim:

1. A herbicidal composition containing at least one substituted pyrido[2,3-d]pyrimidine of the formula I as safener

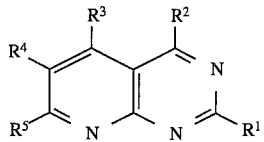

I where $R^1$ and $R^2$ are each hydrogen; $C_1$–$C_8$-alkyl; $C_1$–$C_8$-haloalkyl; $C_1$–$C_6$-alkoxy; $C_1$–$C_6$-haloalkoxy; $C_1$–$C_4$-alkoxy-$C_1$–$C_6$-alkyl; $C_1$–$C_8$-alkylamino; $C_2$–$C_8$-alkenyl; $C_2$–$C_8$-alkynyl; $C_3$–$C_8$-cycloalkyl with which a benzene radical may be fused, where this group may furthermore carry from one to three of the following radicals: hydroxyl, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

phenyl, naphthyl, phenyl-$C_1$–$C_6$-alkyl, a 5-membered aromatic ring which, in addition to carbon atoms, may contain from one to three nitrogen atoms and one oxygen or one sulfur atom as hetero atoms or which, in addition to carbon atoms, may contain from one to three nitrogen atoms or one oxygen or one sulfur atom as heteroatoms, a 6-membered aromatic ring which, in addition to carbon atoms, may contain from one to three nitrogen atoms as heteroatoms, where a benzene ring may be fused with the abovementioned 5-membered and 6-membered heteroaromatics and where the aromatic and heteroaromatic radicals may additionally carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkylthio, $C_3$–$C_6$-alkenyl and $C_3$–$C_6$-alkynyl;

$R^3$ is hydroxyl; amino; halogen; $C_1$–$C_6$-alkythio; di-$C_1$–$C_8$-alkylamino; $C_3$–$C_8$-cycloalkylamino; $C_1$–$C_8$-alkoxycarbonyl or one of the groups stated for $R^1$;

$R^4$ is one of the groups stated for $R^1$;

CN; $NO_2$; COOH; CSOH; Di-$C_1$–$C_4$-alkylamino-$C_1$–$C_4$-alkyl;

$SO_2$—$R^6$; C(=X)—$R^7$; C(=Y)—$R^8$ or $R^7$—C($YR^9$)—$ZR^{10}$;

$R^6$ is one of the groups stated for $R^1$;
hydroxyl; amino; di-$C_1$–$C_8$-alkylamino; $C_3$–$C_8$-cycloalkylamino; $C_1$–$C_6$-alkylthio;

$R^7$ amino; hydroxyamino (—NH—OH ); $C_1$–$C_8$-alkylamino;
di-$C_1$–$C_8$-alkylamino; $C_3$–$C_8$-cycloalkylamino; $C_1$–$C_8$-alkoxy; $C_1$–$C_6$-alkylthio; phenylamino;

$R^8$ is one of the groups stated for $R^1$;

$R^9$ and $R^{10}$ are each $C_1$–$C_8$-alkyl; $C_1$–$C_6$-haloalkyl; $C_1$–$C_4$-alkoxy-$C_2$–$C_6$-alkyl or $C_2$–$C_8$-alkenyl, or $R^9$ and $R^{10}$ together form —$CH_2CH_2$—, —$CH_2CH_2CH_2$— or —$CH_2CH_2CH_2CH_2$—, where one or two hydrogen atoms in these groups may be replaced by the following radicals: =O, $C_1$–$C_8$-alkyl, $C_1$–$C_6$-haloalkyl or $C_1$–$C_6$-alkoxy;

X is oxygen, sulfur or $NR^{11}$, where $R^{11}$ is one of the groups stated for $R^1$ or has the following meanings:
hydrogen; hydroxyl; amino; di-$C_1$–$C_8$-alkylamino; $C_3$–$C_8$-cycloalkylamino;
phenoxy, naphthyloxy, phenylamino or naphthylamino, where the aromatic radicals may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkylthio, $C_3$–$C_6$-alkenyl and $C_3$–$C_6$-alkynyl; and Y is oxygen or sulfur;

$R^5$ is one of the groups stated for $R^1$;
hydroxyl; amino; halogen; $C_1$–$C_6$-alkylthio; di-$C_1$–$C_8$-alkylamino; $C_3$–$C_8$-cycloalkylamino; pyrrolidin-1-yl; piperidin-1-yl; morpholin-1-yl; $C_1$–$C_8$-alkylcarbonyloxy; $C_1$–$C_4$-haloalkylcarbonyloxy; $C_1$–$C_8$-alkylsulfonyloxy; $C_1$–$C_8$-haloalkylsulfonyloxy;
phenoxy, napthyloxy, phenylamino, naphthylamino, benzyloxy, benzylamino, benzoyloxy, 2-naphthoyloxy or phenylsulfonyloxy, where the aromatic radicals may carry from one to three of the following groups: halogen, $C_1$–$C_4$-alkyl, $C_1$–$C_4$-haloalkyl and $C_1$–$C_4$-alkoxy;
$N(R^{12})$—$SO_2$—$R^{13}$; $N(R^{12})$—CO—$R^{14}$; $N(R^{12})$—CS—$R^{14}$;

$R^{12}$ is hydrogen; $C_1$–$C_4$-alkyl;
  phenyl, which may carry from one to three of the following radicals: halogen, $C_1$–$C_4$-alkyl, $C_1$–$C_4$-haloalkyl and $C_1$–$C_4$-alkoxy;
$R^{13}$ is one of the groups stated for $R^1$;
  amino, di-$C_1$–$C_8$-alkylamino or $C_3$–$C_8$-cycloalkylamino;
$R^{14}$ is one of the groups stated for $R^1$;
  amino; hydroxyamino (—NH—OH); di-$C_1$–$C_6$-alkylamino or $C_3$–$C_8$-cycloalkylamino,
and the plant-tolerated salts of those compounds I in which at least one of the substituents $R^1$ to $R^5$ is an acidic or basic group, and at least one herbicidal active ingredient selected from A) the group consisting of the cylcohexenone derivatives of the formula II

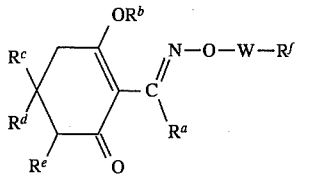

where
$R^a$ is $C_1$–$C_6$-alkyl;
$R^b$ is hydrogen;
  one equivalent of an agriculturally useful cation;
  $C_1$–$C_8$-alkylcarbonyl; $C_1$–$C_{10}$-alkylsulfonyl; $C_1$–$C_{10}$-alkylphosphonyl;
  benzoyl, benzenesulfonyl or benzenephosphonyl, where the aromatic rings may carry from 1 to 5 halogen atoms;
$R^c$ is hydrogen; CN; CHO;
  $C_1$–$C_6$-alkyl which may carry one of the following radicals: $C_1$–$C_4$-alkoxy, $C_1$–$C_4$-alkylthio, phenoxy, phenylthio, pyridyloxy or pyridylthio, where the aromatic radicals in turn may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy or $NR^g R^h$;
$R^g$ is hydrogen; $C_1$–$C_4$-alkyl; $C_3$–$C_6$-alkenyl; $C_3$–$C_6$-alkynyl; $C_1$–$C_6$-alkylcarbonyl;
  benzoyl which may carry from one to three of the following radicals: nitro, cyano, halogen, $C_1$–$C_4$-alkyl, $C_1$–$C_4$-haloalkyl, $C_1$–$C_4$-alkoxy and $C_1$–$C_4$-alkylthio;
$R^h$ is hydrogen; $C_1$–$C_4$-alkyl; $C_3$–$C_6$-alkenyl; $C_3$–$C_6$-alkynyl;
$R^c$ is furthermore
  $C_3$–$C_7$-cycloalkyl or $C_5$–$C_7$-cycloalkenyl, where these rings may carry from one to three of the following radicals: hydroxyl, halogen, $C_1$–$C_4$-alkyl, $C_1$–$C_4$-haloalkyl, $C_1$–$C_4$-alkoxy, $C_1$–$C_4$-alkylthio, benzylthio, $C_1$–$C_4$-alkylsulfonyl, $C_1$–$C_4$-alkylsulfenyl and $C_1$–$C_4$-alkylsulfinyl;
  a 5-membered saturated ring which, in addition to carbon ring members, contains one or two oxygen or sulfur atoms or one oxygen and one sulfur atom and may carry from one to three of the following radicals: $C_1$–$C_4$-alkyl, $C_1$–$C_4$-haloalkyl, $C_1$–$C_4$-alkoxy and $C_1$–$C_4$-alkylthio;
  a 6- or 7-membered saturated or monounsaturated or diunsaturated ring which, in addition to carbon ring members, contains one or two oxygen or sulfur atoms or one oxygen and one sulfur atom and may carry from one to three of the following radicals: hydroxyl, halogen, $C_1$–$C_4$-alkyl, $C_1$–$C_4$-haloalkyl, $C_1$–$C_4$-alkoxy and $C_1$–$C_4$-alkylthio;
  a 5-membered aromatic ring which, in addition to carbon ring members, contains one or two nitrogen atoms and one oxygen or sulfur atom or from one to three nitrogen atoms or one oxygen or one sulfur atom and may carry from one to three of the following radicals: cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkythio, $C_2$–$C_6$-alkenyl, $C_2$–$C_6$-alkenyloxy, $C_2$–$C_6$-alkynyl, $C_2$–$C_6$-alkynyloxy and $C_1$–$C_4$-alkoxy-$C_1$–$C_4$-alkyl;
  phenyl or pyridyl, where these rings may carry from one to three of the following radicals: nitro, formyl, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_2$–$C_6$-alkenyl, $C_2$–$C_6$-alkenyloxy, $C_3$–$C_6$-alkynyl, $C_3$–$C_6$-alkynyloxy and $NR^k R^l$;
$R^k$ is hydrogen; $C_1$–$C_4$-alkyl; $C_3$–$C_6$-alkenyl; $C_3$–$C_6$-alkynyl;
$R^l$ is hydrogen; $C_1$–$C_4$-alkyl; $C_3$–$C_6$-alkenyl; $C_3$–$C_6$-alkynyl; $C_1$–$C_6$-alkylcarbonyl;
  benzoyl, which may carry from one to three of the following radicals: nitro, cyano, halogen, $C_1$–$C_4$-alkyl, $C_1$–$C_4$-haloalkyl, $C_1$–$C_4$-alkoxy and $C_1$–$C_4$-alkylthio;
$R^d$ is hydrogen, hydroxyl or, if $R^c$ is $C_1$–$C_6$-alkyl, also $C_1$–$C_6$-alkyl;
$R^e$ is hydrogen; cyano; halogen; $C_1$–$C_4$-alkoxycarbonyl; $C_1$–$C_4$-alkylketoxime;
W is $C_1$–$C_6$-alkylene, $C_3$–$C_6$-alkenylene or alkynylene, where these groups may carry a methylene group (=$C_2$) and/or from one to three of the following radicals: halogen and $C_1$–$C_3$-alkyl;
  $C_3$–$C_6$-alkylene or $C_3$–$C_6$-alkenylene, in each of which radicals a methylene group is replaced with oxygen, sulfur, SO, $SO_2$ or $NR^i$ and from one to three hydrogen atoms may be replaced with $C_1$–$C_3$-alkyl radicals;
$R^i$ is hydrogen; $C_1$–$C_4$-alkyl; $C_3$–$C_6$-alkenyl; $C_3$–$C_6$-alkynyl; and
$R^f$ is hydrogen; CH=C—$Z^1$, where
$Z^1$ is hydrogen; cyano; carboxyl; halogen; $C_1$–$C_4$-alkyl; $C_1$–$C_4$-haloalkyl; $C_1$–$C_4$-alkoxy; $C_1$–$C_8$-alkoxycarbonyl; benzyloxycarbonyl;
  $C_3$–$C_6$-cycloalkyl which in turn may carry from one to three of the following radicals: hydroxyl, halogen, $C_1$–$C_4$-alkyl, $C_1$–$C_4$-haloalkyl and $C_1$–$C_4$-alkoxy;
  phenyl, halophenyl, dihalophenyl, thienyl or pyridyl, where these radicals may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$alkylthio or $C_3$–$C_6$-cycloalkyl, where the cyclic radical in turn may furthermore carry from one to three of the following groups: halogen, $C_1$–$C_4$-alkyl, $C_1$–$C_4$-haloalkyl and $C_1$–$C_4$-alkoxy;
$R^f$ is furthermore
  Ethynyl, which may carry one of the following radicals: $C_1$–$C_4$-alkyl, or $C_3$–$C_6$-cycloalkyl, where these groups may furthermore carry from one to three of the following radicals: hydroxyl, halogen, $C_1$–$C_4$-alkyl, $C_1$–$C_4$-haloalkyl and $C_1$–$C_4$-alkoxy;
  ethynyl which carries one of the following radicals: phenyl, thienyl or pyridyl, where the aromatic radicals may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

phenyl, a 5-membered aromatic ring which, in addition to carbon members, contains one or two nitrogen atoms and one oxygen or sulfur atom or from one to three nitrogen atoms or one oxygen or one sulfur atom, or a 6-membered aromatic ring which, in addition to carbon ring members, contains from one to four nitrogen atoms, where these aromatic and heteroaromatic groups may carry from one to three of the following radicals: nitro, $C_1$–$C_4$-alkoxy, $C_1$–$C_4$-haloalkoxy, $C_1$–$C_4$-alkylthio, $C_1$–$C_4$-haloalkylthio or the radicals stated for $Z^1$ and $NR^k R^l$ where $R^k$ and $R^l$ have the abovementioned meanings; or B) the group consisting of the 2-(4-hetaryloxy)- or 2-(4-aryloxy)-phenoxycarboxylic acid derivatives of the formula III

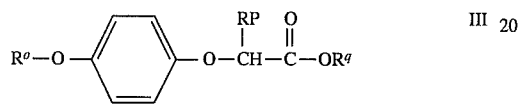

where $R^o$ is phenyl, pyridyl, benzoxazolyl, benzothiazolyl or benzopyrazinyl, where these aromatic and heteroaromatic ring systems may carry one or two of the following radicals: nitro, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^p$ is hydrogen or methyl;

$R^q$ is hydrogen; $C_1$–$C_4$-alkyl; $C_3$–$C_4$-alkenyl; $C_3$–$C_4$-alkynyl; $C_1$–$C_4$-alkoxy-$C_1$–$C_4$-alkyl; $C_3$–$C_4$-alkylideneiminoxy-$C_2$–$C_3$-alkyl; teztrahydrofuranylmethyl; isoxazolidinyl;

or one equivalent of an agriculturally useful cation.

2. The herbicidal composition as claimed in claim 1, wherein $R^5$ is one of the radicals stated for $R^1$, hydroxyl, —$N(R^{12})$—$SO_2$—$R^{13}$ or —$N(R^{12})$—$C(X)R^{14}$.

3. The herbicidal composition as claimed in claim 1, wherein $R^1$ and $R^2$ have the following meanings:

hydrogen; $C_1$–$C_6$-alkyl; $C_1$–$C_4$-haloalkyl; $C_1$–$C_4$-alkoxy-$C_1$–$C_6$-alkyl; $C_2$–$C_8$-alkenyl; $C_2$–$C_8$-alkynyl;

$C_3$–$C_8$-cycloalkyl to which a benzene radical may be fused, where this group may furthermore carry from one to three of the following radicals: hydroxyl, halogen, $C_1$–$C_4$-alkyl, $C_1$–$C_4$-haloalkyl, $C_1$–$C_4$-alkoxy and $C_1$–$C_4$-alkylthio;

phenyl, naphthyl, phenyl-$C_1$–$C_6$-alkyl, a 5-membered aromatic ring which, in addition to carbon atoms, may contain from one to three nitrogen atoms and one oxygen or one sulfur atom as hetero atoms or which, in addition to carbon atoms, may contain from one to three nitrogen atoms or one oxygen or one sulfur atom as hetero atoms, a 6-membered aromatic ring which, in addition to carbon atoms, may contain from one to three nitrogen atoms as hetero atoms, where a benzene ring may be fused to the abovementioned 5-membered and 6-membered heteroaromatics, and where the aromatic and heteroaromatic radicals may additionally carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkylthio, $C_3$–$C_6$-alkenyl and $C_3$–$C_6$-alkynyl.

4. A herbicidal composition as claimed in claim 1, containing at least one substituted pyrido[2,3-d]pyrimidine I and at least one herbicide II or one herbicide III in a weight ratio from 0.01:1 to 10:1.

5. A substituted pyrido(2,3,-d)pyrimidine of the formula I'

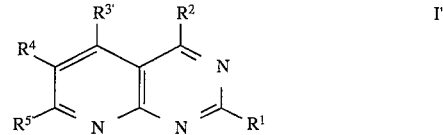

where $R^1$ is a member selected from $C_1$–$C_8$-alkylamino and one of the groups stated for $R^2$;

$R^2$ is a member selected from the group consisting of hydrogen; $C_1$–$C_8$-alkyl; $C_1$–$C_8$-haloalkyl; $C_1$–$C_6$-alkyoxy; $C_1$–$C_6$-haloalkoxy; $C_1$–$C_4$-alkoxy-$C_1$–$C_6$-alkyl; $C_2$–$C_8$-alkenyl; $C_2$–$C_8$-alkynyl; $C_3$–$C_8$-cycloalkyl with which a benzene radical may be fused, where this group may furthermore carry from one to three of the following radicals: hydroxyl, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

phenyl, naphthyl, phenyl-$C_1$–$C_6$-alkyl, a 5-membered aromatic ring which, in addition to carbon atoms, may contain from one to three nitrogen atoms and one oxygen or one sulfur atom as hetero atoms or which, in addition to carbon atoms, may contain from one to three nitrogen atoms or one oxygen or one sulfur atom as heteroatoms, a 6-membered aromatic ring which, in addition to carbon atoms, may contain from one to three nitrogen atoms as heteroatoms, where a benzene ring may be fused with the abovementioned 5-membered and 6-membered heteroaromatics and where the aromatic and heteroaromatic radicals may additionally carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkylthio, $C_3$–$C_6$-alkenyl and $C_3$–$C_6$-alkynyl;

$R^4$ is one of the groups stated for $R^1$; CN; $NO_2$; COOH; CSOH; di-$C_1$–$C_4$-alkylamino-$C_1$–$C_4$-alkyl; $SO_2R^6$; C(=X)—$R^7$; C(=Y)—$R^8$ or $R^7$—C($YR^9$)—$ZR^{10}$;

$R^6$ is one of the groups stated for $R^1$; hydroxyl; amino; di-$C_1$–$C_8$-alkylamino; $C_3$–$C_8$-cycloalkylamino; $C_1$–$C_6$-alkylthio;

$R^7$ amino; hydroxyamino (—NH—OH); $C_1$–$C_8$-alkylamino; di-$C_1$–$C_8$-alkylamino; $C_3$–$C_8$-cycloalkylamino; $C_1$–$C_8$-alkoxy; $C_1$–$C_8$-alkylthio; phenylamino;

$R^8$ is one of the groups stated for $R^1$;

$R^9$ and $R^{10}$ are each $C_1$–$C_8$-alkyl; $C_1$–$C_6$-haloalkyl; $C_1$–$C_4$-alkoxy-$C_2$–$C_6$-alkyl or $C_2$–$C_8$-alkenyl, or $R^9$ and $R^{10}$ together form —$CH_2$—$CH_2$—, $CH_2$—$CH_2$—$CH_2$ or $CH_2$—$CH_2$—$CH_2$—$CH_2$, where one or two hydrogen atoms in these groups may be replaced by the following radicals: =O, $C_1$–$C_8$-alkyl, $C_1$–$C_6$-haloalkyl or $C_1$–$C_6$-alkoxy;

X is oxygen, sulfur or $NR^{11}$, where $R^{11}$ is one of the groups stated for $R^1$ or has the following meanings:

hydrogen; hydroxyl; amino; di-$C_1$–$C_8$-alkylamino; $C_3$–$C_8$-cycloalkylamino;

phenoxy, naphthyloxy, phenylamino or naphthylamino, where the aromatic radicals may carry from one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl, $C_1$–$C_4$-alkylthio, $C_3$–$C_6$-alkenyl and $C_3$–$C_6$-alkynyl; and Y is oxygen or sulfur;

$R^{3'}$ is halogen, $C_1$–$C_6$-alkylthio or one of the groups stated for $R^1$;

$R^{5'}$ is one of the groups stated for $R^2$; hydroxyl; halogen; $C_1$–$C_6$-alkylthio; $C_1$–$C_8$-alkylcarbonyloxy; $C_1$–$C_8$-alkylsulfonyloxy; phenoxy; benzyloxy; phenylsulfonyloxy; where the aromatic radical may carry from one to three of the following groups: halogen, $C_1$–$C_4$-alkyl, $C_1$–$C_4$-haloalkyl and $C_1$–$C_4$-alkoxy;

with the proviso that $R^l$ and $R^{3'}$ are not simultaneously hydrogen when $R^2$ is hydrogen or phenyl and $R^4$ is phenyl or $R^{5'}$ is phenyl, halophenyl, naphthyl or pyridyl, and with the proviso that $R^2$, $R^{3'}$, $R^4$ and $R^{5'}$ are not simultaneously hydrogen when $R^l$ is hydrogen or pyridyl, and with the proviso that $R^2$ may not be alkoxy when $R^1$, $R^{3'}$, $R^4$ and $R^5$ are simultaneously hydrogen;

and the plant-tolerated salts of those compounds I' in which at least one of the substituents $R^l$, $R^2$, $R^{3'}$, $R^4$ and $R^{5'}$, is an acidic or basic group.

6. A method for controlling undesirable plant growth, wherein at least one substituted pyrido[2,3-d]pyrimidine safener of formula I and at least A) one herbicidal cyclohexenone derivative of the formula II or B) one herbicidal 2-(4-heteroaryloxy)- or 2-(4-aryloxy)-phenoxycarboxylic acid derivative of the formula III as claimed in claim 1, are applied simultaneously or in succession, before, during or after the sowing of the crop plants or before or during the emergence of the crop plants.

7. A method for selectively controlling undesirable plant growth, wherein the leaves of the crop plants and of the weeds are treated simultaneously or in succession by the post emergence method with at least one substituted pyrido[2,3-d]pyrimidine safener of formula I and at least A) one herbicidal cyclohexenone derivative of the formula II or B) one herbicidal 2-(4-heteroaryloxy)- or 2-(4-aryloxy)-phenoxycarboxylic acid derivative of the formula III as claimed in claim 1.

8. A method for preventing damage to crop plants by

A) herbicidal cyclohexenone derivatives of the formula II or

B) herbicidal 2-(4-heteroaryloxy)- or 2-(4-aryloxy)-phenoxycarboxylic acid derivatives of the formula III as claimed in claim 1, wherein the seed of the crop plants is treated with an antagonistic amount of the substituted pyrido[2,3-d]pyrimidine of the formula I.weeds are treated simultaneously or in succession by the post emergence method with at least one substituted pyrido[2,3-d]pyrimidine safener of formula I and at least A) one herbicidal cyclohexenone derivative of the formula II or B) one herbicidal 2-(4-heteroaryloxy)- or 2-(4-aryloxy)-phenoxycarboxylic acid derivative of the formula III as claimed in claim 1.

8. A method for preventing damage to crop plants by

A) herbicidal cyclohexenone derivatives of the formula II or

B) herbicidal 2-(4-heteroaryloxy)- or 2-(4-aryloxy)-phenoxycarboxylic acid derivatives of the formula III as claimed in claim 1, wherein the seed of the crop plants is treated with an antagonistic amount of the substituted pyrido [2,3-d]pyrimidine of the formula I.

9. A method as claimed in claim 6, wherein the crop plants are barley, wheat, corn, millet and rice.

* * * * *

UNITED STATES PATENT AND TRADEMARK OFFICE
CERTIFICATE OF CORRECTION

PATENT NO.: 5,597,776

DATED: January 28, 1997

INVENTOR(S): BRATZ et al.

It is certified that error appears in the above-identified patent and that said Letters Patent is hereby corrected as shown below:

On the cover page, item [57], in the Abstract, after formula I, insert
--where $R^1$, $R^2$, $R^3$, $R^4$ and $R^5$ have the meanings in the specification,--.

Column 121, claim 1, line 15, "cylcohexenone" should be --cyclohexenone--.

Column 123, claim 1, line 20, in formula III "RP" should be --$R^p$--.

Column 125, claim 5, lines 11, 15 and 21, "$R^\ell$" should be --$R^1$--.

Column 126, the first claim 8 on lines 7-24 should be deleted.

Signed and Sealed this

Sixth Day of May, 1997

Attest:

BRUCE LEHMAN

*Attesting Officer*      *Commissioner of Patents and Trademarks*